United States Patent [19]
Jastrzebski et al.

[11] Patent Number: 5,218,530
[45] Date of Patent: Jun. 8, 1993

[54] METHOD OF DISPLAYING AND ANALYZING NONLINEAR, DYNAMIC BRAIN SIGNALS

[76] Inventors: George B. Jastrzebski, 824 McGuire Dr., Modesto, Calif. 95355; Lowell R. Wedemeyer, 3112 Thatcher Ave., Marina Del Rey, Calif. 90292

[21] Appl. No.: 405,331
[22] Filed: Sep. 11, 1989
[51] Int. Cl.$^5$ ............................................. G06F 15/42
[52] U.S. Cl. ............................... 364/413.05; 395/119; 395/125; 364/413.06
[58] Field of Search ....................... 364/413.05, 413.06, 364/413.07, 521; 395/119, 125, 128

[56] References Cited

U.S. PATENT DOCUMENTS

| | | | |
|---|---|---|---|
| 4,603,703 | 8/1986 | McGill et al. | 128/731 |
| 4,736,307 | 4/1988 | Salb | 364/518 |
| 4,744,029 | 5/1988 | Raviv et al. | 364/413.05 |
| 4,753,246 | 1/1988 | Freeman | 128/731 |
| 5,003,986 | 4/1991 | Finitzo et al. | 128/731 |
| 5,041,973 | 8/1991 | Lebron et al. | 364/413.05 |

OTHER PUBLICATIONS

Packard, N. H.; Crutchfield, J. P.; Farmer, J. Doyne; and Shaw R. S.; *Geometry of a Time Series*, Physical Review Letters, vol. 47 p. 712 (1980).

Wadlinger, E. Alan, A computer program to fit hyperellipses to a set of phase space points in as many as six dimensions, Department of Energy, Los Alamos Scientific Laboratory, 1980. For sale by the National Technical Information Services, Series Title L.A.; 8271-MS, Springfield, Va.

Takens, F., *Detecting Strange Attractors in Turbulence*, Lecture Notes in Mathematics 898, Dynamical Systems and Turbulence, Warwick 1980, D. A. Rand and L. S. Young, Eds., (Berlin, Springer-Verlag, 1981.).

Froehling, H.; Crutchfield, J. P.; Farmer, J. Doyne; Packard, N. H.; and Shaw, R. S., *On Determining the Dimension of Chaotic Flows*, Physica 3D, pp. 605-617, (1981).

Farmer, J. Doyne; Ott, E.; Yorke, J. A., *The Dimension of Chaotic Attractors*, Physica 7D (1983) 153-180.

Albano, A. M.; Smilowitz, L.; Rapp, P. E.; de Guzman, G. C.; Bashore, T. R., *Dimension Calculations in a Minimal Embedding Space: Low-Dimensional Attractors for Human Electroencephalograms*, in Lecture Notes in Physics 278, The Physics of Phase Space, University of Maryland, May 20-23, 1986, Springer-Verlag, Berlin: New York. (Note additional references in bibliography of this article.).

Ritter, H. J.; Martinez, T. M.; Schulten, K. J., *Topology—Conserving Maps for Learning Visuo-Motor—Coordination*, Neural Networks, vol. 2, pp. 159-168 (1989) (received Sep. 16, 1988; revised and accepted Oct. 18, 1988).

*Is It Healthy to Be Chaotic?* and *The Footprints of Chaos*, Science, vol. 243, pp. 604-607, Feb. 8, 1989.

Goldberger, Ary L.; *Cardiac Chaos*, Science, Mar. 17, 1989, Letters, p. 1419.

*Chaos Theory: How Big an Advance*, Science, vol. 245, pp. 26-28, Jul. 7, 1989.

Primary Examiner—Roy N. Envall, Jr.
Assistant Examiner—A. Bodendorf
Attorney, Agent, or Firm—Lowell R. Wedemeyer

[57] ABSTRACT

The invention is a method to aid analysis of signals, such as electroencephalograms, pursuant to modern mathematical theories of nonlinear dynamical processes, sometimes referred to as chaotic dynamics or chaos theory. It employs graphic display and visual inspection of relatively less filtered, non-averaged raw test data, including raw data heretofore considered random or asynchronous 'noise'. The invention enables reversible decomposition of selected elements of graphic portraits of raw signal data to identify subsets of the depicted raw data which correspond to visually-identified, manually-selected patterns from within the graphic portrait. The identified subsets of raw data can be segregated even though a precise mathematical description of the visually identified pattern is unknown. The invention further comprises a variety of techniques for displaying four or more variables and for enhancing visual discrimination of patterns within computer generated graphic phase space portraits, and conceptions for overlaying symbols onto graphic points representing stimulus and response events concurring with particular signal samples in the phase space portrait. The invention also comprises subsets of pattern-generating signal data identified by the method of the invention and thus made available for further computer or other operations separately from the full data set.

27 Claims, 1 Drawing Sheet

METHOD OF DISPLAYING AND ANALYZING NONLINEAR, DYNAMIC BRAIN SIGNALS

There are no related applications. No federally-sponsored research and development is involved.

SUMMARY OF THE INVENTION

The invention is a method for applying the new theories of chaotic dynamics to brain signals. It enables a computer operator to automatically identify in a recorded stream of brain signal data the subsets of signal data which correspond to manually-selected patterns observed in multi-variable, reversibly-transformable, phase space portraits. The data selection is enabled even though no algorithm describing the observed pattern is known. This data selection capability is combined with enhanced capabilities to display and manipulate multi-variable phase space portraits, thereby increasing the ability to visually discriminate patterns in the stream of data for selection.

The invention draws a large number of variables into a graphic phase space portrait for display on a computer monitor. It then enables manual selection of subsets of drawing elements from within the displayed portrait corresponding to visually identified patterns, and automatically decomposes the selected drawing elements to identify the subset of signal data corresponding to the visually-identified patterns. Each phase space portrait can simultaneously display multiple variables, including three spatial coordinates corresponding to three separate signal detectors, plus scalar magnitude, direction of change, and color-coded time sequence. In principle, such portraits also could display another variable corresponding to drawing line type and could superpose symbols to depict stimulus and response events relative to the time sequence of recorded signals, though the current model does not implement these features.

The invention also creates and depicts composite phase space portraits of larger sets of four or more signal detectors by means of overlays of simultaneous phase space portraits from a plurality of three-detector subsets. Variable colors serve to visually distinguish the contributions of each layer to the composite, thus enabling visual discrimination of the particular subsets of detectors which provide the signals of most interest. In principle, variable line types also could be used to distinguish layers.

One aspect of the invention may be viewed as a computer-assisted manual sieve to identify from a stream of data the subsets of data which correspond to an observed pattern where no algorithm describing the observed pattern is known. The resulting subsets of pattern-containing data then are available for more intensive analysis and other operations, including efforts to define a descriptive algorithm for the observed pattern and efforts to create a 'template' for automated computer-aided pattern recognition.

BACKGROUND OF THE INVENTION

The field of this invention is analytic methods for depiction and analysis of brain signals. Electric potentials have been measured on scalps or with implanted electrodes for decades. The subjects of such measurements have been both human and animal. The current method, commonly called an electroencephalogram or EEG, measures and records a data stream comprised of the electric potentials between each of a plurality of detection electrodes distributed across the subject's scalp and a reference electrode attached to some other portion of the subject's head. A common reference electrode, such as one on an earlobe, may be used.

The relationship between a given electrode and the reference electrode is customarily called a "channel". It has been recognized that the placement of the plurality of electrodes affects the signal collection. Therefore, conventions, such as the "ten-twenty", have been agreed upon to guide the geographic distribution of electrodes about the scalp for collection of EEGs for clinical use.

The data stream of electric potentials from each channel is electronically amplified to strengths suitable for computer analysis and recorded. In modern practice the data stream usually is digitized for use in digital computers, but the data stream can be analyzed by analog computer if desired. The amplified electric potentials usually are electronically 'filtered' to limit the collected signal to selected electronic frequencies. The data stream also frequently is 'averaged' to eliminate more-random or asynchronous data that has been assumed to be meaningless 'noise'.

In digital computer analysis the data stream sometimes is passed through a Fast Fourier Transform, or FFT. Less commonly, the data may be analyzed through a Mellin or 'double' Fourier Transform.

The Fourier Transform and related transforms assume as a mathematical premise that the collected signal can be represented as the sum of a series of sine waves. The Fast Fourier Transform is a computer-implemented technique employing this mathematical premise.

The electroencephalogram has a number of characteristics which limit its discrimination among brain signals. The 'filtering' and 'averaging' both eliminate portions of the collected signal. This elimination process employs the unverified assumption that the data which is thereby eliminated is meaningless 'noise'. That is, it commonly is assumed that the signal of interest is 'non-random' and that data which is "random" is meaningless 'noise'. The filtering and averaging have as their purpose the extraction of the 'non-random' signal from 'noise'. This assumption has been driven by the practical necessity that no better way of analyzing and depicting the entire data set has existed. That is, the discarded data was arbitrarily treated as 'meaningless' due to the lack of a method of ascertaining its meaning, but with no practical method of evaluating whether or not the discarded data in fact is intrinsically meaningless.

A compelling practical reason for use of filtering and averaging is the lack of computer-implemented algorithms which can represent a mathematically true transform of the entire data set of collectible electric potentials without such filtering and averaging.

Some filtering is designed to eliminate signals external to the subject. An example is the 60 hertz 'notch' filter which is intended to eliminate radiated signals from electric transmission lines and devices that transmit about the 60 hertz frequency. However, other filtering is employed to eliminate portions of the collected signal which truly emanate from the human or animal subject.

An analytic disadvantage of the current computer techniques is that discarding portions of the raw data set through filtering and averaging renders the transform of the raw data into the displayed signal irreversible. That is, a depicted EEG image cannot be reversibly re-transformed into the original raw data from which it was drawn due to the destruction of part of the original data set by "filtering" and "averaging". Consequently, mathematically precise, reproducible decompositions of differing graphic depictions of mathematical transforms of the identical raw data stream can not readily be analytically verified to be true equivalents.

In recent years new mathematical techniques have been developed for analysis of nonlinear dynamical processes, sometimes referred to as the mathematics of chaos or chaotic dynamics. These new techniques search for patterns, and frequently for those patterns mathematically defined as strange attractors. These new techniques employ computer generated 'phase space portraits' to visually depict a data stream, and then attempt to infer an appropriate mathematical description of the data stream from patterns visually detected in the graphic 'phase space portraits'. Early examples of this technique are as follows: N. H. Packard, J. P. Crutchfield, J. Doyne Farmer, and R. S. Shaw, "Geometry of a Time Series", Physical Review Letters, 47 (1980), p. 712; F. Takens, "Detecting Strange Attractors in Turbulence" in *Lecture Notes in Mathematics* 898, D. A. Rand and L. S. Young, eds., (Berlin: Springer-Verlag, 1981), p. 336; J. P. Crutchfield, J. Doyne Farmer, N. H. Packard, and R. S. Shaw, "On Determining the Dimension of Chaotic Flows", *Physica 3D*, (1981), pp. 605-17.

Recent publications disclose efforts to apply phase space portraits to both electrocardiograms, EKGs, and electroencephalograms, EEGs. "Is it Healthy to be Chaotic" and "The Footprints of Chaos", *Science*, Vol. 243, pp. 604-607, 8 Feb. 1989. "Chaos Theory: How Big an Advance", *Science*, Vol. 245, pp. 26-28, 7 Jul. 1989.

THE PROBLEMS ADDRESSED BY THE INVENTION

A problem experienced in efforts to apply the new mathematics of nonlinear or chaotic dynamics to brain signals is that the signals must be taken at extremely short time intervals, on the order of milliseconds or less, resulting in an extremely high volume of data in a very short period of time. This necessitates use of a computer to collect and record such signals and to correlate the data stream with stimulus and response events.

The signals recorded from scalp electrodes appear to be a complex composite of several different biological processes of poorly defined origin. Signals reflecting muscular processes, including heartbeat, breathing and voluntary muscle contraction, are mixed in with and to a large extent obscure other signals of interest concerning brain function. In addition, signals from multiple processes within the brain itself may form a portion of the composite signal. Furthermore, the electrodes, or the subject's body, may also be acting antennas collecting signals from the environment.

Prior methods of extracting signals from the background have generally employed some form of averaging to limit the signal to nonrandom patterns, thereby deliberately discarding more random data from the signal. These prior methods also employ 'artifact rejection' which in practice means that signals exceeding a pre-defined amplitude are assumed to be "artifact", such as the signal of a muscular movement, and are "rejected" or deleted from the data stream before averaging. According to the new mathematics of nonlinear or chaotic dynamics it may be postulated that such 'random' and 'artifact' data is in fact part of the genuine brain signal, the meaning of which must be deciphered to understand the entire signal. Under these postulates, "averaging" to eliminate non-random portions of the signal eliminates chaotic data which is in fact a part of the true signal of brain function. In particular, averaging may obscure the transitions from chaotic to ordered states, and vice versa. However, programmable algorithms describing such chaotic data sufficient to employ automated computer pattern recognition or signal analysis have not yet been found.

Thus, the problem is to identify nonlinear dynamic characteristics of cognitive and other brain signals which distinguish such elements from the composite signal when no descriptive, programmable algorithms are known. Since the characteristic attributes of signals denoting cognitive brain functions are not yet known, empirical tools are needed to search for such distinctive characteristics so that such signals can be extracted from the background data. The invention is conceived as such a tool.

It is known that patterns sometimes can be visually recognized in phase space portraits even though such patterns cannot be described with mathematical precision sufficient to define an algorithm for automatic computer recognition of such patterns. The invention is designed to allow manual screening of raw data for visually recognizable patterns, manual selection of the drawing elements which form such patterns, and identification of the raw data which is reflected in the selected patterns.

Because the subset of raw data so identified contains the visually recognized pattern extracted to some degree from the background data, that subset of data can be subjected to more intensive and more efficient processing and analysis to find the best mathematical description to describe the observed pattern.

Once a pattern has been visually recognized and the data including that pattern segregated, it is possible to guide the search for an algorithm describing the pattern by reference to the known phase space portraits of a variety of mathematical formulae. See "Geometry from a Time Series".

It is known that patterns sometimes may appear in graphic phase space portraits of data reflecting nonlinear dynamic processes only when a sufficiently large number of variable dimensions is reflected in the graphic portrait. For this reason it is desirable in phase space portraits to visually depict as many variable dimensions as can be achieved.

OBJECTIVES AND FEATURES OF THE INVENTION

A feature of the invention is the methods employed to increase the number of visually distinctive dimensions which can be displayed in a mathematically precise graphic portrait. In addition to the three physical dimensions which can be displayed in Cartesian coordinates, the invention enables other visually-distinctive dimensions by use of layers to create composite phase space portraits, use of colors to denote time sequence, use of colors to distinguish between the layers in a composite portrait, and use of time-linked color sequences to visually display time sequence and to seek periodicities within graphic phase space drawings. In principle, distinctive line types also could be employed to distinguish between layers in a composite portrait.

The power of the invention to point out subsets of raw data corresponding to visually-identified patterns thus is combined with enhanced ability to display patterns which arises from the capacity to graphically depict a large number of variable dimensions.

It is known that patterns sometimes can be made to appear more visibly distinctive when the phase space diagram is rotated in three dimensions, or otherwise manipulated through mathematically precise transformations. It is a feature of the invention that the graphic portraits can be passed into commercially available computer-aided drawing, design and engineering programs wherein they can be rotated, viewed in mirror image, and otherwise viewed after mathematically precise, reversible transformations.

It is an objective of the invention to enable analytic depiction of the 'raw' amplified stream of electric potentials collected from a plurality of electrode channels, while reducing filtering of the raw data stream and eliminating the mathematical processing called 'averaging'. It is a feature of the invention that it enables analytic depiction of the entire data stream, including within the analytically depicted data set so-called 'random' data which prior analytic methods discarded as non-analyzable.

It is an objective of the invention to enable testing of the assumption that apparently 'random' brain signal data, heretofore eliminated as 'noise' or 'artifact' through filtering and averaging, are meaningless. It is a feature of the invention that it reflects visually detectible patterns in the data stream, without first imposing patterns on the data by the assumption that it can properly be represented by a Fourier transform. It also displays signals of large magnitude heretofore rejected as "artifact".

It is a further objective of the invention to enable the depiction of brain signal data in more than three dimensions, e.g. more than wave amplitude and phase over time as previously enabled by the continuous sine-like wave in an electroencephalogram. It is a feature of the invention that it enables depiction of change over time of a unique point in two or three dimensional space defined by simultaneously-recorded electric potentials, respectively, of two or three different electrode channels. It is a further feature of Applicant's invention that a single drawing line entity can simultaneously depict three drawing coordinates, a direction, an amplitude corresponding to line length, a unique color and a unique line type. Two successive drawing line entities also form an angle, which may be employed in pattern characterization. Each drawing line entity can be placed within a color-coded time sequence in the phase space portrait. In principle, symbols denoting stimulus and response events could also be superposed upon the time sequence. In principle, another variable dimension could be depicted by use of unique line types. See AutoCAD Manual, Sec. 7.9, et seq., pp. 192-195.

It is a further feature of the invention that it enables composite depiction of a plurality of layers wherein each such layer reflects the data stream from a unique different subset of two or three signal channels drawn from a larger set of channels. For example, from a set of four electrodes, layer one can depict a three-electrode combination 1,2,4; layer 2 can depict electrode combination 3,2,4; layer 3 depict electrode combination 2,1,3; and layer 4 depict electrode combination 4,1,3. In this example, a compound visual image can be assembled by overlays of layers 1 through 4, or any subset of them.

A particular layer might be thought of as a "slice" through the skull on a plane defined by the physical placement of the three detection electrodes, relative to the reference electrode, whose data streams are employed to define that particular layer. The composite graphic phase space portrait formed by the overlay of two or more layers might be thought of as a series of slices cut at different angles through the skull.

Each layer in a composite image can be assigned a different color so that the comparative contributions of different layers to the composite image can be visually distinguished on a color computer monitor. This enables rapid visual focus on those layers which produce the most dramatic display of distinctive patterns. Because layers can be turned on and off in any combination, the most dramatic presentations can quickly be identified, while parsimony in data presentation can be achieved by turning off those layers which contribute least to visual discrimination of patterns.

The limitation on the number of electrode combinations which can be so depicted in a composite image is practically limited by the number of channels recorded, by the capacity of the computer, and by the graphic capacity of its monitor, but not by the analytic method. The permutations of electrode combinations which can be depicted rises as a function of the number of electrodes recorded.

It is a feature of the invention that it enables visual inspection for empirically reproducible patterns in a stream of signal data, with less restrictive assumptions than previously employed concerning the mathematical formula which will best describe the data stream. That is, patterns are allowed to manifest themselves in the graphic portrait even though algorithms which describe the visible patterns are unknown.

It is a feature of the invention that it enables mathematically reversible transformations of the raw data set, without discarding any of the data set. It is a feature of the invention that it enables reversible transforms of the identical raw data set into a wide variety of mathematically-comparable, visually-inspectible graphic portraits. The transformations available in commercial CAD software include mirror imaging, and three-dimensional rotations. See AutoCAD Manual, Sec. 5.25, p. 117 and Chap. 14, pp. 309-311; AutoCAD Reference Manual Supplement, Release 9.0, Sec. 1.13, p. 9. This enables identification of those transforms which provide more distinctive depictions of unique features or patterns in the data set.

It is a feature of the invention that distinctive drawing "entities" depicted in the visual image can be "selected" and decomposed with mathematical precision into the subset of the raw data from which the selected drawing entity was created. For example, a drawing structure from within a phase space portrait displayed on the computer monitor can be selected by pointing with a computer mouse to the drawing entities which compose the structure. A computer program specially developed by the Inventors for this purpose then identifies the precise subset of raw data points upon which the selected drawing structure is based. See the PICK.LSP program listing appended hereto.

Visually identified distinctive patterns can be extracted as a "block" from the displayed phase diagram and decomposed into the subset of raw data which produced that block, thus enabling visually-directed identification of pattern-producing subsets of the raw data. See the GRAB.LSP program listing appended hereto.

Identification of the raw data point which produced a pattern enables segregation of that subset of raw data for more efficient, intensive analysis to find a descriptive algorithm. This feature of the invention enhances efforts to focus the search for a descriptive algorithm on classes of mathematical formulae whose graphs are known to approximate the pattern segregated from the phase space portrait. See "Geometry from a Time Series", above.

A feature of the invention allows correlation of a subset of raw data with presentation of an external stimulus to the brain being monitored. "Event flags" or markers, indicating by their content the type of stimulus and by their location in the data sequence the time of presentation of stimuli to the human or animal whose brain signals are being recorded, could be inserted into the recorded stream of raw data. For example, if there were four detector channels being simultaneously recorded in parallel, the recorded computer data file would contain sets of four data points each time the detectors are simultaneously sampled, one point for each detector. The four-point data sets would be iterated for as many sampling times as desired. The data sets could be expanded to six points per set, assigning one additional point to stimulus events and the other additional point to response events. When a distinctive drawing structure displayed on screen was decomposed into the raw data it then could be temporally related with mathematical precision to stimulus and response events through inspection of the stimulus and response data points embedded in the raw data stream. These same flags embedded in the data stream could also be employed to place a distinctive marker in the graphic phase portrait on or close to the point entity formed from the signals in the data set in which the flag appears.

A feature of the invention is that the elements of the graphic display of the data may be considered virtual vectors calculated from the data streams of electrodes which are geographically dispersed over the subject's scalp. That is, a given drawing line entity possesses both a scalar magnitude and a direction. This allows inferences to be drawn from such virtual vectors about the geographic distribution within the head of the electric phenomena which are being graphically depicted.

A further feature of the invention is that a series of permutations, comprised of combinations of different sets of three electrodes drawn from a larger set of electrodes distributed over the whole head, can be depicted as overlays in a composite image. The resulting composite image reflects the virtual vectors of a broader geography of the head than can a subset of only three electrodes, thus enabling the drawing of more sophisticated inferences about the geographic distribution of phenomena within the head.

A feature of the invention is that the data stream can be depicted as a 'tree' structure emanating radially from the center of a three dimensional phase space. Alternatively, the data stream can be depicted as emanations from corners of a cube along the cube's walls and within the interior space of the cube. The 'tree' or center-based structure tends to reduce overlapping of the larger magnitude elements of the drawing structure making such larger magnitude images more readily distinguishable. The cube corner structure tends to reduce overlapping near the origins at the corners of the cube thus making lower amplitude drawing structures near the origins more readily discernable.

THE INVENTION

Figure 1:
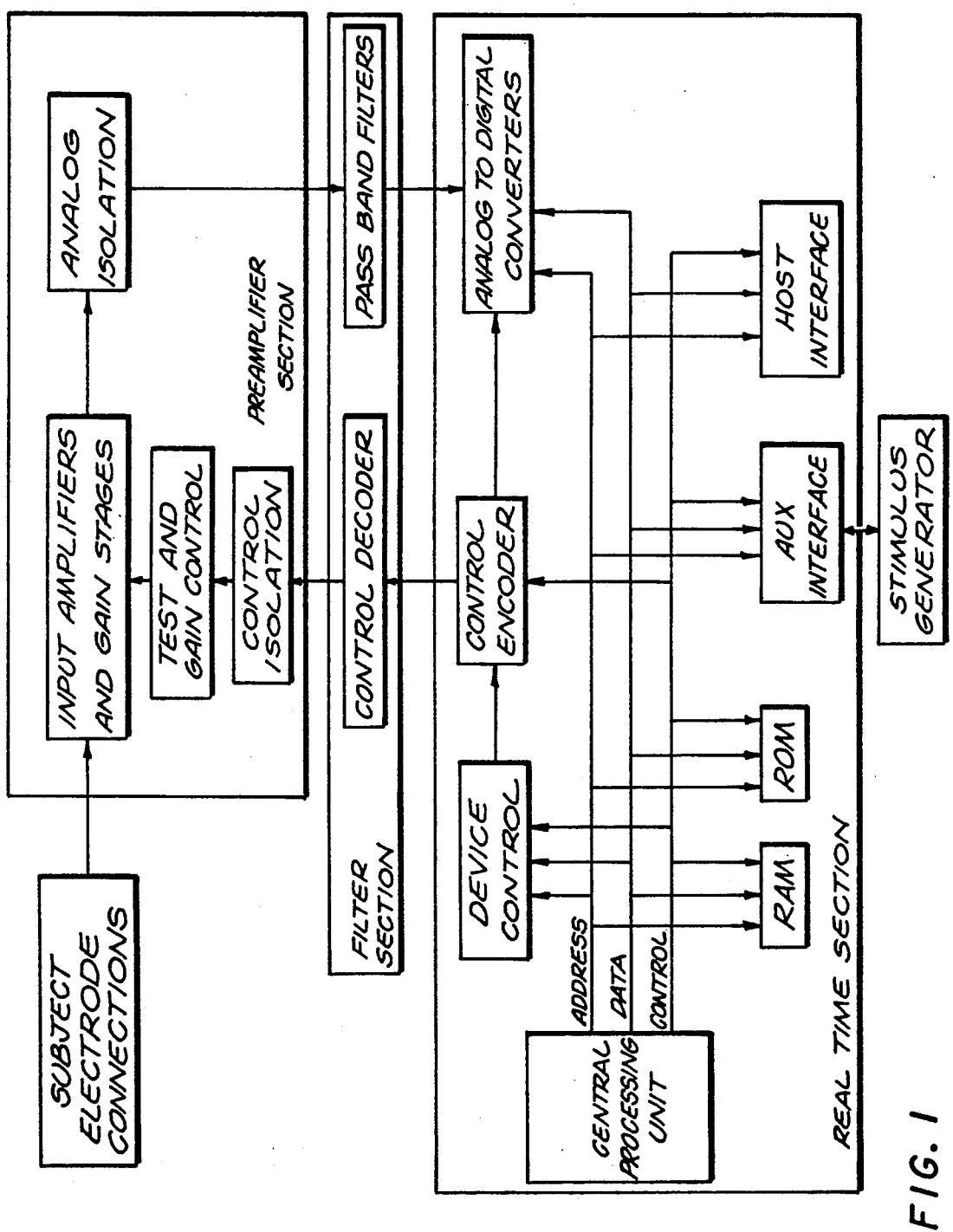
FIG. 1 is a schematic diagram of a signal collection system.

The invention employs specially developed computer programs to format a stream of raw electronically-recorded brain signal data into ASCII DXF, or Drawing eXchange Files. See the DXFROW.EXE and DXFBOX.EXE computer program listings appended hereto. A data "point entity" in three dimensional space is defined by assigning from the raw data stream the signals recorded substantially simultaneously from three different detection electrodes as the 'x', 'y', and 'z' coordinates, respectively. For example, the potential recorded from electrode 1 is the 'x' dimension, that from electrode 2 is the 'y' dimension, and that from electrode 4 is the 'z' dimension, thereby defining a unique point in the three dimensional phase space. A "line entity" then is defined as the line connecting two successive data "point entities". These point and line entities are defined within recognized conventions for graphic computer displays, such as the Drawing eXchange Format standard or DXF convention. Alternatively, various curved drawing entities instead of lines could be employed to connect the data points. The drawing "line entity" so defined can be thought of as a virtual vector reflecting the scalar value and the direction of the change over time of the electric potential from one data point to the succeeding data point. It is, of course, possible in principle to transform the drawing structures from Cartesian coordinates to polar coordinates, though the current software does not do so.

When so formatted the signal data can be imported into commercially available computer-aided design or CAD computer software programs. Formatting in accord with the ASCII DXF definition system enables mathematically reversible graphic display of the raw data in a wide variety of engineering computer-aided design programs such as AutoCad (R). It further enables manipulations of the raw data stream through three dimensional rotations and other image transformations using the capabilities of commercially available CAD programs. In principle, the formatted data could be translated into Initial Graphics Exchange Standard (IGES) files for use on other systems. See AutoCAD Manual, Sec. C.3, p. 383.

A variety of capabilities within such commercial CAD software is employed to enhance the number of visually displayed variable dimensions within the phase space portrait. From within the commercial CAD program a computer mouse is employed to manually point out the drawing entities within a graphic portrait which form visually identified patterns. A set of commands within the CAD program then forms a 'selection-set' of the identified drawing entities.

The invention then employs specially developed computer programs to decompose the 'selection-set' of drawing entities to identify the subset of raw signal data from which the manually-selected patterns were constructed. See the PICK.LSP computer program listing appended hereto.

DETAILED DESCRIPTION

"Signal detector" means a device for detection of phenomena of interest such that signal data can be collected through the device. A signal detection device in the case of electroencephalograms means metallic electrodes; and the signal is the electric potential measured between a pair of electrodes, one attached to the scalp and compared to a reference electrode attached elsewhere on the subject's head. An example of an electrode is the type E6GH gold disc electrode from Grass Instrument Company, Quincy, Mass. 02169.

"Automatic collection of signal data" by computer means detection of the signal through electrodes and electronic amplification to voltages suitable for computer processing. Drawing 1 is a schematic diagram of a signal collection system. The amplified signal is digitized for use in digital computers. Signal amplification and digitization are both well known electronic techniques. Electronic circuits for analog to digital conversions of a stream of signals, commonly called A/D circuits, are well known. A plurality of A/D converters in parallel under the control of a single timer can be employed for substantially simultaneous, parallel data collection from a plurality of signal detectors for display and analysis according to the invention. The Inventors estimate that the time intervals currently employed are approximately 1500 microseconds more or less between trigger signals. That is, that a data sample set is latched approximately every 1500 microseconds, though this time interval can be adjusted if desired. The Inventors estimate that the amplitude of scalp signal resolution currently employed for signal collection is approximately 3200 nanovolts, or 3.2 microvolts, though the gain is adjustable in a range above and below that value if desired.

"Substantially simultaneous" collection of signal data from several detectors is achieved by a common triggering signal from a timer controlled by a central or "host" processor to each of the several data detector "channels" which operate in parallel, resulting in substantially simultaneous initiation of data gathering and 'latching' of a data value in every channel. This is followed by serial polling of the parallel data channels by a central processor to collect the latched data from each channel for recordation and/or further processing. The signal data then is serially written to storage media, such as a hard disk, in sets comprising a data value for each detector plus one or more additional items per set to represent any stimulus or other event which occurred during the same sampling period. The required file structure into which the collected raw data must be written to enable operation of the listed computer programs is described in the "RAW DATA FILE FORMAT" in Appendix 1 hereto.

Construction of computer graphic drawing entities, including drawing point entities and drawing line entities among others, is defined in accord with recognized computer conventions such as the ASCII DXF file format.

The invention employs computer software programs specially written for the invention to translate the collected raw signal data into computer graphic drawing "point" and "line" entities, to define drawing "layers", and to assign color attributes to the drawing layers. See the DXFROW.EXE and DXFBOX.EXE computer program listings appended hereto. Where it is desired that a single drawing line entity have a separate color, that single drawing line entity is drawn on its own separate layer and the color is assigned to the layer. See the DXFCOL.EXE computer program listing appended hereto.

The image resulting from translation of a set of signal values into a series of computer graphic drawing entities is referred to as a "graphic phase space portrait" of such set of signal values.

Coordinates means a Cartesian, polar or relative coordinate system. See AutoCAD Manual, sec. 2.9, et seq., pp. 39–40. Thus, in a three dimensional Cartesian coordinate system, a point P would be defined by "x", "y" and "z" coordinates.

The Inventors limit each individual phase space portrait or "frame" to approximately 100 samples, or less, to avoid excessive overlapping of drawing entities, enhance visual discrimination of drawing patterns, and permit more reliable selection of particular drawing entities with the computer mouse. The number of samples per frame is adjustable. Individual frames are then lined up in rows and columns according to time sequence. Within AutoCAD an individual frame, or any portion of it, can be 'windowed' for 'zoom' magnification to inspect smaller details of the phase space portrait.

Visual identification of patterns means to visually inspect the computer generated graphic image as displayed on the computer monitor screen. The invention employs commercially available AutoCAD (R) software to process ASCII DXF files into the computer, display the graphic images, to manually point to and select drawing entities, to turn layers on and off in connection with composite phase space portraits, and to rotate and otherwise manipulate the graphic images. References herein to AutoCAD commands and functions refer to the AutoCAD (R) Drafting Package Reference Manual, Jul. 11, 1986, (Copyright 1982, 1983, 1984, 1985, 1986 Autodesk, Inc.), referred to herein as "AutoCAD Manual". The invention currently employs AutoCAD Release 9.0, AutoCAD Reference Manual Supplement Release 9.0, and AUTOLISP (TM) Version 2.6 Programmer's Reference.

The invention currently employs a Compaq DESKPRO 386 (TM) personal computer with math-coprocessor and extended memory to operate both AutoCAD and the invention's special software programs.

Manual selection of drawing entities is achieved by use of a 'pointing device' such as a computer mouse or the cursor control keyboard keys. A variety of drawing "entity selection" commands is available in publicly available drawing programs, such as those in the AutoCAD Manual, Sec. 2.10, pp. 45–49. The collection of drawing objects so identified is referred to as a "selection-set" in AutoCAD.

The invention employs specially developed copyrighted computer software to compare the AutoCAD "selection-set" to the ASCII DXF file and the original raw data file and to identify the subset of raw data which was used to create the selected drawing entities. See the PICK.LSP computer program listing appended hereto. The identified subset of raw data could then be written to a separate file if desired for further processing.

Colors, line types and layers are defined on pages 14 and 16 of the AutoCAD Manual and generally explained in Chapter 7, pp. 181–195 of the AutoCAD Manual.

Examples of point drawing symbols, which could be employed to mark the timing of events within a graphic portrait, may be found in the AutoCAD Manual, Section 4.2, p. 75. Note that the reference is to the types of symbols, not necessarily to the PDMODE and PDSIZE commands of AutoCAD, though those commands could be employed to some extent within their limitations.

As used in the claims the term "event" which is flagged within a data stream can refer to either a stimulus or a response. For example, one type of flag could be inserted into the data stream to reflect the triggering of a stimulus, such as presentation of a visual image to the test subject; and another type of flag could be inserted to reflect the time at which the test subject activates a trigger or some recording device detects a signal in response to perception or recognition of the stimulus. The detection device could be any of a wide variety of mechanical or biometric detectors for such things as respiration, blood pressure, muscular contraction or relaxation or motion. Various categories of events can be given unique, visually distinctive point symbols within a graphic phase space drawing.

COMPUTER PROGRAM AND FILE LISTINGS

APPENDIX 1 hereto contains a listing of computer programs and files employed in connection with one or more aspects of the invention. These programs and files were programmed by G. E. Somerville under directions from the inventors. The listings are as follows:

ACAD.LSP; COLBAR.LSP; GET.LSP; GRAB.LSP; LAYER.LSP; PICK.LSP; RAW FILE FORMAT; CHGCOLOR; DXFCOL; DXFROW; CRT03MN; CVN03MN; IOR03MN; and VIEW.

Programs with the .LSP suffix are written in accord with AUTOLISP (TM) Version 2.6 PROGRAMMER'S REFERENCE, copyright Autodesk, Inc. 1985, 1986, 1987. They are designed to employ the invention with AUTOCAD (R).

Programs with the .EXE suffix are written in binary code, executable format, for use on an IBM-compatible personal computer. IBM is a registered trademark of International Business Machines. The listed programs perform the following functions:

The RAW DATA FILE FORMAT describes the structure of file into which raw data must be written to enable the DXFROW.EXE program to opera on the raw data. User-defined data conversion programs may be necessary to convert the file format of various collection devices to the RAW DATA FILE FORMAT before DXFROW.EXE can be employed. Drawing 1 appended hereto is a schematic generally illustrating data collection.

DXFROW.EXE transforms raw data from files already formatted in the RAW DATA FILE FORMAT into ASCII DXF drawing entities, and creates rows of phase space portraits, one for each "trial". Within the RAW DATA FILE a "trial" means a stimulus flag and its concurrent data sample set, plus data sample sets immediately following it up to but not including the next stimulus flag. DXFROW.EXE creates four subfiles:

[FILENAME]H.DXF which creates a 'header' structure required by AutoCAD;

[FILENAME]E.DXF is an 'entities' file which contains the drawing entities defined from the raw data;

[FILENAME].LSP which includes the LOADPARAM data required for PICK.LSP to identify raw data from selected drawing entities;

[FILENAME].SCR is a 'script' file written for use by invoking the AutoCAD command "script" from within the AutoCAD program and entering [FILENAME].SCR at the AutoCAD command prompt. It automatically calls into AutoCAD the header and entity files, and loads the LOADPARAM data for use by the PICK.LSP program, resulting in display of the phase space portraits ready for manipulation within an AutoCAD drawing.

DXFCOL.EXE restructures drawing files created by DXFROW.EXE to impose a color-code in according with signal time sequence upon the drawing entities on a selected layer. DXFCOL.EXE employs whatever color code is in a data file named COLORS.DAT which defines the desired sequence in a color code.

CHGCOL.EXE is employed to define color codes in the format required for the COLORS.DAT file. It enables definition of a series of color codes. The color code of choice is copied to the COLOR.DAT file prior to running DXFCOL.EXE.

ACAD.LSP contains a series of definitions in a file format which is automatically read by AutoCAD when initiating a drawing. These definitions enable operation with AutoCAD of various programs developed under the direction of the inventors.

COLBAR.LSP allows display of the current color code sequence as a bar on the graphics monitor when a color-coded time sequence is imposed on a phase space portrait.

GET.LSP enables selection or deletion of a series of drawing entities in a time sequence between two selected drawing entities.

GRAB.LSP is employed in conjunction with AutoCAD to segregate a plurality of 'blocks' of drawing entities. It must be loaded into AutoCAD by the command LOADGRAB. Then the command GRABBASE is given, which refers to all drawing entities displayed on the screen by AutoCAD at the time the command is given. Various commands from within AutoCAD can be employed to turn off layers, zoom to larger or smaller windows, delete drawing entities and otherwise eliminate unwanted drawing entities from the screen either before or after the GRABBASE command is given. Then those remaining entities for which raw data identification is sought can be pointed out by use of a computer mouse and a 'window' to select the entities, and the command GRABVIEW is given, resulting in automatic identification of the raw data points.

LAYER.LSP facilitates rapid switching of groups of drawing layers on or off within AutoCAD. It is loaded into AutoCAD by the command LOADLAYER, following which the command SETLAYER is given. Thereafter the commands ONLAYER and OFFLAYER are available.

PICK.LS is employed in conjunction with AutoCAD (R) (C) to manually point out a single drawing entity displayed on the computer monitor screen and to automatically identify the raw data points from which the selected drawing structure is formed. It must be loaded into AutoCAD by the command LOADPICK. Thereafter its operating commands are SETPICK, which refers to drawing entities displayed on screen by AutoCAD at the time the command is given, and PICKENT which thereafter is employed to point out and automatically identify the raw data from which selected entities are drawn.

CRT03MN.LIB, CVN03MN.LIB and IOR03MN.LIB comprise a library of standardized subroutines called by the main program. They are written in accord with Microsoft (R) Macro Assembler Version 5.10. The use of these subroutines is transparent to the user. They are copyrighted programs of G. E. Somerville, who has licensed them to the inventors, and they are included herein with his permission.

VIEW.EXE parses a GRAB VIEW file.

CONCEIVED USES OF THE INVENTION

One of the Inventors' conceptions is that a human subject can be given a switch to insert flags or markers into the signal data stream corresponding to the moment the subject experiences conscious thoughts, perceptions of external stimuli, or other conscious processes. Similarly, the host computer can trigger a stimulus and simultaneously insert a flag denoting the stimulus into the collected data stream. Thus, both stimulus and response events can be recorded within the data stream in conjunction with simultaneously collected brain signals.

Another of the Inventors' conceptions is that the invention enables computer-assisted manual identification of pattern-generating subsets of raw data. The identified subsets of raw data can then be segregated to serve as empirical data patterns against which computer-aided pattern comparison can be made, even though no precise mathematical description of the segregated raw data can be programmed into the computer. The Inventors further conceive, for example, that such segregated subsets of pattern-generating raw data can be used to 'train' computer neural networks to recognize the patterns in such raw data subsets without first defining a descriptive mathematical formula for such raw data subsets.

The Inventors conceive that an empirical library of subsets of raw data comprising brain activity reflecting responses to stimuli, perceptions, and thought processes, can be created by so selecting such visually distinctive, patterned subsets of raw data out of the displayed phase space portraits. The Inventors further conceive that such subsets can be employed as computer-recognizable patterns pattern recognition programs.

The Inventors conceive that the development of computer recognizable patterns in brain signals, in turn, will enable 'on-the-fly' or real time analysis of brain signals by computer-aided pattern comparison to such an empirical library of brain signal patterns.

SYNTAX CONVENTIONS

The following conventions are employed in the syntax of the claims:

"Signal detectors" are assigned the capital letter "D", followed by a numeral indicating a particular detector in the sequence, such as, D1, D2 and D3.

"Discrete times" are indicated by lower case "t" followed by a numeral indicating the particular place in the time sequence, such as, t1, t2, and t3. Signal values are assigned a capital letter "S" followed by a numeral indicating the time the signal was taken. For example signal S1 was collected at time t1. Signal values are further assigned a letter and number to indicate the particular detector from which the signal was collected, such as, D1S1, meaning the signal value collected from detector D1 at time t1.

A "series" of indeterminate length is indicated by listing the first few members of the series followed by four periods and the 'nth' member of the series.

An example is the time series "t1, t2, t3, .... tn.

Another example is the signal detector series "D1, D2, D3, .... Dn". Alphabetic series of indefinite length are denoted by the first few letters followed by four periods and the letter 'x'. An example is the alphabetic series "Da, Db, Dc, .... Dx."

Drawing "point entities" are referred to by the capital letter "P" followed by a numeral indicating the time at which the signal data establishing the coordinates of the point was collected. Thus, point "P1" is defined by the signal data collected at time t1. The three coordinates of a point are defined by signal data collected substantially simultaneously from three different detectors. For example, "x" could be the signal data from detector D1, "y" the signal data from detector D2, and "z" the signal data from detector D3.

Drawing "line entities" are referred to by the capital letters "LI" followed by a numeral indicating the time of the first point entity, such as "LI1" referring to the line connecting points P1 and P2, which starts at time t1 and extends to time t2. "LI2" refers to the line connecting points P2 and P3, starting at time t2.

Drawing "layers" are referred to by the capital letters "LA" followed by a numeral indicating place in the sequence of a series of layers, such as LA1, LA2, and LA3. Point entities drawn on different layers are designated by a capital "P" followed by a numeral designating time, by the capital letters "LA" and a numeral indicate which layer in the sequence. For example, "P1LA2" means Point 1 on Layer 2, whose coordinates are defined by signal data taken at time t1, from the unique subset 2 of detectors whose signal data is employed to define the points on Layer 2.

"Color-time" sequences employ the syntax capital "C" followed by a numeral for a distinctive color, followed by lower case "t" followed by a numeral for a discrete time. Thus, "C1t1" means the color 1 is assigned to time t1 in a pre-determined table. Where colors are employed to visually illustrate a time sequence, the sequence of colors is pre-determined in a table. The relationship of a particular color to a particular discrete time in the table is entirely arbitrary. For example, one might choose to arrange the colors in accord with the natural spectrum or rainbow because of the intuitive ease of following the colors of the rainbow in the correct sequence. The first seven numbers have been assigned to standard colors by convention. AutoCAD Manual, sec. 7.1.2, p. 181. For computer programming purposes, colors are identified by numbers in accord with generally recognized color conventions for computer graphics. For non-spectral colors, a possible arrangement is the chromatic sequence in the color circle employed in the Farnsworth-Munsell 100 hue test.

"Prime number" means a number divisible only by the number 1 and itself. Examples are 2, 3, 5, 7, 11, and 13.

In principle, periodicities might appear in the graphic portraits corresponding to multiples of one of the prime numbers, providing either (i) that the period is nearly an exact multiple of the time interval (t2−t1) between data samples, or (ii) that such time interval (t2−t1) is extremely small relative to the period.

APPENDIX 1.        COMPUTER PROGRAM AND FILE LISTINGS

```
FILE LISTING:    ACAD.LSP  . . . . . . . . . . . . . . . . .  35

FILE LISTING:    COLBAR.LSP  . . . . . . . . . . . . . . . .  36

FILE LISTING:    GET.LSP . . . . . . . . . . . . . . . . . .  38

FILE LISTING:    GRAB.LSP  . . . . . . . . . . . . . . . . .  41

PROGRAM LISTING: LAYER.LSP . . . . . . . . . . . . . . . . .  42

PROGRAM LISTING: PICK.LSP  . . . . . . . . . . . . . . . . . 45

LISTING:   RAW FILE FORMAT  . . . . . . . . . . . . . . . .  47

PROGRAM LISTING: CHGCOLOR  . . . . . . . . . . . . . . . . . 49

PROGRAM LISTING: DXFCOL  . . . . . . . . . . . . . . . . . . 64

PROGRAM LISTING: DXFROW  . . . . . . . . . . . . . . . . .  108

PROGRAM LISTING: CRT03MN . . . . . . . . . . . . . . . . .  168

PROGRAM LISTING: CVN03MN . . . . . . . . . . . . . . . . .  179

PROGRAM LISTING: IOR03MN . . . . . . . . . . . . . . . . .  208

PROGRAM LISTING: VIEW.EXE  . . . . . . . . . . . . . . . .  219
```

FILE LISTING: ACAD.LSP
DATE: Sept. 7, 1989

Upon initiation of a drawing session, AutoCAD (R) loads the file named "ACAD.LSP" if it exists and evaluates the functions defined therein. See AUTOLISP (tm) VERSION 2.6 PROGRAMMER'S REFERENCE, sec. 2.4, p. 5. The invention employs the following copyrighted command definitions within the ACAD.LSP file to provide the interface between AutoCAD and the inventors' programs. The following definitions are copyrighted, by George Jastrzebski and Lowell R. Wedemeyer, doing business as GEOLOW PARTNERS. COPYRIGHT (C), September 1, 1989, all rights reserved. Programming by G.E. Somerville.

```
(defun c:loadgrab ()
   (load "grab")
)
(defun c:loadlayer ()
   (load "layer")
)
(defun c:loadpick ()
   (load "pick")
)
(DEFUN C:LOADCOLBAR()
   (LOAD "COLBAR")
   (setq cbar 0)
)
(DEFUN C:LOADGET()
   (LOAD "GET")
)
(defun c:loadparam (/ fnam)
   (setq fnam (getstring "Enter basic filename:"))
   (load fnam)
)
^Z
```

FILE LISTING: COLBAR.LSP
DATE: 9/7/89
COPYRIGHT GEORGE B. JASTRZEBSKI AND LOWELL R. WEDEMEYER DOING BUSINESS AS GEOLOW PARTNERS, SEPTEMBER 6, 1989. ALL RIGHTS RESERVED.
Programming by G.E. Somerville.
This program enables display on the CRT of the currently effective color code for use in connection with color-coded time sequences.

```
(DEFUN C:COLBAR(/ M PS PE HDST VDST HSPC VSPC LP A B PM)
   (WHILE (= CBAR 0)
      (SETQ M (GETVAR "BLIPMODE"))
      (SETVAR "BLIPMODE" 0)
```

```
13         (SETQ PS (GETPOINT"STARTING POINT  "))
14         (SETQ PE (GETPOINT PS "END POINT"))
15         (SETQ HDST (- (CAR PE) (CAR PS)))
16         (SETQ HSPC (/ HDST 16.0))
17         (SETQ VDST (- (CADR PE) (CADR PS)))
18         (SETQ VSPC (/ VDST 16.0))
19         (SETQ LP 1)
20         (WHILE (<= LP 16)
21             (SETQ A (+ (CAR PS) HSPC))
22             (SETQ B (+ (CADR PS) VSPC))
23             (SETQ PM (LIST A B))
24             (COMMAND "COLOR" LP)
25             (COMMAND "LINE" PS PM)
26             (COMMAND)
27             (SETQ PS (LIST A B))
28             (SETQ LP (1+ LP))
29         )
30         (SETVAR "BLIPMODE" M)
31     (SETQ CBAR 1)
32     )
33 )
34 (DEFUN C:DELBAR(/ LP)
35     (WHILE (= CBAR 1)
36         (SETQ LP 1)
1          (WHILE (<= LP 16)
2              (COMMAND "ERASE" "L")
3              (COMMAND "")
4              (SETQ LP (1+ LP))
5          )
6      (SETQ CBAR 0)
7      )
8 )
9 ^Z
```

1 FILE LISTING:  GET.LSP
2 DATE: 9/7/89
3 THIS FILE DEFINES CERTAIN DRAWING ENTITY SELECTION COMMANDS FOR USE
4 OF THE INVENTION WITH AutoCAD (R).  COPYRIGHT, GEORGE B. JASTRZEBSKI
5 AND LOWELL R. WEDEMEYER, DOING BUSINESS AS GEOLOW PARTNERS, 9/6/89.
6 ALL RIGHTS RESERVED.  Programming by G.E. Somerville.
7
```
8 (DEFUN C:RESTENTS ()
9     (LOOPDEL)
10 )
11 (DEFUN C:DELENTS ()
12     (GETENTS)
```

```
13      (SETQ DDEL NIL)
14      (LOOPDEL)
15  )
16  (DEFUN C:DELOTHER ()
17      (GETENTS)
18      (SETQ DDEL T)
19      (LOOPDEL)
20  )
21  (DEFUN GETENTS ()
22      (PRINT "FIRST SELECT ALL ENTITIES WITH A WINDOW")
23      (SETQ LFLG NIL DSET (SSGET))
24      (SETQ NDEL (SSLENGTH DSET))
25      (PRIN1)
26      (SETQ FDEL (ENTSEL "PICK STARTING ENTITY: ") FDEL (CAR FDEL))
27      (PRIN1)
28      (SETQ LDEL (ENTSEL "PICK LAST ENTITY:") LDEL (CAR LDEL))
29      (IF FDEL (SETQ FNUM (1- NDEL)) (SETQ FNUM -2) )
30      (WHILE FDEL
31           (IF (EQUAL FDEL (SSNAME DSET FNUM)) (SETQ FDEL NIL)
32           (SETQ FNUM (1- FNUM))
33           )
34           (IF (= FNUM -2) (SETQ FDEL NIL))
35      )
36      (IF LDEL (SETQ LNUM (1- NDEL)) (SETQ LNUM -2) )
1       (WHILE LDEL
2            (IF (EQUAL LDEL (SSNAME DSET LNUM)) (SETQ LDEL NIL)
3            (SETQ LNUM (1- LNUM))
4            )
5            (IF (= LNUM -2) (SETQ LDEL NIL))
6       )
7       (IF (= FNUM -2) (PRINT "CAN'T FIND FIRST ENTITY")
8            (IF (= LNUM -2) (PRINT "CAN'T FIND LAST ENTITY")
9                 (PROGN
10                 (IF (< LNUM FNUM) (SETQ N FNUM FNUM LNUM LNUM N))
11                 (SETQ LFLG 1)
12                 )
13            )
14      )
15  )
16  (DEFUN LOOPDEL()
17      (IF LFLG
18           (PROGN
19           (SETQ LP 0)
20           (IF DDEL
21                (WHILE (< LP NDEL)
```

```
22                  (PROGN
23                     (IF (< LP FNUM) (ENTDEL (SSNAME DSET LP)))
24                     (IF (< LNUM LP) (ENTDEL (SSNAME DSET LP)))
25                     (SETQ LP (1+ LP))
26                  )
27               )
28               (WHILE (< LP NDEL)
29                  (PROGN
30                     (IF (>= LP FNUM)
31                         (IF (<= LP LNUM)
32                             (ENTDEL (SSNAME DSET LP))
33                         )
34                     )
35                     (SETQ LP (1+ LP))
36                  )
 1               )
 2            )
 3         )
 4      )
 5 )
 6 ^Z
 1 FILE LISTING: GRAB.LSP
 2 DATE: September 7, 1989.
 3 THIS FILE DEFINES CERTAIN DRAWING ENTITY SELECTION COMMANDS FOR USE
 4 OF THE INVENTION WITH AUTOCAD (R).  COPYRIGHT GEORGE B. JASTRZEBSKI
 5 AND LOWELL R. WEDEMEYER, DOING BUSINESS AS GEOLOW PARTNERS, SEPTEMBER
 6 6, 1989.  ALL RIGHTS RESERVED.
 7
 8 (defun c:grabbase ()
 9    (setq fnam (getstring"Enter grab base file name:"))
10    (setq s "GRABBASE")
11    (grab)
12 )
13 (defun c:grabview ()
14    (setq fnam (getstring"Enter grab view file name:"))
15    (setq s "GRABVIEW")
16    (grab)
17 )
18 (defun grab (/ sset b c)
19    (setq fnum (open fnam "w"))
20    (print s fnum)
21    (print "Select objects with a Window")
22    (prin1)
23    (setq sset (ssget))
24    (setq c (sslength sset))
```

```
25      (setq b -1)
26      (repeat c (setq b(+ b 1))(print (ssname sset b) fnum))
27      (print "ENDGRAB" fnum)
28      (write-char 13 fnum)
29      (write-char 10 fnum)
30      (write-char 26 fnum)
31      (close fnum)
32      (prin1)
33  )
34  ^z
 1  PROGRAM LISTING: LAYER.LSP
 2  DATE: 9/7/89
 3  COPYRIGHT (C) 6/6/89 GEORGE B. JASTRZEBSKI AND LOWELL R. WEDEMEYER
 4  DOING BUSINESS AS GEOLOW PARTNERS.  ALL RIGHTS RESERVED.
 5  This file enables rapid turning of multiple layers on and off within
 6  AUTOCAD (R).
 7
 8  (defun c:setlayer (/ a)
 9      (setq a 1 llist nil lstg nil)
10      (setq num (getint"Enter last layer number:"))
11      (setq sets (getint"Enter number of channel pairs:"))
12      (while (<= a num)
13          (setq llist (cons (itoa a) llist))
14          (setq a (1+ a))
15      )
16      (setq llist (reverse llist))
17      (setq nlyr num llayr llist)
18      (prin1)
19  )
20  (defun c:offlayer (/ seton layoff loops nset a b c fset lset lstg
21  nstg)
22      (setq a 1 llayr nil)
23      (setq seton (getint"Enter ON pair number:"))
24      (setq loops (/ num sets))
25      (setq fset (1- seton))
26      (setq lset (- sets seton))
27      (setq nlyr (* (+ fset lset) loops))
28      (setq layoff 0)
29      (while (<= a loops)
30          (setq b 1 c 1)
31          (while (<= b fset)
32              (setq llayr (cons (nth layoff llist) llayr))
33              (setq layoff (1+ layoff))
34              (setq b (1+ b))
35          )
36          (setq layoff (1+ layoff))
```

```
        (setq a (1+ a))
        (while (<= c lset)
                (setq llayr (cons (nth layoff llist) llayr))
                (setq layoff (1+ layoff))
                (setq c (1+ c))
        )
    )
    (setq llayr (reverse llayr))
    (setq a 1 lstg nil)
    (setq lstg (nth 0 llayr))
    (setq nstg lstg)
    (command "layer" "set" "0" "")
    (while (< a nlyr)
        (setq lstg (strcat lstg "," (nth a llayr)))
        (setq a (1+ a))
        (if (> (strlen lstg) 250)
            (progn
                (command "layer" "off" lstg "")
                (setq lstg nstg)
            )
        )
    )
    (if (> (strlen lstg) 1)
        (command "layer" "off" lstg "")
    )
    (prin1)
)
(defun c:onlayer (/ a lstg nstg)
    (setq a 1 lstg nil)
    (setq lstg (nth 0 llayr))
    (setq nstg lstg)
    (while (< a nlyr)
        (setq lstg (strcat lstg "," (nth a llayr)))
        (setq a (1+ a))
        (if (> (strlen lstg) 250)
            (progn
                (command "layer" "on" lstg "")
                (setq lstg nstg)
            )
        )
    )
    (if (> (strlen lstg) 1)
        (command "layer" "on" lstg "")
    )
    (prin1)
)
^Z
```

```
1   PROGRAM LISTING:  PICK.LSP
2   DATE: 9/6/89
3   COPYRIGHT (C), 9/06/89, GEORGE B. JASTRZEBSKI AND LOWELL R. WEDEMEYER,
4   DOING BUSINESS AS GEOLOW PARTNERS.  ALL RIGHTS RESERVED.
5
6   (defun c:setpick ()
7       (setq pset nil)
8       (print "Select all entities with a Window")
9       (prin1)
10      (setq pset (ssget))
11      (setq nent (sslength pset))
12  )
13  (defun c:pickent (/ c d e f trl smp set)
14      (setq e (entsel "pick an entity:"))
15      (setq e (car e))
16      (setq f (eval e))
17      (if e (setq c (1- nent))
18          (setq c -2)
19      )
20      (while e
21          (if (equal e (ssname pset c)) (setq e nil)
22          (setq c (1- c))
23          )
24          (if (= c -2) (setq e nil)
25          )
26      )
27      (if (= c -2) (print "can't find")
28          (progn
29          (setq c (- nent c))
30          (setq d (* nset nsmps))
31          (setq e (rem c d))
32          (setq trl (/ c d))
33          (if (> e 0)(setq trl (1+ trl))
34          )
35          (while (> c d)
36              (setq c (- c d))
1           )
2           (setq d (rem c nset))
3           (setq smp (/ c nset))
4           (if (> d 0)(setq smp (+ smp d))
5           )
6           (if (= d 0) (setq d nset)
7           )
8           (prin1 "trial ")
9           (prin1 trl)
```

```
10          (prin1 "  sample ")
11          (prin1 smp)
12          (prin1 "  set ")
13          (prin1 d)
14          )
15      )
16      (prin1)
17  )
18  ^Z
```

1  LISTING: RAW FILE FORMAT
2  DATE: 9/7/89
3  COPYRIGHT (C) GEORGE B. JASTRZEBSKI AND LOWELL R. WEDEMEYER, DOING
4  BUSINESS AS GEOLOW PARTNERS, June 27, 1989.  ALL RIGHTS RESERVED.
5
6      The following is the format into which raw signal data is placed
7  for use by the DXFROW program.  The file structure comprises an 80
8  byte header followed by numerous sets of 5 bytes each.  These 5 byte
9  sets represent one time sample.
10
11 HEADER
12 The header consists of 37 words (DW) and 6 bytes (DB). All
13 information is in binary format.
14
15 DW    Year
16 DB    Date
17 DB    month
18 DB    minutes
19 DB    hour
20 DB    tens/secs
21 DB    seconds
22 DW    conversion mode
23 DW    number conversions
24 DW    channel 1 on/off
25 DW    channel 2 on/off
26 DW    channel 3 on/off
27 DW    channel 4 on/off
28 DW    operating mode
29 DW    CRT page
30 DW    horizontal size
31 DW    vertical size
32 DW    frame count
33 DW    page count
34 DW    blanking count
35 DW    contrast
36 DW    artifact level

```
1    DW      artifact limit
2    DW      number sweeps
3    DW      number sweeps mode 4
4    DW      sweep rate
5    DW      resolution
6    DW      resolution mode 4
7    DW      gain channel 1
8    DW      gain channel 2
9    DW      gain channel 3
10   DW      gain channel 4
11   DW      LP filter 1/2
12   DW      LP filter 3/4
13   DW      HF 1/2
14   DW      Q 1/2
15   DW      absolute delay 1/2
16   DW      HF 3/4
17   DW      Q 3/4
18   DW      absolute delay 3/4
19   DW      noise count
20   DW      external port latch
21   DW      impedance frequency
22   SAMPLES
23   Each 5 byte set consists of the four channels and a flag, collectively
24   referred to as a "sample set".
25   DB      channel 1 (0 to 255)
26   DB      channel 2 (0 to 255)
27   DB      channel 3 (0 to 255)
28   DB      channel 4 (0 to 255)
29   DB      flag
30   Note: If more than four signal channels are employed, then the sample
31   set format must increased to provide a byte for each channel.  In
32   addition, if a response channel is employed an additional byte must
33   be provided in each sample set for such response.  In that event, the
34   DXFROW, CHGCOLOR, AND DXFCOL programs must be modified to read such
35   larger sample set format.
1    PROGRAM LISTING:   CHGCOLOR
2    DATE:  9/7/89
3    ^HMicrosoft (R) Macro Assembler Version 5.10                    8/25/89
4    12:42:33
5    CREATES MULTILAYER DXF FILE FROM ROW OR BOX                     Page
6    1-1
7         1                      .8086
8         2                              NAME CHGCOLOR
9         3                              PAGE 62,120
10        4                              TITLE     CREATES MULTILAYER DXF FILE
```

```
11  FROM ROW OR BOX
12      5                              ;
13      6                              COMMENT *
14      7
15  ;;;;;;;;;;;;;;;;;;;;;;;;;;;;;;;;;;;;;;;;;;;;;;;;;;;;;;;;;;;;;;;;
16  ;;;;;;;
17      8                              COPYRIGHT (C) 1989 GEOLOW PARTNERS. ALL
18  RIGHTS RESERVED. NO PART OF PROGRAM
19      9                              OR    PUBLICATION    MAY    BE
20  TRANSCRIBED,REPRODUCED, TRANSMITTED, OR TRANSLATED
21      10                             INTO ANY LANGUAGE OR COMPUTER LANGUAGE BY
22  ANY MEANS ELECTRONIC, MECHANICAL,
23      11                             MAGNETIC, CHEMICAL, OPTICAL, MANUAL OR
24  OTHERWISE OR IN ANY FORM, WITHOUT
25      12                             THE PRIOR WRITTEN PERMISSION OF LOWELL
26  WEDEMEYER, 3112 THATCHER AVE,
27      13                             MARINA DEL REY CALIFORNIA, 90292.
28      14
29  ;;;;;;;;;;;;;;;;;;;;;;;;;;;;;;;;;;;;;;;;;;;;;;;;;;;;;;;;;;;;;;;;
30  ;;;;;;;
31      15
32      16                             PROGRAMMING BY G. E. SOMERVILLE, 7315
33  BROCADE DR., CITRUS HEIGHTS, CA 95621
34      17               *
35      18                              ;
36      19 = 000D                      CR      EQU     0DH
 1      20 = 000A                      LF      EQU     0AH
 2      21 = 0021                      DOSINT  EQU     21H
 3      22                              ;
 4      23                             INCLUDELIB      IOR03MN
 5      24                             INCLUDELIB      CVN03MN
 6      25                             INCLUDELIB      CRT03MN
 7      26                              ;
 8      27 0000                        DATA SEGMENT    PUBLIC     'DATA'
 9      28                              ;
10      29 0000   49 6E 73 75 66 66    MSG0 DB    'Insufficient memory$'
11      30        69 63 69 65 6E 74
12      31        20 6D 65 6D 6F 72
13      32        79 24
14      33 0014   45 6E 74 65 72 20    MSG1 DB    'Enter color file name in
15  full: $'
16      34        63 6F 6C 6F 72 20
17      35        66 69 6C 65 20 6E
18      36        61 6D 65 20 69 6E
19      37        20 66 75 6C 6C 3A
```

| | | | | |
|---|---|---|---|---|
| 20 | 38 | 20 24 | | |
| 21 | 39 0034 | 41 63 63 65 73 73 | MSG2 DB | 'Access denied or invalid$' |
| 22 | | | | |
| 23 | 40 | 20 64 65 6E 69 65 | | |
| 24 | 41 | 64 20 6F 72 20 69 | | |
| 25 | 42 | 6E 76 61 6C 69 64 | | |
| 26 | 43 | 24 | | |
| 27 | 44 004D | 54 6F 6F 20 6D 61 | MSG3 DB | 'Too many files open$' |
| 28 | 45 | 6E 79 20 66 69 6C | | |
| 29 | 46 | 65 73 20 6F 70 65 | | |
| 30 | 47 | 6E 24 | | |
| 31 | 48 0061 | 4E 65 77 20 66 69 | MSG4 DB | 'New file Y(CR) or N=$' |
| 32 | 49 | 6C 65 20 59 28 43 | | |
| 33 | 50 | 52 29 20 6F 72 20 | | |
| 34 | 51 | 4E 3D 24 | | |
| 35 | 52 0076 | 50 61 74 68 20 6E | MSG5 DB | 'Path not found$' |
| 36 | 53 | 6F 74 20 66 6F 75 | | |
| 1 | 54 | 6E 64 24 | | |
| 2 | 55 0085 | 4E 6F 20 66 69 6C | MSG6 DB | 'No file open$' |
| 3 | 56 | 65 20 6F 70 65 6E | | |
| 4 | 57 | 24 | | |
| 5 | 58 0092 | 4F 6C 64 20 66 69 | MSG7 DB | 'Old file Y(CR) or N=$' |
| 6 | | | | |

1 ^HMicrosoft (R) Macro Assembler Version 5.10                8/25/89
2 12:42:33
3 CREATES MULTILAYER DXF FILE FROM ROW OR BOX                Page
4 1-2
5
6

| | | | | |
|---|---|---|---|---|
| 7 | 59 | 6C 65 20 59 28 43 | | |
| 8 | 60 | 52 29 20 6F 72 20 | | |
| 9 | 61 | 4E 3D 24 | | |
| 10 | 62 00A7 | 3A 24 | MSG8 DB | ':$' |
| 11 | 63 00A9 | 20 20 20 20 20 20 | MSG9 DB | ' |
| 12 | $' | | | |
| 13 | 64 | 20 20 20 20 20 20 | | |
| 14 | 65 | 20 20 20 20 20 20 | | |
| 15 | 66 | 20 20 20 20 20 20 | | |
| 16 | 67 | 20 20 20 20 24 | | |
| 17 | 68 00C6 | 41 74 74 65 6D 70 | MSG10 DB | 'Attempt to read past |
| 18 | end of file$' | | | |
| 19 | 69 | 74 20 74 6F 20 72 | | |
| 20 | 70 | 65 61 64 20 70 61 | | |
| 21 | 71 | 73 74 20 65 6E 64 | | |

```
22           72           20 6F 66 20 66 69
23           73           6C 65 24
24           74 00E7      45 6E 74 65 72 20    MSG11      DB      'Enter    number    of
25  colors to process :$'
26           75           6E 75 6D 62 65 72
27           76           20 6F 66 20 63 6F
28           77           6C 6F 72 73 20 74
29           78           6F 20 70 72 6F 63
30           79           65 73 73 20 3A 24
31           80 010B      55 6E 61 62 6C 65    MSG12      DB      'Unable    to    open
32  file.$'
33           81           20 74 6F 20 6F 70
34           82           65 6E 20 66 69 6C
35           83           65 2E 24
 1           84 0120      56 61 6C 75 65 20    MSG13      DB      'Value too high or
 2  non-numeric$'
 3           85           74 6F 6F 20 68 69
 4           86           67 68 20 6F 72 20
 5           87           6E 6F 6E 2D 6E 75
 6           88           6D 65 72 69 63 24
 7           89 013E      20 20 20 20 20 3A    MSG14      DB      '      :$'
 8           90           24
 9           91 0145      45 72 72 6F 72 20    MSG15      DB      'Error    writing    to
10  file$'
11           92           77 72 69 74 69 6E
12           93           67 20 74 6F 20 66
13           94           69 6C 65 24
14           95                                ;
15           96 015B      0000 R 0014 R 0034 R    MSGTAB   DW
16  MSG0,MSG1,MSG2,MSG3,MSG4,MSG5,MSG6,MSG7,MSG8
17           97           004D R 0061 R 0076 R
18           98           0085 R 0092 R 00A7 R
19           99 016D      00A9 R 00C6 R 00E7 R                 DW
20  MSG9,MSG10,MSG11,MSG12,MSG13,MSG14,MSG15
21          100           010B R 0120 R 013E R
22          101           0145 R
23          102                                ;
24          103 017B      43 48 47 43 4F 4C    VERS       DB     'CHGCOLOR VERSION 1.0 DXF
25  FILE FOR COLORS '
26          104           4F 52 20 56 45 52
27          105           53 49 4F 4E 20 31
28          106           2E 30 20 20 44 58
29          107           46 20 46 49 4C 45
30          108           20 46 4F 52 20 43
31          109           4F 4C 4F 52 53 20
```

```
32      110        20
33      111 01A6   43 4F 50 59 52 49   CPYRHT   DB   'COPYRIGHT      GEOLOW
34 PARTNERS',0DH,0AH,0AH,'$'
35      112        47 48 54 20 47 45
36      113        4F 4C 4F 57 20 50
 1      114        41 52 54 4E 45 52
 2      115        53 0D 0A 0A 24
 3      116                            ;
 4

1  ^HMicrosoft (R) Macro Assembler Version 5.10              8/25/89
 2  12:42:33
 3  CREATES MULTILAYER DXF FILE FROM ROW OR BOX               Page
 4  1-3
 5
 6
 7      117 01C3   20             CLRBUF   DB   ' '
 8      118 01C4   20 20 20 0D 0A          OUTBUF   DB   '   ',CR,LF
 9      119                        ;
10      120 01C9   41             FLNAME   DB   65      ;MAX PATH BYTES
11      121 01CA   00             FLNMLN   DB   ?       ;BYTES READ IN
12      122 01CB   0041[          FILNAM   DB   65 DUP(?) ;FILE NAME
13 BUFFER
14      123        ??
15      124              ]
16      125
17      126                        ;
18      127 020C   0000           FHANDL   DW   ?       ;FILE HANDLE
19      128                        ;
20      129 020E   02             REPLY    DB   2       ;ONE RESPONSE BYTE
21      130 020F   00                      DB   ?
22      131 0210   0002[                   DB   2 DUP(?) ;RESPONSE
23      132        ??
24      133              ]
25      134
26      135                        ;
27      136 0212   0064[          BUFF DB   100 DUP(?)
28      137        ??
29      138              ]
30      139
31      140 0276   0000           NCLRS    DW   ?       ;# OF COLORS
32      141 0278   0000           NVAL DW   ?
33      142                        ;
34      143                        PUBLIC   BUFF,FHANDL,MSG0,MSGTAB
35      144                        EXTRN    MSGNM:WORD
36      145                        ;
```

```
146 027A                    DATA    ENDS
147                         ;
148 0000                    STACK   SEGMENT STACK   'STACK'
149 0000  0400[             DW      1024 DUP(?)
150       ????
151            ]
152
153 0800                    STKTOP  LABEL   WORD
154 0800                    STACK   ENDS
155                         ;
156                         DGROUP  GROUP   DATA,STACK
157                         CGROUP  GROUP   CODE
158 0000                    CODE    SEGMENT PUBLIC  'CODE'
159                         ASSUME  CS:CGROUP,DS:DGROUP,SS:DGROUP
160                         ;
161                         EXTRN   BNASC4:NEAR,BNASC6:NEAR,BNASC8:NEAR,CLRHDL:NEAR,CRTMSG:NEAR
162                         EXTRN   D32B16:NEAR,DIRMSG:NEAR,DISCMD:NEAR
163                         EXTRN   RCVVAL:NEAR,RDIND:NEAR,SNDLF:NEAR,UPRCAS:NEAR,WRTIND:NEAR
164                         ;
165 0000                    START   LABEL   NEAR
166 0000  B8 ---- R          MOV    AX,DGROUP
167 0003  8E D8              MOV    DS,AX
168 0005  8E D0              MOV    SS,AX
169 0007  BC 0800 R          MOV    SP,OFFSET DGROUP:STKTOP
170 000A  BE 017B R          MOV    SI,OFFSET DGROUP:VERS
171 000D  E8 0000 E          CALL   DIRMSG          ;DISPLAY VERSION
172 0010  E9 00D9 R          JMP    MAINPG          ;JMP TO MAIN PROGRAM
173                         ;
174                         ;
```

Microsoft (R) Macro Assembler Version 5.10                    8/25/89 12:42:33
CREATES MULTILAYER DXF FILE FROM ROW OR BOX                   Page 1-4

```
175                         ;THIS GETS OLD/NEW RESPONSE FROM MESSAGE IN MSGNM
176                         ;NZ FOR NO AND Z FOR YES
```

```
10      177 0013                        REPCHK  PROC NEAR
11      178 0013  E8 0000 E                     CALL SNDLF
12      179 0016  E8 0000 E                     CALL DISCMD     ;ASK QUESTION
13      180 0019  BA 020E R                     MOV  DX,OFFSET DGROUP:REPLY
14      181 001C  B0 0A                         MOV  AL,0AH
15      182 001E  B4 0C                         MOV  AH,0CH
16      183 0020  CD 21                         INT  DOSINT     ;GET REPLY
17      184 0022  8A 26 020F R                  MOV  AH,REPLY+1  ;# BYTES
18 READ
19      185 0026  0A E4                         OR   AH,AH
20      186 0028  74 0C                         JZ   REPOK      ;JMP IF CR
21      187 002A  8A 26 0210 R                  MOV  AH,REPLY+2  ;GET REPLY
22 BYTE
23      188 002E  80 FC 59                      CMP  AH,'Y'
24      189 0031  74 03                         JZ   REPOK      ;JMP IF Y
25      190 0033  80 FC 79                      CMP  AH,'y'
26      191 0036  C3              REPOK:        RET
27      192 0037                        REPCHK  ENDP
28      193                               ;
29      194                               ;THIS OPENS THE DESTINATION FILE.
30 CY=ERR
31      195 0037                        MAKFIL  PROC NEAR
32      196 0037  E8 0000 E                     CALL CRTMSG
33      197 003A  BA 01C9 R                     MOV  DX,OFFSET DGROUP:FLNAME
34      198 003D  B0 0A                         MOV  AL,0AH
35      199 003F  B4 0C                         MOV  AH,0CH
 1      200 0041  CD 21                         INT  DOSINT     ;G E T   F I L E
 2 PATH/NAME
 3      201 0043  E8 0000 E                     CALL SNDLF
 4      202 0046  80 3E 01CA R 00               CMP  FLNMLN,0
 5      203 004B  75 0E                         JNE  MKF0
 6      204 004D  C7 06 0000 E 0002             MOV  MSGNM,2    ;NO ACCESS
 7      205 0053  E8 0000 E                     CALL CRTMSG
 8      206 0056  E8 0000 E                     CALL SNDLF
 9      207 0059  F9              STC
10      208 005A  C3              RET
11      209                               ;
12      210 005B  8A 0E 01CA R    MKF0:  MOV  CL,FLNMLN ;# BYTES IN
13 NAME
14      211 005F  32 ED                         XOR  CH,CH
15      212 0061  BF 01CB R                     MOV  DI,OFFSET DGROUP:FILNAM
16      213 0064  E8 0000 E                     CALL UPRCAS     ;ALL UPPER CASE
17      214 0067  8A 0E 01CA R                  MOV  CL,FLNMLN
18      215 006B  32 ED                         XOR  CH,CH
19      216 006D  BB 01CB R                     MOV  BX,OFFSET DGROUP:FILNAM
```

```
217 0070  03 D9              ADD   BX,CX       ;POINT TO END OF NAME
218 0072  C6 07 00            MOV   BYTE PTR [BX],00H
219 0075  BA 01CB R           MOV   DX,OFFSET DGROUP:FILNAM
220 0078  B4 4E               MOV   AH,4EH
221 007A  33 C9               XOR   CX,CX
222 007C  CD 21               INT   DOSINT      ;SEARCH FOR FILE
223 007E  3C 00               CMP   AL,0
224 0080  75 0F               JNE   MKF2 ;JMP IF FILE NOT FOUND 225 0082  C7 06 0000 E 0007   MOV   MSGNM,7
226 0088  53                  PUSH  BX    ;HOLD FILE NAME ADDR
227 0089  E8 0013 R           CALL  REPCHK  ;SEE IF OK TO DESTROY EXISTING FILES
228 008C  5B                  POP   BX
229 008D  74 02               JZ    MKF2 ;JMP IF OKAY
230 008F  F9                  STC
231 0090  C3                  RET
232                           ;
```

`HMicrosoft (R) Macro Assembler Version 5.10                8/25/89 12:42:33
CREATES MULTILAYER DXF FILE FROM ROW OR BOX                 Page 1-5

```
233 0091  BA 01CB R     MKF2:  MOV DX,OFFSET DGROUP:FILNAM
234 0094  B4 3C                MOV  AH,3CH
235 0096  33 C9                XOR  CX,CX
236 0098  CD 21                INT  DOSINT      ;OPEN FILE
237 009A  72 05                JC   MKF4 ;JMP IF ERR
238 009C  A3 020C R            MOV  FHANDL,AX ;SAVE FILE HANDLE 239 009F  F8                   CLC
240 00A0  C3                   RET
241                            ;
242 00A1  C7 06 0000 E 000C MKF4: MOV MSGNM,12
243 00A7  E8 0000 E            CALL CRTMSG  ;UNABLE TO OPEN
244 00AA  B4 4C                MOV  AH,4CH  ;STOP PROGRAM
245 00AC  CD 21                INT  DOSINT
246                            ;
247 00AE              MAKFIL   ENDP
248                            ;
249                            ;THIS GETS A VALUE FROM KEYBOARD.
```

```
26  CY=ERR
27      250                             ;MSGNM=MESSAGE.  255=MAXIMUM VALUE
28      251 00AE                        GETVAL   PROC NEAR
29      252 00AE  E8 0000 E                 CALL SNDLF
30      253 00B1  E8 0000 E                 CALL CRTMSG
31      254 00B4  E8 0000 E                 CALL RCVVAL    ;GET VALUE
32      255 00B7  72 15                     JC   GTERR     ;JMP IF ERR
33      256 00B9  81 FE 00FF                CMP  SI,255
34      257 00BD  77 0F                     JA   GTERR     ;JMP IF OVER MAX
35      258 00BF  89 36 0278 R              MOV  NVAL,SI   ;RESULT TO AX AND
36  SI
 1      259 00C3  BB 0278 R                 MOV  BX,OFFSET DGROUP:NVAL
 2      260 00C6  BF 01C3 R                 MOV  DI,OFFSET DGROUP:CLRBUF
 3      261 00C9  E8 0000 E                 CALL BNASC4    ;POST ASCII
 4      262 00CC  F8                        CLC
 5      263 00CD  C3                        RET
 6      264 00CE  C7 06 0000 E 000D  GTERR: MOV  MSGNM,13
 7      265 00D4  E8 0000 E                 CALL CRTMSG
 8      266 00D7  F9                        STC
 9      267 00D8  C3                        RET
10      268 00D9                        GETVAL   ENDP
11      269                             ;
12      270                             ;THIS IS THE START OF THE MAIN
13  PROGRAM
14      271 00D9                        MAINPG:
15      272 00D9  E8 0000 E             MPG0:    CALL SNDLF
16      273 00DC  C7 06 0000 E 0001         MOV  MSGNM,1   ;DEST FILE MSG
17      274 00E2  E8 0037 R                 CALL MAKFIL    ;OPEN THEM
18      275 00E5  72 F2                     JC   MPG0 ;JMP IF ERROR
19      276 00E7  E8 0000 E                 CALL SNDLF
20      277                             ;
21      278 00EA  C7 06 0000 E 000B  MPG1:  MOV  MSGNM,11
22      279 00F0  E8 00AE R                 CALL GETVAL    ;GET # TO DO
23      280 00F3  72 F5                     JC   MPG1 ;JMP IF ERR
24      281 00F5  A1 0278 R                 MOV  AX,NVAL
25      282 00F8  A3 0276 R                 MOV  NCLRS,AX
26      283                             ;
27      284 00FB  E8 0000 E                 CALL SNDLF
28      285 00FE  8B 0E 0276 R              MOV  CX,NCLRS  ;# TO DO
29      286 0102  C7 06 0276 R 0001         MOV  NCLRS,1   ;1ST ONE
30      287 0108  51               MPG2:    PUSH CX
31      288 0109  BB 0276 R                 MOV  BX,OFFSET DGROUP:NCLRS
32      289 010C  BF 013E R                 MOV  DI,OFFSET DGROUP:MSG14
33      290 010F  E8 0000 E                 CALL BNASC4    ;ENTRY #
34
```

Microsoft (R) Macro Assembler Version 5.10                          8/25/89
12:42:33
CREATES MULTILAYER DXF FILE FROM ROW OR BOX                          Page
1-6

```
291 0112  C7 06 0000 E 000E  MPG3:    MOV  MSGNM,14
292 0118  E8 00AE R                    CALL GETVAL    ;GET COLOR #
293 011B  73 02                        JNC  MPG4 ;JMP IF NO ERR
294 011D  EB F3                        JMP  MPG3
295                                    ;
296 011F  8B 1E 020C R       MPG4:    MOV  BX,FHANDL
297 0123  BA 01C4 R                    MOV  DX,OFFSET DGROUP:OUTBUF
298 0126  B9 0005                      MOV  CX,5
299 0129  E8 0000 E                    CALL WRTIND    ;COLOR TO FILE
300 012C  72 09                        JC   MPG8 ;JMP IF ERR
301 012E  FF 06 0276 R                 INC  NCLRS
302 0132  59                  POP  CX
303 0133  E2 D3                        LOOP MPG2 ;JMP IF MORE
304 0135  EB 09                        JMP  SHORT MPG9
305                                    ;
306 0137  C7 06 0000 E 000F  MPG8:    MOV  MSGNM,15
307 013D  E8 0000 E                    CALL CRTMSG    ;FILE ERROR
308 0140  E8 0000 E          MPG9:    CALL CLRHDL    ; C L O S E  OUTPUT FILE
309 0143  B4 4C                        MOV  AH,4CH
310 0145  CD 21                        INT  DOSINT
311                                    ;
312 0147                               CODE ENDS
313                                    END  START

236 Source  Lines
    236 Total   Lines
     74 Symbols

47176 + 382947 Bytes symbol space free

0 Warning Errors
      0 Severe  Errors
```

NOTE: For use by the DXFCOL program the file created by CHGCOL must be named COLORS.DAT in response to the prompt at line 33. Alternatively, a library of color files can be created and the particular color sequence required may be copied into a file named COLORS.DAT when needed.

PROGRAM LISTING: DXFCOL
DATE: 9/7/89
^HMicrosoft (R) Macro Assembler Version 5.10          8/29/89 12:40:44
CREATES MULTILAYER DXF FILE FROM ROW OR BOX           Page 1-1

```
        1                       .8086
        2                       NAME DXFCOL
        3                       PAGE 62,120
        4                       TITLE   CREATES MULTILAYER DXF FILE FROM ROW OR BOX
        5                       ;
        6                       COMMENT *
        7
;;;;;;;;;;;;;;;;;;;;;;;;;;;;;;;;;;;;;;;;;;;;;;;;;;;;;;;;;;;;;;;;;;;;;
        8                       COPYRIGHT (C) 1989 GEOLOW PARTNERS. ALL RIGHTS RESERVED. NO PART OF PROGRAM
        9                       OR  PUBLICATION  MAY  BE TRANSCRIBED, REPRODUCED, TRANSMITTED, OR TRANSLATED
       10                       INTO ANY LANGUAGE OR COMPUTER LANGUAGE BY ANY MEANS ELECTRONIC, MECHANICAL,
       11                       MAGNETIC, CHEMICAL, OPTICAL, MANUAL OR OTHERWISE OR IN ANY FORM, WITHOUT
       12                       THE PRIOR WRITTEN PERMISSION OF LOWELL WEDEMEYER, 3112 THATCHER AVE,
       13                       MARINA DEL REY CALIFORNIA, 90292.
       14
;;;;;;;;;;;;;;;;;;;;;;;;;;;;;;;;;;;;;;;;;;;;;;;;;;;;;;;;;;;;;;;;;;;;;
       15
       16                       PROGRAMMING BY G. E. SOMERVILLE, 7315 BROCADE DR., CITRUS HEIGHTS, CA 95621
       17                       *
       18                       ;
       19 = 000D                CR      EQU     0DH
       20 = 000A                LF      EQU     0AH
       21 = 0021                DOSINT  EQU     21H
       22                       ;
       23                       INCLUDELIB      IOR03MN
       24                       INCLUDELIB      CVN03MN
       25                       INCLUDELIB      CRT03MN
       26                       ;
       27 0000                  DATA SEGMENT    PUBLIC  'DATA'
```

```
 9      28                                       ;
10      29 0000    30 0D 0A 4C 41 59   LAYR DB    '0',CR,LF,'LAYER',CR,LF
11      30         45 52 0D 0A
12      31 000A    32 0D 0A                 DB    '2',CR,LF
13      32 000D    20 20 20 31 0D 0A   LNUM DB    '   1',CR,LF
14      33                                       ;
15      34 0013    37 30 0D 0A 30 0D        DB    '70',CR,LF,'0',CR,LF
16      35         0A
17      36 001A    36 32 0D 0A              DB    '62',CR,LF
18      37 001E    20 20 31 0D 0A      LCOL DB    '  1',CR,LF
19      38 0023    36 0D 0A 43 4F 4E        DB
20  '6',CR,LF,'CONTINUOUS',CR,LF
21      39         54 49 4E 55 4F 55
22      40         53 0D 0A
23      41 = 0032                      LLNGH    EQU  $-LAYR
24      42                                       ;
25      43 0032    30 0D 0A 45 4E 44   EOFILE   DB
26  '0',CR,LF,'ENDTAB',CR,LF
27      44         54 41 42 0D 0A
28      45 003D    30 0D 0A 45 4E 44   ENDFIL   DB
29  '0',CR,LF,'ENDSEC',CR,LF
30      46         53 45 43 0D 0A
31      47 0048    30 0D 0A 45 4F 46        DB    '0',CR,LF,'EOF',CR,LF
32      48         0D 0A
33      49 = 001E                      LEOF  EQU  $-EOFILE
34      50 = 0013                      LENDF EQU  $-ENDFIL
35      51                                       ;
36      52 0050    49 6E 73 75 66 66   MSG0 DB    'Insufficient memory$'
 1      53         69 63 69 65 6E 74
 2      54         20 6D 65 6D 6F 72
 3      55         79 24
 4      56 0064    45 6E 74 65 72 20   MSG1 DB    'Enter DXF source file name
 5  (omit .DXF): $'
 6      57         44 58 46 20 73 6F
 7      58         75 72 63 65 20 66
 8
 1  ^HMicrosoft (R) Macro Assembler Version 5.10           8/29/89
 2  12:40:44
 3  CREATES MULTILAYER DXF FILE FROM ROW OR BOX                Page
 4  1-2
 5
 6
 7      59         69 6C 65 20 6E 61
 8      60         6D 65 20 28 6F 6D
```

```
 9         61         69 74 20 2E 44 58
10         62         46 29 3A 20 24
11         63 008D    41 63 63 65 73 73  MSG2  DB    'Access denied or invalid$'
12
13         64         20 64 65 6E 69 65
14         65         64 20 6F 72 20 69
15         66         6E 76 61 6C 69 64
16         67         24
17         68 00A6    54 6F 6F 20 6D 61  MSG3  DB    'Too many files open$'
18         69         6E 79 20 66 69 6C
19         70         65 73 20 6F 70 65
20         71         6E 24
21         72 00BA    4E 65 77 20 66 69  MSG4  DB    'New file Y(CR) or N=$'
22         73         6C 65 20 59 28 43
23         74         52 29 20 6F 72 20
24         75         4E 3D 24
25         76 00CF    50 61 74 68 20 6E  MSG5  DB    'Path not found$'
26         77         6F 74 20 66 6F 75
27         78         6E 64 24
28         79 00DE    4E 6F 20 66 69 6C  MSG6  DB    'No file open$'
29         80         65 20 6F 70 65 6E
30         81         24
31         82 00EB    4F 6C 64 20 66 69  MSG7  DB    'Old file Y(CR) or N=$'
32         83         6C 65 20 59 28 43
33         84         52 29 20 6F 72 20
34         85         4E 3D 24
35         86 0100    3A 24              MSG8  DB    ':$'
 1         87 0102    20 20 20 20 20 20  MSG9  DB    '
 2   $'
 3         88         20 20 20 20 20 20
 4         89         20 20 20 20 20 20
 5         90         20 20 20 20 20 20
 6         91         20 20 20 20 24
 7         92 011F    41 74 74 65 6D 70  MSG10       DB    'Attempt to read past
 8   end of file$'
 9         93         74 20 74 6F 20 72
10         94         65 61 64 20 70 61
11         95         73 74 20 65 6E 64
12         96         20 6F 66 20 66 69
13         97         6C 65 24
14         98 0140    45 6E 74 65 72 20  MSG11       DB    'Enter    destination
15   file name (omit .DXF):$'
16         99         64 65 73 74 69 6E
17        100         61 74 69 6F 6E 20
18        101         66 69 6C 65 20 6E
```

```
19       102          61 6D 65 20 28 6F
20       103          6D 69 74 20 2E 44
21       104          58 46 29 3A 24
22       105 0169     4E 75 6D 62 65 72 MSG12    DB    'Number of sets or
23 channel pairs=    $'
24       106          20 6F 66 20 73 65
25       107          74 73 20 6F 72 20
26       108          63 68 61 6E 6E 65
27       109          6C 20 70 61 69 72
28       110          73 3D 20 20 20 20
29       111          20 24
30       112 018F     4E 75 6D 62 65 72 MSG13    DB    'Number of trials per
31 set=    $'
32       113          20 6F 66 20 74 72
33       114          69 61 6C 73 20 70
34       115          65 72 20 73 65 74
35       116          3D 20 20 20 20 20
36
 1 ^HMicrosoft (R) Macro Assembler Version 5.10                    8/29/89
 2 12:40:44
 3 CREATES MULTILAYER DXF FILE FROM ROW OR BOX                     Page
 4 1-3
 5
 6
 7       117          24
 8       118 01AE     4E 75 6D 62 65 72 MSG14    DB    'Number of samples per
 9 trial=    $'
10       119          20 6F 66 20 73 61
11       120          6D 70 6C 65 73 20
12       121          70 65 72 20 74 72
13       122          69 61 6C 3D 20 20
14       123          20 20 20 24
15       124 01D0     45 6E 74 65 72 20 MSG15    DB    'Enter desired set
16 number :$'
17       125          64 65 73 69 72 65
18       126          64 20 73 65 74 20
19       127          6E 75 6D 62 65 72
20       128          20 3A 24
21       129 01EB     45 6E 74 65 72 20 MSG16    DB    'Enter number of
22 trials per set :$'
23       130          6E 75 6D 62 65 72
24       131          20 6F 66 20 74 72
25       132          69 61 6C 73 20 70
26       133          65 72 20 73 65 74
27       134          20 3A 24
```

```
28      135 020C  45 6E 74 65 72 20  MSG17    DB    'Enter    number    of
29  samples per trial :$'
30      136       6E 75 6D 62 65 72
31      137       20 6F 66 20 73 61
32      138       6D 70 6C 65 73 20
33      139       70 65 72 20 74 72
34      140       69 61 6C 20 3A 24
35      141 0230  45 6E 74 65 72 20  MSG18    DB    'Enter    number    of
36  trials to process :$'
 1      142       6E 75 6D 62 65 72
 2      143       20 6F 66 20 74 72
 3      144       69 61 6C 73 20 74
 4      145       6F 20 70 72 6F 63
 5      146       65 73 73 20 3A 24
 6      147 0254  45 72 72 6F 72 20  MSG19    DB    'Error reading .LSP
 7  input file$'
 8      148       72 65 61 64 69 6E
 9      149       67 20 2E 4C 53 50
10      150       20 69 6E 70 75 74
11      151       20 66 69 6C 65 24
12      152 0272  45 72 72 6F 72 20  MSG20    DB    'Error    reading
13  COLORS.DAT file$'
14      153       72 65 61 64 69 6E
15      154       67 20 43 4F 4C 4F
16      155       52 53 2E 44 41 54
17      156       20 66 69 6C 65 24
18      157 0290  45 72 72 6F 72 20  MSG21    DB    'Error reading/writing
19  H.DXF file$'
20      158       72 65 61 64 69 6E
21      159       67 2F 77 72 69 74
22      160       69 6E 67 20 48 2E
23      161       44 58 46 20 66 69
24      162       6C 65 24
25      163 02B1  56 61 6C 75 65 20  MSG22    DB    'Value  too  high  or
26  non-numeric$'
27      164       74 6F 6F 20 68 69
28      165       67 68 20 6F 72 20
29      166       6E 6F 6E 2D 6E 75
30      167       6D 65 72 69 63 24
31      168                                           ;
32      169 02CF  0050 R 0064 R 008D R   MSGTAB   DW
33  MSG0,MSG1,MSG2,MSG3,MSG4,MSG5,MSG6,MSG7,MSG8
34      170       00A6 R 00BA R 00CF R
35      171       00DE R 00EB R 0100 R
```

```
172 02E1  0102 R 011F R 0140 R         DW
    MSG9,MSG10,MSG11,MSG12,MSG13,MSG14,MSG15,MSG16
173       0169 R 018F R 01AE R
174       01D0 R 01EB R
```

Microsoft (R) Macro Assembler Version 5.10                    8/29/89 12:40:44
CREATES MULTILAYER DXF FILE FROM ROW OR BOX                   Page 1-4

```
175 02F1  020C R 0230 R 0254 R         DW
    MSG17,MSG18,MSG19,MSG20,MSG21,MSG22
176       0272 R 0290 R 02B1 R
177                                    ;
178 02FD  44 58 46 43 4F 4C   VERS  DB   'DXFCOL VERSION 1.0   DXF FILE FOR COLORS '
179       20 56 45 52 53 49
180       4F 4E 20 31 2E 30
181       20 20 44 58 46 20
182       46 49 4C 45 20 46
183       4F 52 20 43 4F 4C
184       4F 52 53 20 20
185 0326  43 4F 50 59 52 49   CPYRHT  DB  'COPYRIGHT    GEOLOW PARTNERS',0DH,0AH,0AH,'$'
186       47 48 54 20 47 45
187       4F 4C 4F 57 20 50
188       41 52 54 4E 45 52
189       53 0D 0A 0A 24
190                                    ;
191 0343  2E 4C 53 50 00      LISP  DB   '.LSP',00H
192 0348  2E 44 58 46 00      DXF   DB   '.DXF',00H
193 034D  2E 53 43 52 00      SCRP  DB   '.SCR',00H
194                                    ;
195 0352  28 53 45 54 51 20   STQTRL  DB  '(SETQ    NTRLS    )',0DH,0AH
196       4E 54 52 4C 53 20
197       20 20 20 20 29 0D
198       0A
199 0365  28 53 45 54 51 20   STQSMP  DB  '(SETQ    NSMPS    )',0DH,0AH
200       4E 53 4D 50 53 20
201       20 20 20 20 29 0D
202       0A
203 0378  28 53 45 54 51 20   STQSET  DB  '(SETQ    NSET
```

```
5     )',0DH,0AH
6         204        4E 53 45 54 20 20
7         205        20 20 20 29 0D 0A
8         206 = 0038                      LNSTQ    EQU    $-STQTRL
9         207                             ;
10        208 038A   44 58 46 49 4E 0D   SCRIN    DB     'DXFIN',0DH,0AH
11        209        0A
12        210 0391   0008[                HNAM DB  8 DUP(0)
13        211           00
14        212                    ]
15        213
16        214 0399   0D 0A 44 58 46 49    DB      0DH,0AH,'DXFIN',0DH,0AH
17        215        4E 0D 0A
18        216 03A2   0008[                ENAM DB  8 DUP(0)
19        217           00
20        218                    ]
21        219
22        220 03AA   0D 0A 4C 4F 41 44    DB      0DH,0AH,'LOADPARAM',0DH,0AH
23
24        221        50 41 52 41 4D 0D
25        222        0A
26        223 03B7   0008[                LNAM DB  8 DUP(0)
27        224           00
28        225                    ]
29        226
30        227 03BF   0D 0A 5A 4F 4F 4D    DB
31  0DH,0AH,'ZOOM',0DH,0AH,'E',0DH,0AH
32        228        0D 0A 45 0D 0A
33        229 03CA   5A 4F 4F 4D 0D 0A    DB      'ZOOM',0DH,0AH,'D',0DH,0AH
34        230        44 0D 0A
35        231 = 0049                      LNSCR    EQU    $-SCRIN
36        232                             ;
37
```

1 ^HMicrosoft (R) Macro Assembler Version 5.10                              8/29/89
2 12:40:44
3 CREATES MULTILAYER DXF FILE FROM ROW OR BOX                               Page
4 1-5

```
5         233 03D3   41                  FLNAME   DB     65    ;MAX PATH BYTES
6         234 03D4   00                  FLNMLN   DB     ?     ;BYTES READ IN
7         235 03D5   0041[               FILNAM   DB     65 DUP(?) ;FILE NAME
8  BUFFER
9         236           ??
10        237                    ]
11        238
```

```
12      239                         ;
13      240 0416  0000      FHANDL  DW    ?     ;FILE HANDLE
14      241 0418  0000      EIHAND  DW    ?     ;ENTITIES IN FILE
15 HANDLE
16      242 041A  0000      HIHAND  DW    ?     ;HEADER IN FILE
17 HANDLE
18      243 041C  0000      LIHAND  DW    ?     ;LSP  IN  FILE
19 HANDLE
20      244                         ;
21      245 041E  0000      EOHAND  DW    ?     ;ENTITIES    OUT
22 FILE HANDLE
23      246 0420  0000      HOHAND  DW    ?     ;HEADER OUT FILE
24 HANDLE
25      247 0422  0000      LOHAND  DW    ?     ;LSP  OUT  FILE
26 HANDLE
27      248 0424  0000      SOHAND  DW    ?     ;SCRIPT OUT FILE
28 HANDLE
29      249                         ;
30      250 0426  43 4F 4C 4F 52 53 CFILE   DB
31 'COLORS.DAT',00H,'$'    ;COLORS FILE
32      251       2E 44 41 54 00 24
33      252                         ;
34      253 0432  02        REPLY   DB    2     ;ONE RESPONSE BYTE
35      254 0433  00                DB    ?
36      255 0434  0002[             DB    2 DUP(?) ;RESPONSE
 1      256       ??
 2      257              ]
 3      258
 4      259                         ;
 5      260 0436  000F[    MSGBUF   DB    15 DUP(?)
 6      261       ??
 7      262              ]
 8      263
 9      264                         ;
10      265 0445  0000     NSETS   DW    ?     ;# SETS
11      266 0447  0000     NSMPS   DW    ?     ;# SAMPLES/TRIAL
12      267 0449  0000     NTRLS   DW    ?     ;# TRIALS/SET
13      268                         ;
14      269 044B  0000     NSET DW      ?     ;SET # TO FIND
15      270 044D  0000     NSMP DW      ?     ;# SAMPLES/TRIAL
16      271 044F  0000     NTRL DW      ?     ;# TRIALS/SET
17      272 0451  0000     NLYR DW      ?
18      273 0453  0000     CLYR DW      ?     ;CURR LAYER
19      274                         ;
20      275 0455  0000     GSET DW      ?     ;LAST SET
```

```
21      276 0457  0000                LSMP   DW    ?          ;LAST SAMP
22      277 0459  0000                LTRL   DW    ?          ;LAST TRIAL
23      278                                  ;
24      279 045B  0002[               FSIZ   DW    2 DUP(?)   ;BYTES IN FILE
25      280       ????
26      281                 ]
27      282
28      283 045F  0002[               BYTSRD    DW  2 DUP(?)  ;BYTES READ
29      284       ????
30      285                 ]
31      286
32      287 0463  0000                BUFSIZ    DW  ?          ;BYTES IN BUFF
33      288 0465  0000                BUFRD     DW  ?          ;BYTES READ
34      289 0467  0000                BUFPTR    DW  ?          ;NEXT BUFF ADR
35      290
36
 1  ^HMicrosoft (R) Macro Assembler Version 5.10                   8/29/89
 2  12:40:44
 3  CREATES MULTILAYER DXF FILE FROM ROW OR BOX                    Page
 4  1-6
 5
 6
 7      291 0469  8000[               FBUF   DB    32768 DUP(?)
 8      292       ??
 9      293                 ]
10      294
11      295 8469  0064[               BUFF   DB    100 DUP(?)
12      296       ??
13      297                 ]
14      298
15      299 84CD  0000                NCLRS     DW  ?          ;# OF COLORS
16      300 84CF  0000                CLRPTR    DW  ?
17      301 84D1  02FD[               COLORS    DB  765 DUP(?)
18      302       ??
19      303                 ]
20      304
21      305                                   ;
22      306                           PUBLIC    BUFF,FHANDL,MSG0,MSGTAB
23      307                           EXTRN     MSGNM:WORD
24      308                                   ;
25      309 87CE                      DATA ENDS
26      310                                   ;
27      311 0000                      STACK     SEGMENT   STACK     'STACK'
28
29      312 0000  0400[                         DW   1024 DUP(?)
```

```
313            ????
314                    ]
315
316 0800                         STKTOP   LABEL    WORD
317 0800                         STACK    ENDS
318                              ;
319                              DGROUP   GROUP    DATA,STACK
320                              CGROUP   GROUP    CODE
321 0000                         CODE SEGMENT      PUBLIC   'CODE'
322                              ASSUME
     CS:CGROUP,DS:DGROUP,SS:DGROUP
323                              ;
324                              EXTRN
     BNASC4:NEAR,BNASC6:NEAR,BNASC8:NEAR,CLRHDL:NEAR,CRTMSG:NEAR
325                              EXTRN
     D32B16:NEAR,DIRMSG:NEAR,DISCMD:NEAR
326                              EXTRN
     RCVVAL:NEAR,RDIND:NEAR,SNDLF:NEAR,UPRCAS:NEAR,WRTIND:NEAR
327                              ;
328 0000                         START    LABEL    NEAR
329 0000  B8 ---- R              MOV      AX,DGROUP
330 0003  8E D8                  MOV      DS,AX
331 0005  8E D0                  MOV      SS,AX
332 0007  BC 0800 R              MOV      SP,OFFSET DGROUP:STKTOP
333 000A  BE 02FD R              MOV      SI,OFFSET DGROUP:VERS
334 000D  E8 0000 E              CALL     DIRMSG       ;DISPLAY VERSION
335 0010  BA 0426 R              MOV      DX,OFFSET DGROUP:CFILE
336 0013  B4 3D                  MOV      AH,3DH
337 0015  B0 02                  MOV      AL,2
338 0017  CD 21                  INT      DOSINT       ;OPEN FILE
339 0019  72 03                  JC       BADCOL       ;JMP IF NO COLOR FILE
340 001B  E9 05A3 R              JMP      MAINPG       ;JMP TO MAIN PROGRAM
341                              ;
342                              ;
343 001E  C7 06 0000 E 0014 BADCOL:  MOV   MSGNM,20    ;BAD ACCESS
344 0024  E8 0000 E              CALL     CRTMSG
345 0027  E8 0000 E              CALL     SNDLF
346 002A  BF 0426 R              MOV      DI,OFFSET DGROUP:CFILE
347 002D  E8 0000 E              CALL     DIRMSG
348 0030  E8 0000 E              CALL     SNDLF
```

```
`HMicrosoft (R) Macro Assembler Version 5.10                    8/29/89
12:40:44
CREATES MULTILAYER DXF FILE FROM ROW OR BOX                     Page
1-7

349   0033   B4 4C                  MOV  AH,4CH      ;STOP PROGRAM
        350   0035   CD 21                  INT  DOSINT
        351                                 ;
        352                                 ;THIS GETS OLD/NEW RESPONSE FROM MESSAGE IN MSGNM
        353                                 ;NZ FOR NO AND Z FOR YES
        354   0037                  REPCHK  PROC NEAR
        355   0037   E8 0000 E              CALL SNDLF
        356   003A   E8 0000 E              CALL DISCMD     ;ASK QUESTION
        357   003D   BA 0432 R              MOV  DX,OFFSET DGROUP:REPLY
        358   0040   B0 0A                  MOV  AL,0AH
        359   0042   B4 0C                  MOV  AH,0CH
        360   0044   CD 21                  INT  DOSINT     ;GET REPLY
        361   0046   8A 26 0433 R           MOV  AH,REPLY+1   ;# BYTES READ
        362   004A   0A E4                  OR   AH,AH
        363   004C   74 0C                  JZ   REPOK      ;JMP IF CR
        364   004E   8A 26 0434 R           MOV  AH,REPLY+2  ;GET REPLY BYTE
        365   0052   80 FC 59               CMP  AH,'Y'
        366   0055   74 03                  JZ   REPOK      ;JMP IF Y
        367   0057   80 FC 79               CMP  AH,'y'
        368   005A   C3            REPOK:   RET
        369   005B                  REPCHK  ENDP
        370                                 ;
        371                                 ;THIS OPENS THE SOURCE FILES. CY=ERR
        372   005B                  GETFIL  PROC NEAR
        373   005B   E8 0000 E              CALL CRTMSG
        374   005E   BA 03D3 R              MOV  DX,OFFSET DGROUP:FLNAME
        375   0061   B0 0A                  MOV  AL,0AH
        376   0063   B4 0C                  MOV  AH,0CH
        377   0065   CD 21                  INT  DOSINT     ;GET FILE PATH/NAME
        378   0067   E8 0000 E              CALL SNDLF
        379   006A   8A 0E 03D4 R           MOV  CL,FLNMLN  ;# BYTES IN NAME
        380   006E   80 F9 00               CMP  CL,0
        381   0071   74 28                  JE   GTF4       ;JMP IF JUST CR
        382   0073   32 ED                  XOR  CH,CH
        383   0075   BF 03D5 R              MOV  DI,OFFSET DGROUP:FILNAM
```

```
10      384 0078  E8 0000 E              CALL  UPRCAS      ;ALL UPPER CASE
11      385 007B  BB 03D5 R              MOV   BX,OFFSET DGROUP:FILNAM
12      386 007E  8A 0E 03D4 R           MOV   CL,FLNMLN
13      387 0082  32 ED                  XOR   CH,CH
14      388 0084  03 D9                  ADD   BX,CX       ;BX=EXT LOCATION
15      389 0086  8B FB                  MOV   DI,BX
16      390 0088  BE 0343 R              MOV   SI,OFFSET DGROUP:LISP
17      391 008B  B9 0005                MOV   CX,5
18      392 008E  F3/ A4           REP   MOVSB             ;ADD .LSP EXT
19      393 0090  BA 03D5 R              MOV   DX,OFFSET DGROUP:FILNAM
20      394 0093  B4 3D                  MOV   AH,3DH
21      395 0095  B0 02                  MOV   AL,2
22      396 0097  CD 21                  INT   DOSINT      ;OPEN FILE
23      397 0099  73 17                  JNC   GTF5 ;JMP IF EXISTS
24      398                         ;
25      399 009B  C7 06 0000 E 0002 GTF4: MOV   MSGNM,2    ;BAD ACCESS
26      400 00A1  E8 0000 E              CALL  CRTMSG
27      401 00A4  E8 0000 E              CALL  SNDLF
28      402 00A7  BF 03D5 R              MOV   DI,OFFSET DGROUP:FILNAM
29      403 00AA  E8 0000 E              CALL  DIRMSG
30      404 00AD  E8 0000 E              CALL  SNDLF
31      405 00B0  F9                     STC
32      406 00B1  C3                     RET
33

1  ^HMicrosoft (R) Macro Assembler Version 5.10              8/29/89
 2  12:40:44
 3  CREATES MULTILAYER DXF FILE FROM ROW OR BOX             Page
 4  1-8
 5
 6
 7      407                         ;
 8      408 00B2  A3 041C R        GTF5:   MOV   LIHAND,AX ;SAVE LISP
 9  IN FILE HANDLE
10      409 00B5  8B FB                  MOV   DI,BX
11      410 00B7  C6 05 45               MOV   BYTE PTR [DI],'E'
12      411 00BA  47                     INC   DI
13      412 00BB  BE 0348 R              MOV   SI,OFFSET DGROUP:DXF
14      413 00BE  B9 0005                MOV   CX,5
15      414 00C1  F3/ A4           REP   MOVSB             ;ADD .DXF EXT
16      415 00C3  BA 03D5 R              MOV   DX,OFFSET DGROUP:FILNAM
17      416 00C6  B4 3D                  MOV   AH,3DH
18      417 00C8  B0 02                  MOV   AL,2
19      418 00CA  CD 21                  INT   DOSINT      ;OPEN FILE
20      419 00CC  72 CD                  JC    GTF4 ;JMP IF DOESNT EXIST
21      420 00CE  A3 0418 R              MOV   EIHAND,AX ;SAVE  ENTITIES
```

```
22  IN FILE HANDLE
23       421                              ;
24       422  00D1  8B FB                 MOV   DI,BX
25       423  00D3  C6 05 48              MOV   BYTE PTR [DI],'H'
26       424  00D6  47              INC   DI
27       425  00D7  BE 0348 R             MOV   SI,OFFSET DGROUP:DXF
28       426  00DA  B9 0005               MOV   CX,5
29       427  00DD  F3/ A4          REP   MOVSB           ;ADD .DXF EXT
30       428  00DF  BA 03D5 R             MOV   DX,OFFSET DGROUP:FILNAM
31       429  00E2  B4 3D                 MOV   AH,3DH
32       430  00E4  B0 02                 MOV   AL,2
33       431  00E6  CD 21                 INT   DOSINT     ;OPEN FILE
34       432  00E8  72 B1                 JC    GTF4 ;JMP IF DOESNT EXIST
35       433  00EA  A3 041A R             MOV   HIHAND,AX  ;SAVE HEADER IN
36  FILE HANDLE
 1       434  00ED  F8              CLC
 2       435  00EE  C3              RET
 3       436  00EF            GETFIL    ENDP
 4       437                              ;
 5       438                              ;THIS OPENS THE DESTINATION FILES.
 6  CY=ERR
 7       439  00EF            MAKFIL    PROC NEAR
 8       440  00EF  E8 0000 E             CALL  CRTMSG
 9       441  00F2  BA 03D3 R             MOV   DX,OFFSET DGROUP:FLNAME
10       442  00F5  B0 0A                 MOV   AL,0AH
11       443  00F7  B4 0C                 MOV   AH,0CH
12       444  00F9  CD 21                 INT   DOSINT     ;G E T    F I L E
13  PATH/NAME
14       445  00FB  E8 0000 E             CALL  SNDLF
15       446  00FE  80 3E 03D4 R 00       CMP   FLNMLN,0
16       447  0103  75 0E                 JNE   MKF0
17       448  0105  C7 06 0000 E 0002     MOV   MSGNM,2    ;NO ACCESS
18       449  010B  E8 0000 E             CALL  CRTMSG
19       450  010E  E8 0000 E             CALL  SNDLF
20       451  0111  F9              STC
21       452  0112  C3              RET
22       453                              ;
23       454  0113  8A 0E 03D4 R    MKF0: MOV   CL,FLNMLN  ;# BYTES IN
24  NAME
25       455  0117  32 ED                 XOR   CH,CH
26       456  0119  BF 03D5 R             MOV   DI,OFFSET DGROUP:FILNAM
27       457  011C  E8 0000 E             CALL  UPRCAS     ;ALL UPPER CASE
28       458  011F  8A 0E 03D4 R          MOV   CL,FLNMLN
29       459  0123  32 ED                 XOR   CH,CH
30       460  0125  BB 03D5 R             MOV   BX,OFFSET DGROUP:FILNAM
```

```
31      461 0128  03 D9                ADD   BX,CX       ;POINT TO END OF
32 NAME
33      462 012A  8B FB                MOV   DI,BX
34      463 012C  BE 0343 R            MOV   SI,OFFSET DGROUP:LISP
35      464 012F  B9 0005              MOV   CX,5
36
```

ˆHMicrosoft (R) Macro Assembler Version 5.10                8/29/89
12:40:44
CREATES MULTILAYER DXF FILE FROM ROW OR BOX                  Page
1-9

```
        465 0132  F3/ A4               REP   MOVSB       ;ADD .LSP EXT
        466                             ;
        467 0134  BA 03D5 R            MOV   DX,OFFSET DGROUP:FILNAM
        468 0137  B4 4E                MOV   AH,4EH
        469 0139  33 C9                XOR   CX,CX
        470 013B  CD 21                INT   DOSINT      ;SEARCH FOR FILE
        471 013D  3C 00                CMP   AL,0
        472 013F  75 0F                JNE   MKF2  ;JMP IF FILE NOT FOUND 473 0141  C7 06 0000 E 0007    MOV   MSGNM,7
        474 0147  53                   PUSH  BX    ;HOLD FILE NAME ADDR
        475 0148  E8 0037 R            CALL  REPCHK      ;SEE IF OK TO
DESTROY EXISTING FILES
        476 014B  5B                   POP   BX
        477 014C  74 02                JZ    MKF2 ;JMP IF OKAY
        478 014E  F9                   STC
        479 014F  C3                   RET
        480                             ;
        481 0150  BA 03D5 R            MKF2:  MOV  DX,OFFSET
DGROUP:FILNAM
        482 0153  B4 3C                MOV   AH,3CH
        483 0155  33 C9                XOR   CX,CX
        484 0157  CD 21                INT   DOSINT      ;OPEN FILE
        485 0159  72 55                JC    MKF4 ;JMP IF ERR
        486 015B  A3 0422 R            MOV   LOHAND,AX ;SAVE LSP OUT
FILE HANDLE
        487                             ;
        488 015E  8B FB                MOV   DI,BX
        489 0160  BE 034D R            MOV   SI,OFFSET DGROUP:SCRP
        490 0163  B9 0005              MOV   CX,5
```

```
491 0166  F3/ A4              REP  MOVSB              ;ADD .SCR EXT
492 0168  BA 03D5 R                MOV  DX,OFFSET DGROUP:FILNAM
493 016B  B4 3C                    MOV  AH,3CH
494 016D  33 C9                    XOR  CX,CX
495 016F  CD 21                    INT  DOSINT             ;OPEN FILE
496 0171  72 3D                    JC   MKF4 ;JMP IF ERR
497 0173  A3 0424 R                MOV  SOHAND,AX ;SAVE SCR OUT FILE HANDLE
498                               ;
499 0176  8B FB                    MOV  DI,BX
500 0178  C6 05 45                 MOV  BYTE PTR [DI],'E'
501 017B  47                  INC  DI
502 017C  BE 0348 R                MOV  SI,OFFSET DGROUP:DXF
503 017F  B9 0005                  MOV  CX,5
504 0182  F3/ A4              REP  MOVSB              ;ADD .DXF EXT
505 0184  BA 03D5 R                MOV  DX,OFFSET DGROUP:FILNAM
506 0187  B4 3C                    MOV  AH,3CH
507 0189  33 C9                    XOR  CX,CX
508 018B  CD 21                    INT  DOSINT             ;OPEN FILE
509 018D  72 21                    JC   MKF4 ;JMP IF ERR
510 018F  A3 041E R                MOV  EOHAND,AX ;SAVE ENTITIES OUT FILE HANDLE
511                               ;
512 0192  8B FB                    MOV  DI,BX
513 0194  C6 05 48                 MOV  BYTE PTR [DI],'H'
514 0197  47                  INC  DI
515 0198  BE 0348 R                MOV  SI,OFFSET DGROUP:DXF
516 019B  B9 0005                  MOV  CX,5
517 019E  F3/ A4              REP  MOVSB              ;ADD .DXF EXT
518 01A0  BA 03D5 R                MOV  DX,OFFSET DGROUP:FILNAM
519 01A3  B4 3C                    MOV  AH,3CH
520 01A5  33 C9                    XOR  CX,CX
521 01A7  CD 21                    INT  DOSINT             ;OPEN FILE
522 01A9  72 05                    JC   MKF4 ;JMP IF ERR
```

Microsoft (R) Macro Assembler Version 5.10                8/29/89 12:40:44
CREATES MULTILAYER DXF FILE FROM ROW OR BOX               Page 1-10

```
523 01AB  A3 0420 R                MOV  HOHAND,AX ;SAVE HEADER OUT FILE HANDLE
524 01AE  F8                       CLC
525 01AF  C3                       RET
```

```
11      526                             ;
12      527 01B0  B4 4C         MKF4:   MOV   AH,4CH     ; S T O P
PROGRAM
14      528 01B2  CD 21                 INT   DOSINT
15      529                             ;
16      530 01B4                MAKFIL  ENDP
17      531                             ;
18      532                             ;THIS GETS A VALUE FROM KEYBOARD.
CY=ERR
20      533                             ;MSGNM=MESSAGE.  AX=MAXIMUM VALUE
21      534 01B4                GETVAL  PROC  NEAR
22      535 01B4  50            PUSH AX       ;HOLD MAX
23      536 01B5  E8 0000 E             CALL  SNDLF
24      537 01B8  E8 0000 E             CALL  CRTMSG
25      538 01BB  E8 0000 E             CALL  RCVVAL     ;GET VALUE
26      539 01BE  58            POP   AX
27      540 01BF  72 08                 JC    GTERR      ;JMP IF ERR
28      541 01C1  3B F0                 CMP   SI,AX
29      542 01C3  77 04                 JA    GTERR      ;JMP IF OVER MAX
30      543 01C5  8B C6                 MOV   AX,SI      ;RESULT TO AX AND
SI
32      544 01C7  F8                    CLC
33      545 01C8  C3                    RET
34      546 01C9  C7 06 0000 E 0016 GTERR:  MOV  MSGNM,22
35      547 01CF  E8 0000 E             CALL  CRTMSG
36      548 01D2  F9                    STC
1       549 01D3  C3                    RET
2       550 01D4                GETVAL  ENDP
3       551                             ;
4       552                             ;THIS CREATES THE LISP FILE
5       553 01D4                WRTPAR  PROC  NEAR
6       554 01D4  C7 06 045F R 0001     MOV   BYTSRD,1   ;TEMPY
7       555 01DA  BB 045F R             MOV   BX,OFFSET DGROUP:BYTSRD
8       556 01DD  BF 0383 R             MOV   DI,OFFSET DGROUP:STQSET+11
9       557 01E0  E8 0000 E             CALL  BNASC4     ;POST CHAN PAIRS
10      558 01E3  BB 044F R             MOV   BX,OFFSET DGROUP:NTRL
11      559 01E6  BF 035E R             MOV   DI,OFFSET DGROUP:STQTRL+12
12      560 01E9  E8 0000 E             CALL  BNASC4     ;POST TRIALS TO
LISP
14      561 01EC  BB 044D R             MOV   BX,OFFSET DGROUP:NSMP
15      562 01EF  BF 0371 R             MOV   DI,OFFSET DGROUP:STQSMP+12
16      563 01F2  E8 0000 E             CALL  BNASC4     ;POST # SAMPS
17      564 01F5  B9 0038               MOV   CX,LNSTQ   ;# CHARS
18      565 01F8  BA 0352 R             MOV   DX,OFFSET DGROUP:STQTRL
;1ST ADR
```

```
566 01FB  8B 1E 0422 R        MOV   BX,LOHAND   ;LSP FIL HANDLE
567 01FF  E8 0000 E           CALL  WRTIND      ;TO FILE
568 0202  89 1E 0416 R        MOV   FHANDL,BX
569 0206  E8 0000 E           CALL  CLRHDL      ;CLEAR HANDLE
570 0209  C3              RET
571 020A                  WRTPAR   ENDP
572                       ;
573                       ;THIS CREATES THE SCRIPT FILE
574 020A                  WRTSCR   PROC NEAR
575 020A  8A 0E 03D4 R        MOV   CL,FLNMLN   ;BASIC FILE NAME LENGTH
576 020E  32 ED               XOR   CH,CH
577 0210  51              PUSH CX
578 0211  BF 03B7 R           MOV   DI,OFFSET DGROUP:LNAM
579 0214  BE 03D5 R           MOV   SI,OFFSET DGROUP:FILNAM
580 0217  F3/ A4          REP  MOVSB             ;POST LSP NAME
```

Microsoft (R) Macro Assembler Version 5.10                    8/29/89 12:40:44
CREATES MULTILAYER DXF FILE FROM ROW OR BOX                   Page 1-11

```
581 0219  59              POP  CX
582 021A  51              PUSH CX
583 021B  BF 0391 R           MOV   DI,OFFSET DGROUP:HNAM
584 021E  BE 03D5 R           MOV   SI,OFFSET DGROUP:FILNAM
585 0221  F3/ A4          REP  MOVSB             ;POST HEADER NAME 586 0223  C6 05 48            MOV   BYTE PTR [DI],'H'
587 0226  59              POP  CX
588 0227  BF 03A2 R           MOV   DI,OFFSET DGROUP:ENAM
589 022A  BE 03D5 R           MOV   SI,OFFSET DGROUP:FILNAM
590 022D  F3/ A4          REP  MOVSB             ;POST ENTITIES NAME
591 022F  C6 05 45            MOV   BYTE PTR [DI],'E'
592 0232  BA 038A R           MOV   DX,OFFSET DGROUP:SCRIN
593 0235  B9 0049             MOV   CX,LNSCR
594 0238  8B 1E 0424 R        MOV   BX,SOHAND   ;SCR FILE HANDLE
595 023C  E8 0000 E           CALL  WRTIND
596 023F  89 1E 0416 R        MOV   FHANDL,BX
597 0243  E8 0000 E           CALL  CLRHDL      ;CLOSE FILE
598 0246  C3              RET
599 0247                  WRTSCR   ENDP
600                       ;
```

```
29      601                             ;THIS READS AND WRITES LINES TO OUT
30 FILE
31      602                             ;BX=HANDLE. SI=SOURCE. CX=# LINES
32      603 0247                        WRTLIN   PROC NEAR
33      604 0247 8B D6                     MOV   DX,SI        ;HOLD ADR
34      605 0249 4E                     DEC   SI             ;BACK ONE BYTE
35      606 024A 33 FF                     XOR   DI,DI        ;0 BYTES
36      607 024C 47        WL1:         INC   DI             ;ADD A BYTE
 1      608 024D 46                        INC   SI
 2      609 024E 80 3C 0A                  CMP   BYTE
 3 PTR[SI],LF       ;GET NEXT BYTE
 4      610 0251 75 F9                     JNE   WL1          ;JMP IF NOT EOLINE
 5      611 0253 E2 F7                     LOOP  WL1          ;JUMP IF NOT LAST LINE
 6
 7      612 0255 8B CF                     MOV   CX,DI        ;GET # BYTES
 8      613 0257 E8 0000 E                 CALL  WRTIND       ;WRITE TO FILE
 9      614 025A 29 3E 0463 R              SUB   BUFSIZ,DI    ;BYTES LEFT
10      615 025E 01 3E 0467 R              ADD   BUFPTR,DI    ;NEXT ADR
11      616 0262 C3                     RET
12      617 0263                        WRTLIN   ENDP
13      618                             ;
14      619                             ;THIS WRITES THE NEW HEADER FILE FROM
15
16      620                             ;THE OLD HEADER FILE.
17      621 0263                        WRTHDR   PROC NEAR
18      622 0263 8B 1E 041A R              MOV   BX,HIHAND
19      623 0267 BA 0469 R                 MOV   DX,OFFSET DGROUP:FBUF
20 ;1ST ADR
21      624 026A 89 16 0467 R              MOV   BUFPTR,DX
22      625 026E B9 8000                   MOV   CX,32768
23      626 0271 E8 0000 E                 CALL  RDIND        ;READ   INPUT
24 HEADER FILE
25      627 0274 73 03                     JNC   WH0          ;JMP IF NO ERR
26      628 0276 E9 0334 R                 JMP   WHERR
27      629 0279 A3 0463 R     WH0:        MOV   BUFSIZ,AX    ;CURR SIZE
28      630 027C 8B 1E 041A R              MOV   BX,HIHAND
29      631 0280 89 1E 0416 R              MOV   FHANDL,BX
30      632 0284 E8 0000 E                 CALL  CLRHDL       ;CLOSE HDR IN
31 FILE
32      633 0287 8B 1E 0420 R              MOV   BX,HOHAND    ;HEADER OUT FILE
33 HANDLE
34      634 028B 8B 36 0467 R              MOV   SI,BUFPTR    ;1ST SOURCE ADR
35      635 028F B9 0017                   MOV   CX,23        ;23 LINES
36      636 0292 E8 0247 R                 CALL  WRTLIN       ;WRITE LINES
```

```
637 0295  73 03              JNC  WH00  ;JMP IF NO ERR
638 0297  E9 0334 R           JMP  WHERR
```

`^HMicrosoft (R) Macro Assembler Version 5.10                    8/29/89 12:40:44`
CREATES MULTILAYER DXF FILE FROM ROW OR BOX                Page 1-12

```
639 029A  BB 0451 R       WH00:  MOV  BX,OFFSET DGROUP:NLYR
640 029D  BF 0469 R              MOV  DI,OFFSET DGROUP:FBUF
641 02A0  E8 0000 E              CALL BNASC4    ;# LAYERS TO ASC
642 02A3  C6 06 046D R 0D        MOV  BYTE PTR FBUF+4,CR
643 02A8  C6 06 046E R 0A        MOV  BYTE PTR FBUF+5,LF
644 02AD  BF 0469 R              MOV  DI,OFFSET DGROUP:FBUF
645 02B0  B9 0006                MOV  CX,6 ;6 CHARS
646 02B3  80 3D 20        WH1:   CMP  BYTE PTR [DI],' '
647 02B6  75 04                  JNE  WH2  ;JMP IF NOT LEADING SPACE
648 02B8  47                     INC  DI
649 02B9  49                     DEC  CX
650 02BA  EB F7                  JMP  WH1
651                              ;
652 02BC  8B D7           WH2:   MOV  DX,DI
653 02BE  8B 1E 0420 R           MOV  BX,HOHAND
654 02C2  E8 0000 E              CALL WRTIND    ;WRITE # LAYERS
655 02C5  72 6D                  JC   WHERR     ;JMP IF ERR
656 02C7  8B 0E 0451 R           MOV  CX,NLYR   ;# LAYERS
657 02CB  C7 06 0453 R 0001      MOV  CLYR,1    ;1ST LAYER
658 02D1  BF 84D1 R              MOV  DI,OFFSET DGROUP:COLORS
659 02D4  89 3E 84CF R           MOV  CLRPTR,DI ;COLOR POINTER
660 02D8  51              WH3:   PUSH CX
661 02D9  BB 0453 R              MOV  BX,OFFSET DGROUP:CLYR
662 02DC  BF 000D R              MOV  DI,OFFSET DGROUP:LNUM
663 02DF  E8 0000 E              CALL BNASC4    ;POST CURR LAYER #
664 02E2  FF 06 0453 R           INC  CLYR ;BUMP LAYER
665                              ;
666 02E6  BE 000D R              MOV  SI,OFFSET DGROUP:LNUM
667 02E9  80 3C 20        WH4:   CMP  BYTE PTR [SI],' '
668 02EC  75 11                  JNE  WH5  ;JMP IF NOT LEADING SPACE
669 02EE  8B 44 01               MOV  AX,[SI+1]
670 02F1  89 04                  MOV  [SI],AX
671 02F3  8A 44 03               MOV  AL,[SI+3]
```

```
 7      672 02F6    88 44 02                MOV    [SI+2],AL
 8      673 02F9    C6 44 03 00             MOV    BYTE PTR [SI+3],00H
 9      674 02FD    EB EA                   JMP    WH4
10      675                         ;
11      676 02FF    8B 36 84CF R    WH5:    MOV    SI,CLRPTR   ;NEXT COLOR
12      677 0303    BF 001E R               MOV    DI,OFFSET DGROUP:LCOL
13      678 0306    B9 0003                 MOV    CX,3
14      679 0309    F3/ A4          REP     MOVSB              ;POST COLOR
15      680 030B    89 36 84CF R            MOV    CLRPTR,SI
16      681 030F    BA 0000 R               MOV    DX,OFFSET DGROUP:LAYR
17      682 0312    B9 0032                 MOV    CX,LLNGH
18      683 0315    8B 1E 0420 R            MOV    BX,HOHAND
19      684 0319    E8 0000 E               CALL   WRTIND      ;WRITE LAYER TO
20 FILE
21      685 031C    72 16                   JC     WHERR       ;JMP IF ERR
22      686 031E    59              POP     CX
23      687 031F    E2 B7                   LOOP   WH3         ;JMP IF MORE
24      688 0321    BA 0032 R               MOV    DX,OFFSET DGROUP:EOFILE
25      689 0324    B9 001E                 MOV    CX,LEOF
26      690 0327    E8 0000 E               CALL   WRTIND      ;WRITE FILE END
27      691 032A    72 08                   JC     WHERR       ;JMP IF ERR
28      692 032C    89 1E 0416 R            MOV    FHANDL,BX
29      693 0330    E8 0000 E               CALL   CLRHDL      ;CLOSE   HEADER
30 FILE
31      694 0333    C3                      RET
32      695                         ;
33      696 0334    C7 06 0000 E 0015  WHERR:   MOV  MSGNM,21
34
 1   ^HMicrosoft (R) Macro Assembler Version 5.10                    8/29/89
 2   12:40:44
 3   CREATES MULTILAYER DXF FILE FROM ROW OR BOX                     Page
 4   1-13
 5
 6
 7      697 033A    E8 0000 E               CALL   CRTMSG
 8      698 033D    E8 0000 E               CALL   SNDLF
 9      699 0340    B4 4C                   MOV    AH,4CH      ;STOP PGM
10      700 0342    CD 21                   INT    DOSINT
11      701 0344    C3                      RET
12      702 0345                    WRTHDR  ENDP
13      703                         ;
14      704                         ;THIS READS LINES FROM WBUF
15      705                         ;SI=SOURCE. CX=# LINES
16      706 0345            GETLIN  PROC NEAR
17      707 0345    8B D6                   MOV    DX,SI       ;HOLD ADR
```

| | | | | | |
|---|---|---|---|---|---|
| 18 | 708 0347 | 4E | | DEC SI | ;BACK ONE BYTE |
| 19 | 709 0348 | 33 FF | | XOR DI,DI | ;0 BYTES |
| 20 | 710 034A | 47 | GL1: | INC DI | ;ADD A BYTE |
| 21 | 711 034B | 46 | | INC SI | |
| 22 | 712 034C | 80 3C 0A | | CMP BYTE PTR[SI],LF | ;GET NEXT BYTE |
| 24 | 713 034F | 75 F9 | | JNE GL1 | ;JMP IF NOT EOLINE |
| 25 | 714 0351 | E2 F7 | | LOOP GL1 | ;JUMP IF NOT LAST LINE |
| 27 | 715 0353 | 29 3E 0463 R | | SUB BUFSIZ,DI | ;BYTES LEFT |
| 28 | 716 0357 | 01 3E 0467 R | | ADD BUFPTR,DI | ;NEXT ADR |
| 29 | 717 035B | C3 | | RET | |
| 30 | 718 035C | | | GETLIN ENDP | |
| 31 | 719 | | | ; | |
| 32 | 720 | | | ;THIS FILLS THE INPUT BUFFER | |
| 33 | 721 035C | | | FILLBF PROC NEAR | |
| 34 | 722 035C | BB 8000 | | MOV BX,32768 | ;MAX SIZE |
| 35 | 723 035F | 8B 0E 0463 R | | MOV CX,BUFSIZ | ;CURR SIZE |
| 36 | 724 0363 | BF 0469 R | | MOV DI,OFFSET DGROUP:FBUF | |
| 1 | 725 0366 | 83 F9 00 | | CMP CX,0 | |
| 2 | 726 0369 | 74 06 | | JE FBF0 | ;JMP IF EMPTY |
| 3 | 727 036B | 8B 36 0467 R | | MOV SI,BUFPTR | ;NXT DATA ADR |
| 4 | 728 036F | F3/ A4 | | REP MOVSB | ;DATA TO HEAD OF BUFFER |
| 6 | 729 0371 | 89 3E 0467 R | FBF0: | MOV BUFPTR,DI | ;NXT DATA ADR |
| 8 | 730 0375 | 2B 1E 0463 R | | SUB BX,BUFSIZ | ;SPACE AVAIL |
| 9 | 731 0379 | 8B 0E 045B R | | MOV CX,FSIZ | ;GET FILE SIZE |
| 10 | 732 037D | 8B 16 045D R | | MOV DX,FSIZ+2 | |
| 11 | 733 0381 | 2B 0E 045F R | | SUB CX,BYTSRD | ;LESS BYTES READ |
| 12 | 734 0385 | 1B 16 0461 R | | SBB DX,BYTSRD+2 | |
| 13 | 735 0389 | 0B D2 | | OR DX,DX | |
| 14 | 736 038B | 75 08 | | JNZ FBF1 | ;JMP IF OVER 65535 |
| 15 | 737 038D | 0B C9 | | OR CX,CX | |
| 16 | 738 038F | 74 29 | | JZ FBF5 | ;JMP IF DONE |
| 17 | 739 0391 | 3B CB | | CMP CX,BX | |
| 18 | 740 0393 | 72 02 | | JB FBF2 | ;JMP IF LT SPACE AVAIL |
| 20 | 741 0395 | 8B CB | FBF1: | MOV CX,BX | ;SET TO MAX |
| 21 | 742 0397 | 8B 1E 0418 R | FBF2: | MOV BX,EIHAND | |
| 22 | 743 039B | 8B 16 0467 R | | MOV DX,BUFPTR | ;1ST ADR |
| 23 | 744 039F | E8 0000 E | | CALL RDIND | ;READ INPUT FILE |
| 24 | 745 03A2 | 72 16 | | JC FBF5 | ;JMP IF ERR |
| 25 | 746 03A4 | 01 06 0463 R | | ADD BUFSIZ,AX | ;CURR SIZE |
| 26 | 747 03A8 | 01 06 045F R | | ADD BYTSRD,AX | ;TOTAL BYTES READ |

```
28      748 03AC  83 16 0461 R 00              ADC  BYTSRD+2,0
29      749 03B1  BE 0469 R              MOV  SI,OFFSET DGROUP:FBUF
30      750 03B4  89 36 0467 R           MOV  BUFPTR,SI
31      751 03B8  F8                     CLC
32      752 03B9  C3                     RET
33      753 03BA  F9            FBF5:    STC
34      754 03BB  C3                     RET
35
```

^HMicrosoft (R) Macro Assembler Version 5.10          8/29/89
12:40:44
CREATES MULTILAYER DXF FILE FROM ROW OR BOX           Page
1-14

```
 7      755 03BC                         FILLBF  ENDP
 8      756                              ;
 9      757                              ;THIS PARSES THE ENTITIES FILE
10      758 03BC                         PARSE   PROC NEAR
11      759 03BC  A1 0449 R              MOV  AX,NTRLS   ;GET MAX TRIALS
12      760 03BF  2B 06 044F R           SUB  AX,NTRL    ;LESS TRIALS TO WRITE
14      761 03C3  A3 0459 R              MOV  LTRL,AX    ;AS LAST TRIAL INDEX
16      762 03C6  8B 0E 0449 R           MOV  CX,NTRLS
17      763 03CA  51            DOTRLS:  PUSH CX         ;TRIALS LOOP
18      764 03CB  3B 0E 0459 R           CMP  CX,LTRL
19      765 03CF  77 03                  JA   DOT1 ;JMP IF NOT LAST
20      766 03D1  59                     POP  CX
21      767 03D2  F8                     CLC
22      768 03D3  C3                     RET
23      769                              ;
24      770 03D4  A1 0447 R     DOT1:    MOV  AX,NSMPS   ;MAX SAMPLES
26      771 03D7  2B 06 044D R           SUB  AX,NSMP    ;LESS SAMPS TO WRITE
28      772 03DB  A3 0457 R              MOV  LSMP,AX    ;AS LAST SAMPLE INDEX
30      773 03DE  C7 06 84CF R 0001      MOV  CLRPTR,1   ;SET FOR LAYER 1
32      774 03E4  8B 0E 0447 R           MOV  CX,NSMPS
33      775 03E8  51            DOSMPS:  PUSH CX         ;SAMPLES LOOP
34      776 03E9  3B 0E 0457 R           CMP  CX,LSMP
35      777 03ED  77 03                  JA   DOS1 ;JMP IF NOT LAST
36      778 03EF  E9 04A9 R              JMP  CLSETS     ;AS CLEAR SETS
```

```
779                         ;
780 03F2  A1 0445 R      DOS1:    MOV  AX,NSETS    ;MAX SETS
781 03F5  2B 06 044B R            SUB  AX,NSET     ;LESS DESIRED SET 782 03F9  40                      INC  AX
783 03FA  A3 0455 R               MOV  GSET,AX     ;SET # TO DO
784 03FD  8B 0E 0445 R            MOV  CX,NSETS
785 0401  51             DOSETS:  PUSH CX          ;SET LOOP
786 0402  3B 0E 0455 R            CMP  CX,GSET
787 0406  74 02                   JE   DOST1       ;JMP IF GOOD SET
788 0408  EB 6F                   JMP  SHORT DOSRD ;ELSE SKIP SET
789                         ;
790 040A  83 3E 0463 R 50  DOST1:   CMP  BUFSIZ,80
791 040F  77 08                    JA   DOST2      ;JMP IF ROOM IN BUFF
792 0411  E8 035C R                CALL FILLBF     ;ELSE GET MORE
793 0414  73 03                    JNC  DOST2      ;JMP IF NO ERR
794 0416  E9 04CC R                JMP  RET3
795 0419  8B 36 0467 R    DOST2:   MOV  SI,BUFPTR  ;POINT TO BUFF
796 041D  8B 1E 041E R             MOV  BX,EOHAND
797 0421  B9 0003                  MOV  CX,3
798 0424  E8 0247 R                CALL WRTLIN     ;XSFR 3 LINES
799 0427  73 03                    JNC  DOST3      ;JMP IF NO ERR
800 0429  E9 04CC R                JMP  RET3
801 042C  B9 0001         DOST3:   MOV  CX,1
802 042F  8B 36 0467 R             MOV  SI,BUFPTR
803 0433  E8 0345 R                CALL GETLIN     ;GET LAYER # LINE 804 0436  BB 84CF R                MOV  BX,OFFSET DGROUP:CLRPTR  ;LAYER #
805 0439  BF 0469 R                MOV  DI,OFFSET DGROUP:FBUF    ;TEMPY
806 043C  E8 0000 E                CALL BNASC4     ;LAYER AS ASCII
807 043F  C6 06 046D R 0D          MOV  BYTE PTR FBUF+4,CR
808 0444  C6 06 046E R 0A          MOV  BYTE PTR FBUF+5,LF
809 0449  BF 046A R                MOV  DI,OFFSET DGROUP:FBUF+1
810 044C  B9 0005                  MOV  CX,5
811                          ;
812 044F  80 3D 20        DOST3A:  CMP  BYTE PTR [DI],' '
```

^HMicrosoft (R) Macro Assembler Version 5.10                8/29/89 12:40:44
CREATES MULTILAYER DXF FILE FROM ROW OR BOX                 Page 1-15

```
813 0452  75 04              JNE     DOST3B    ;JMP IF NO LEADING SPACE
814 0454  47                 INC     DI
815 0455  49                 DEC     CX
816 0456  EB F7              JMP     DOST3A
817                          ;
818 0458  8B D7       DOST3B: MOV    DX,DI
819 045A  8B 1E 041E R       MOV     BX,EOHAND
820 045E  E8 0000 E          CALL    WRTIND    ;WRITE LAYER #
821 0461  73 03              JNC     DOST3C    ;JMP IF NO ERR
822 0463  EB 67 90           JMP     RET3
823 0466  FF 06 84CF R DOST3C: INC   CLRPTR    ;BUMP LAYER #
824 046A  B9 000C            MOV     CX,12
825 046D  8B 36 0467 R       MOV     SI,BUFPTR
826 0471  E8 0247 R          CALL    WRTLIN    ;XSFR 12 LINES
827 0474  73 1C              JNC     DOSTRT    ;JMP IF NO ERR
828 0476  EB 54 90           JMP     RET3
829                          ;
830 0479  83 3E 0463 R 50 DOSRD: CMP  BUFSIZ,80
831 047E  77 08              JA      DOST4     ;JMP IF ROOM IN BUFF
832 0480  E8 035C R          CALL    FILLBF    ;ELSE GET MORE
833 0483  73 03              JNC     DOST4     ;JMP IF NO ERR
834 0485  EB 45 90           JMP     RET3
835 0488  8B 36 0467 R DOST4: MOV    SI,BUFPTR ;POINT TO BUFF
836 048C  B9 0010            MOV     CX,16
837 048F  E8 0345 R          CALL    GETLIN    ;CLR SET FROM BUFF
838                          ;
839 0492  59          DOSTRT: POP    CX        ;GET SETS TO DO
840 0493  49                 DEC     CX
841 0494  74 03              JZ      DOSRT     ;JMP IF DONE
842 0496  E9 0401 R          JMP     DOSETS    ;JMP IF MORE
843                          ;
844 0499  59          DOSRT:  POP    CX        ;GET SMPS TO DO
845 049A  49                 DEC     CX
846 049B  74 03              JZ      DOTRT
```

```
847 049D  E9 03E8 R              JMP   DOSMPS    ;JMP IF MORE
848                          ;
849 04A0  59              DOTRT:   POP   CX    ;GET TRIALS TO DO
850 04A1  49                      DEC   CX
851 04A2  74 03                   JZ    DONE
852 04A4  E9 03CA R               JMP   DOTRLS   ;JMP IF MORE
853 04A7  F8              DONE:    CLC
854 04A8  C3                      RET
855                          ;
856 04A9  8B 0E 0445 R    CLSETS:  MOV   CX,NSETS
857 04AD  51              CLS1:    PUSH  CX    ;SET LOOP
858 04AE  83 3E 0463 R 50          CMP   BUFSIZ,80
859 04B3  77 08                   JA    CLS2 ;JMP IF ROOM IN BUFF
860 04B5  E8 035C R               CALL  FILLBF   ;ELSE GET MORE
861 04B8  73 03                   JNC   CLS2 ;JMP IF NO ERR
862 04BA  EB 10 90                JMP   RET3
863 04BD  8B 36 0467 R    CLS2:    MOV   SI,BUFPTR ;POINT TO BUFF
864 04C1  B9 0010                 MOV   CX,16
865 04C4  E8 0345 R               CALL  GETLIN   ;CLR SET FROM BUFF
866 04C7  59                      POP   CX
867 04C8  E2 E3                   LOOP  CLS1 ;JMP IF MORE
868 04CA  EB CD                   JMP   DOSRT
869                          ;
870 04CC  59              RET3:    POP   CX
871 04CD  59                      POP   CX
872 04CE  59                      POP   CX
873 04CF  C3                      RET
874                          ;
875 04D0                  PARSE    ENDP
876                          ;
877                          ;THIS PARSES A LINE TO FIND NUMERIC VALUE
878                          ;SI=SOURCE ADR. AX=RESULT
879 04D0                  PARLIN   PROC NEAR
880 04D0  B7 0D                   MOV   BH,CR    ;SET TO CARR RET
881 04D2  33 C0                   XOR   AX,AX    ;ZERO RESULT
```

```
19    882 04D4  80 3C 2F        PL1: CMP  BYTE PTR [SI],2FH
20    883 04D7  77 07                 JA   PL2  ;JMP IF 0 UP
21    884 04D9  38 3C                 CMP  [SI],BH
22    885 04DB  74 1C                 JE   PL4  ;JMP IF EOL
23    886 04DD  46              INC   SI
24    887 04DE ·EB F4                 JMP  PL1  ;TRY AGAIN
25    888                       ;
26    889 04E0  80 3C 3A        PL2: CMP  BYTE PTR [SI],3AH
27    890 04E3  72 03                 JB   PL3  ;JMP IF 0-9
28    891 04E5  46              INC   SI
29    892 04E6  EB EC                 JMP  PL1  ;TRY AGAIN
30    893                       ;
31    894 04E8  B9 000A         PL3: MOV  CX,10
32    895 04EB  F7 E1                 MUL  CX   ;RESULT TIMES 10
33    896 04ED  8A 0C                 MOV  CL,[SI]
34    897 04EF  80 E9 30              SUB  CL,30H
35    898 04F2  32 ED                 XOR  CH,CH
36    899 04F4  03 C1                 ADD  AX,CX
 1    900 04F6  46              INC   SI
 2    901 04F7  EB DB                 JMP  PL1  ;TRY AGAIN
 3    902                       ;
 4    903 04F9  46          PL4: INC SI    ;SKIP CARR RET
 5    904                       ;
 6    905 04FA  C3                    RET
 7    906 04FB                  PARLIN     ENDP
 8    907                       ;
 9    908                       ;THIS GETS THE PARAMETERS FROM THE
10   LISP FILE
11    909 04FB                  CHKLSP     PROC NEAR
12    910 04FB  8B 1E 041C R          MOV  BX,LIHAND ;GET  LSP  FILE
13   HANDLE
14    911 04FF  B9 0064               MOV  CX,100
15    912 0502  BA 0469 R             MOV  DX,OFFSET DGROUP:FBUF
16    913 0505  E8 0000 E             CALL RDIND     ;READ LSP FILE
17    914 0508  72 20                 JC   LSPERR    ;JMP IF ERR
18    915 050A  A3 045F R             MOV  BYTSRD,AX ;GET # BYTES
19    916 050D  89 1E 0416 R          MOV  FHANDL,BX
20    917 0511  E8 0000 E             CALL CLRHDL    ;CLEAR   FILE
21   HANDLE
22    918 0514 ·BE 0469 R             MOV  SI,OFFSET DGROUP:FBUF
23    919 0517  E8 04D0 R             CALL PARLIN    ;GET # TRLS
24    920 051A  A3 0449 R             MOV  NTRLS,AX
25    921 051D  E8 04D0 R             CALL PARLIN    ;GET # SAMPLES
26    922 0520· A3 0447 R             MOV  NSMPS,AX
27    923 0523  E8 04D0 R             CALL PARLIN    ;GET # SETS
```

```
28      924 0526  A3 0445 R              MOV   NSETS,AX
29      925 0529  C3                     RET
30      926                              ;
31      927 052A  C7 06 0000 E 0013  LSPERR: MOV MSGNM,19
32      928 0530  E8 0000 E              CALL  CRTMSG
```

HMicrosoft (R) Macro Assembler Version 5.10                8/29/89
12:40:44
CREATES MULTILAYER DXF FILE FROM ROW OR BOX                Page 1-17

```
 7      929 0533  E8 0000 E              CALL  SNDLF
 8      930 0536  B4 4C                  MOV   AH,4CH     ;STOP PGM
 9      931 0538  CD 21                  INT   DOSINT
10      932 053A                 CHKLSP  ENDP
11      933                              ;
12      934                              ;THIS GETS LAYER COLORS FROM DATA FILE
14      935 053A                 GCOLOR  PROC NEAR
15      936 053A  8B 1E 0422 R           MOV   BX,LOHAND  ;GET COLORS FILE HANDLE
17      937 053E  B9 0500                MOV   CX,1280
18      938 0541  BA 0469 R              MOV   DX,OFFSET DGROUP:FBUF
19      939 0544  E8 0000 E              CALL  RDIND      ;READ COLORS FILE
21      940 0547  73 01                  JNC   GC0        ;JMP IF NO ERR
22      941 0549  C3                     RET
23      942                              ;
24      943 054A  A3 045F R      GC0:    MOV   BYTSRD,AX  ;GET # BYTES
25      944 054D  89 1E 0416 R           MOV   FHANDL,BX
26      945 0551  E8 0000 E              CALL  CLRHDL     ;CLEAR FILE HANDLE
28      946 0554  C7 06 84CD R 0000      MOV   NCLRS,0    ;CLR COUNTER
29      947 055A  BE 0469 R              MOV   SI,OFFSET DGROUP:FBUF
30      948 055D  BF 84D1 R              MOV   DI,OFFSET DGROUP:COLORS ;COLOR TABLE
32      949 0560  B9 0003        GC1:    MOV   CX,3
33      950 0563  F3/ A4                 REP   MOVSB      ;XSFR 3 CHARS
34      951 0565  83 C6 02               ADD   SI,2       ;SKIP CRLF
35      952 0568  FF 06 84CD R           INC   NCLRS
36      953 056C  83 2E 045F R 05        SUB   BYTSRD,5
```

```
954 0571  74 02              JZ    GC2   ;JMP IF NONE LEFT
955 0573  79 EB              JNS   GC1   ;JMP IF MORE
956                          ;
957 0575  8B 1E 0422 R  GC2: MOV   BX,LOHAND
958 0579  89 1E 0416 R       MOV   FHANDL,BX
959 057D  E8 0000 E          CALL  CLRHDL  ;CLOSE FILE
960 0580  C7 06 0422 R 0000  MOV   LOHAND,0
961                          ;
962 0586  8B 0E 84CD R       MOV   CX,NCLRS  ;GET # COLORS
963 058A  BE 84D1 R          MOV   SI,OFFSET DGROUP:COLORS
964 058D  80 3C 20      GC3: CMP   BYTE PTR [SI],' '
965 0590  75 0B              JNE   GC4   ;JMP IF NOT LEADING SPACE
966 0592  8B 44 01           MOV   AX,[SI+1]
967 0595  89 04              MOV   [SI],AX
968 0597  C6 44 02 00        MOV   BYTE PTR [SI+2],00H
969 059B  EB F0              JMP   GC3
970                          ;
971 059D  83 C6 03      GC4: ADD   SI,3
972 05A0  E2 EB              LOOP  GC3   ;JMP IF MORE
973 05A2  C3                 RET
974 05A3                     GCOLOR ENDP
975                          ;
976                          ;THIS IS THE START OF THE MAIN PROGRAM
977 05A3  A3 0422 R     MAINPG: MOV  LOHAND,AX ;TEMPY FILE HANDLE
978 05A6  8C D8              MOV   AX,DS
979 05A8  8E C0              MOV   ES,AX
980 05AA  FC                 CLD
981 05AB  E8 053A R          CALL  GCOLOR  ;GET LAYER COLORS 982 05AE  C7 06 0000 E 0001  MOV   MSGNM,1  ;SOURCE FILE MSG
983 05B4  E8 005B R          CALL  GETFIL  ;OPEN THEM
984 05B7  73 04              JNC   MPG1 ;JMP IF NO ERROR
985 05B9  B4 4C              MOV   AH,4CH  ;STOP PROGRAM
986 05BB  CD 21              INT   DOSINT
```

Microsoft (R) Macro Assembler Version 5.10                    8/29/89 12:40:44
CREATES MULTILAYER DXF FILE FROM ROW OR BOX

```
987                          ;
```

```
 8      988 05BD  E8 0000 E           MPG1:     CALL SNDLF
 9      989 05C0  C7 06 0000 E 000B             MOV  MSGNM,11    ;DEST FILE MSG
10      990 05C6  E8 00EF R                     CALL MAKFIL      ;OPEN THEM
11      991 05C9  72 F2                         JC   MPG1 ;JMP IF ERROR
12      992                             ;
13      993 05CB  E8 0000 E                     CALL SNDLF
14      994 05CE  E8 04FB R                     CALL CHKLSP      ;G E T   F I L E
15 PARAMETERS
16      995 05D1  BB 0445 R                     MOV  BX,OFFSET DGROUP:NSETS
17      996 05D4  BF 0189 R                     MOV  DI,OFFSET DGROUP:MSG12+32
18      997 05D7  E8 0000 E                     CALL BNASC4
19      998 05DA  E8 0000 E                     CALL SNDLF
20      999 05DD  C7 06 0000 E 000C             MOV  MSGNM,12
21     1000 05E3  E8 0000 E                     CALL CRTMSG      ;DISPLAY # SETS
22     1001 05E6  E8 0000 E                     CALL SNDLF
23     1002 05E9  BB 0449 R                     MOV  BX,OFFSET DGROUP:NTRLS
24     1003 05EC  BF 01A8 R                     MOV  DI,OFFSET DGROUP:MSG13+25
25     1004 05EF  E8 0000 E                     CALL BNASC4
26     1005 05F2  C7 06 0000 E 000D             MOV  MSGNM,13
27     1006 05F8  E8 0000 E                     CALL CRTMSG      ;DISPLAY # TRIALS
28
29     1007 05FB  E8 0000 E                     CALL SNDLF
30     1008 05FE  BB 0447 R                     MOV  BX,OFFSET DGROUP:NSMPS
31     1009 0601  BF 01CA R                     MOV  DI,OFFSET DGROUP:MSG14+28
32     1010 0604  E8 0000 E                     CALL BNASC4
33     1011 0607  C7 06 0000 E 000E             MOV  MSGNM,14
34     1012 060D  E8 0000 E                     CALL CRTMSG      ;DISPLAY # SETS
35     1013 0610  E8 0000 E                     CALL SNDLF
36     1014                             ;
 1     1015 0613  C7 06 0000 E 000F MPG2:       MOV  MSGNM,15
 2     1016 0619  A1 0445 R                     MOV  AX,NSETS    ;# SETS
 3     1017 061C  E8 01B4 R                     CALL GETVAL      ;GET SET #
 4     1018 061F  72 F2                         JC   MPG2 ;JMP IF ERR
 5     1019 0621  0B C0                         OR   AX,AX
 6     1020 0623  74 EE                         JZ   MPG2 ;JMP IF ZERO
 7     1021 0625  A3 044B R                     MOV  NSET,AX
 8     1022                             ;
 9     1023 0628  C7 06 0000 E 0010 MPG3:       MOV  MSGNM,16
10     1024 062E  A1 0449 R                     MOV  AX,NTRLS
11     1025 0631  E8 01B4 R                     CALL GETVAL      ;GET # TRIALS PER
12 SET
13     1026 0634  72 F2                         JC   MPG3 ;JMP IF ERR
14     1027 0636  0B C0                         OR   AX,AX
15     1028 0638  74 EE                         JZ   MPG3 ;JMP IF ZERO
16     1029 063A  A3 044F R                     MOV  NTRL,AX
```

```
17      1030                                    ;
18      1031 063D  C7 06 0000 E 0011  MPG4:    MOV   MSGNM,17
19      1032 0643  A1 0447 R                   MOV   AX,NSMPS
20      1033 0646  E8 01B4 R                   CALL  GETVAL    ;GET # SAMPLES
21  PER TRIAL
22      1034 0649  72 F2                       JC    MPG4
23      1035 064B  0B C0                       OR    AX,AX
24      1036 064D  74 EE                       JZ    MPG4  ;JMP IF ZERO
25      1037 064F  A3 044D R                   MOV   NSMP,AX
26      1038 0652  A3 0451 R                   MOV   NLYR,AX   ;# LAYERS IS #
27  SAMPS
28      1039 0655  E8 01D4 R                   CALL  WRTPAR    ;WRITE PARAM FILE
29
30      1040 0658  E8 020A R                   CALL  WRTSCR    ;WRITE  SCRIPT
31  FILE
32      1041 065B  E8 0263 R                   CALL  WRTHDR    ;WRITE  HEADER
33  FILE
34      1042                                    ;
35      1043 065E  8B 1E 0418 R                MOV   BX,EIHAND
36      1044 0662  33 C9                       XOR   CX,CX
37
 1  ^HMicrosoft (R) Macro Assembler Version 5.10                    8/29/89
 2  12:40:44
 3  CREATES MULTILAYER DXF FILE FROM ROW OR BOX                     Page
 4  1-19
 5
 6
 7      1045 0664  33 D2                       XOR   DX,DX
 8      1046 0666  B0 02                       MOV   AL,2
 9      1047 0668  B4 42                       MOV   AH,42H
10      1048 066A  CD 21                       INT   DOSINT    ;GET END OF FILE
11      1049 066C  A3 045B R                   MOV   FSIZ,AX   ;POST FILE SIZE
12      1050 066F  89 16 045D R                MOV   FSIZ+2,DX
13      1051 0673  33 C9                       XOR   CX,CX
14      1052 0675  33 D2                       XOR   DX,DX
15      1053 0677  32 C0                       XOR   AL,AL
16      1054 0679  B4 42                       MOV   AH,42H
17      1055 067B  CD 21                       INT   DOSINT    ;SET  START  OF
18  FILE
19      1056 067D  BE 0469 R                   MOV   SI,OFFSET DGROUP:FBUF
20      1057 0680  89 36 0467 R                MOV   BUFPTR,SI ;SET INIT BUFF
21  ADR
22      1058 0684  C7 06 0463 R 0000           MOV   BUFSIZ,0
23      1059 068A  E8 035C R                   CALL  FILLBF    ;READ SOME DATA
24  INTO BUFF
```

```
25    1060 068D  72 38              JC   MPG22      ;JMP IF END OR
26 ERR
27    1061 068F  8B 1E 041E R       MOV  BX,EOHAND  ;HEADER OUT FILE
28 HANDLE
29    1062 0693  8B 36 0467 R       MOV  SI,BUFPTR  ;1ST SOURCE ADR
30    1063 0697  B9 0004            MOV  CX,4 ;4 LINES
31    1064 069A  E8 0247 R          CALL WRTLIN     ;WRITE LINES
32    1065 069D  72 28              JC   MPG22      ;JMP IF ERR
33    1066                          ;
34    1067 069F  E8 03BC R          CALL PARSE      ;PROCESS   THE
35 BUFFER
36    1068 06A2  72 23              JC   MPG22      ;JMP IF ERR
 1    1069                          ;
 2    1070 06A4  8B 1E 041E R  MPG20: MOV BX,EOHAND
 3    1071 06A8  89 1E 0416 R       MOV  FHANDL,BX
 4    1072 06AC  B9 0013            MOV  CX,LENDF
 5    1073 06AF  BA 003D R          MOV  DX,OFFSET DGROUP:ENDFIL
 6    1074 06B2  E8 0000 E          CALL WRTIND     ;WRT END OF FILE
 7    1075 06B5  E8 0000 E          CALL CLRHDL     ;CLOSE FILE
 8    1076 06B8  8B 1E 0418 R       MOV  BX,EIHAND
 9    1077 06BC  89 1E 0416 R       MOV  FHANDL,BX
10    1078 06C0  E8 0000 E          CALL CLRHDL     ;CLOSE INPUT FILE
11
12    1079 06C3  B4 4C              MOV  AH,4CH
13    1080 06C5  CD 21              INT  DOSINT
14    1081                          ;
15    1082 06C7  8B 1E 041E R  MPG22: MOV BX,EOHAND
16    1083 06CB  89 1E 0416 R       MOV  FHANDL,BX
17    1084 06CF  E8 0000 E          CALL CLRHDL     ;CLOSE FILE
18    1085 06D2  8B 1E 0418 R       MOV  BX,EIHAND
19    1086 06D6  89 1E 0416 R       MOV  FHANDL,BX
20    1087 06DA  E8 0000 E          CALL CLRHDL     ;CLOSE INPUT FILE
21
22    1088 06DD  B4 4C              MOV  AH,4CH
23    1089 06DF  CD 21              INT  DOSINT
24    1090
25    1091                          ;
26    1092 06E1                     CODE ENDS
27    1093                          END  START
28
 1 ^HMicrosoft (R) Macro Assembler Version 5.10              8/29/89
 2 12:40:44
 3 CREATES MULTILAYER DXF FILE FROM ROW OR BOX               Page
 4 1-20
```

```
 8       927 Source   Lines
 9       927 Total    Lines
10       184 Symbols
11
12     47050 + 349760 Bytes symbol space free
13
14         0 Warning Errors
15         0 Severe  Errors
16
 1  PROGRAM LISTING: DXFROW
 2  DATE: 9/7/89
 3  ^HMicrosoft (R) Macro Assembler Version 5.10                    8/29/89
 4  12:31:51
 5  CREATES DXF FILE WITH Z AXIS FOR AUTOCAD                         Page
 6  1-1
 7
 8
 9       1                    .8086
10       2                          NAME DXFROW
11       3                          PAGE 62,120
12       4                          TITLE     CREATES DXF FILE WITH Z
13  AXIS FOR AUTOCAD
14       5                          ;
15       6                          COMMENT *
16       7
17  ;;;;;;;;;;;;;;;;;;;;;;;;;;;;;;;;;;;;;;;;;;;;;;;;;;;;;;;;;;;;;;;
18  ;;;;;;;
19       8                          COPYRIGHT (C) 1989 GEOLOW PARTNERS. ALL
20  RIGHTS RESERVED. NO PART OF PROGRAM
21       9                          OR   PUBLICATION   MAY   BE
22  TRANSCRIBED,REPRODUCED, TRANSMITTED, OR TRANSLATED
23       10                         INTO ANY LANGUAGE OR COMPUTER LANGUAGE BY
24  ANY MEANS ELECTRONIC, MECHANICAL,
25       11                         MAGNETIC, CHEMICAL, OPTICAL, MANUAL OR
26  OTHERWISE OR IN ANY FORM, WITHOUT
27       12                         THE PRIOR WRITTEN PERMISSION OF LOWELL
28  WEDEMEYER, 3112 THATCHER AVE,
29       13                         MARINA DEL REY CALIFORNIA, 90292.
30       14
31  ;;;;;;;;;;;;;;;;;;;;;;;;;;;;;;;;;;;;;;;;;;;;;;;;;;;;;;;;;;;;;;;
32  ;;;;;;;
33       15
34       16                         PROGRAMMING BY G. E. SOMERVILLE, 7315
35  BROCADE DR., CITRUS HEIGHTS, CA 95621
36       17                         *
```

```
 1     18                                  ;
 2     19 = 000D                     CR      EQU     0DH
 3     20 = 000A                     LF      EQU     0AH
 4     21 = 0021                     DOSINT  EQU     21H
 5     22                                  ;
 6     23                             INCLUDELIB    IOR03MN
 7     24                             INCLUDELIB    CVN03MN
 8     25                             INCLUDELIB    CRT03MN
 9     26                                  ;
10     27 0000                       DATA SEGMENT   PUBLIC    'DATA'
11     28                                  ;
12     29 0000   30 0D 0A 53 45 43   SECT DB   '0',CR,LF,'SECTION',CR,LF
13     30        54 49 4F 4E 0D 0A
14     31 000C   32 0D 0A 45 4E 54        DB   '2',CR,LF,'ENTITIES',CR,LF
15     32        49 54 49 45 53 0D
16     33        0A
17     34 = 0019                     LSECT   EQU   $-SECT
18     35                                  ;
19     36 0019   30 0D 0A 33 44 4C   LINE DB
20  '0',CR,LF,'3DLINE',CR,LF,'8',CR,LF
21     37        49 4E 45 0D 0A 38
22     38        0D 0A
23     39 = 000E                     LLINE   EQU   $-LINE
24     40                                  ;
25     41 0027   31 30 0D 0A         XPNT DB   '10',CR,LF
26     42 002B   32 30 0D 0A         YPNT DB   '20',CR,LF
27     43 002F   33 30 0D 0A         ZPNT DB   '30',CR,LF
28     44 0033   31 31 0D 0A         NXPNT     DB   '11',CR,LF
29     45 0037   32 31 0D 0A         NYPNT     DB   '21',CR,LF
30     46 003B   33 31 0D 0A         NZPNT     DB   '31',CR,LF
31     47                                  ;
32     48 003F   30 0D 0A 45 4E 44   EOFILE    DB
33  '0',CR,LF,'ENDSEC',CR,LF
34     49        53 45 43 0D 0A
35     50 004A   30 0D 0A 45 4F 46        DB   '0',CR,LF,'EOF',CR,LF
36     51        0D 0A
 1     52 = 0013                     LEOF EQU    $-EOFILE
 2     53                                  ;
 3     54 0052   30 0D 0A 53 45 43   TABL DB   '0',CR,LF,'SECTION',CR,LF
 4     55        54 49 4F 4E 0D 0A
 5     56 005E   32 0D 0A 48 45 41        DB   '2',CR,LF,'HEADER',CR,LF
 6     57        44 45 52 0D 0A
 7     58 0069   39 0D 0A 24 43 45        DB   '9',CR,LF,'$CELTYPE',CR,LF
 8
```

```
 1  ^HMicrosoft (R) Macro Assembler Version 5.10              8/29/89
 2  12:31:51
 3  CREATES DXF FILE WITH Z AXIS FOR AUTOCAD                  Page
 4  1-2
 5
 6
 7       59           4C 54 59 50 45 0D
 8       60           0A
 9       61 0076      36 0D 0A 42 59 4C      DB      '6',CR,LF,'BYLAYER',CR,LF
10       62           41 59 45 52 0D 0A
11       63 0082      39 0D 0A 24 43 45      DB      '9',CR,LF,'$CECOLOR',CR,LF
12       64           43 4F 4C 4F 52 0D
13       65           0A
14       66 008F      36 32 0D 0A 32 35      DB      '62',CR,LF,'256',CR,LF
15       67           36 0D 0A
16       68 0098      30 0D 0A 45 4E 44      DB      '0',CR,LF,'ENDSEC',CR,LF
17       69           53 45 43 0D 0A
18       70 00A3      30 0D 0A 53 45 43      DB      '0',CR,LF,'SECTION',CR,LF
19       71           54 49 4F 4E 0D 0A
20       72 00AF      32 0D 0A 54 41 42      DB      '2',CR,LF,'TABLES',CR,LF
21       73           4C 45 53 0D 0A
22       74 00BA      30 0D 0A 54 41 42      DB      '0',CR,LF,'TABLE',CR,LF
23       75           4C 45 0D 0A
24       76 00C4      32 0D 0A 4C 41 59      DB      '2',CR,LF,'LAYER',CR,LF,'
25  70',CR,LF
26       77           45 52 0D 0A 20 37
27       78           30 0D 0A
28       79 00D3      32 0D 0A        NLAYRS   DB      '2',CR,LF
29       80 = 0084                    LTABL    EQU     $-TABL
30       81                                    ;
31       82 00D6      30 0D 0A 4C 41 59 LAYR  DB      '0',CR,LF,'LAYER',CR,LF
32       83           45 52 0D 0A
33       84 00E0      32 0D 0A                 DB      '2',CR,LF
34       85 = 000D                    LLAYR    EQU     $-LAYR
35       86                                    ;
36       87 00E3      37 30 0D 0A 30 0D LTYP  DB      '70',CR,LF,'0',CR,LF
 1       88           0A
 2       89 00EA      36 32 0D 0A 20 20      DB      '62',CR,LF,'     '
 3       90           20 20 20
 4       91 00F3      37 0D 0A         LCOL   DB      '7',CR,LF
 5       92 00F6      36 0D 0A 43 4F 4E      DB
 6  '6',CR,LF,'CONTINUOUS',CR,LF
 7       93           54 49 4E 55 4F 55
 8       94           53 0D 0A
 9       95 = 0022                    LLTYP    EQU     $-LTYP
```

```
10       96                                    ;
11       97 0105  30 0D 0A 45 4E 44  ETABL  DB  '0',CR,LF,'ENDTAB',CR,LF
13       98       54 41 42 0D 0A
14       99 0110  30 0D 0A 45 4E 44         DB  '0',CR,LF,'ENDSEC',CR,LF
15      100       53 45 43 0D 0A
16      101 011B  30 0D 0A 45 4F 46         DB  '0',CR,LF,'EOF',CR,LF
17      102       0D 0A
18      103 = 001E                    LETABL  EQU  $-ETABL
19      104                                  ;
20      105 0123  0000                NXTADR  DW   ?
21      106 0125  0024[               PTRTAB  DW   36 DUP(?) ;WRITE BUFF PTRS
23      107       ????
24      108            ]
25      109
26      110 016D  0012[               NXYZTB  DW   18 DUP(?)
27      111       ????
28      112            ]
29      113
30      114 0191  0000                NXBIN   DW   ?
31      115 0193  0000                NYBIN   DW   ?
32      116 0195  0000                NZBIN   DW   ?
```

Microsoft (R) Macro Assembler Version 5.10          8/29/89 12:31:51
CREATES DXF FILE WITH Z AXIS FOR AUTOCAD             Page 1-3

```
 7      117 0197  0000                XBIN  DW   ?
 8      118 0199  0000                YBIN  DW   ?
 9      119 019B  0000                ZBIN  DW   ?
10      120                                  ;
11      121 019D  01DB[               WBUFF  DB   475 DUP(?)
12      122       ??
13      123            ]
14      124
15      125 0378  01DB[               WBUF DB   475 DUP(?)
16      126       ??
17      127            ]
18      128
19      129 0553  0000                LWBUF  DW   ?
20      130                                  ;
21      131 0555  0000                CPOS DW   0   ;CURR POSITION
```

```
22      132  0557  0000              HOR     DW      0
23      133  0559  0000              VRT     DW      0
24      134  055B  80          CBOX  DB      128     ;CENTER OF BOX
25      135  055C  00          HFLG  DB      0
26      136                          ;
27      137  055D  0003[       LNAME1        DB      3 DUP(00H)      ;   3
28  CHARS
29      138        00
30      139              ]
31      140
32      141  0560  0003[       LNAME2        DB      3 DUP(00H)      ;   3
33  CHARS
34      142        00
35      143              ]
36      144
1       145  0563  0003[       LNAME3        DB      3 DUP(00H)      ;   3
2   CHARS
3       146        00
4       147              ]
5       148
6       149  0566  0003[       LNAME4        DB      3 DUP(00H)      ;   3
7   CHARS
8       150        00
9       151              ]
10      152
11      153  0569  0003[       LNAME5        DB      3 DUP(00H)      ;   3
12  CHARS
13      154        00
14      155              ]
15      156
16      157  056C  0003[       LNAME6        DB      3 DUP(00H)      ;   3
17  CHARS
18      158        00
19      159              ]
20      160
21      161                          ;
22      162  056F  37 37 37 37 37 37 COLTAB   DB      '777777'
23      163                          ;
24      164  0575  49 6E 73 75 66 66 MSG0     DB      'Insufficient memory$'
25      165        69 63 69 65 6E 74
26      166        20 6D 65 6D 6F 72
27      167        79 24
28      168  0589  45 6E 74 65 72 20 MSG1     DB      'Enter source file name:
29  $'
30      169        73 6F 75 72 63 65
```

| | | | | |
|---|---|---|---|---|
| 31 | 170 | | 20 66 69 6C 65 20 | |
| 32 | 171 | | 6E 61 6D 65 3A 20 | |
| 33 | 172 | | 24 | |
| 34 | 173 | 05A2 | 41 63 63 65 73 73 | MSG2 DB 'Access denied or invalid$' |
| 35 | | | | |
| 36 | 174 | | 20 64 65 6E 69 65 | |
| 37 | | | | |

```
 1  ^HMicrosoft (R) Macro Assembler Version 5.10                   8/29/89
 2  12:31:51
 3  CREATES DXF FILE WITH Z AXIS FOR AUTOCAD                       Page
 4  1-4
 5
 6
 7       175          64 20 6F 72 20 69
 8       176          6E 76 61 6C 69 64
 9       177          24
10       178  05BB    54 6F 6F 20 6D 61   MSG3  DB   'Too many files open$'
11       179          6E 79 20 66 69 6C
12       180          65 73 20 6F 70 65
13       181          6E 24
14       182  05CF    4E 65 77 20 66 69   MSG4  DB   'New file Y(CR) or N=$'
15       183          6C 65 20 59 28 43
16       184          52 29 20 6F 72 20
17       185          4E 3D 24
18       186  05E4    50 61 74 68 20 6E   MSG5  DB   'Path not found$'
19       187          6F 74 20 66 6F 75
20       188          6E 64 24
21       189  05F3    4E 6F 20 66 69 6C   MSG6  DB   'No file open$'
22       190          65 20 6F 70 65 6E
23       191          24
24       192  0600    4F 6C 64 20 66 69   MSG7  DB   'Old file Y(CR) or N=$'
25       193          6C 65 20 59 28 43
26       194          52 29 20 6F 72 20
27       195          4E 3D 24
28       196  0615    3A 24               MSG8  DB   ':$'
29       197  0617    20 20 20 20 20 20   MSG9  DB   '
30  $'
31       198          20 20 20 20 20 20
32       199          20 20 20 20 20 20
33       200          20 20 20 20 20 20
34       201          20 20 20 20 24
35       202  0634    41 74 74 65 6D 70   MSG10      DB    'Attempt to read past
36  end of file$'
```

| | | | |
|---|---|---|---|
| 203 | 74 20 74 6F 20 72 | | |
| 204 | 65 61 64 20 70 61 | | |
| 205 | 73 74 20 65 6E 64 | | |
| 206 | 20 6F 66 20 66 69 | | |
| 207 | 6C 65 24 | | |
| 208 0655 | 45 6E 74 65 72 20 | MSG11 DB | 'Enter number of channel pairings (max 6) :$' |
| 209 | 6E 75 6D 62 65 72 | | |
| 210 | 20 6F 66 20 63 68 | | |
| 211 | 61 6E 6E 65 6C 20 | | |
| 212 | 70 61 69 72 69 6E | | |
| 213 | 67 73 20 28 6D 61 | | |
| 214 | 78 20 36 29 20 3A | | |
| 215 | 24 | | |
| 216 0680 | 45 6E 74 65 72 20 | MSG12 DB | 'Enter channel channel number for X :$' |
| 217 | 63 68 61 6E 6E 65 | | |
| 218 | 6C 20 63 68 61 6E | | |
| 219 | 6E 65 6C 20 6E 75 | | |
| 220 | 6D 62 65 72 20 66 | | |
| 221 | 6F 72 20 58 20 3A | | |
| 222 | 24 | | |
| 223 06A5 | 45 6E 74 65 72 20 | MSG13 DB | 'Enter channel channel number for Y :$' |
| 224 | 63 68 61 6E 6E 65 | | |
| 225 | 6C 20 63 68 61 6E | | |
| 226 | 6E 65 6C 20 6E 75 | | |
| 227 | 6D 62 65 72 20 66 | | |
| 228 | 6F 72 20 59 20 3A | | |
| 229 | 24 | | |
| 230 06CA | 07 24 | MSG14 DB | 07H,'$' |
| 231 06CC | 45 6E 74 65 72 20 | MSG15 DB | 'Enter layer color (0-7) :$' |
| 232 | 6C 61 79 65 72 20 | | |

^HMicrosoft (R) Macro Assembler Version 5.10       8/29/89 12:31:51
CREATES DXF FILE WITH Z AXIS FOR AUTOCAD       Page 1-5

| | | | |
|---|---|---|---|
| 233 | 63 6F 6C 6F 72 20 | | |
| 234 | 28 30 2D 37 29 20 | | |
| 235 | 3A 24 | | |
| 236 06E6 | 45 6E 74 65 72 20 | MSG16 DB | 'Enter DXF basic |

```
11       (drive:\path\) filename: $'
12       237          44 58 46 20 62 61
13       238          73 69 63 20 28 64
14       239          72 69 76 65 3A 5C
15       240          70 61 74 68 5C 29
16       241          20 66 69 6C 65 6E
17       242          61 6D 65 3A 20 24
18       243  0710    41 70 70 72 6F 78  MSG17       DB    'Approximate number
19  of samples per trial='
20       244          69 6D 61 74 65 20
21       245          6E 75 6D 62 65 72
22       246          20 6F 66 20 73 61
23       247          6D 70 6C 65 73 20
24       248          70 65 72 20 74 72
25       249          69 61 6C 3D
26       250  0738    20 20 20 20 20 20              DB    '            to          $'
27       251          20 20 20 74 6F 20
28       252          20 20 20 20 20 20
29       253          20 20 20 24
30       254  074E    45 6E 74 65 72 20  MSG18       DB    'Enter number of
31  trials to process :$'
32       255          6E 75 6D 62 65 72
33       256          20 6F 66 20 74 72
34       257          69 61 6C 73 20 74
35       258          6F 20 70 72 6F 63
36       259          65 73 73 20 3A 24
 1       260  0772    45 6E 74 65 72 20  MSG19       DB    'Enter starting trial
 2  number :$'
 3       261          73 74 61 72 74 69
 4       262          6E 67 20 74 72 69
 5       263          61 6C 20 6E 75 6D
 6       264          62 65 72 20 3A 24
 7       265  0790    45 6E 74 65 72 20  MSG20       DB    'Enter starting sample
 8  number (0=all) :$'
 9       266          73 74 61 72 74 69
10       267          6E 67 20 73 61 6D
11       268          70 6C 65 20 6E 75
12       269          6D 62 65 72 20 28
13       270          30 3D 61 6C 6C 29
14       271          20 3A 24
15       272  07B7    45 6E 74 65 72 20  MSG21       DB    'Enter ending sample
16  number :$'
17       273          65 6E 64 69 6E 67
18       274          20 73 61 6D 70 6C
19       275          65 20 6E 75 6D 62
```

```
20      276         65 72 20 3A 24
21      277 07D4    41 70 70 72 6F 78  MSG22   DB   'Approximate number
22 of trials in file=         $'
23      278         69 6D 61 74 65 20
24      279         6E 75 6D 62 65 72
25      280         20 6F 66 20 74 72
26      281         69 61 6C 73 20 69
27      282         6E 20 66 69 6C 65
28      283         3D 20 20 20 20 20
29      284         20 20 20 20 20 20
30      285         24
31      286 0805    45 6E 74 65 72 20  MSG23   DB   'Enter channel channel
32 number for Z :$'
33      287         63 68 61 6E 6E 65
34      288         6C 20 63 68 61 6E
35      289         6E 65 6C 20 6E 75
36      290         6D 62 65 72 20 66
```

Microsoft (R) Macro Assembler Version 5.10               8/29/89 12:31:51
CREATES DXF FILE WITH Z AXIS FOR AUTOCAD                 Page 1-6

```
 7      291         6F 72 20 5A 20 3A
 8      292         24
 9      293 082A    44 6F 20 6E 6F 74  MSG24   DB   'Do not enter file
10 name extension$'
11      294         20 65 6E 74 65 72
12      295         20 66 69 6C 65 20
13      296         6E 61 6D 65 20 65
14      297         78 74 65 6E 73 69
15      298         6F 6E 24
16      299 084B    43 65 6E 74 65 72  MSG25   DB   'Center of box to be
17 center point. Y(CR) or N=$'
18      300         20 6F 66 20 62 6F
19      301         78 20 74 6F 20 62
20      302         65 20 63 65 6E 74
21      303         65 72 20 70 6F 69
22      304         6E 74 2E 20 59 28
23      305         43 52 29 20 6F 72
24      306         20 4E 3D 24
25      307                             ;
26      308 0879    0575 R 0589 R 05A2 R  MSGTAB  DW
```

```
27      MSG0,MSG1,MSG2,MSG3,MSG4,MSG5,MSG6,MSG7,MSG8
28          309           05BB R  05CF R  05E4 R
29          310           05F3 R  0600 R  0615 R
30          311 088B      0617 R  0634 R  0655 R              DW
31      MSG9,MSG10,MSG11,MSG12,MSG13,MSG14,MSG15,MSG16
32          312           0680 R  06A5 R  06CA R
33          313           06CC R  06E6 R
34          314 089B      0710 R  074E R  0772 R              DW
35      MSG17,MSG18,MSG19,MSG20,MSG21,MSG22,MSG23,MSG24,MSG25
36          315           0790 R  07B7 R  07D4 R
 1          316           0805 R  082A R  084B R
 2          317                           ;
 3          318 08AD      44 58 46 52 4F 57   VERS   DB   'DXFROW VERSION 1.0   DXF
 4      FILE WITH TRIALS IN ROWS  '
 5          319           20 56 45 52 53 49
 6          320           4F 4E 20 31 2E 30
 7          321           20 20 44 58 46 20
 8          322           46 49 4C 45 20 57
 9          323           49 54 48 20 54 52
10          324           49 41 4C 53 20 49
11          325           4E 20 52 4F 57 53
12          326           20 20
13          327 08DF      43 4F 50 59 52 49   CPYRHT DB   'COPYRIGHT       GEOLOW
14      PARTNERS',0DH,0AH,0AH,'$'
15          328           47 48 54 20 47 45
16          329           4F 4C 4F 57 20 50
17          330           41 52 54 4E 45 52
18          331           53 0D 0A 0A 24
19          332                           ;
20          333 08FC      2E 4C 53 50 00      LISP   DB   '.LSP',00H
21          334 0901      2E 44 58 46 00      DXF    DB   '.DXF',00H
22          335 0906      2E 53 43 52 00      SCRP   DB   '.SCR',00H
23          336                           ;
24          337 090B      28 53 45 54 51 20   STQTRL DB   '(SETQ   NTRLS
25      )',0DH,0AH
26          338           4E 54 52 4C 53 20
27          339           20 20 20 20 29 0D
28          340           0A
29          341 091E      28 53 45 54 51 20   STQSMP DB   '(SETQ   NSMPS
30      )',0DH,0AH
31          342           4E 53 4D 50 53 20
32          343           20 20 20 20 29 0D
33          344           0A
34          345 0931      28 53 45 54 51 20   STQSET DB   '(SETQ   NSET
35      )',0DH,0AH
```

```
36    346        4E 53 45 54 20 20
 1    347        20 20 20 29 0D 0A
 2    348 = 0038                       LNSTQ    EQU   $-STQTRL
```

`^H`Microsoft (R) Macro Assembler Version 5.10                8/29/89
12:31:51
CREATES DXF FILE WITH Z AXIS FOR AUTOCAD                    Page 1-7

```
 7    349                              ;
 8    350 0943  44 58 46 49 4E 0D  SCRIN    DB    'DXFIN',0DH,0AH
 9    351        0A
10    352 094A  0008[              HNAM DB    8 DUP(0)
11    353        00
12    354                    ]
13    355
14    356 0952  0D 0A 44 58 46 49      DB    0DH,0AH,'DXFIN',0DH,0AH
15    357        4E 0D 0A
16    358 095B  0008[              ENAM DB    8 DUP(0)
17    359        00
18    360                    ]
19    361
20    362 0963  0D 0A 4C 4F 41 44      DB    0DH,0AH,'LOADPARAM',0DH,0AH
21
22    363        50 41 52 41 4D 0D
23    364        0A
24    365 0970  0008[              LNAM DB    8 DUP(0)
25    366        00
26    367                    ]
27    368
28    369 0978  0D 0A 5A 4F 4F 4D      DB
29   0DH,0AH,'ZOOM',0DH,0AH,'E',0DH,0AH
30    370        0D 0A 45 0D 0A
31    371 0983  5A 4F 4F 4D 0D 0A      DB    'ZOOM',0DH,0AH,'D',0DH,0AH
32    372        44 0D 0A
33    373 = 0049                   LNSCR    EQU   $-SCRIN
34    374                              ;
35    375 098C  0000               NPAIR    DW    ?
 1    376 098E  000C[              PAIRTB   DW    12 DUP(?) ;X AND Y
 2   PAIRING
 3    377        ????
 4    378                    ]
 5    379
 6    380 09A6  0006[              ZTAB DW    6 DUP(?)   ;Z AXIS
```

```
  7      381           ????
  8      382                            ]
  9      383
 10      384                            ;
 11      385 09B2  41         FLNAME   DB    65        ;MAX PATH BYTES
 12      386 09B3  00         FLNMLN   DB    ?         ;BYTES READ IN
 13      387 09B4  0041[               FILNAM   DB    65 DUP(?) ;FILE NAME
 14 BUFFER
 15      388           ??
 16      389                            ]
 17      390
 18      391 09F5  0041[               INPNAM   DB    65 DUP(?) ;INPUT FILE
 19 NAME
 20      392           ??
 21      393                            ]
 22      394
 23      395 0A36  0041[               HDRNAM   DB    65 DUP(?) ;HEADER FILE
 24 NAME
 25      396           ??
 26      397                            ]
 27      398
 28      399 0A77  0041[               ENTNAM   DB    65 DUP(?) ;ENTITY FILE
 29 NAME
 30      400           ??
 31      401                            ]
 32      402
 33      403 0AB8  0041[               SCRNAM   DB    65 DUP(?) ;SCRIPT FILE
 34 NAME
 35      404           ??
 36      405                            ]
  1      406
  2
  1  ^HMicrosoft (R) Macro Assembler Version 5.10                    8/29/89
  2  12:31:51
  3  CREATES DXF FILE WITH Z AXIS FOR AUTOCAD                           Page
  4  1-8
  5
  6
  7      407                            ;
  8      408 0AF9  0000        PHANDL   DW    ?         ;PARAM    FILE
  9 HANDLE
 10      409 0AFB  0000        EHANDL   DW    ?         ;ENTITIES FILE
 11 HANDLE
 12      410 0AFD  0000        HHANDL   DW    ?         ;HEADER   FILE
 13 HANDLE
```

```
14      411  0AFF  0000         IHANDL    DW    ?       ;INPUT    FILE
15  HANDLE
16      412  0B01  0000         FHANDL    DW    ?       ;FILE HANDLE
17      413  0B03  0000         SHANDL    DW    ?       ;SCRIPT   FILE
18  HANDLE
19      414                               ;
20      415                               ;
21      416  0B05  02           REPLY     DB    2       ;ONE RESPONSE BYTE
22      417  0B06  00                     DB    ?
23      418  0B07  0002[                  DB    2 DUP(?) ;RESPONSE
24      419         ??
25      420                 ]
26      421
27      422                               ;
28      423  0B09  000F[        MSGBUF    DB    15 DUP(?)
29      424         ??
30      425                 ]
31      426
32      427                               ;
33      428  0B18  0000         NSMP DW   ?     ;# SAMPLES/TRIAL
34      429  0B1A  0000         NTRLS     DW    ?       ;# TRIALS TO DO
35      430  0B1C  0000         FTRL DW   ?     ;FIRST TRIAL #
36      431  0B1E  0000         FSMP DW   ?     ;FIRST SAMPLE TO DO
 1      432  0B20  0000         LSMP DW   ?     ;LAST SAMPLE TO DO
 2      433  0B22  0002[        NTRL DW   2 DUP(?)
 3      434         ????
 4      435                 ]
 5      436
 6      437  0B26  0000         NLYR DW   ?
 7      438                               ;
 8      439  0B28  0002[        FSIZ DW   2 DUP(?)  ;BYTES IN FILE
 9      440         ????
10      441                 ]
11      442
12      443  0B2C  0002[        BYTSRD    DW    2 DUP(?)   ;BYTES READ
13      444         ????
14      445                 ]
15      446
16      447  0B30  0000         BUFSIZ    DW    ?       ;BYTES IN BUFF
17      448  0B32  0000         BUFRD     DW    ?       ;BYTES READ
18      449  0B34  0000         BUFPTR    DW    ?       ;NEXT BUFF ADR
19      450                               ;
20      451  0B36  4000[        FBUF DB   16384 DUP(?)
21      452         ??
```

| | | | | | | |
|---|---|---|---|---|---|---|
| 22 | 453 | | | ] | | |
| 23 | 454 | | | | | |
| 24 | 455 | 4B36 | 0064[ | BUFF DB | 100 DUP(?) | |
| 25 | 456 | | ?? | | | |
| 26 | 457 | | | ] | | |
| 27 | 458 | | | | | |
| 28 | 459 | | | ; | | |
| 29 | 460 | | | PUBLIC | BUFF,FHANDL,MSG0,MSGTAB | |
| 30 | 461 | | | EXTRN | MSGNM:WORD | |
| 31 | 462 | | | ; | | |
| 32 | 463 | 4B9A | | DATA ENDS | | |
| 33 | 464 | | | ; | | |

^HMicrosoft (R) Macro Assembler Version 5.10           8/29/89
12:31:51
CREATES DXF FILE WITH Z AXIS FOR AUTOCAD                Page
1-9

| | | | | | | |
|---|---|---|---|---|---|---|
| 7 | 465 | 0000 | | STACK | SEGMENT | STACK | 'STACK' |
| 9 | 466 | 0000 | 0400[ | DW | 1024 DUP(?) | |
| 10 | 467 | | ???? | | | |
| 11 | 468 | | | ] | | |
| 12 | 469 | | | | | |
| 13 | 470 | 0800 | | STKTOP | LABEL | WORD |
| 14 | 471 | 0800 | | STACK | ENDS | |
| 15 | 472 | | | ; | | |
| 16 | 473 | | | DGROUP | GROUP | DATA,STACK |
| 17 | 474 | | | CGROUP | GROUP | CODE |
| 18 | 475 | 0000 | | CODE SEGMENT | PUBLIC | 'CODE' |
| 19 | 476 | | | ASSUME | | |

CS:CGROUP,DS:DGROUP,SS:DGROUP

| | | | | | |
|---|---|---|---|---|---|
| 21 | 477 | | | ; | |
| 22 | 478 | | | EXTRN | |

BNASC4:NEAR,BNASC6:NEAR,BNASC8:NEAR,CLRHDL:NEAR,CRTMSG:NEAR

| | | | |
|---|---|---|---|
| 24 | 479 | | EXTRN |

D32B16:NEAR,DIRMSG:NEAR,DISCMD:NEAR

| | | | |
|---|---|---|---|
| 26 | 480 | | EXTRN |

RCVVAL:NEAR,RDIND:NEAR,SNDLF:NEAR,UPRCAS:NEAR,WRTFIL:NEAR

| | | | | | |
|---|---|---|---|---|---|
| 28 | 481 | | | ; | |
| 29 | 482 | 0000 | | START | LABEL | NEAR |
| 30 | 483 | 0000 | B8 ---- R | | MOV | AX,DGROUP |
| 31 | 484 | 0003 | 8E D8 | | MOV | DS,AX |
| 32 | 485 | 0005 | 8E D0 | | MOV | SS,AX |

```
33        486 0007  BC 0800   R        MOV   SP,OFFSET DGROUP:STKTOP
34        487 000A  BE 08AD   R        MOV   SI,OFFSET DGROUP:VERS
35        488 000D  E8 0000   E        CALL  DIRMSG      ;DISPLAY VERSION
 1        489 0010  E9 0651   R        JMP   MAINPG      ;JMP TO MAIN
 2 PROGRAM
 3        490                           ;
 4        491                           ;THIS GETS OLD/NEW RESPONSE FROM
 5 MESSAGE IN MSGNM
 6        492                           ;NZ FOR NO AND Z FOR YES
 7        493 0013                      REPCHK  PROC NEAR
 8        494 0013  E8 0000   E            CALL SNDLF
 9        495 0016  E8 0000   E            CALL DISCMD   ;ASK QUESTION
10        496 0019  BA 0B05   R            MOV  DX,OFFSET DGROUP:REPLY
11        497 001C  B0 0A                  MOV  AL,0AH
12        498 001E  B4 0C                  MOV  AH,0CH
13        499 0020  CD 21                  INT  DOSINT   ;GET REPLY
14        500 0022  8A 26 0B06 R           MOV  AH,REPLY+1  ;# BYTES
15 READ
16        501 0026  0A E4                  OR   AH,AH
17        502 0028  74 0C                  JZ   REPOK    ;JMP IF CR
18        503 002A  8A 26 0B07 R           MOV  AH,REPLY+2  ;GET REPLY
19 BYTE
20        504 002E  80 FC 59               CMP  AH,'Y'
21        505 0031  74 03                  JZ   REPOK    ;JMP IF Y
22        506 0033  80 FC 79               CMP  AH,'y'
23        507 0036  C3              REPOK:  RET
24        508 0037                      REPCHK  ENDP
25        509                           ;
26        510                           ;THIS OPENS THE SOURCE FILE. CY=ERR
27        511 0037                      GETFIL  PROC NEAR
28        512 0037  E8 0000   E            CALL CRTMSG
29        513 003A  BA 09B2   R            MOV  DX,OFFSET DGROUP:FLNAME
30        514 003D  B0 0A                  MOV  AL,0AH
31        515 003F  B4 0C                  MOV  AH,0CH
32        516 0041  CD 21                  INT  DOSINT   ;G E T   F I L E
33 PATH/NAME
34        517 0043  E8 0000   E            CALL SNDLF
35        518 0046  8A 1E 09B3 R           MOV  BL,FLNMLN ;# BYTES IN NAME
36        519 004A  32 FF                  XOR  BH,BH
 1        520 004C  C6 87 09B4 R 00        MOV  B Y T E   P T R
 2 [FLNAME+BX+2],0      ;ASCZ
 3        521 0051  8B CB                  MOV  CX,BX
 4        522 0053  83 F9 00               CMP  CX,0
 5
```

Microsoft (R) Macro Assembler Version 5.10      8/29/89
12:31:51
CREATES DXF FILE WITH Z AXIS FOR AUTOCAD                Page
1-10

```
        523 0056  74 20                     JE   GTF4 ;JMP IF JUST CR
        524 0058  BF 09B4 R                 MOV  DI,OFFSET DGROUP:FILNAM
        525 005B  E8 0000 E                 CALL UPRCAS    ;ALL UPPER CASE
        526 005E  BF 09F5 R                 MOV  DI,OFFSET DGROUP:INPNAM
        527 0061  BE 09B4 R                 MOV  SI,OFFSET DGROUP:FILNAM
        528 0064  8A 0E 09B3 R              MOV  CL,FLNMLN ;NAME LENGTH
        529 0068  32 ED                     XOR  CH,CH
        530 006A  41                        INC  CX
        531 006B  F3/ A4                    REP  MOVSB      ;XSFR NAME
        532 006D  BA 09B4 R                 MOV  DX,OFFSET DGROUP:FILNAM
        533 0070  B4 3D                     MOV  AH,3DH
        534 0072  B0 02                     MOV  AL,2
        535 0074  CD 21                     INT  DOSINT    ;OPEN FILE
        536 0076  73 0E                     JNC  GTF5 ;JMP IF EXISTS
        537 0078  C7 06 0000 E 0002  GTF4:  MOV  MSGNM,2   ;BAD ACCESS
        538 007E  E8 0000 E                 CALL CRTMSG
        539 0081  E8 0000 E                 CALL SNDLF
        540 0084  F9                        STC
        541 0085  C3                        RET
        542 0086  A3 0AFF R          GTF5:  MOV  IHANDL,AX ;SAVE FILE HANDLE
        543 0089  F8                        CLC
        544 008A  C3                        RET
        545 008B                     GETFIL ENDP
        546                                 ;
        547                                 ;THIS OPENS THE DXF FILE. CY=ERR
        548 008B                     MAKFIL PROC NEAR
        549 008B  E8 0000 E                 CALL CRTMSG
        550 008E  BA 09B2 R                 MOV  DX,OFFSET DGROUP:FLNAME
        551 0091  B0 0A                     MOV  AL,0AH
        552 0093  B4 0C                     MOV  AH,0CH
        553 0095  CD 21                     INT  DOSINT   ;GET FILE PATH/NAME
        554 0097  E8 0000 E                 CALL SNDLF
        555 009A  80 3E 09B3 R 00           CMP  FLNMLN,0
        556 009F  75 03                     JNE  MKF
        557 00A1  E9 0173 R                 JMP  MKF3 ;JMP IF NO NAME
        558 00A4  8A 0E 09B3 R       MKF:   MOV  CL,FLNMLN ;GET # CHARS
        559 00A8  32 ED                     XOR  CH,CH
```

```
10      560 00AA  BF 09B4 R              MOV   DI,OFFSET DGROUP:FILNAM
11      561 00AD  B0 2E                  MOV   AL,'.'
12      562 00AF  F2/ AE          REPNE  SCASB
13      563 00B1  E3 17                  JCXZ  MKF0 ;JMP IF NO EXT
14      564 00B3  C7 06 0000 E 0018      MOV   MSGNM,24
15      565 00B9  E8 0000 E              CALL  SNDLF
16      566 00BC  E8 0000 E              CALL  CRTMSG      ;NO EXT ALLOWED
17      567 00BF  E8 0000 E              CALL  SNDLF
18      568 00C2  C7 06 0000 E 0010      MOV   MSGNM,16
19      569 00C8  EB C1                  JMP   MAKFIL
20      570                              ;
21      571 00CA  8A 0E 09B3 R    MKF0:  MOV   CL,FLNMLN ;# BYTES IN
22  NAME
23      572 00CE  32 ED                  XOR   CH,CH
24      573 00D0  BF 09B4 R              MOV   DI,OFFSET DGROUP:FILNAM
25      574 00D3  E8 0000 E              CALL  UPRCAS      ;ALL UPPER CASE
26      575 00D6  8A 0E 09B3 R           MOV   CL,FLNMLN
27      576 00DA  32 ED                  XOR   CH,CH
28      577 00DC  BE 09B4 R              MOV   SI,OFFSET DGROUP:FILNAM
29      578 00DF  BF 0A36 R              MOV   DI,OFFSET DGROUP:HDRNAM
30      579 00E2  51                     PUSH  CX    ;HOLD # CHARS
31      580 00E3  56                     PUSH  SI    ;HOLD SOURCE ADR
32
 1  ^HMicrosoft (R) Macro Assembler Version 5.10              8/29/89
 2  12:31:51
 3  CREATES DXF FILE WITH Z AXIS FOR AUTOCAD                 Page
 4  1-11
 5
 6
 7      581 00E4  F3/ A4           REP   MOVSB           ;COPY TO HEADER
 8  NAME
 9      582 00E6  C6 05 48               MOV   BYTE PTR [DI],'H'
10      583 00E9  5E                     POP   SI
11      584 00EA  59                     POP   CX
12      585 00EB  BF 0A77 R              MOV   DI,OFFSET DGROUP:ENTNAM
13      586 00EE  51                     PUSH  CX
14      587 00EF  56                     PUSH  SI
15      588 00F0  F3/ A4           REP   MOVSB           ;COPY TO ENTITY
16  NAME
17      589 00F2  C6 05 45               MOV   BYTE PTR [DI],'E'
18      590 00F5  5E                     POP   SI
19      591 00F6  59                     POP   CX
20      592 00F7  BF 0AB8 R              MOV   DI,OFFSET DGROUP:SCRNAM
21      593 00FA  51                     PUSH  CX
22      594 00FB  56                     PUSH  SI
```

```
23      595 00FC    F3/ A4      REP   MOVSB              ;COPY TO SCRIPT
24 NAME
25      596 00FE    5F                POP  DI            ;GET SOURCE AS DEST
26      597 00FF    59                POP  CX
27      598 0100    03 F9             ADD  DI,CX         ;END OF SOURCE
28      599 0102    51                PUSH CX
29      600 0103    BE 08FC R         MOV  SI,OFFSET DGROUP:LISP
30 ;EXT
31      601 0106    B9 0005           MOV  CX,5
32      602 0109    F3/ A4      REP   MOVSB              ;PARAM FILE NAME
33      603 010B    59                POP  CX
34      604 010C    BF 0AB8 R         MOV  DI,OFFSET DGROUP:SCRNAM
35      605 010F    03 F9             ADD  DI,CX
36      606 0111    51                PUSH CX
 1      607 0112    BE 0906 R         MOV  SI,OFFSET DGROUP:SCRP
 2      608 0115    B9 0005           MOV  CX,5
 3      609 0118    F3/ A4      REP   MOVSB              ;POST EXT
 4      610 011A    59                POP  CX
 5      611 011B    41                INC  CX            ;PLUS LETTER
 6      612 011C    BF 0A36 R         MOV  DI,OFFSET DGROUP:HDRNAM
 7      613 011F    03 F9             ADD  DI,CX
 8      614 0121    51                PUSH CX
 9      615 0122    BE 0901 R         MOV  SI,OFFSET DGROUP:DXF
10      616 0125    56                PUSH SI
11      617 0126    B9 0005           MOV  CX,5
12      618 0129    F3/ A4      REP   MOVSB              ;HEADER FILE NAME
13
14      619 012B    5E                POP  SI
15      620 012C    59                POP  CX
16      621 012D    BF 0A77 R         MOV  DI,OFFSET DGROUP:ENTNAM
17      622 0130    03 F9             ADD  DI,CX
18      623 0132    F3/ A4      REP   MOVSB              ;ENTITY FILE NAME
19
20      624                           ;
21      625 0134    BA 09B4 R         MOV  DX,OFFSET DGROUP:FILNAM
22      626 0137    B4 3C             MOV  AH,3CH
23      627 0139    33 C9             XOR  CX,CX
24      628 013B    CD 21             INT  DOSINT        ;OPEN FILE
25      629 013D    72 2A             JC   MKF2          ;JMP IF ERR
26      630 013F    A3 0AF9 R         MOV  PHANDL,AX     ;SAVE PARAM FILE
27 HANDLE
28      631                           ;
29      632 0142    BA 0AB8 R         MOV  DX,OFFSET DGROUP:SCRNAM
30      633 0145    B4 3C             MOV  AH,3CH
31      634 0147    33 C9             XOR  CX,CX
```

```
32      635 0149  CD 21              INT  DOSINT    ;OPEN FILE
33      636 014B  72 1C              JC   MKF2 ;JMP IF ERR
34      637 014D  A3 0B03 R          MOV  SHANDL,AX ;SAVE SCRIPT FILE
35 HANDLE
36      638                          ;
37
 1 ^HMicrosoft (R) Macro Assembler Version 5.10              8/29/89
 2 12:31:51
 3 CREATES DXF FILE WITH Z AXIS FOR AUTOCAD                  Page
 4 1-12
 5
 6
 7      639 0150  BA 0A36 R          MOV  DX,OFFSET DGROUP:HDRNAM
 8      640 0153  B4 3C              MOV  AH,3CH
 9      641 0155  33 C9              XOR  CX,CX
10      642 0157  CD 21              INT  DOSINT    ;OPEN FILE
11      643 0159  72 0E              JC   MKF2 ;JMP IF ERR
12      644 015B  A3 0AFD R          MOV  HHANDL,AX ;SAVE HEADER FILE
13 HANDLE
14      645                          ;
15      646 015E  BA 0A77 R          MOV  DX,OFFSET DGROUP:ENTNAM
16      647 0161  B4 3C              MOV  AH,3CH
17      648 0163  33 C9              XOR  CX,CX
18      649 0165  CD 21              INT  DOSINT    ;OPEN FILE
19      650 0167  73 18              JNC  MKF5 ;JMP IF NO ERR
20      651                          ;
21      652 0169  C7 06 0000 E 0005  MKF2:  MOV MSGNM,5   ;BAD PATH
22      653 016F  3C 03              CMP  AL,3
23      654 0171  74 06              JE   MKF4 ;JMP IF NO PATH
24      655 0173  C7 06 0000 E 0002  MKF3:  MOV MSGNM,2   ;NO ACCESS
25      656 0179  E8 0000 E          MKF4:  CALL CRTMSG
26      657 017C  E8 0000 E                 CALL SNDLF
27      658 017F  F9                        STC
28      659 0180  C3                        RET
29      660 0181  F8                 MKF5:  CLC
30      661 0182  C3                        RET
31      662 0183                     MAKFIL   ENDP
32      663                          ;
33      664                          ;THIS GETS A VALUE FROM KEYBOARD.
34 CY=ERR
35      665                          ;MSGNM=MESSAGE.  AX=MAXIMUM VALUE
36      666 0183                     GETVAL   PROC NEAR
 1      667 0183  50                 PUSH AX    ;HOLD MAX
 2      668 0184  E8 0000 E                 CALL SNDLF
 3      669 0187  E8 0000 E                 CALL CRTMSG
```

```
 670 018A  E8 0000 E              CALL RCVVAL      ;GET VALUE
 671 018D  58                     POP  AX
 672 018E  72 08                  JC   GTERR       ;JMP IF ERR
 673 0190  3B F0                  CMP  SI,AX
 674 0192  77 04                  JA   GTERR       ;JMP IF OVER MAX
 675 0194  8B C6                  MOV  AX,SI       ;RESULT TO AX AND SI
 676 0196  F8                     CLC
 677 0197  C3                     RET
 678 0198  C7 06 0000 E 000E  GTERR:  MOV MSGNM,14
 679 019E  E8 0000 E              CALL CRTMSG
 680 01A1  F9                     STC
 681 01A2  C3                     RET
 682 01A3                  GETVAL  ENDP
 683                       ;
 684                       ;THIS WRITES THE INITIAL DXF FILE HEADER
 685 01A3                  WRTHDR  PROC NEAR
 686 01A3  B9 0084                MOV  CX,LTABL
 687 01A6  BA 0052 R              MOV  DX,OFFSET DGROUP:TABL
 688 01A9  E8 0000 E              CALL WRTFIL      ;TABLE START
 689 01AC  8B 0E 098C R           MOV  CX,NPAIR    ;GET # LAYERS
 690 01B0  C7 06 0555 R 0000      MOV  CPOS,0      ;FIRST LAYER
 691 01B6  51           WHD1:     PUSH CX
 692 01B7  B9 000D                MOV  CX,LLAYR
 693 01BA  BA 00D6 R              MOV  DX,OFFSET DGROUP:LAYR
 694 01BD  E8 0000 E              CALL WRTFIL      ;NXT LAYER
 695 01C0  A1 0555 R              MOV  AX,CPOS     ;GET LAYER #
 696 01C3  B9 0003                MOV  CX,3
```

^HMicrosoft (R) Macro Assembler Version 5.10           8/29/89 12:31:51
CREATES DXF FILE WITH Z AXIS FOR AUTOCAD                      Page 1-13

```
 697 01C6  F7 E1                  MUL  CX          ;GET OFFSET
 698 01C8  BE 055D R              MOV  SI,OFFSET DGROUP:LNAME1
 699 01CB  03 F0                  ADD  SI,AX       ;LAYER NAME ADR
 700 01CD  BF 0B09 R              MOV  DI,OFFSET DGROUP:MSGBUF
 701 01D0  32 E4                  XOR  AH,AH
 702 01D2  B9 0003                MOV  CX,3        ;MAX CHARS
 703 01D5  8A 04        WHD2:     MOV  AL,[SI]     ;GET NXT CHAR
 704 01D7  3C 00                  CMP  AL,0
```

```
16   705 01D9  74 08                    JE   WHD3  ;JMP IF ASCIIZ
17   706 01DB  88 05                    MOV  [DI],AL   ;POST NXT CHAR
18   707 01DD  FE C4                    INC  AH    ;COUNT IT
19   708 01DF  47               INC  DI
20   709 01E0  46               INC  SI
21   710 01E1  E2 F2                    LOOP WHD2
22   711                        ;
23   712 01E3  C6 05 0D         WHD3:   MOV  BYTE PTR [DI],CR
24   713 01E6  47               INC  DI
25   714 01E7  C6 05 0A                 MOV  BYTE PTR [DI],LF
26   715 01EA  80 C4 02                 ADD  AH,2
27   716 01ED  8A CC                    MOV  CL,AH    ;# CHARS
28   717 01EF  32 ED                    XOR  CH,CH
29   718 01F1  BA 0B09 R                MOV  DX,OFFSET DGROUP:MSGBUF
30   719 01F4  E8 0000 E                CALL WRTFIL   ;NXT LAYER NAME
31   720 01F7  BF 056F R                MOV  DI,OFFSET DGROUP:COLTAB
32   721 01FA  A1 0555 R                MOV  AX,CPOS   ;CURR LAYER
33   722 01FD  03 F8                    ADD  DI,AX    ;CURR COLOR
34   723 01FF  8A 05                    MOV  AL,[DI]
35   724 0201  A2 00F3 R                MOV  LCOL,AL   ;POST COLOR
36   725 0204  B9 0022                  MOV  CX,LLTYP
 1   726 0207  BA 00E3 R                MOV  DX,OFFSET DGROUP:LTYP
 2   727 020A  E8 0000 E                CALL WRTFIL   ;NXT LAYER COLOR
 3   728 020D  FF 06 0555 R             INC  CPOS
 4   729 0211  59              POP  CX
 5   730 0212  E2 A2                    LOOP WHD1  ;JMP IF MORE
 6   731 0214  B9 001E                  MOV  CX,LETABL
 7   732 0217  BA 0105 R                MOV  DX,OFFSET DGROUP:ETABL
 8   733 021A  E8 0000 E                CALL WRTFIL   ;END OF TABLE
 9   734 021D  C3              RET
10   735 021E             WRTHDR    ENDP
11   736                   ;
12   737                   ;THIS CREATES THE LISP FILE
13   738 021E             WRTPAR    PROC NEAR
14   739 021E  BB 098C R                MOV  BX,OFFSET DGROUP:NPAIR
15   740 0221  BF 093C R                MOV  DI,OFFSET DGROUP:STQSET+11
16   741 0224  E8 0000 E                CALL BNASC4   ;POST CHAN PAIRS
17   742 0227  A1 0B1E R                MOV  AX,FSMP   ;1ST SAMPLE
18   743 022A  8B 1E 0B20 R             MOV  BX,LSMP   ;LAST SAMPLE
19   744 022E  2B D8                    SUB  BX,AX    ;DIFF
20   745 0230  43              INC  BX
21   746 0231  89 1E 0B18 R             MOV  NSMP,BX
22   747 0235  BB 0B18 R                MOV  BX,OFFSET DGROUP:NSMP
23   748 0238  BF 092A R                MOV  DI,OFFSET DGROUP:STQSMP+12
24   749 023B  E8 0000 E                CALL BNASC4   ;POST # SAMPS
```

```
25      750 023E  B9 0038           MOV     CX,LNSTQ    ;# CHARS
26      751 0241  BA 090B R         MOV     DX,OFFSET DGROUP:STQTRL
27  ;1ST ADR
28      752 0244  E8 0000 E         CALL    WRTFIL      ;TO FILE
29      753 0247  C3                RET
30      754 0248                    WRTPAR  ENDP
31
 1  ^HMicrosoft (R) Macro Assembler Version 5.10                8/29/89
 2  12:31:51
 3  CREATES DXF FILE WITH Z AXIS FOR AUTOCAD                Page
 4  1-14
 5
 6
 7      755                         ;
 8      756                         ;THIS CREATES THE SCRIPT FILE
 9      757 0248                    WRTSCR  PROC NEAR
10      758 0248  8A 0E 09B3 R        MOV   CL,FLNMLN ;BASIC FILE NAME
11  LENGTH
12      759 024C  32 ED               XOR   CH,CH
13      760 024E  51                PUSH    CX
14      761 024F  BF 0970 R           MOV   DI,OFFSET DGROUP:LNAM
15      762 0252  BE 09B4 R           MOV   SI,OFFSET DGROUP:FILNAM
16      763 0255  F3/ A4            REP     MOVSB       ;POST LSP NAME
17      764 0257  59                POP     CX
18      765 0258  41                INC     CX    ;PLUS LETTER
19      766 0259  51                PUSH    CX
20      767 025A  BF 094A R           MOV   DI,OFFSET DGROUP:HNAM
21      768 025D  BE 0A36 R           MOV   SI,OFFSET DGROUP:HDRNAM
22      769 0260  F3/ A4            REP     MOVSB       ;POST HEADER NAME
23
24      770 0262  59                POP     CX
25      771 0263  BF 095B R           MOV   DI,OFFSET DGROUP:ENAM
26      772 0266  BE 0A77 R           MOV   SI,OFFSET DGROUP:ENTNAM
27      773 0269  F3/ A4            REP     MOVSB       ;POST ENTITIES
28  NAME
29      774 026B  BA 0943 R           MOV   DX,OFFSET DGROUP:SCRIN
30      775 026E  B9 0049             MOV   CX,LNSCR
31      776 0271  E8 0000 E           CALL  WRTFIL
32      777 0274  C3                RET
33      778 0275                    WRTSCR  ENDP
34      779                         ;
35      780                         ;THIS MAKES THE WRITE BUFFER FOR
36  LINES
 1      781 0275                    MAKBUF  PROC NEAR
 2      782 0275  BE 0125 R           MOV   SI,OFFSET DGROUP:PTRTAB
```

```
783 0278  89 36 0123 R          MOV  NXTADR,SI    ;HOLD POINTER ADR 784 027C  8B 0E 098C R          MOV  CX,NPAIR     ;GET # LAYERS
785 0280  C7 06 0555 R 0000     MOV  CPOS,0       ;FIRST LAYER
786 0286  BF 0378 R             MOV  DI,OFFSET DGROUP:WBUF
787 0289  51            MBF1:   PUSH CX
788 028A  B9 000E               MOV  CX,LLINE
789 028D  BE 0019 R             MOV  SI,OFFSET DGROUP:LINE
790 0290  F3/ A4                REP  MOVSB        ;LINE HEADER
791 0292  57                    PUSH DI  ;HOLD CURR BUFF ADR
792 0293  A1 0555 R             MOV  AX,CPOS      ;GET LAYER #
793 0296  B9 0003               MOV  CX,3
794 0299  F7 E1                 MUL  CX   ;GET OFFSET
795 029B  BE 055D R             MOV  SI,OFFSET DGROUP:LNAME1
796 029E  03 F0                 ADD  SI,AX        ;LAYER NAME ADR
797 02A0  BF 0B09 R             MOV  DI,OFFSET DGROUP:MSGBUF
798 02A3  32 E4                 XOR  AH,AH
799 02A5  B9 0003               MOV  CX,3 ;MAX CHARS
800 02A8  8A 04         MBF2:   MOV  AL,[SI]  ;GET   NXT CHAR
801 02AA  3C 00                 CMP  AL,0
802 02AC  74 08                 JE   MBF3 ;JMP IF ASCIIZ
803 02AE  88 05                 MOV  [DI],AL  ;POST NXT CHAR
804 02B0  FE C4                 INC  AH   ;COUNT IT
805 02B2  47                    INC  DI
806 02B3  46                    INC  SI
807 02B4  E2 F2                 LOOP MBF2
808                             ;
809 02B6  C6 05 0D      MBF3:   MOV  BYTE PTR [DI],CR
810 02B9  47                    INC  DI
811 02BA  C6 05 0A              MOV  BYTE PTR [DI],LF
812 02BD  80 C4 02              ADD  AH,2
```

ˉHMicrosoft (R) Macro Assembler Version 5.10                    8/29/89 12:31:51
CREATES DXF FILE WITH Z AXIS FOR AUTOCAD                        Page 1-15

```
813 02C0  8A CC                 MOV  CL,AH        ;# CHARS
814 02C2  32 ED                 XOR  CH,CH
815 02C4  BE 0B09 R             MOV  SI,OFFSET DGROUP:MSGBUF
816 02C7  5F                    POP  DI   ;GET BUFF ADR
817 02C8  F3/ A4                REP  MOVSB        ;NXT NAME TO BUFF
```

```
13      818 02CA   BE 0027 R          MOV   SI,OFFSET DGROUP:XPNT
14      819 02CD   B9 0004            MOV   CX,4
15      820 02D0   F3/ A4       REP   MOVSB          ;X LABEL
16      821 02D2   8B 36 0123 R       MOV   SI,NXTADR ;GET    VALUE
17 POINTER ADR
18      822 02D6   89 3C              MOV   [SI],DI   ;SAVE X VALUE
19 POINTER
20      823 02D8   83 C6 02                 ADD  SI,2
21      824 02DB   89 36 0123 R       MOV   NXTADR,SI
22      825 02DF   83 C7 06                 ADD  DI,6 ;SPACE  FOR  X
23 VALUE
24      826 02E2   C6 05 0D                 MOV   BYTE PTR [DI],CR
25      827 02E5   47           INC   DI
26      828 02E6   C6 05 0A                 MOV   BYTE PTR [DI],LF
27      829 02E9   47           INC   DI
28      830 02EA   BE 002B R          MOV   SI,OFFSET DGROUP:YPNT
29      831 02ED   B9 0004            MOV   CX,4
30      832 02F0   F3/ A4       REP   MOVSB          ;Y LABEL
31      833 02F2   8B 36 0123 R       MOV   SI,NXTADR ;GET    VALUE
32 POINTER ADR
33      834 02F6   89 3C              MOV   [SI],DI   ;SAVE Y VALUE
34 POINTER
35      835 02F8   83 C6 02                 ADD  SI,2
36      836 02FB   89 36 0123 R       MOV   NXTADR,SI
 1      837 02FF   83 C7 06                 ADD  DI,6 ;SPACE  FOR  Y
 2 VALUE
 3      838 0302   C6 05 0D                 MOV   BYTE PTR [DI],CR
 4      839 0305   47           INC   DI
 5      840 0306   C6 05 0A                 MOV   BYTE PTR [DI],LF
 6      841 0309   47           INC   DI
 7      842 030A   BE 002F R          MOV   SI,OFFSET DGROUP:ZPNT
 8      843 030D   B9 0004            MOV   CX,4
 9      844 0310   F3/ A4       REP   MOVSB          ;Z LABEL
10      845 0312   8B 36 0123 R       MOV   SI,NXTADR ;GET    VALUE
11 POINTER ADR
12      846 0316   89 3C              MOV   [SI],DI   ;SAVE Z VALUE
13 POINTER
14      847 0318   83 C6 02                 ADD  SI,2
15      848 031B   89 36 0123 R       MOV   NXTADR,SI
16      849 031F   83 C7 06                 ADD  DI,6 ;SPACE  FOR  Z
17 VALUE
18      850 0322   C6 05 0D                 MOV   BYTE PTR [DI],CR
19      851 0325   47           INC   DI
20      852 0326   C6 05 0A                 MOV   BYTE PTR [DI],LF
21      853 0329   47           INC   DI
```

```
22      854 032A  BE 0033 R           MOV  SI,OFFSET DGROUP:NXPNT
23      855 032D  B9 0004             MOV  CX,4
24      856 0330  F3/ A4          REP MOVSB            ;NX LABEL
25      857 0332  8B 36 0123 R        MOV  SI,NXTADR ;GET    VALUE
26 POINTER ADR
27      858 0336  89 3C               MOV  [SI],DI  ;SAVE NX VALUE
28 POINTER
29      859 0338  83 C6 02                 ADD SI,2
30      860 033B  89 36 0123 R        MOV  NXTADR,SI
31      861 033F  83 C7 06                 ADD DI,6 ;SPACE FOR NX
32 VALUE
33      862 0342  C6 05 0D            MOV  BYTE PTR [DI],CR
34      863 0345  47              INC  DI
35      864 0346  C6 05 0A            MOV  BYTE PTR [DI],LF
36      865 0349  47              INC  DI
 1      866 034A  BE 0037 R           MOV  SI,OFFSET DGROUP:NYPNT
 2      867 034D  B9 0004             MOV  CX,4
 3      868 0350  F3/ A4          REP MOVSB            ;NY LABEL
 4      869 0352  8B 36 0123 R        MOV  SI,NXTADR ;GET    VALUE
 5 POINTER ADR
 6      870 0356  89 3C               MOV  [SI],DI  ;SAVE NY VALUE
 7 POINTER
 8
 1 ^HMicrosoft (R) Macro Assembler Version 5.10                    8/29/89
 2 12:31:51
 3 CREATES DXF FILE WITH Z AXIS FOR AUTOCAD                         Page
 4 1-16
 5
 6
 7      871 0358  83 C6 02                 ADD SI,2
 8      872 035B  89 36 0123 R        MOV  NXTADR,SI
 9      873 035F  83 C7 06                 ADD DI,6 ;SPACE FOR NY
10 VALUE
11      874 0362  C6 05 0D            MOV  BYTE PTR [DI],CR
12      875 0365  47              INC  DI
13      876 0366  C6 05 0A            MOV  BYTE PTR [DI],LF
14      877 0369  47              INC  DI
15      878 036A  BE 003B R           MOV  SI,OFFSET DGROUP:NZPNT
16      879 036D  B9 0004             MOV  CX,4
17      880 0370  F3/ A4          REP MOVSB            ;NZ LABEL
18      881 0372  8B 36 0123 R        MOV  SI,NXTADR ;GET    VALUE
19 POINTER ADR
20      882 0376  89 3C               MOV  [SI],DI  ;SAVE NZ VALUE
21 POINTER
22      883 0378  83 C6 02                 ADD SI,2
```

```
23      884 037B   89 36 0123 R           MOV   NXTADR,SI
24      885 037F   83 C7 06                ADD   DI,6    ;SPACE FOR NZ
25 VALUE
26      886 0382   C6 05 0D                MOV   BYTE PTR [DI],CR
27      887 0385   47                      INC   DI
28      888 0386   C6 05 0A                MOV   BYTE PTR [DI],LF
29      889 0389   47                      INC   DI
30      890 038A   FF 06 0555 R            INC   CPOS    ;NEXT PAIR
31      891 038E   59               POP   CX
32      892 038F   49               DEC   CX      ;COUNT A PAIRING
33      893 0390   74 03                   JZ    MBF4    ;JMP IF DONE
34      894 0392   E9 0289 R               JMP   MBF1
35      895 0395   BE 0378 R        MBF4:  MOV   SI,OFFSET DGROUP:WBUF
 1      896 0398   2B FE                   SUB   DI,SI   ;GET NUMBER CHARS
 2 IN BUFF
 3      897 039A   89 3E 0553 R            MOV   LWBUF,DI ;POST
 4      898 039E   C3                RET
 5      899 039F              MAKBUF    ENDP
 6      900                          ;
 7      901                          ;THIS FILLS THE INPUT BUFFER
 8      902 039F              FILLBF    PROC NEAR
 9      903 039F   BB 4000                MOV   BX,16384  ;MAX SIZE
10      904 03A2   8B 0E 0B30 R           MOV   CX,BUFSIZ ;CURR SIZE
11      905 03A6   BF 0B36 R              MOV   DI,OFFSET DGROUP:FBUF
12      906 03A9   83 F9 00               CMP   CX,0
13      907 03AC   74 06                  JE    FBF0 ;JMP IF EMPTY
14      908 03AE   8B 36 0B34 R           MOV   SI,BUFPTR ;NXT DATA ADR
15      909 03B2   F3/ A4          REP    MOVSB          ;DATA TO HEAD OF
16 BUFFER
17      910 03B4   89 3E 0B34 R    FBF0:  MOV   BUFPTR,DI ;NXT DATA
18 ADR
19      911 03B8   2B 1E 0B30 R           SUB   BX,BUFSIZ ;SPACE AVAIL
20      912 03BC   8B 0E 0B28 R           MOV   CX,FSIZ   ;GET FILE SIZE
21      913 03C0   8B 16 0B2A R           MOV   DX,FSIZ+2
22      914 03C4   2B 0E 0B2C R           SUB   CX,BYTSRD ;LESS BYTES READ
23      915 03C8   1B 16 0B2E R           SBB   DX,BYTSRD+2
24      916 03CC   0B D2                  OR    DX,DX
25      917 03CE   75 08                  JNZ   FBF1 ;JMPIF OVER 65535
26      918 03D0   0B C9                  OR    CX,CX
27      919 03D2   74 29                  JZ    FBF5 ;JMP IF DONE
28      920 03D4   3B CB                  CMP   CX,BX
29      921 03D6   72 02                  JB    FBF2 ;JMP IF LT SPACE AVAIL
30
31      922 03D8   8B CB            FBF1: MOV   CX,BX    ;SET TO MAX
32      923 03DA   8B 1E 0AFF R     FBF2: MOV   BX,IHANDL
```

```
33    924 03DE  8B 16 0B34 R          MOV  DX,BUFPTR  ;1ST ADR
34    925 03E2  E8 0000 E             CALL RDIND      ;READ INPUT FILE
35    926 03E5  72 16                 JC   FBF5 ;JMP IF ERR
36    927 03E7  01 06 0B30 R          ADD  BUFSIZ,AX  ;CURR SIZE
 1    928 03EB  01 06 0B2C R          ADD  BYTSRD,AX  ;TOTAL BYTES READ
 2
 3
```

1  ^HMicrosoft (R) Macro Assembler Version 5.10                    8/29/89
2  12:31:51
3  CREATES DXF FILE WITH Z AXIS FOR AUTOCAD                        Page
4  1-17
5
6

```
 7    929 03EF  83 16 0B2E R 00       ADC  BYTSRD+2,0
 8    930 03F4  BE 0B36 R             MOV  SI,OFFSET DGROUP:FBUF
 9    931 03F7  89 36 0B34 R          MOV  BUFPTR,SI  ;SET INIT BUFF
10 ADR
11    932 03FB  F8                    CLC
12    933 03FC  C3                    RET
13    934 03FD  F9            FBF5:   STC
14    935 03FE  C3                    RET
15    936 03FF                FILLBF  ENDP
16    937                             ;
17    938                             ;THIS GETS CURR PAIR FROM BUFFER
18    939                             ;BX=BUFF POINTER
19    940 03FF                PAIRS   PROC NEAR
20    941 03FF  BF 09A6 R             MOV  DI,OFFSET DGROUP:ZTAB
21    942 0402  A1 0555 R             MOV  AX,CPOS    ;GET CURR POS
22    943 0405  D1 E0                 SHL  AX,1 ;CURR POS *2
23    944 0407  50                    PUSH AX         ;HOLD
24    945 0408  03 F8                 ADD  DI,AX      ;POINT TO Z
25    946 040A  8B 35                 MOV  SI,[DI]    ;GET Z CHAN
26    947 040C  8A 10                 MOV  DL,[BX][SI]    ;GET Z VALUE
27
28    948 040E  02 16 055B R          ADD  DL,CBOX    ;CORRECT POLARITY
29
30    949 0412  32 F6                 XOR  DH,DH
31    950 0414  03 16 0557 R          ADD  DX,HOR     ;PLUS   DISPLAY
32 OFFSETS
33    951 0418  89 16 019B R          MOV  ZBIN,DX    ;SAVE
34    952 041C  D1 E0                 SHL  AX,1 ;CURR POS *4
35    953 041E  50                    PUSH AX         ;HOLD OFFSET
36    954 041F  BF 098E R             MOV  DI,OFFSET DGROUP:PAIRTB
 1    955 0422  03 F8                 ADD  DI,AX      ;POINT TO PAIR
 2    956 0424  8B 35                 MOV  SI,[DI]    ;GET X CHAN
```

```
957 0426  8B 45 02              MOV   AX,[DI+2]   ;AND Y CHAN
958 0429  8B F8           MOV   DI,AX
959 042B  8A 00           MOV   AL,[BX][SI]   ;GET X VALUE 960 042D  02 06 055B R          ADD   AL,CBOX   ;CORRECT POLARITY 961 0431  8A 11           MOV   DL,[BX][DI]   ;GET Y VALUE 962 0433  02 16 055B R          ADD   DL,CBOX   ;CORRECT POLARITY 963 0437  32 E4                 XOR   AH,AH
964 0439  32 F6                 XOR   DH,DH
965 043B  03 06 0557 R          ADD   AX,HOR    ;PLUS    DISPLAY OFFSETS
966 043F  03 16 0559 R          ADD   DX,VRT
967 0443  A3 0197 R             MOV   XBIN,AX   ;SAVE
968 0446  89 16 0199 R          MOV   YBIN,DX
969 044A  58              POP   AX    ;GET POS OFFSET *4
970 044B  5A              POP   DX    ;GET POS OFFSET *2
971 044C  C3              RET
972 044D                  PAIRS   ENDP
973                       ;
974                       ;THIS PARSES INPUT BUFFER
975 044D                  PARSE   PROC NEAR
976 044D  83 3E 0B30 R 04       CMP   BUFSIZ,4
977 0452  77 02                JA    PAR0  ;JMP IF BYTES FOR A SAMPLE
978 0454  F8              CLC
979 0455  C3              RET
980 0456  8B 1E 0B34 R    PAR0:   MOV   BX,BUFPTR ;GET NXT ADR 981 045A  80 7F 04 01           CMP   BYTE PTR [BX+4],1
982 045E  74 02                JE    PAR1  ;JMP IF NEW TRIAL
983 0460  EB 79                JMP   SHORT PAR3
984                       ;
985 0462  C7 06 0B18 R 0000 PAR1:  MOV   NSMP,0   ;R E S E T SAMPLE COUNTER
986 0468  FF 06 0B22 R          INC   NTRL  ;COUNT A TRIAL
```

^HMicrosoft (R) Macro Assembler Version 5.10                8/29/89 12:31:51
CREATES DXF FILE WITH Z AXIS FOR AUTOCAD                    Page 1-18

```
  7       987 046C  A1 0B22 R                MOV    AX,NTRL
  8       988 046F  3B 06 0B1C R             CMP    AX,FTRL
  9       989 0473  73 03                    JAE    PAR00         ;JMP IF TRIAL IN
 10  RANGE
 11       990 0475  E9 0577 R                JMP    PAR10         ;SKIP  TO  NEXT
 12  TRIAL
 13       991                                ;
 14       992 0478  FF 0E 0B1A R      PAR00: DEC    NTRLS         ;COUNT     A
 15  TRIAL
 16       993 047C  79 02                    JNS    PAR000        ;JMP IF NOT DONE
 17       994 047E  F9                       STC
 18       995 047F  C3                       RET
 19       996                                ;
 20       997 0480  81 3E 0557 R 07D0 PAR000: CMP   HOR,2000
 21       998 0486  74 0F                    JE     PAR2 ;JMP IF 5 HORIZ BOXES
 22       999 0488  80 3E 055C R 00          CMP    HFLG,0
 23      1000 048D  74 14                    JE     SHORT PAR2A   ;JMP IF JUST
 24  STARTING
 25      1001 048F  81 06 0557 R 01F4        ADD    HOR,500       ;ELSE   NEW
 26  BOX
 27      1002 0495  EB 0C                    JMP    SHORT PAR2A
 28      1003                                ;
 29      1004 0497  81 06 0559 R 01F4 PAR2:  ADD    VRT,500    ; N E X T
 30  VERTICAL LINE
 31      1005 049D  C7 06 0557 R 0000        MOV    HOR,0         ;START HORIZ OVER
 32
 33      1006 04A3  C6 06 055C R 01   PAR2A: MOV    HFLG,1
 34      1007 04A8  C7 06 0555 R 0000        MOV    CPOS,0
 35      1008 04AE  B9 0006                  MOV    CX,6
 36      1009 04B1  BF 016D R                MOV    DI,OFFSET DGROUP:NXYZTB
  1      1010 04B4  51                PAR2B: PUSH   CX
  2      1011 04B5  57                       PUSH   DI
  3      1012 04B6  E8 03FF R                CALL   PAIRS         ;GET    INITIAL
  4  VALUES
  5      1013 04B9  5F                       POP    DI
  6      1014 04BA  A1 0197 R                MOV    AX,XBIN
  7      1015 04BD  89 05                    MOV    [DI],AX       ;  S  E  T
  8  STARTING POINTS
  9      1016 04BF  A1 0199 R                MOV    AX,YBIN
 10      1017 04C2  89 45 02                 MOV    [DI+2],AX
 11      1018 04C5  A1 019B R                MOV    AX,ZBIN
 12      1019 04C8  89 45 04                 MOV    [DI+4],AX
 13      1020 04CB  83 C7 06                 ADD    DI,6
 14      1021 04CE  FF 06 0555 R             INC    CPOS
 15      1022 04D2  59                       POP    CX
```

```
16      1023 04D3  E2 DF                    LOOP PAR2B
17      1024 04D5  C7 06 0B18 R 0000        MOV  NSMP,0    ;FIRST SAMPLE
18      1025                          ;
19      1026
20      1027 04DB  A1 0B22 R        PAR3:   MOV  AX,NTRL
21      1028 04DE  3B 06 0B1C R             CMP  AX,FTRL
22      1029 04E2  73 03                    JAE  PAR3A     ;JMP IF TRIAL IN
23 RANGE
24      1030 04E4  E9 0577 R                JMP  PAR10     ;ELSE SKIP TO
25 NEXT TRIAL
26      1031 04E7  A1 0B18 R        PAR3A:  MOV  AX,NSMP   ;GET CURR
27 SMP #
28      1032 04EA  3B 06 0B1E R             CMP  AX,FSMP
29      1033 04EE  73 03                    JAE  PAR3B     ;JMP IF WITHIN
30 RANGE
31      1034 04F0  E9 0577 R                JMP  PAR10     ;ELSE SKIP SAMPLE
32
33      1035 04F3  3B 06 0B20 R     PAR3B:  CMP  AX,LSMP
34      1036 04F7  76 03                    JBE  PAR3C     ;JMP IF OKAY
35      1037 04F9  EB 7C 90                 JMP  PAR10     ;JMP IF TOO
36 HIGH
 1      1038                          ;
 2      1039 04FC  C7 06 0555 R 0000 PAR3C: MOV  CPOS,0    ; F I R S T
 3 PAIRING
 4      1040 0502  8B 0E 098C R             MOV  CX,NPAIR  ;# TO DO
 5      1041 0506  51               PAR4:   PUSH CX
 6      1042 0507  53                       PUSH BX
 7      1043 0508  E8 03FF R                CALL PAIRS     ;GET VALUES
 8      1044 050B  03 C2                    ADD  AX,DX     ;*6
 9
 1 ^HMicrosoft (R) Macro Assembler Version 5.10              8/29/89
 2 12:31:51
 3 CREATES DXF FILE WITH Z AXIS FOR AUTOCAD                  Page
 4 1-19
 5
 6
 7      1045 050D  50                       PUSH AX
 8      1046 050E  BE 016D R                MOV  SI,OFFSET DGROUP:NXYZTB
 9      1047 0511  03 F0                    ADD  SI,AX
10      1048 0513  8B 04                    MOV  AX,[SI]   ;GET PREV X
11      1049 0515  A3 0191 R                MOV  NXBIN,AX
12      1050 0518  8B 44 02                 MOV  AX,[SI+2] ;GET PREV
13 Y
14      1051 051B  A3 0193 R                MOV  NYBIN,AX
15      1052 051E  8B 44 04                 MOV  AX,[SI+4] ;GET PREV
```

```
16  Z
17      1053 0521  A3 0195 R           MOV   NZBIN,AX
18      1054 0524  A1 0197 R           MOV   AX,XBIN
19      1055 0527  89 04               MOV   [SI],AX      ;SAVE CURR X
20      1056 0529  A1 0199 R           MOV   AX,YBIN
21      1057 052C  89 44 02            MOV   [SI+2],AX  ;SAVE CURR
22  Y
23      1058 052F  A1 019B R           MOV   AX,ZBIN
24      1059 0532  89 44 04            MOV   [SI+4],AX  ;SAVE CURR
25  Z
26      1060 0535  58            POP   AX    ;GET POS OFFSET
27      1061 0536  D1 E0               SHL   AX,1 ;*12
28      1062 0538  BE 0125 R           MOV   SI,OFFSET DGROUP:PTRTAB
29      1063 053B  03 F0               ADD   SI,AX       ;DEST ADR FOR X
30      1064 053D  8B 3C               MOV   DI,[SI]
31      1065 053F  BB 0191 R           MOV   B X ,  O F F S E T
32  DGROUP:NXBIN ;SOURCE OF X
33      1066 0542  BE 000C             MOV   SI,12       ;OFFSET TO Y DEST
34
35      1067 0545  B9 0006             MOV   CX,6 ;6 VALUES
36      1068 0548  E8 0000 E           CALL  BNASC6      ;CNVT TO ASCII
 1      1069 054B  FF 06 0555 R        INC   CPOS ;NXT POS
 2      1070 054F  5B            POP   BX
 3      1071 0550  59            POP   CX
 4      1072 0551  49            DEC   CX
 5      1073 0552  74 02               JZ    PAR5 ;JMP IF DONE
 6      1074 0554  EB B0               JMP   PAR4 ;JMP IF MORE
 7      1075                     ;
 8      1076 0556  8B 0E 0553 R  PAR5: MOV   CX,LWBUF
 9      1077 055A  33 D2               XOR   DX,DX
10      1078 055C  BE 0378 R           MOV   SI,OFFSET DGROUP:WBUF
11      1079 055F  BF 019D R           MOV   DI,OFFSET DGROUP:WBUFF
12      1080 0562  8A 04         PAR6: MOV   AL,[SI]     ;GET NXT CHR
13
14      1081 0564  3C 20               CMP   AL,' '
15      1082 0566  74 04               JE    PAR7 ;JMP IF SPACE
16      1083 0568  88 05               MOV   [DI],AL
17      1084 056A  47            INC   DI
18      1085 056B  42            INC   DX
19      1086 056C  46            PAR7: INC   SI
20      1087 056D  E2 F3               LOOP  PAR6
21      1088                     ;
22      1089 056F  8B CA               MOV   CX,DX
23      1090 0571  BA 019D R           MOV   DX,OFFSET DGROUP:WBUFF
24      1091 0574  E8 0000 E           CALL  WRTFIL      ;NXT LINE TO FILE
```

```
 26    1092 0577  83 06 0B34 R 05         PAR10:   ADD  BUFPTR,5    ;NEXT SAMPLE ADR
 28    1093 057C  83 2E 0B30 R 05                  SUB  BUFSIZ,5
 29    1094 0581  FF 06 0B18 R                     INC  NSMP
 30    1095 0585  E9 044D R                        JMP  PARSE       ;TRY NEXT SAMPLE
 31    1096                                        ;
 32    1097 0588                          PARSE    ENDP
 33    1098                                        ;
 34    1099                                        ;THIS CHECKS FILE FOR NUMBER OF SAMPLES AND TRIALS
 36    1100 0588                          CHKFIL   PROC NEAR
  1    1101 0588  8B 1E 0AFF R                     MOV  BX,IHANDL
  2    1102 058C  33 C9                            XOR  CX,CX
```

^HMicrosoft (R) Macro Assembler Version 5.10                  8/29/89 12:31:51
CREATES DXF FILE WITH Z AXIS FOR AUTOCAD                      Page 1-20

```
  7    1103 058E  33 D2                            XOR  DX,DX
  8    1104 0590  B0 02                            MOV  AL,2
  9    1105 0592  B4 42                            MOV  AH,42H
 10    1106 0594  CD 21                            INT  DOSINT      ;GET END OF FILE
 11    1107 0596  A3 0B28 R                        MOV  FSIZ,AX     ;POST FILE SIZE
 12    1108 0599  89 16 0B2A R                     MOV  FSIZ+2,DX
 13    1109 059D  8B 1E 0AFF R                     MOV  BX,IHANDL
 14    1110 05A1  BA 0050                          MOV  DX,80       ;40 WORD HEADER
 15    1111 05A4  89 16 0B2C R                     MOV  BYTSRD,DX
 16    1112 05A8  33 C9                            XOR  CX,CX
 17    1113 05AA  32 C0                            XOR  AL,AL
 18    1114 05AC  B4 42                            MOV  AH,42H
 19    1115 05AE  CD 21                            INT  DOSINT      ;SET START OF DATA
 21    1116                                        ;
 22    1117 05B0  8B 1E 0AFF R                     MOV  BX,IHANDL
 23    1118 05B4  BA 0B36 R                        MOV  DX,OFFSET DGROUP:FBUF
 24    1119 05B7  B9 2710                          MOV  CX,10000
 25    1120 05BA  E8 0000 E                        CALL RDIND       ;GET START OF FILE
 27    1121 05BD  73 02                            JNC  CF0         ;JMP IF NO ERR
 28    1122 05BF  F9                      STC
 29    1123 05C0  C3                      RET
 30    1124 05C1  B9 07D0                 CF0:     MOV  CX,2000
```

```
31   1125 05C4  33 D2              XOR  DX,DX      ;CLEAR COUNTER
32   1126 05C6  33 DB              XOR  BX,BX      ;CLR MAX SMPS
33   1127 05C8  B8 0FFF            MOV  AX,0FFFH   ;CLR MIN SMPS
34   1128 05CB  BE 0B3A R          MOV  SI,OFFSET DGROUP:FBUF+4
35   1129 05CE  80 3C 01      CF1: CMP  BYTE PTR [SI],1
36   1130 05D1  74 07              JE   CF2   ;JMP IF TRIAL FLAG
 1   1131 05D3  83 C6 05           ADD  SI,5  ;ELSE NEXT FLAG
 2   1132 05D6  E2 F6              LOOP CF1   ;JMP IF MORE
 3   1133 05D8  F9            STC
 4   1134 05D9  C3            RET
 5   1135                     ;
 6   1136 05DA  42       CF2: INC  DX    ;COUNT A SAMPLE
 7   1137 05DB  83 C6 05         ADD  SI,5
 8   1138 05DE  80 3C 01    CF3: CMP  BYTE PTR [SI],1
 9   1139 05E1  74 08            JE   CF4   ;JMP IF TRIAL FLAG
10   1140 05E3  83 C6 05         ADD  SI,5
11   1141 05E6  42               INC  DX    ;ADD A SAMP
12   1142 05E7  E2 F5            LOOP CF3   ;JMP IF MORE
13   1143 05E9  EB 10            JMP  SHORT CF7
14   1144                   ;
15   1145 05EB  3B D0     CF4: CMP  DX,AX
16   1146 05ED  77 02          JA   CF5   ;JMP IF ABOVE MINIMUM
17   1147 05EF  8B C2          MOV  AX,DX     ;ELSE REPLACE
18   1148 05F1  3B D3     CF5: CMP  DX,BX
19   1149 05F3  72 02          JB   CF6   ;JMP IF BELOW MAXIMUM
20   1150 05F5  8B DA          MOV  BX,DX     ;ELSE REPLACE
21   1151 05F7  33 D2     CF6: XOR  DX,DX     ;CLR COUNTER
22   1152 05F9  EB DF          JMP  CF2   ;START NEXT TRIAL
23   1153                ;
24   1154 05FB  A3 0B18 R  CF7: MOV  NSMP,AX   ;SAVE MINIMUM #
25 SAMPLES PER TRIAL
26   1155 05FE  89 1E 0B20 R     MOV  LSMP,BX   ;SAVE MAXIMUM IN
27 TEMPY
28   1156 0602  8B C3            MOV  AX,BX
29   1157 0604  B9 0005          MOV  CX,5
30   1158 0607  F7 E1            MUL  CX    ;# SETS
31   1159 0609  8B D8            MOV  BX,AX
32   1160 060B  A1 0B28 R        MOV  AX,FSIZ    ;GET FILE SIZE
33
 1  ^HMicrosoft (R) Macro Assembler Version 5.10           8/29/89
 2  12:31:51
 3  CREATES DXF FILE WITH Z AXIS FOR AUTOCAD              Page
 4  1-21
 5
 6
```

```
 7      1161 060E  8B 16 0B2A R              MOV   DX,FSIZ+2
 8      1162 0612  E8 0000 E                 CALL  D32B16     ;DIV BY MAXIMUM
 9   # SETS PER TRIAL
10      1163 0615  A3 0B22 R                 MOV   WORD PTR NTRL,AX    ;HOLD
11   TRIALS PER FILE
12      1164 0618  89 16 0B24 R              MOV   WORD PTR NTRL+2,DX
13      1165 061C  BB 0B22 R                 MOV   BX,OFFSET DGROUP:NTRL
14      1166 061F  BF 07FA R                 MOV   DI,OFFSET DGROUP:MSG22+38
15      1167 0622  E8 0000 E                 CALL  BNASC8     ;POST # TRIALS
16      1168 0625  BB 0B18 R                 MOV   BX,OFFSET DGROUP:NSMP
17      1169 0628  BF 0739 R                 MOV   DI,OFFSET DGROUP:MSG17+41
18      1170 062B  B9 0001                   MOV   CX,1
19      1171 062E  E8 0000 E                 CALL  BNASC4     ;POST # SAMPLES
20   MIN
21      1172 0631  BB 0B20 R                 MOV   BX,OFFSET DGROUP:LSMP
22      1173 0634  BF 0745 R                 MOV   DI,OFFSET DGROUP:MSG17+53
23      1174 0637  B9 0001                   MOV   CX,1
24      1175 063A  E8 0000 E                 CALL  BNASC4     ;POST # SAMPLES
25   MAX
26      1176 063D  E8 0000 E                 CALL  SNDLF
27      1177 0640  BE 0710 R                 MOV   SI,OFFSET DGROUP:MSG17
28      1178 0643  E8 0000 E                 CALL  DIRMSG     ;DISPLAY    #
29   SAMPLES
30      1179 0646  E8 0000 E                 CALL  SNDLF
31      1180 0649  BE 07D4 R                 MOV   SI,OFFSET DGROUP:MSG22
32      1181 064C  E8 0000 E                 CALL  DIRMSG     ;DISPLAY # TRIALS
33
34      1182 064F  F8                 CLC
35      1183 0650  C3                 RET
36      1184 0651             CHKFIL   ENDP
 1      1185                       ;
 2      1186 0651  8C D8       MAINPG:  MOV  AX,DS
 3      1187 0653  8E C0                MOV  ES,AX
 4      1188 0655  FC                   CLD
 5      1189 0656  C7 06 0000 E 0001    MOV  MSGNM,1    ;SOURCE FILE MSG
 6      1190 065C  E8 0037 R            CALL GETFIL     ;OPEN IT
 7      1191 065F  72 F0                JC   MAINPG     ;JMP IF ERROR
 8      1192 0661  C7 06 0000 E 0010 MPG1:  MOV  MSGNM,16  ;DXF FILE
 9   MSG
10      1193 0667  E8 008B R            CALL MAKFIL     ;OPEN IT
11      1194 066A  72 F5                JC   MPG1  ;JMP IF ERROR
12      1195 066C  A3 0AFB R            MOV  EHANDL,AX  ;FILE HANDLE
13      1196 066F  A3 0B01 R            MOV  FHANDL,AX
14      1197                       ;
15      1198 0672  C7 06 0000 E 0019    MOV  MSGNM,25
```

```
16      1199 0678  E8 0013 R                 CALL    REPCHK      ;BOX CENTER MSG
17      1200 067B  74 05                     JZ      MPG1A       ;JMP IF CENTERED
18      1201 067D  C6 06 055B R 00           MOV     CBOX,0      ;ELSE CORNER
19
20      1202                          ;
21      1203 0682  E8 0000 E        MPG1A:   CALL    SNDLF
22      1204 0685  E8 0588 R                 CALL    CHKFIL      ;GET FILE SPECS
23      1205 0688  73 03                     JNC     MPG2 ;JMP IF NO ERR
24      1206 068A  E9 0840 R                 JMP     MPG20
25      1207 068D  C7 06 0000 E 0012 MPG2:   MOV     MSGNM,18
26      1208 0693  A1 0B22 R                 MOV     AX,NTRL     ;LIMIT
27      1209 0696  E8 0183 R                 CALL    GETVAL      ;GET # TRIALS TO
28 DO
29      1210 0699  72 F2                     JC      MPG2 ;JMP IF ERR
30      1211 069B  0B C0                     OR      AX,AX
31      1212 069D  75 0B                     JNZ     MPG2A
32      1213 069F  C7 06 0000 E 000E         MOV     MSGNM,14
33      1214 06A5  E8 0000 E                 CALL    CRTMSG
34      1215 06A8  EB E3                     JMP     MPG2
35      1216 06AA  A3 0B1A R        MPG2A:   MOV     NTRLS,AX
36      1217 06AD  BB 0B1A R                 MOV     BX,OFFSET DGROUP:NTRLS
 1      1218 06B0  BF 0917 R                 MOV     DI,OFFSET DGROUP:STQTRL+12
 2
 1  ^HMicrosoft (R) Macro Assembler Version 5.10                        8/29/89
 2  12:31:51
 3  CREATES DXF FILE WITH Z AXIS FOR AUTOCAD                            Page
 4  1-22
 5
 6
 7      1219 06B3  E8 0000 E                 CALL    BNASC4      ;POST TRIALS TO
 8 LISP
 9      1220 06B6  C7 06 0000 E 0013 MPG3:   MOV     MSGNM,19
10      1221 06BC  A1 0B22 R                 MOV     AX,NTRL
11      1222 06BF  E8 0183 R                 CALL    GETVAL      ;GET   STARTING
12 TRIAL #
13      1223 06C2  72 F2                     JC      MPG3 ;JMP IF ERR
14      1224 06C4  A3 0B1C R                 MOV     FTRL,AX
15      1225 06C7  3D 0000                   CMP     AX,0
16      1226 06CA  75 06                     JNE     MPG4 ;JMP IF NOT 0
17      1227 06CC  C7 06 0B1C R 0001         MOV     FTRL,1      ;ELSE SET TO 1
18      1228 06D2  C7 06 0000 E 0014 MPG4:   MOV     MSGNM,20
19      1229 06D8  A1 0B18 R                 MOV     AX,NSMP
20      1230 06DB  E8 0183 R                 CALL    GETVAL      ;GET FIRST SAMPLE
21 #
22      1231 06DE  72 F2                     JC      MPG4
```

```
23      1232 06E0  A3 0B1E R              MOV   FSMP,AX
24      1233 06E3  0B C0                  OR    AX,AX
25      1234 06E5  75 0D                  JNZ   MPG4A        ;JMP IF NOT ZERO
26      1235 06E7  FF 06 0B1E R           INC   FSMP
27      1236 06EB  A1 0B18 R              MOV   AX,NSMP      ;GET MIN SMPS
28      1237 06EE  48              DEC    AX
29      1238 06EF  A3 0B20 R              MOV   LSMP,AX      ;SET TO MIN LESS
30   1
31      1239 06F2  EB 17                  JMP   SHORT MPG4B
32      1240                        ;
33      1241 06F4  C7 06 0000 E 0015 MPG4A: MOV MSGNM,21
34      1242 06FA  A1 0B18 R              MOV   AX,NSMP
35      1243 06FD  E8 0183 R              CALL  GETVAL       ;GET LAST SAMPLE
36   #
 1      1244 0700  72 F2                  JC    MPG4A
 2      1245 0702  A3 0B20 R              MOV   LSMP,AX
 3      1246 0705  3B 06 0B1E R           CMP   AX,FSMP
 4      1247 0709  72 E9                  JB    MPG4A
 5      1248                        ;
 6      1249 070B  C7 06 0000 E 000B MPG4B: MOV MSGNM,11
 7      1250 0711  B8 0006                MOV   AX,6 ;MAX VALUE
 8      1251 0714  E8 0183 R              CALL  GETVAL       ;GET # PAIRINGS
 9      1252 0717  72 F2                  JC    MPG4B        ;JMP IF ERR
10      1253 0719  0B C0                  OR    AX,AX
11      1254 071B  75 0B                  JNZ   MPG4C
12      1255 071D  C7 06 0000 E 000E      MOV   MSGNM,14
13      1256 0723  E8 0000 E              CALL  CRTMSG
14      1257 0726  EB E3                  JMP   MPG4B
15      1258 0728  A3 098C R       MPG4C: MOV   NPAIR,AX     ;SAVE
16      1259 072B  04 30                  ADD   AL,30H       ;AS ASCII
17      1260 072D  A2 00D3 R              MOV   NLAYRS,AL    ;SAVE
18      1261 0730  8B CE                  MOV   CX,SI        ;GET PAIRS AGAIN
19      1262 0732  C7 06 0555 R 0000      MOV   CPOS,0       ;FIRST POSITION
20      1263 0738  C7 06 0B26 R 0001      MOV   NLYR,1       ;1ST LAYER
21      1264 073E  BE 098E R              MOV   SI,OFFSET DGROUP:PAIRTB
22      1265 0741  BF 09A6 R              MOV   DI,OFFSET DGROUP:ZTAB
23      1266 0744  51              MPG5:  PUSH  CX           ;HOLD # TO DO
24      1267 0745  57                     PUSH  DI
25      1268 0746  56                     PUSH  SI
26      1269 0747  C7 06 0000 E 000C MPG6: MOV  MSGNM,12
27      1270 074D  B8 0005                MOV   AX,5 ;MAX 5 CHS
28      1271 0750  E8 0183 R              CALL  GETVAL       ;GET CHAN # FOR
29   X
30      1272 0753  72 F2                  JC    MPG6 ;JMP IF ERR
31      1273 0755  0B C0                  OR    AX,AX
```

```
32      1274 0757  75 0B                   JNZ   MPG6A
33      1275 0759  C7 06 0000 E 000E       MOV   MSGNM,14
34      1276 075F  E8 0000 E               CALL  CRTMSG
35
 1  ^HMicrosoft (R) Macro Assembler Version 5.10          8/29/89
 2  12:31:51
 3  CREATES DXF FILE WITH Z AXIS FOR AUTOCAD              Page
 4  1-23
 5
 6
 7      1277 0762  EB E3                   JMP   MPG6
 8      1278 0764  5E              MPG6A:  POP   SI
 9      1279 0765  48                      DEC   AX       ;1=0 ETC
10      1280 0766  89 04                   MOV   [SI],AX
11      1281 0768  83 C6 02                ADD   SI,2
12      1282 076B  56                      PUSH  SI
13      1283                        ;
14      1284 076C  C7 06 0000 E 000D MPG7: MOV   MSGNM,13
15      1285 0772  B8 0005                 MOV   AX,5     ;MAX 5 CHS
16      1286 0775  E8 0183 R               CALL  GETVAL   ;GET CHAN # FOR
17  Y
18      1287 0778  72 F2                   JC    MPG7     ;JMP IF ERR
19      1288 077A  0B C0                   OR    AX,AX
20      1289 077C  75 0B                   JNZ   MPG7A
21      1290 077E  C7 06 0000 E 000E       MOV   MSGNM,14
22      1291 0784  E8 0000 E               CALL  CRTMSG
23      1292 0787  EB E3                   JMP   MPG7
24      1293 0789  5E              MPG7A:  POP   SI
25      1294 078A  48                      DEC   AX       ;1=0 ETC
26      1295 078B  89 04                   MOV   [SI],AX  ;POST CH #
27      1296 078D  83 C6 02                ADD   SI,2
28      1297 0790  56                      PUSH  SI
29      1298                        ;
30      1299 0791  C7 06 0000 E 0017 MPG7B: MOV  MSGNM,23
31      1300 0797  B8 0005                 MOV   AX,5     ;MAX 5 CHS
32      1301 079A  E8 0183 R               CALL  GETVAL   ;GET CHAN # FOR
33  Z
34      1302 079D  72 F2                   JC    MPG7B    ;JMP IF ERR
35      1303 079F  0B C0                   OR    AX,AX
36      1304 07A1  75 0B                   JNZ   MPG7C
 1      1305 07A3  C7 06 0000 E 000E       MOV   MSGNM,14
 2      1306 07A9  E8 0000 E               CALL  CRTMSG
 3      1307 07AC  EB E3                   JMP   MPG7B
 4      1308 07AE  5E              MPG7C:  POP   SI
 5      1309 07AF  5F                      POP   DI
```

```
 6    1310 07B0  48              DEC  AX      ;1=0 ETC
 7    1311 07B1  89 05           MOV  [DI],AX ;POST CH #
 8    1312 07B3  83 C7 02        ADD  DI,2
 9    1313 07B6  57              PUSH DI
10    1314 07B7  56              PUSH SI
11    1315                       ;
12    1316 07B8  A1 0555 R   MPG8: MOV AX,CPOS ;GET LAYER #
14    1317 07BB  B9 0003         MOV  CX,3
15    1318 07BE  F7 E1           MUL  CX      ;GET OFFSET
16    1319 07C0  BF 055D R       MOV  DI,OFFSET DGROUP:LNAME1
17    1320 07C3  03 F8           ADD  DI,AX   ;LAYER NAME ADR
18    1321 07C5  57              PUSH DI
19    1322 07C6  BB 0B26 R       MOV  BX,OFFSET DGROUP:NLYR
20    1323 07C9  BF 4B36 R       MOV  DI,OFFSET DGROUP:BUFF
21    1324 07CC  E8 0000 E       CALL BNASC4  ;LAYER # TO ASCII
22
23    1325 07CF  8B F3           MOV  SI,BX
24    1326 07D1  5F              POP  DI
25    1327 07D2  F3/ A4          REP  MOVSB   ;POST LAYER
26    1328                       ;
27    1329 07D4  C7 06 0000 E 000F  MPG9: MOV MSGNM,15
28    1330 07DA  B8 0007         MOV  AX,7    ;MAX 7 COLORS
29    1331 07DD  E8 0183 R       CALL GETVAL  ;GET COLOR FOR LAYER
31    1332 07E0  72 F2           JC   MPG9    ;JMP IF ERR
32    1333 07E2  8A D8           MOV  BL,AL   ;GET COLOR
33    1334 07E4  80 C3 30        ADD  BL,30H  ;AS ASCII
```

Microsoft (R) Macro Assembler Version 5.10                    8/29/89 12:31:51
CREATES DXF FILE WITH Z AXIS FOR AUTOCAD

```
 7    1335 07E7  A1 0555 R       MOV  AX,CPOS ;GET CURR POS
 8    1336 07EA  BE 056F R       MOV  SI,OFFSET DGROUP:COLTAB
 9    1337 07ED  03 F0           ADD  SI,AX   ;COLOR ADR
10    1338 07EF  88 1C           MOV  [SI],BL ;POST COLOR
11    1339                       ;
12    1340 07F1  FF 06 0555 R    INC  CPOS    ;NEXT POSITION
13    1341 07F5  FF 06 0B26 R    INC  NLYR    ;NEXT LAYER
14    1342 07F9  5E              POP  SI
15    1343 07FA  5F              POP  DI
16    1344 07FB  59              POP  CX
```

```
17      1345 07FC  49                  DEC  CX
18      1346 07FD  74 03               JZ   MPG10      ;JMP IF DONE
19      1347 07FF  E9 0744 R           JMP  MPG5 ;JMP IF MORE
20      1348                           ;
21      1349 0802  B9 0019       MPG10:  MOV  CX,LSECT
22      1350 0805  BA 0000 R           MOV  DX,OFFSET DGROUP:SECT
23      1351 0808  E8 0000 E           CALL WRTFIL     ;START    OF
24 ENTITIES
25      1352 080B  8B 1E 0AFF R        MOV  BX,IHANDL
26      1353 080F  BA 0050             MOV  DX,80      ;40 WORD HEADER
27      1354 0812  89 16 0B2C R        MOV  BYTSRD,DX
28      1355 0816  33 C9               XOR  CX,CX
29      1356 0818  32 C0               XOR  AL,AL
30      1357 081A  B4 42               MOV  AH,42H
31      1358 081C  CD 21               INT  DOSINT     ;SET   START   OF
32 DATA
33      1359 081E  BE 0B36 R           MOV  SI,OFFSET DGROUP:FBUF
34      1360 0821  89 36 0B34 R        MOV  BUFPTR,SI  ;SET INIT BUFF
35 ADR
36      1361                           ;
1       1362 0825  E8 0275 R           CALL MAKBUF     ;CREATE    WRITE
2 BUFFER
3       1363 0828  C7 06 0B22 R 0000   MOV  NTRL,0     ;CLR    TRIAL
4 COUNTER
5       1364 082E  C7 06 0B18 R 0000   MOV  NSMP,0     ;SET   TO   FIRST
6 SAMPLE
7       1365 0834  E8 039F R     MPG12:  CALL FILLBF   ;READ SOME
8 DATA INTO BUFF
9       1366 0837  72 07               JC   MPG20      ;JMP IF END OR
10 ERR
11      1367 0839  E8 044D R           CALL PARSE     ;PROCESS    THE
12 BUFFER
13      1368 083C  72 02               JC   MPG20      ;JMP IF BAD FLAG
14      1369 083E  EB F4               JMP  MPG12
15      1370                           ;
16      1371 0840  B9 0013       MPG20:  MOV  CX,LEOF
17      1372 0843  BA 003F R           MOV  DX,OFFSET DGROUP:EOFILE
18      1373 0846  E8 0000 E           CALL WRTFIL     ;WRT END OF FILE
19      1374 0849  E8 0000 E           CALL CLRHDL     ;CLOSE DXF FILE
20      1375 084C  8B 1E 0AFF R        MOV  BX,IHANDL
21      1376 0850  89 1E 0B01 R        MOV  FHANDL,BX
22      1377 0854  E8 0000 E           CALL CLRHDL     ;CLOSE INPUT FILE
23
24      1378 0857  A1 0AFD R           MOV  AX,HHANDL ;GET    HEADER
25 HANDLE
```

```
     1379 085A  A3 0B01 R            MOV  FHANDL,AX
     1380 085D  E8 01A3 R            CALL WRTHDR      ;WRITE   HEADER
FILE
     1381 0860  E8 0000 E            CALL CLRHDL
     1382 0863  A1 0AF9 R            MOV  AX,PHANDL   ;PARAM HANDLE
     1383 0866  A3 0B01 R            MOV  FHANDL,AX
     1384 0869  E8 021E R            CALL WRTPAR      ;WRITE PARAM FILE 1385 086C  E8 0000 E            CALL CLRHDL
     1386 086F  A1 0B03 R            MOV  AX,SHANDL   ;SCRIPT HANDLE
     1387 0872  A3 0B01 R            MOV  FHANDL,AX
     1388 0875  E8 0248 R            CALL WRTSCR      ;WRITE   SCRIPT
FILE
     1389 0878  E8 0000 E            CALL CLRHDL
     1390 087B  B4 4C                MOV  AH,4CH
     1391 087D  CD 21                INT  DOSINT
     1392                            ;
```

`HMicrosoft (R) Macro Assembler Version 5.10                    8/29/89 12:31:51
CREATES DXF FILE WITH Z AXIS FOR AUTOCAD                        Page 1-25

1393 087F                       CODE ENDS
     1394                            END  START

1133 Source  Lines
   1133 Total   Lines
    227 Symbols

47086 + 366653 Bytes symbol space free

0 Warning Errors
       0 Severe  Errors

PROGRAM LISTING: CRT03MN
DATE: 9/7/89
`HMicrosoft (R) Macro Assembler Version 5.10                    9/2/89 09:09:28

CRT LIBRARY ROUTINES                                            Page 1-1

```
10       1                    .8086
11       2                       NAME    CRT03MN
12       3                       PAGE    62,120
13       4                       TITLE   CRT LIBRARY ROUTINES
14       5                       ;
15       6                    COMMENT *
16       7
17  ;;;;;;;;;;;;;;;;;;;;;;;;;;;;;;;;;;;;;;;;;;;;;;;;;;;;;;;;;;;;
18       8                       COPYRIGHT (C) 1989 GESTRON ENGRG. ALL
19  RIGHTS RESERVED. NO PART OF
20       9                       PUBLICATION  OR  PROGRAM  MAY  BE
21  TRANSCRIBED,REPRODUCED, TRANSMITTED,
22       10                      OR  TRANSLATED  INTO  ANY  LANGUAGE  OR
23  COMPUTER LANGUAGE BY ANY MEANS:
24       11                      ELECTRONIC,   MECHANICAL,   MAGNETIC,
25  CHEMICAL, OPTICAL, MANUAL OR
26       12                      OTHERWISE OR IN ANY FORM, WITHOUT THE
27  PRIOR WRITTEN PERMISSION OF
28       13                      G. E. SOMERVILLE, 7315 BROCADE DRIVE,
29  CITRUS HEIGHTS CALIF. 95621.
30       14
31  ;;;;;;;;;;;;;;;;;;;;;;;;;;;;;;;;;;;;;;;;;;;;;;;;;;;;;;;;;;;;
32       15
33       16
34  ;;;;;;;;;;;;;;;;;;;;;;;;;;;;;;;;;;;;;;;;;;;;;;;;;;;;;;;;;;;;
35  ;;;
 1       17                      LICENSE  TO  USE  THESE  ROUTINES  WITH
 2  PROGRAMS WRITTEN BY G. E. SOMERVILLE
 3       18                      FOR GEOLOW PARTNERS IS GRANTED TO GEOLOW
 4  PARTNERS BY G. E. SOMERVILLE
 5       19
 6  ;;;;;;;;;;;;;;;;;;;;;;;;;;;;;;;;;;;;;;;;;;;;;;;;;;;;;;;;;;;;
 7  ;;;
 8       20                   *
 9       21 = 0010             ROMVID    EQU     10H
10       22                       ;
11       23                    DGROUP    GROUP   DATA
12       24 0000               DATA      SEGMENT  PUBLIC    'DATA'
13       25 0000               DATA      ENDS
14       26                    CGROUP    GROUP   CODE
15       27 0000               CODE      SEGMENT  PUBLIC    'CODE'
16       28                              ASSUME
17  CS:CGROUP,DS:DGROUP,SS:DGROUP
18       29                       ;
19       30                       EXTRN    CRTMSG:NEAR
```

```
31              ;
32              PUBLIC    DISCMD
33              ;
34              COMMENT *
35              DESCRIPTION: DISPLAYS COMMAND MESSAGE AND CHECKS CURSOR
36              INPUT:     MSGNUM=MESSAGE NUMBER
37              OUTPUT:
38              DATA:
39              REGISTERS: AX,BX,CX,DX,SI
40              *
41 0000                 DISCMD    PROC NEAR
42 0000 B4 15               MOV  AH,15H
43 0002 CD 10               INT  ROMVID    ;GET MODE
44 0004 3C 02               CMP  AL,2
45 0006 74 17               JE   DISC2     ;JMP IF TEXT
46 0008 B4 03           DISC1:  MOV  AH,3
47 000A 32 FF               XOR  BH,BH
48 000C CD 10               INT  ROMVID    ;GET CRS POSITION
49 000E 80 FE 17            CMP  DH,23
50 0011 72 0C               JC   DISC2     ;JMP IF LINE 15-22
51 0013 FE CE               DEC  DH        ;ELSE DROP A LINE
52 0015 B0 01               MOV  AL,1
53 0017 E8 0023 R           CALL SCRLGR    ;SCROLL ONE LINE
54 001A E8 009B R           CALL SETCRS
55 001D EB E9               JMP  DISC1     ;TRY AGAIN
56                  ;
57 001F E8 0000 E   DISC2:  CALL CRTMSG    ;MSG TO CRT
58 0022 C3                  RET
```

`HMicrosoft (R) Macro Assembler Version 5.10                9/2/89 09:09:28

CRT LIBRARY ROUTINES                                            Page 1-2

```
59 0023                 DISCMD    ENDP
60              ;
61              COMMENT *
62              DESCRIPTION: SEE INDIVIDUAL ROUTINES
63              INPUT:       SEE INDIVIDUAL ROUTINES
64              OUTPUT:
```

```
 14    65                     DATA:
 15    66                     REGISTERS:    SEE INDIVIDUAL ROUTINES
 16    67                     *
 17    68                           ;THIS PROCEDURE SCROLLS THE LOWER
 18 PORTION
 19    69                           ;OF GRAPHICS DISPLAY PER VALUE IN AL.
 20
 21    70                           ;USES REGS AX,BX,CX
 22    71                     PUBLIC   SCRLGR
 23    72 0023                SCRLGR   PROC NEAR
 24    73 0023 52             PUSH DX      ;HOLD CURR ROW
 25    74 0024 B5 0F                MOV  CH,15    ;UPPER LINE
 26    75 0026 B6 18                MOV  DH,24    ;LOWER LINE
 27    76 0028 32 C9                XOR  CL,CL    ;LEFT COLUMN
 28    77 002A B2 36                MOV  DL,54    ;RIGHT COL
 29    78 002C B4 06                MOV  AH,6 ;SCROLL UP
 30    79 002E 32 FF                XOR  BH,BH
 31    80 0030 CD 10                INT  ROMVID   ;BLANK LINE 24
 32    81 0032 5A             POP  DX      ;RETRIEVE CURR ROW
 33    82 0033 C3             RET
 34    83 0034                SCRLGR   ENDP
 35    84                     ;
  1    85                           ;THIS PROCEDURE CHECKS THE CURRENT
  2 CURSOR POSITION
  3    86                           ;AND SCROLLS UP IF AT BOTTOM.
  4    87                           ;USES REGS  AX,BX,CX,DX
  5    88                     PUBLIC   CHKCRS,SCLGRF,CLRTXT,CLRGRF
  6
  7    89 0034                CHKCRS   PROC NEAR
  8    90 0034 B4 0F                MOV  AH,15
  9    91 0036 CD 10                INT  ROMVID   ;GET VIDEO MODE
 10    92 0038 3C 06                CMP  AL,6
 11    93 003A 74 03                JZ   CURS0    ;JMP IF HR
 12 GRAPHICS
 13    94 003C EB 21 90             JMP  CURS3    ;ELSE JMP
 14 TEXT MODE
 15    95 003F B4 03          CURS0:   MOV AH,3
 16    96 0041 32 FF                XOR  BH,BH
 17    97 0043 CD 10                INT  ROMVID   ;GET CURR CURSOR
 18 POS
 19    98 0045 80 FE 0F             CMP  DH,15
 20    99 0048 72 0E                JC   CURS2    ;JMP IF BELOW
 21 LINE 15
 22   100 004A 80 FE 17             CMP  DH,23
```

```
23      101 004D  73 09              JNC   CURS2      ;JMP IF 23 OR
24 HIGHER
25      102 004F  80 FA 00           CMP   DL,0 ;CHK COL
26      103 0052  74 46              JZ    CRSRET     ;JMP IF 0
27      104 0054  FE C6               INC  DH    ;BUMP ROW
28      105 0056  EB 3F               JMP  SHORT CURS5    ;SET NEW ROW
29
30      106                          ;
31      107 0058  B0 01        CURS2: MOV  AL,1 ;ONE LINE
32      108 005A  E8 0023 R          CALL  SCRLGR     ;SCROLL UP
33      109 005D  EB 38              JMP   SHORT CURS5    ;SET CURSOR
34      110                          ;
35      111 005F  B4 03        CURS3: MOV  AH,3
36      112 0061  32 FF              XOR   BH,BH
 1      113 0063  CD 10              INT   ROMVID     ;GET CURR CURSOR
 2 POS
 3      114 0065  80 FE 18           CMP   DH,24
 4      115 0068  73 09              JNC   CURS4      ;JMP IF 24 OR
 5 HIGHER
 6      116 006A  80 FA 00           CMP   DL,0 ;CHK COL
 7
 1 ^HMicrosoft (R) Macro Assembler Version 5.10                9/2/89
 2 09:09:28
 3
 4 CRT LIBRARY ROUTINES                                         Page
 5 1-3
 6
 7
 8      117 006D  74 2B              JZ    CRSRET     ;JMP IF 0
 9      118 006F  FE C6              INC   DH    ;BUMP ROW
10      119 0071  EB 24              JMP   SHORT CURS5    ;SET NEW ROW
11
12      120                          ;
13      121 0073  B0 01        CURS4: MOV  AL,1 ;ONE LINE
14      122 0075  B7 07              MOV   BH,7
15      123 0077  EB 10              JMP   SHORT SCRL
16      124                          ;
17      125                          ;THIS IS A PARTIAL TEXT CLEAR.
18 CH=UPPER LINE
19      126                          ;USES REGS AX,BH,CX,DX
20      127 0079               CLRTXT       LABEL       NEAR
21      128 0079  32 C0              XOR   AL,AL
22      129 007B  B7 07              MOV   BH,7
23      130 007D  EB 0C 90           JMP   SCRLT
```

```
24      131                          ;
25      132                          ;THIS IS A PARTIAL GRAPHICS CLEAR.
26 CH=UPPER LINE
27      133                          ;USES REGS   AX,BH,CX,DX
28      134 0080                     CLRGRF     LABEL    NEAR
29      135 0080  32 C0                  XOR   AL,AL
30      136 0082  32 FF                  XOR   BH,BH
31      137 0084  EB 05 90               JMP   SCRLT
32      138                          ;
33      139                          ;THIS IS THE FULL SCREEN GRAPHICS
34 SCROLL. AL=# LINES
35      140                          ;USES REGS   AX,BH,CX,DX
36      141 0087                     SCLGRF     LABEL    NEAR
 1      142 0087  32 FF                  XOR   BH,BH
 2      143                          ;
 3      144                          ;THIS SCROLLS PER AL AND ATRB IN BH
 4      145                          ;USES REGS   AX,BH,CX,DX
 5      146 0089  32 ED              SCRL:  XOR  CH,CH       ;UPPER LINE
 6      147 008B  B6 18              SCRLT: MOV  DH,24       ;LOWER LINE
 7      148 008D  32 C9                  XOR   CL,CL    ;LEFT COLUMN
 8      149 008F  B2 4F                  MOV   DL,79    ;RIGHT COL
 9      150 0091  B4 06                  MOV   AH,6 ;SCROLL UP
10      151 0093  CD 10                  INT   ROMVID   ;BLANK LINES
11      152 0095  B6 18                  MOV   DH,24    ;CURSOR TO LINE
12 24
13      153                          ;
14      154 0097  E8 009B R          CURS5:  CALL SETCRS    ;SET CURSOR
15 POS
16      155 009A  C3                 CRSRET:  RET
17      156 009B                     CHKCRS    ENDP
18      157                          ;
19      158                          COMMENT *
20      159                          DESCRIPTION:   THESE PROCEDURES SET THE
21 CURSOR POSITION
22      160                          INPUT:   DH=ROW.  DL=COL FOR POSCRS. DL
23 ZEROED FOR SETCRS
24      161                          OUTPUT:
25      162                          DATA:
26      163                          REGISTERS:      AX,BX,DX
27      164                          *
28      165                               PUBLIC   SETCRS,POSCRS,FIXCRS,SNDLF
29      166 009B                     SETCRS    PROC NEAR
30      167 009B  32 D2                  XOR   DL,DL
31      168                          ;
32      169                          ;THIS SETS CURSOR TO COL IN DL AND
```

```
33  ROW IN DH
34      170 009D                      POSCRS    LABEL      NEAR
35      171 009D   B4 02                MOV  AH,2
36      172 009F   32 FF                XOR  BH,BH
 1      173 00A1   CD 10                INT  ROMVID     ;SET CURSOR LINE
 2      174 00A3   C3                 RET
 3

1  ^HMicrosoft (R) Macro Assembler Version 5.10                    9/2/89
 2  09:09:28
 3
 4  CRT LIBRARY ROUTINES                                            Page
 5  1-4
 6
 7
 8      175 00A4                      SETCRS    ENDP
 9      176                           ;
10      177                           ;THIS PROCEDURE FIXES CURSOR POSITION
11
12      178 00A4                      FIXCRS    PROC NEAR
13      179 00A4   B4 0F                MOV  AH,0FH
14      180 00A6   CD 10                INT  ROMVID     ;GET VIDEO MODE
15      181 00A8   3C 06                CMP  AL,6
16      182 00AA   75 17                JNZ  FIXRET     ;JMP IF TEXT
17      183 00AC   B4 03              FIX1:   MOV  AH,3
18      184 00AE   32 FF                XOR  BH,BH
19      185 00B0   CD 10                INT  ROMVID     ;GET   CURSOR
20  POSITION
21      186 00B2   80 FE 17             CMP  DH,23
22      187 00B5   72 0C                JC   FIXRET     ;JMP IF     LINE
23  15-22
24      188 00B7   FE CE                DEC  DH   ;ELSE DROP A LINE
25      189 00B9   B0 01                MOV  AL,1
26      190 00BB   E8 0023 R            CALL SCRLGR    ;SCROLL ONE LINE
27      191 00BE   E8 009B R            CALL SETCRS    ;SET CURSOR POS
28      192 00C1   EB E9                JMP  FIX1 ;TRY AGAIN
29      193                           ;
30      194 00C3   C3               FIXRET:   RET
31      195 00C4                      FIXCRS    ENDP
32      196                           ;
33      197                           ;THIS PROCEDURE SENDS A LINE FEED
34  THEN CHECKS CURSOR
35      198 00C4                      SNDLF     PROC NEAR
36      199 00C4   B0 0A                MOV  AL,0AH
```

```
 207                              5,218,530                              208
200 00C6  B4 0E              MOV     AH,0EH
201 00C8  B3 07              MOV     BL,7
202 00CA  CD 10              INT     ROMVID     ;SEND LF
203 00CC  E8 0034 R          CALL    CHKCRS
204 00CF  C3                 RET
205 00D0                     SNDLF   ENDP
206                          ;
207 00D0                     CODE    ENDS
208                          END

208 Source  Lines
    208 Total   Lines
     33 Symbols

47350 + 388917 Bytes symbol space free

0 Warning Errors
      0 Severe  Errors
```

1 PROGRAM LISTING: CVN03MN
2 DATE: 9/7/89
3 ^HMicrosoft (R) Macro Assembler Version 5.10                                9/2/89
4 09:11:14
5
6 CONVERSION LIBRARY ROUTINES                                                  Page
7 1-1
8
9
10        1                   .8086
11        2                           NAME    CVN03MN
12        3                           PAGE    62,120
13        4                           TITLE   CONVERSION LIBRARY ROUTINES
14
15        5                           ;
16        6                           COMMENT *
17        7
18 ;;;;;;;;;;;;;;;;;;;;;;;;;;;;;;;;;;;;;;;;;;;;;;;;;;;;;;;;;;;;;;;
19        8                           COPYRIGHT (C) 1989 GESTRON ENGRG. ALL
20 RIGHTS RESERVED. NO PART OF
21        9                           PUBLICATION   OR    PROGRAM    MAY   BE
22 TRANSCRIBED, REPRODUCED, TRANSMITTED,
23       10                           OR   TRANSLATED   INTO   ANY   LANGUAGE   OR
24 COMPUTER LANGUAGE BY ANY MEANS:
25       11                           ELECTRONIC,    MECHANICAL,    MAGNETIC,
26 CHEMICAL, OPTICAL, MANUAL OR
27       12                           OTHERWISE OR IN ANY FORM, WITHOUT THE

```
28 PRIOR WRITTEN PERMISSION OF
29      13                    G. E. SOMERVILLE, 7315 BROCADE DRIVE,
30 CITRUS HEIGHTS CALIF. 95621.
31      14
32 ;;;;;;;;;;;;;;;;;;;;;;;;;;;;;;;;;;;;;;;;;;;;;;;;;;;;;;;;;;;;;
33      15
34      16
35 ;;;;;;;;;;;;;;;;;;;;;;;;;;;;;;;;;;;;;;;;;;;;;;;;;;;;;;;;;;;;;;;
36 ;;;
1       17                    LICENSE TO USE THESE ROUTINES WITH
2  PROGRAMS WRITTEN BY G. E. SOMERVILLE
3       18                    FOR GEOLOW PARTNERS IS GRANTED TO GEOLOW
4  PARTNERS BY G. E. SOMERVILLE
5       19
6  ;;;;;;;;;;;;;;;;;;;;;;;;;;;;;;;;;;;;;;;;;;;;;;;;;;;;;;;;;;;;;;;
7  ;;;
8       20                        *
9       21                    DGROUP    GROUP    DATA
10      22 0000                DATA SEGMENT    PUBLIC    'DATA'
11      23                        ;
12      24 0000  0000           BUF1 DW    ?
13      25 0002  0000           BUF2 DW    ?
14      26 0004  0000           BUF3 DW    ?
15      27 0006  0007[          BUF7 DB    7 DUP(?)
16      28       ??
17      29             ]
18      30
19      31 000D  00         NFLG DB    ?
20      32 000E  0000           HGHW DW    ?
21      33 0010  0000           LOWW DW    ?
22      34 0012  0000           RSLT DW    ?
23      35 0014  0000                DW    ?
24      36                        ;
25      37                    EXTRN    BUFF:BYTE,MSGNM:WORD
26      38                        ;
27      39 0016               DATA ENDS
28      40                    CGROUP    GROUP    CODE
29      41 0000               CODE SEGMENT    PUBLIC    'CODE'
30      42                    ASSUME
31 CS:CGROUP,DS:DGROUP,SS:DGROUP
32      43                        ;
33      44                    PUBLIC
34 ASCBIN,BCD8B,BCD16B,BCDAGN,BCD24B,BINASC,BINDEC
35      45                    PUBLIC
36 BNASC4,BNASC6,BNASC8,BLKZ8C,BLKZRO,DV16B8,D16B16
```

```
46              PUBLIC
D24B16,D32B16,D32B24,D32B32,HEXASC,UPRCAS
47              ;
48              COMMENT *
49              DESCRIPTION: THIS CONVERTS A 16 BIT BINARY TO ASCII AND
50                           BLANKS LEADING ZEROES. LIMITED TO 9,999
51              INPUT: BX=ADR OF 16 BIT. DI=DEST ADR FOR ASCII.
52              OUTPUT: BX=ADR OF 1ST NON-0 CHAR. CX=# CHARS FOR BX.
53              DATA: ONE WORD
54              REGISTERS: AX,BX,CX,DX,DI
55              *
56 0000         BNASC4   PROC NEAR
57 0000  57             PUSH DI    ;HOLD DEST ADR
58 0001  57             PUSH DI    ;HOLD DEST ADR AGAIN
```

Microsoft (R) Macro Assembler Version 5.10                9/2/89 09:11:14

CONVERSION LIBRARY ROUTINES                               Page 1-2

```
59 0002  E8 024D R      CALL BINDEC    ;BIN TO BCD
60 0005  A3 0004 R      MOV  BUF3,AX   ;RESULTS TO TEMPY BUFFER
61 0008  BB 0005 R      MOV  BX, OFFSET DGROUP:BUF3+1  ;HIGH BYTE ADR
62 000B  5F             POP  DI        ;DEST ADR
63 000C  B9 0002        MOV  CX,2      ;2 BYTES
64 000F  E8 0210 R      CALL HEXASC    ;BCD TO ASC
65 0012  5F             POP  DI        ;DEST ADR
66 0013  B9 0004        MOV  CX,4      ;4 BYTES
67 0016  E8 0235 R      CALL BLKZRO    ;BLANK 0'S
68 0019  C3             RET
69 001A         BNASC4   ENDP
70              ;
71              COMMENT *
72              DESCRIPTION: THIS PROCEDURE CONVERTS A SERIES OF 16 BIT BINARY
73                           WORDS TO A SERIES OF 6 ASCII
```

```
                                     CHARS WITH 1ST CHAR BLANK.
        74                  INPUT:    BX=SOURCE ADR OF BINARY WORD
TABLE.
        75                             DI=DEST ADR FOR ASCII. SI=DEST ADR
OFFSET FOR SERIES.
        76                             CX=NUMBER OF WORDS TO TRANSFER.
        77                  OUTPUT:   DI=DEST ADR FOR NEXT SERIES
        78                  DATA:     TWO WORDS
        79                  REGISTERS: AX,BX,CX,DX,DI,SI
        80                  *
        81 001A                       BNASC6   PROC NEAR
        82 001A 51          BNA1:     PUSH  CX    ;HOLD COUNT
        83 001B 57                    PUSH  DI    ;HOLD DEST ADR
        84 001C 53                    PUSH  BX    ;HOLD SOURCE
        85 001D 57                    PUSH  DI    ;HOLD DEST ADR
        86 001E 57                    PUSH  DI    ;HOLD DEST ADR AGAIN
        87 001F E8 024D R             CALL  BINDEC    ;BIN TO BCD
        88 0022 A3 0000 R             MOV   BUF1,AX   ;RESULTS TO TEMPY
BUFFER
        89 0025 89 16 0002 R          MOV   BUF2,DX   ;REMAINDER
        90 0029 BB 0002 R             MOV   BX,OFFSET DGROUP:BUF2
;BYTE 3 ADR
        91 002C 5F                    POP   DI    ;DEST ADR
        92 002D B9 0003               MOV   CX,3  ;3 BYTES
        93 0030 E8 0210 R             CALL  HEXASC    ;BCD TO ASC
        94 0033 5F                    POP   DI    ;DEST ADR
        95 0034 B9 0006               MOV   CX,6  ;6 DIGITS
        96 0037 E8 0235 R             CALL  BLKZRO    ;BLANK  LEADING
ZEROES
        97 003A 5B                    POP   BX
        98 003B 83 C3 02              ADD   BX,2  ;BUMP SOURCE ADR
        99 003E 5F                    POP   DI    ;GET ORIG DEST ADR
       100 003F 03 FE                 ADD   DI,SI    ;BUMP DEST ADR
       101 0041 59                    POP   CX
       102 0042 E2 D6                 LOOP  BNA1  ;JMP IF MORE
       103 0044 C3                    RET
       104 0045                       BNASC6    ENDP
       105                            ;
       106                  COMMENT *
       107                  DESCRIPTION: THIS CONVERTS A 24 BIT
BINARY TO ASCII AND
       108                             BLANKS LEADING ZEROES AND ADDS
TERMINATER
       109                  INPUT:    BX=ADR OF 32 BIT WORD. DI=DEST
```

```
34  ADR
35       110                        OUTPUT:   DI=ORIG DEST ADR. BX=ADR OF 1ST
36  NON-0 CHAR
 1       111                                  CX=# CHARS AFTER BX
 2       112                        DATA:
 3       113                        REGISTERS:   AX,BX,CX,DX,DI,SI
 4       114                        *
 5       115 0045                   BNASC8    PROC NEAR
 6       116 0045  57                         PUSH DI    ;HOLD DEST ADR
 7
 1  ^HMicrosoft (R) Macro Assembler Version 5.10                          9/2/89
 2  09:11:14
 3
 4  CONVERSION LIBRARY ROUTINES                                           Page
 5  1-3
 6
 7
 8       117 0046  E8 0208 R                  CALL BINASC    ;CONVERT
 9       118 0049  C6 05 24                   MOV  BYTE PTR[DI],'$'
10  ;ADD TERMINATOR
11       119 004C  5F                POP  DI    ;GET ORIG DEST ADR
12       120 004D  57                PUSH DI
13       121 004E  E8 0232 R                  CALL BLKZ8C    ;BLANK LEADING
14  ZEROES
15       122 0051  5F                POP  DI
16       123 0052  C3                RET
17       124 0053                    BNASC8    ENDP
18       125                         ;
19       126                         COMMENT *
20       127                         DESCRIPTION:   THESE ARE INTEGER DIVISION
21  ROUTINES
22       128                         INPUT:   CL:BX BX OR BL =DIVISOR.  DX:AX
23  OR DL:AX OR AX =DIVIDEND
24       129                         OUTPUT: DX:AX
25       130                         DATA:  9 BYTES
26       131                         REGISTERS:   AX,BX,CX,DX,SI
27       132                         *
28       133                         ;LOW    LEVEL    ROUTINES.    USES
29  AX,BX,CL,DX,SI
30       134                         ;8 TO 16 BIT DIVISOR. 16 TO 32 BIT
31  DIVIDEND
32       135 0053                    D32B16    LABEL   NEAR
33       136 0053  C6 06 000D R 00             MOV  NFLG,0    ;SET POS
34  FLAG
35       137 0058  0A F6                       OR   DH,DH
```

```
138  005A  79 39                    JNS   POSNM      ;JMP  IF  POS NUMBER
139  005C  EB 1E                    JMP   SHORT NEGNM
140                          ;
141  005E                    D24B16 LABEL NEAR
142  005E  32 F6                    XOR   DH,DH      ;DL=MSB
143  0060  C6 06 000D R 00          MOV   NFLG,0     ;SET  POS  FLAG
144  0065  0A D2                    OR    DL,DL
145  0067  79 2C                    JNS   POSNM      ;JMP  IF  POS NUMBER
146  0069  F6 D6                    NOT   DH         ;EXTEND SIGN
147  006B  EB 0F                    JMP   SHORT NEGNM
148                          ;
149  006D                    DV16B8 PROC  NEAR
150  006D  32 FF                    XOR   BH,BH      ;BL=DVSR
151  006F                    D16B16 LABEL NEAR
152  006F  33 D2                    XOR   DX,DX      ;DX=0
153  0071  C6 06 000D R 00          MOV   NFLG,0     ;SET  POS  FLAG
154  0076  0A E4                    OR    AH,AH
155  0078  79 1B                    JNS   POSNM      ;JMP  IF  POS NUMBER
156  007A  F7 D2                    NOT   DX         ;EXTEND SIGN
157                          ;
158  007C  83 FB 00                 NEGNM: CMP  BX,0
159  007F  75 05                    JNE   FXNEG      ;JMP IF GOOD DVSR
160  0081  33 C0                    ZRORET: XOR AX,AX
161  0083  33 D2                    XOR   DX,DX
162  0085  C3                       RET
163                          ;
164  0086  C6 06 000D R 01          FXNEG: MOV  NFLG,1    ;NEG  FLAG
165  008B  F7 D0                    NOT   AX         ;2'S COMPLEMENT
166  008D  F7 D2                    NOT   DX
167  008F  05 0001                  ADD   AX,1
168  0092  83 D2 00                 ADC   DX,0
169                          ;
170  0095                    POSNM  LABEL NEAR
171  0095  83 FB 00                 CMP   BX,0
172  0098  75 02                    JNE   POS1 ;JMP IF NOT DIV BY ZERO
```

```
173 009A  EB E5                    JMP   ZRORET
174                          ;
```

Microsoft (R) Macro Assembler Version 5.10                    9/2/89
09:11:14

CONVERSION LIBRARY ROUTINES                                    Page 1-4

```
175 009C  8B C8            POS1:   MOV   CX,AX
176 009E  0B CA                    OR    CX,DX
177 00A0  75 01                    JNZ   POS2     ;JMP IF NOT ZERO DVND
178 00A2  C3                       RET
179 00A3  57               POS2:   PUSH  DI
180 00A4  56                       PUSH  SI
181 00A5  33 FF                    XOR   DI,DI    ;CLR RESULT
182 00A7  33 F6                    XOR   SI,SI
183 00A9  B9 0010                  MOV   CX,16    ;16 SHIFTS
184 00AC  F6 C7 80         NRM8D:  TEST  BH,80H
185 00AF  75 05                    JNZ   NRM8X    ;JMP IF NORMALZD
186 00B1  D1 E3                    SHL   BX,1
187 00B3  41                       INC   CX
188 00B4  EB F6                    JMP   NRM8D
189                          ;
190 00B6  F6 C6 80         NRM8X:  TEST  DH,80H
191 00B9  75 07                    JNZ   CHK8N    ;JMP IF NORMALZD
192 00BB  D1 E0                    SHL   AX,1
193 00BD  D1 D2                    RCL   DX,1
194 00BF  49                       DEC   CX
195 00C0  EB F4                    JMP   NRM8X
196                          ;
197 00C2  F6 C5 80         CHK8N:  TEST  CH,80H
198 00C5  74 08                    JZ    D8AGN    ;JMP IF NOT NEG
199 00C7  C6 06 000D R 00          MOV   NFLG,0
200 00CC  EB 45 90                 JMP   DONE8
201                          ;
202 00CF  89 16 000E R     D8AGN:  MOV   HGHW,DX  ;HOLD DVND
203 00D3  A3 0010 R                MOV   LOWW,AX
204 00D6  2B D3                    SUB   DX,BX    ;SUBT DVSR
205 00D8  73 0A                    JNC   OKAY8    ;JMP IF BORROW
206 00DA  8B 16 000E R             MOV   DX,HGHW  ;RESTORE DVND
207 00DE  A1 0010 R                MOV   AX,LOWW
208 00E1  EB 07 90                 JMP   SHFT8
```

```
209                           ;
210 00E4  83 C6 01        OKAY8:  ADD  SI,1    ;1 TO RESULT 211 00E7  83 D7 00                ADC  DI,0
212 00EA  0B C9           SHFT8:  OR   CX,CX
213 00EC  74 25                   JZ   DONE8    ;JMP IF NO SHIFTS 214 00EE  D1 E6                   SHL  SI,1    ;SHIFT RESULT
215 00F0  D1 D7                   RCL  DI,1
216 00F2  D1 E0                   SHL  AX,1    ;SHIFT DVND
217 00F4  D1 D2                   RCL  DX,1
218 00F6  73 08                   JNC  CHK8    ;JMP IF NO OVERFLOW
219 00F8  83 C6 01                ADD  SI,1    ;1 TO RESULT
220 00FB  83 D7 00                ADC  DI,0
221 00FE  2B D3                   SUB  DX,BX   ;SUBT DVSR
222 0100  A3 000E R       CHK8:   MOV  HGHW,AX
223 0103  09 16 000E R            OR   HGHW,DX
224 0107  74 08                   JZ   ZRO8    ;JMP IF ZERO DVND
225 0109  E2 C4                   LOOP D8AGN   ;JMP IF MORE
226 010B  EB 06                   JMP  SHORT DONE8
227                           ;
228 010D  D1 E6           Z8AGN:  SHL  SI,1    ;SHIFT RESULT
229 010F  D1 D7                   RCL  DI,1
230 0111  E2 FA           ZRO8:   LOOP Z8AGN   ;JMP IF MORE

231                           ;
232 0113  8B C6           DONE8:  MOV  AX,SI   ;GET RESULT
```

Microsoft (R) Macro Assembler Version 5.10        9/2/89 09:11:14

CONVERSION LIBRARY ROUTINES                       Page 1-5

```
233 0115  8B D7                   MOV  DX,DI
234 0117  80 3E 000D R 00         CMP  NFLG,0
235 011C  74 0A                   JE   POS8    ;JMP IF POS NUMBER
236 011E  F7 D0                   NOT  AX      ;ELSE 2'S COMP
237 0120  F7 D2                   NOT  DX
238 0122  05 0001                 ADD  AX,1
239 0125  83 D2 00                ADC  DX,0
240 0128  5E              POS8:   POP  SI
241 0129  5F                      POP  DI
```

```
17      242 012A  C3                        RET
18      243                                 ;
19      244 012B                  DV16B8    ENDP
20      245                                 ;
21      246                       ;HIGH     LEVEL     ROUTINES.    USES
        AX,BX,CX,DX,SI
23      247                       ;24 BIT DIVISOR. 32 BIT DIVIDEND
24      248 012B                  D32B24    PROC NEAR
25      249 012B  32 ED                     XOR  CH,CH     ;CL:BX=DVSR
26      250 012D                  D32B32    LABEL    NEAR
27      251 012D  C6 06 000D R 00           MOV  NFLG,0    ;SET  FLAG
        TO POSITIVE NMBR
29      252 0132  0B D2                     OR   DX,DX
30      253 0134  79 0E                     JNS  NUMPOS    ;JMP IF POS
31      254 0136  F6 16 000D R              NOT  NFLG ;ELSE NEG FLAG
32      255 013A  F7 D0                     NOT  AX   ;2'S COMPLEMENT
33      256 013C  F7 D2                     NOT  DX
34      257 013E  05 0001                   ADD  AX,1
35      258 0141  83 D2 00                  ADC  DX,0
36      259 0144  83 F9 00       NUMPOS:    CMP  CX,0
1       260 0147  75 03                     JNZ  DIV32     ;JMP IF NOT 16
        BIT DVSR
3       261 0149  E9 0095 R                 JMP  POSNM     ;PROCESS AS 16
        BIT DVSR
5       262                                 ;
6       263 014C  57             DIV32:     PUSH DI
7       264 014D  56                        PUSH SI
8       265 014E  8B F0                     MOV  SI,AX
9       266 0150  0B F2                     OR   SI,DX
10      267 0152  75 03                     JNZ  DIVOK     ;JMP IF NOT ZERO
        DVND
12      268 0154  5E                        POP  SI
13      269 0155  5F                        POP  DI
14      270 0156  C3                        RET
15      271                                 ;
16      272 0157  BF 0012 R      DIVOK:     MOV  DI,OFFSET DGROUP:RSLT
17      273 015A  C7 05 0000                MOV  WORD PTR [DI],0    ;CLR
        RESLUT
19      274 015E  C7 45 02 0000             MOV  WORD PTR [DI+2],0
20      275 0163  8B F1                     MOV  SI,CX    ;SI:BX=DVSR
21      276 0165  B9 0020                   MOV  CX,32    ;32 SHIFTS
22      277 0168  F6 C5 80       NRM32D:    TEST CH,80H
23      278 016B  75 07                     JNZ  NRM32X    ;JMP IF NORMLZD
24      279 016D  D1 E3                     SHL  BX,1
25      280 016F  D1 D6                     RCL  SI,1
```

```
26    281 0171  41              INC  CX
27    282 0172  EB F4           JMP  NRM32D
28    283                   ;
29    284 0174  F6 C6 80        NRM32X:  TEST DH,80H
30    285 0177  75 07           JNZ  CHK32N    ;JMP IF NORMLZD
31    286 0179  D1 E0           SHL  AX,1
32    287 017B  D1 D2           RCL  DX,1
33    288 017D  49          DEC  CX
34    289 017E  EB F4           JMP  NRM32X
35    290                   ;
36
```

Microsoft (R) Macro Assembler Version 5.10                              9/2/89
09:11:14

CONVERSION LIBRARY ROUTINES                                             Page 1-6

```
 8    291 0180  F6 C5 80        CHK32N:  TEST CH,80H
 9    292 0183  74 08           JZ   D32AGN    ;JMP IF NOT NEG
10    293 0185  C6 06 000D R 00 MOV  NFLG,0
11    294 018A  EB 4D 90        JMP  DONE32
12    295                   ;
13    296 018D  89 16 000E R    D32AGN:  MOV HGHW,DX   ;HOLD DVND
14    297 0191  A3 0010 R       MOV  LOWW,AX
15    298 0194  2B C3           SUB  AX,BX     ;SUBT DVSR
16    299 0196  1B D6           SBB  DX,SI
17    300 0198  73 0A           JNC  OKAY32    ;JMP IF BORROW
18    301 019A  8B 16 000E R    MOV  DX,HGHW   ;RESTORE DVND
19    302 019E  A1 0010 R       MOV  AX,LOWW
20    303 01A1  EB 08 90        JMP  SHFT32
21    304                   ;
22    305 01A4  83 05 01        OKAY32:  ADD WORD PTR
23 [DI],1 ;1 TO RESULT
24    306 01A7  83 55 02 00     ADC  WORD PTR [DI+2],0
25    307 01AB  0B C9           SHFT32:  OR CX,CX
26    308 01AD  74 2A           JZ   DONE32    ;JMP IF NO SHIFTS
27
28    309 01AF  D1 25           SHL  WORD PTR [DI],1   ;SHIFT
29 RESULT
30    310 01B1  D1 55 02        RCL  WORD PTR [DI+2],1
31    311 01B4  D1 E0           SHL  AX,1 ;SHIFT DVND
32    312 01B6  D1 D2           RCL  DX,1
33    313 01B8  73 0B           JNC  CHK32     ;JMP IF NO
```

```
34          OVERFLOW
35          314 01BA  83 05 01                    ADD   WORD PTR [DI],1     1;
36     TO RESULT
 1          315 01BD  83 55 02 00                 ADC   WORD PTR [DI+2],0
 2          316 01C1  2B C3                       SUB   AX,BX      ;SUBT DVSR
 3          317 01C3  1B D6                       SBB   DX,SI
 4          318 01C5  A3 000E R         CHK32:    MOV   HGHW,AX
 5          319 01C8  09 16 000E R                OR    HGHW,DX
 6          320 01CC  74 09                       JZ    ZRO32      ;JMP IF ZERO DVND
 7
 8          321 01CE  E2 BD                       LOOP  D32AGN     ;JMP IF MORE
 9          322 01D0  EB 07                       JMP   SHORT DONE32
10          323                                   ;
11          324 01D2  D1 25             Z32AGN:   SHL   WORD PTR [DI],1
12     ;SHIFT RESULT
13          325 01D4  D1 55 02                    RCL   WORD PTR [DI+2],1
14          326 01D7  E2 F9             ZRO32:    LOOP  Z32AGN     ;JMP IF MORE
15
16          327                                   ;
17          328 01D9  8B 05             DONE32:   MOV   AX,[DI]    ;GET RESULT
18          329 01DB  8B 55 02                    MOV   DX,[DI+2]
19          330 01DE  80 3E 000D R 00             CMP   NFLG,0
20          331 01E3  74 0A                       JE    POS32      ;JMP IF POS
21     NUMBER
22          332 01E5  F7 D0                       NOT   AX         ;ELSE 2'S COMP
23          333 01E7  F7 D2                       NOT   DX
24          334 01E9  05 0001                     ADD   AX,1
25          335 01EC  83 D2 00                    ADC   DX,0
26          336 01EF  5E                POS32:    POP   SI
27          337 01F0  5F                          POP   DI
28          338 01F1  C3                          RET
29          339                                   ;
30          340 01F2                    D32B24    ENDP
31          341                                   ;
32          342                         COMMENT *
33          343                         DESCRIPTION:   THIS  PROCEDURE  MAKES  A
34     STRING UPPER CASE ONLY.
35          344                         INPUT:    DI=ADR. CX=# CHARS.
36          345                         OUTPUT: DI & CX NOT CHANGED
 1          346                         DATA:
 2          347                         REGISTERS:   AL,CX,DI
 3          348                         *
 4
```

`HMicrosoft (R) Macro Assembler Version 5.10    9/2/89 09:11:14

CONVERSION LIBRARY ROUTINES                                    Page 1-7

```
349 01F2              UPRCAS   PROC NEAR
350 01F2  57                   PUSH DI
351 01F3  51                   PUSH CX
352 01F4  8A 05       UC1:     MOV  AL,[DI]   ;GET NXT CHAR
353 01F6  3C 61                CMP  AL,61H
354 01F8  72 08                JB   UC2       ;JMP IF UPPER CASE
355 01FA  3C 7A                CMP  AL,7AH
356 01FC  77 04                JA   UC2       ;JMP IF NOT LOWER CASE 357 01FE  2C 20                SUB  AL,20H    ;MAKE UPPER CASE
358 0200  88 05                MOV  [DI],AL   ;REPLACE
359 0202  47          UC2:     INC  DI
360 0203  E2 EF                LOOP UC1       ;JMP IF MORE
361 0205  59                   POP  CX
362 0206  5F                   POP  DI
363 0207  C3                   RET
364 0208              UPRCAS   ENDP
365                            ;
366                   COMMENT *
367                   DESCRIPTION: BINASC
368                       THIS CONVERTS 24 BIT BINARY TO BCD THEN TO ASCII
369                   INPUT:   BX=ADDRESS OF 32 BIT WORD. DI=ADDRESS OF DEST
370                   OUTPUT: 2 ASCII CHARS FOR EACH BYTE
371                   DATA:
372                   REGISTERS: AX,BX,CX,DX,DI,SI
373                   ;
374                   DESCRIPTION: HEXASC
375                       THIS CONVERTS BCD TO ASCII. CX=# BYTES
376                   INPUT:   BX=SOURCE ADR OF HIGH BYTE. DI=DEST ADR
377                   OUTPUT:  2 ASCII CHARS FOR EACH BYTE
378                   DATA:
379                   REGISTERS: AL,BX,CX,DI
380                            *
```

```
9     381 0208                      BINASC    PROC NEAR
10    382 0208  57                  PUSH DI        ;SAVE DEST
11    383 0209  E8 02CD R           CALL BCD24B    ;GET PACKED BCD
12    384 020C  5F                  POP  DI        ;GET DEST ADR
13    385 020D  B9 0004             MOV  CX,4      ;4 BYTES
14    386                           ;
15    387 0210                      HEXASC    LABEL    NEAR
16    388 0210  51             HA0: PUSH CX        ;HOLD # BYTES
17    389 0211  B9 0002             MOV  CX,2      ;2 PASSES
18    390 0214  8A 07          HA1: MOV  AL,[BX]   ;GET NXT BYTE
19    391 0216  D0 C8               ROR  AL,1      ;SWAP HALVES
20    392 0218  D0 C8               ROR  AL,1
21    393 021A  D0 C8               ROR  AL,1
22    394 021C  D0 C8               ROR  AL,1
23    395 021E  88 07               MOV  [BX],AL   ;HOLD
24    396 0220  24 0F               AND  AL,0FH    ;CLR LEFT
25    397 0222  04 90               ADD  AL,90H
26    398 0224  27                  DAA
27    399 0225  14 40               ADC  AL,40H
28    400 0227  27                  DAA
29    401 0228  88 05               MOV  [DI],AL   ;SAVE ASCII CHAR
30    402 022A  47                  INC  DI        ;BUMP DEST ADR
31    403 022B  E2 E7               LOOP HA1       ;JMP IF ANOTHER PASS
32    404 022D  4B                  DEC  BX        ;BUMP SOURCE
33    405 022E  59                  POP  CX
34    406 022F  E2 DF               LOOP HA0       ;JMP IF MORE BYTES
35
```

^HMicrosoft (R) Macro Assembler Version 5.10                     9/2/89
09:11:14

CONVERSION LIBRARY ROUTINES                                         Page
1-8

```
8     407 0231  C3                  RET
9     408 0232                      BINASC    ENDP
10    409                           ;
11    410                  COMMENT *
12    411                  DESCRIPTION:   THIS BLANKS LEADING ZEROES.
13
14    412                  INPUT:     DI=1ST ADR OF SOURCE. CX=# DIGITS
16    413                  OUTPUT:    BX=1ST NON-ZERO ADR. CX=# DIGITS
```

```
18    414                              DATA:
19    415                              REGISTERS: AL,BX,CX,DI
20    416                              *
21    417  0232                                BLKZ8C    PROC NEAR
22    418  0232  B9 0008                             MOV  CX,8  ;8 DIGITS
23    419                                         ;
24    420  0235                                BLKZRO    LABEL     NEAR
25    421  0235  8A 05                   BLKZ:   MOV  AL,[DI]    ;GET  NEXT
26 CHAR
27    422  0237  3C 20                           CMP  AL,' '
28    423  0239  74 07                           JE   BLNK ;JMP IF SPACE
29    424  023B  3C 30                           CMP  AL,'0'
30    425  023D  75 0B                           JNE  BLKEND    ;JMP IF NOT 0
31    426  023F  C6 05 20                        MOV  BYTE PTR[DI],' '
32 ;RPLCE 0 WITH SPACE
33    427  0242  47              BLNK:   INC  DI   ;BUMP ADR
34    428  0243  E2 F0                   LOOP BLKZ ;JMP IF MORE
35    429  0245  4F              DEC  DI   ;ELSE BACKUP
 1    430  0246  C6 05 30                        MOV  BYTE PTR[DI],'0'
 2 ;AND SET AS 0
 3    431  0249  41                      INC  CX   ;CORRECT
 4    432  024A  8B DF           BLKEND: MOV  BX,DI     ;BX=1ST NON
 5  0 ADR
 6    433  024C  C3              RET
 7    434  024D                          BLKZ8C    ENDP
 8    435                                          ;
 9    436                              COMMENT *
10    437                              DESCRIPTION:  THIS CONVERTS 16 BIT BIN
11 TO PACKED DEC
12    438                              INPUT:    BX=ADDRESS OF 16 BIT
13    439                              OUTPUT:   OUTPUT AX=PACKED BCD (9,999).
14 DL=REMAINDER
15    440                              DATA:
16    441                              REGISTERS: AX,BX,CX,DX,DI
17    442                              *
18    443  024D                                BINDEC    PROC NEAR
19    444  024D  8B 17                          MOV  DX,[BX]  ;GET BIN
20    445  024F  E8 031F R                      CALL BCD16B   ;GET TENS/UNITS
21    446  0252  32 E4                          XOR  AH,AH
22    447  0254  8B F8                          MOV  DI,AX    ;HOLD
23    448  0256  E8 031F R                      CALL BCD16B   ;GET THOU/HUNDS
24    449  0259  8A E0                          MOV  AH,AL    ;TO HIGH BYTE
25    450  025B  32 C0                          XOR  AL,AL    ;CLR LSD
26    451  025D  03 C7                          ADD  AX,DI    ;ADD IN LOW BYTE
```

```
27    452 025F  C3              RET
28    453 0260                  BINDEC  ENDP
29    454                       ;
30    455                       COMMENT $
31    456                       DESCRIPTION:    ;THIS PROCEDURE CONVERTS ASCII TO BINARY.
33    457                       INPUT:   CX=# CHARS (7 MAX). BX=ASCII ADR. SI=BINARY OUT.
35    458                       OUTPUT:  IF DEC POINT & ONE DIGIT, VALUE IS * TEN
 1    459                                IF RESULT OVER 32,767 IT IS AN ERROR
 2    460                                IF ERROR, CY IS SET AND AX=MSG # FOR CRTMSG ROUTINE
 4    461                       DATA:    SEVEN BYTES
 5    462                       REGISTERS: AX,BX,CX,DI,SI
 6    463                       $
 7    464 0260                  ASCBIN   PROC NEAR
```

Microsoft (R) Macro Assembler Version 5.10         9/2/89 09:11:14

CONVERSION LIBRARY ROUTINES                                Page 1-9

```
 8    465 0260  BE 0000          MOV  SI,0   ;CLR RESULT
 9    466 0263  32 E4            XOR  AH,AH  ;SET TO NO DEC POINT
11    467 0265  80 F9 00         CMP  CL,0
12    468 0268  75 02            JNZ  ASB1   ;JMP IF ENTRY
13    469 026A  F8               CLC
14    470 026B  C3               RET         ;ELSE RET ZERO
15    471                        ;
16    472 026C  BE 0006 R   ASB1:  MOV  SI,OFFSET DGROUP:BUF7
17    473 026F  51             PUSH CX    ;HOLD # DIGITS
18    474 0270  8A 07       ASB2:  MOV  AL,[BX]  ;GET NEXT DIGIT
20    475 0272  3C 2E            CMP  AL,'.'
21    476 0274  75 10            JNE  ASB2A     ;JMP IF NOT DEC POINT
23    477 0276  B4 01            MOV  AH,1  ;SET FOR DEC PNT
24    478 0278  80 F9 02         CMP  CL,2
25    479 027B  74 16            JE   ASB2B     ;JMP IF ONE DGIT
```

```
26  AFTER DEC PNT
27      480 027D  59                          POP   CX      ;CLR STACK
28      481 027E  C7 06 0000 E 0024           MOV   MSGNM,36   ;DEC PNT ERR MSG
29      482 0284  F9                          STC
30      483 0285  C3                          RET
31      484                                   ;
32      485 0286  3C 30             ASB2A:    CMP   AL,30H
33      486 0288  72 3A                       JB    ASB5 ;JMP IF BELOW 0
34      487 028A  3C 3A                       CMP   AL,3AH
35      488 028C  73 36                       JNB   ASB5 ;JMP IF ABOVE 9
36      489 028E  24 0F                       AND   AL,0FH    ;CLR ASCII
 1      490 0290  88 04                       MOV   [SI],AL   ;SAVE
 2      491 0292  46                          INC   SI   ;BUMP DEST ADR
 3      492 0293  43                ASB2B:    INC   BX   ;BUMP SRC ADR
 4      493 0294  E2 DA                       LOOP  ASB2 ;JMP IF MORE
 5      494 0296  4E                          DEC   SI   ;DROP ADR TO LSB
 6      495 0297  59                          POP   CX   ;GET # DIGITS
 7      496 0298  2A CC                       SUB   CL,AH     ;CORRECT IF DEC
 8  PNT
 9      497 029A  8B DE                       MOV   BX,SI
10      498 029C  BE 0000                     MOV   SI,0 ;CLR RESULT
11      499 029F  BF 0001                     MOV   DI,1 ;1ST     POSITION
12  MULTIPLIER
13      500 02A2  8A 07             ASB3:     MOV   AL,[BX]   ;GET NEXT
14  DIGIT
15      501 02A4  4B                          DEC   BX
16      502 02A5  32 E4                       XOR   AH,AH
17      503 02A7  F7 E7                       MUL   DI   ;TIMES POSITION
18      504 02A9  03 F0                       ADD   SI,AX     ;ADD TO PREV
19      505 02AB  B8 000A                     MOV   AX,10
20      506 02AE  F7 E7                       MUL   DI   ;POSITION TIMES 10
21      507 02B0  8B F8                       MOV   DI,AX     ;NEW  POSITION
22  MULTIPLIER
23      508 02B2  E2 EE                       LOOP  ASB3 ;JMP IF MORE
24      509 02B4  F7 C6 8000                  TEST  SI,8000H
25      510 02B8  78 02                       JS    ASB4 ;JMP IF OVER 32,767
26      511 02BA  F8                          CLC
27      512 02BB  C3                          RET        ;RET AS OKAY
28      513 02BC  C7 06 0000 E 0055 ASB4:     MOV   MSGNM,85  ;SET MSG #
29      514 02C2  F9                          STC
30      515 02C3  C3                          RET
31      516 02C4  59                ASB5:     POP   CX   ;CLR STACK
32      517 02C5  C7 06 0000 E 0044           MOV   MSGNM,68  ;SET NON-NUMERIC
33  MSG #
```

```
34      518  02CB  F9                STC
35      519  02CC  C3                RET
36      520  02CD              ASCBIN  ENDP
 1      521                       ;
 2      522                     COMMENT *
 3
```

Microsoft (R) Macro Assembler Version 5.10                    9/2/89 09:11:14

CONVERSION LIBRARY ROUTINES                                    Page 1-10

```
 8      523              DESCRIPTION: THIS CONVERTS FIRST 24 BITS OF 32 BIT WORD TO PACKED BCD.
10      524              INPUT: BX=ADDRESS OF WORD
11      525              OUTPUT: BX=ADDRESS OF BUFFER OF LENGTH 4
12      526              DATA:   EXTERNAL BYTE BUFFER. STARTS AT BUFF+10
14      527              REGISTERS:  AX,BX,CX,DX,DI,SI
15      528              *
16      529  02CD              BCD24B  PROC NEAR
17      530  02CD  8B 07            MOV  AX,[BX]    ;GET LSB
18      531  02CF  8B 4F 02         MOV  CX,[BX+2]  ;GET MSB
19      532  02D2  8A D4            MOV  DL,AH
20      533  02D4  8A F1            MOV  DH,CL      ;DX=16 MSB'S
21      534  02D6  8A E0            MOV  AH,AL
22      535  02D8  8B F8            MOV  DI,AX      ;DI=8 LSB'S
23      536  02DA  BB 000A E        MOV  BX,OFFSET DGROUP:BUFF+10
24      537  02DD  BE FFFD          MOV  SI,-3      ;FOR 4TH BYTE OF BUFFER
26      538  02E0  E8 031F R        CALL BCD16B     ;16 BITS OF TENS/UNITS
28      539  02E3  87 FA            XCHG DI,DX      ;DI=16 BIT RMDR. DH=8 LOW BITS
30      540  02E5  B9 0008          MOV  CX,8
31      541  02E8  E8 0324 R        CALL BCDAGN     ;GET TENS/UNITS
32      542  02EB  88 00            MOV  [BX][SI],AL ;TO BUFFER
33      543  02ED  46               INC  SI
34      544  02EE  8A F2            MOV  DH,DL      ;POSITION RMDR
35      545  02F0  87 FA            XCHG DI,DX      ;DI=8 BIT RMDR. DX=16 BIT RMDR
```

```
546 02F2  E8 031F R           CALL BCD16B      ;16 BITS OF THOU/HUND
547 02F5  87 FA                XCHG DI,DX      ;DI=16 BIT RMDR. DH=8 BIT RMDR
548 02F7  B9 0008              MOV  CX,8
549 02FA  E8 0324 R            CALL BCDAGN     ;GET THOU/HUND
550 02FD  88 00                MOV  [BX][SI],AL ;TO BUFFER
551 02FF  46               INC SI
552 0300  8A F2                MOV  DH,DL      ;POS RMDR
553 0302  87 FA                XCHG DI,DX      ;DI=8 BIT RMDR. DX=16 BIT RMDR
554 0304  E8 031F R            CALL BCD16B     ;16 BITS OF HTHOU/TTHOU
555 0307  87 FA                XCHG DI,DX      ;DI=16 BIT RMDR. DH=8 BIT RMDR
556 0309  B9 0008              MOV  CX,8
557 030C  E8 0324 R            CALL BCDAGN     ;GET HTHOU/TTHOU
558 030F  88 00                MOV  [BX][SI],AL ;TO BUFFER
559 0311  E8 0317 R            CALL BCD8B      ;GET TNMLN/MLN
560 0314  88 07                MOV  [BX],AL    ;TO BUFFER
561 0316  C3                   RET
562 0317                BCD24B  ENDP
563                             ;
564                     COMMENT *
565                     DESCRIPTION: BCD8B   CONVERTS 8 BIT BIN IN DL TO PACKED BCD
566                     INPUT:
567                     OUTPUT: A=LSB'S. DL=MSB OR 8 BIT REMAINDER
568                     DATA:
569                     REGISTERS: AX,BX,CX,DX
570                             ;
571                     DESCRIPTION: BCD16B  THIS CONVERTS 16 BIT BIN IN DX TO PACKED BCD
572                                          SEVERAL PASSES MAY BE REQUIRED
573                     INPUT:
574                     OUTPUT:    OUTPUT A=LSB'S. DX=16 BIT REMAINDER
575                     DATA:
576                     REGISTERS: AX,BX,CX,DX
577                             *
578 0317            BCD8B    PROC NEAR
579 0317  8A F2                MOV  DH,DL      ;MOVE TO HIGH
```

```
        9 BYTE
       10     580 0319  B9 0008              MOV  CX,8  ;8 SHIFTS
       11
```

HMicrosoft (R) Macro Assembler Version 5.10                    9/2/89 09:11:14

CONVERSION LIBRARY ROUTINES                                    Page 1-11

```
        581 031C  EB 04 90                   JMP  BCDCLR
        582                            ;
        583 031F                       BCD16B    LABEL    NEAR
        584 031F  B9 0010                   MOV  CX,16   ;16 SHIFTS
        585 0322  32 C0              BCDCLR:  XOR  AL,AL     ;CLR RESULT
        586                            ;
        587 0324                       BCDAGN    LABEL    NEAR
        588 0324  D1 E2                     SHL  DX,1  ;GET HIGH BIT
        589 0326  12 C0                     ADC  AL,AL    ;DBLE RESLT AND ADD HGH BIT
        590 0328  27                  DAA            ;ADJUST FOR DEC
        591 0329  73 03                     JNC  BCDBIT    ;JMP IF LESS THAN 99
        592 032B  83 C2 01                  ADD  DX,1  ;ELSE  OVERFLOW TO REMAINDER
        593 032E  E2 F4              BCDBIT:  LOOP BCDAGN    ;JMP IF MORE
        594 0330  C3                  RET
        595 0331                       BCD8B     ENDP
        596                            ;
        597 0331                       CODE ENDS
        598                            END

595 Source   Lines
    595 Total    Lines
     87 Symbols

47144 + 376836 Bytes symbol space free

0 Warning Errors
      0 Severe  Errors
```

```
PROGRAM LISTING: IOR03MN
DATE: 9/7/89
^HMicrosoft (R) Macro Assembler Version 5.10                    9/2/89
09:14:42

IN/OUT LIBRARY FUNCTIONS                                          Page 1-1

1                   .8086
        2                       NAME IOR03MN
        3                       PAGE 62,120
        4                       TITLE    IN/OUT LIBRARY FUNCTIONS
        5                       ;
        6                   COMMENT *
        7
;;;;;;;;;;;;;;;;;;;;;;;;;;;;;;;;;;;;;;;;;;;;;;;;;;;;;;;;;;;;;;;;;;
        8                       COPYRIGHT (C) 1989 GESTRON ENGRG. ALL RIGHTS RESERVED. NO PART OF
        9                       PUBLICATION   OR   PROGRAM   MAY   BE TRANSCRIBED,REPRODUCED, TRANSMITTED,
       10                       OR   TRANSLATED   INTO   ANY   LANGUAGE   OR COMPUTER LANGUAGE BY ANY MEANS:
       11                       ELECTRONIC,   MECHANICAL,   MAGNETIC, CHEMICAL, OPTICAL, MANUAL OR
       12                       OTHERWISE OR IN ANY FORM, WITHOUT THE PRIOR WRITTEN PERMISSION OF
       13                       G.  E.  SOMERVILLE, 7315 BROCADE DRIVE, CITRUS HEIGHTS CALIF. 95621.
       14
;;;;;;;;;;;;;;;;;;;;;;;;;;;;;;;;;;;;;;;;;;;;;;;;;;;;;;;;;;;;;;;;;;
       15
       16
;;;;;;;;;;;;;;;;;;;;;;;;;;;;;;;;;;;;;;;;;;;;;;;;;;;;;;;;;;;;;;;;;;;;;
       17                       LICENSE  TO  USE  THESE  ROUTINES  WITH PROGRAMS WRITTEN BY G. E. SOMERVILLE
       18                       FOR GEOLOW PARTNERS IS GRANTED TO GEOLOW PARTNERS BY G. E. SOMERVILLE
       19
;;;;;;;;;;;;;;;;;;;;;;;;;;;;;;;;;;;;;;;;;;;;;;;;;;;;;;;;;;;;;;;;;;;;;
       20                   *
       21 = 0010             ROMVID    EQU    10H    ;ROM   BIOS
```

```
10  INTERRUPT
11       22 = 0021                DOSINT    EQU       21H
12       23                       ;
13       24 0000                  DATA      SEGMENT   PUBLIC    'DATA'
14       25                       ;
15       26 0000 0000             MSGNM     DW        ?
16       27 0002 00               VALIN     DB        ?         ;MAX DIGITS
17       28 0003 00                         DB        ?
18       29 0004 0008[            VALBUF    DB        8 DUP(?)
19       30        ??
20       31              ]
21       32
22       33                       ;
23       34                       PUBLIC    MSGNM
24       35                       EXTRN
25  FHANDL:WORD,MSGTAB:WORD,MSG0:BYTE
26       36                       ;
27       37 000C                  DATA      ENDS
28       38                       DGROUP    GROUP     DATA
29       39                       CGROUP    GROUP     CODE
30       40                       ;
31       41 0000                  CODE      SEGMENT   PUBLIC    'CODE'
32       42                       ASSUME CS:CGROUP,DS:DGROUP,SS:DGROUP
33       43                       ;
34       44                       EXTRN     CHKCRS:NEAR,ASCBIN:NEAR
35       45                       ;
 1       46                       PUBLIC
 2  CLRHDL,CRTMSG,DIRMSG,RCVVAL,RDFIL,RDIND,SNDMSG,MSGOUT
 3       47                       PUBLIC    WRTFIL,WRTIND
 4       48                       ;
 5       49                       COMMENT *
 6       50                       DESCRIPTION: THESE PROCEDURES SEND
 7  MESSAGES FROM MESSAGE
 8       51                          TABLES. THEY ACT AS A TTY. MSG
 9  STOPS ON $.
10       52                          CRTMSG: A MASTER MESSAGE TABLE AT
11  ADDRESS MSGTAB.
12       53                          MSGOUT: A MESSAGE TABLE WITH ADDRESS
13  IN BX.
14       54                          DIRMSG: MESSAGE ADDRESS IN SI.
15       55                       INPUT: CRTMSG: MSGNM=MESSAGE NUMBER.
16       56                          MSGOUT: AL=MESSAGE #.  BX=MESSAGE
17  ADDRESS.
18       57                          DIRMSG: SI=MESSAGE ADDRESS.
19       58                       OUTPUT:
20
```

Microsoft (R) Macro Assembler Version 5.10                              9/2/89
09:14:42

IN/OUT LIBRARY FUNCTIONS                                                Page
1-2

```
   59                       DATA:       ONE WORD
   60                       REGISTERS:  AX,BX,CL,DI,SI
   61                       *
   62                           ;THIS PROCEDURE DISPLAYS A NUMBERED MESSAGE
   63                           ;FROM A SPECIFIC TABLE
   64 0000                  MSGOUT    PROC NEAR
   65 0000  32 E4               XOR  AH,AH
   66 0002  8B F8               MOV  DI,AX
   67 0004  D1 E7               SHL  DI,1   ;DOUBLE MSG #
   68 0006  8B 31               MOV  SI,[BX][DI]     ;MSG OFFSET
   69 0008  E8 001E R           CALL DIRMSG  ;DISPLAY MSG
   70 000B  C3              RET
   71 000C                  MSGOUT    ENDP
   72                       ;
   73                       ;
   74 000C                  CRTMSG    PROC NEAR
   75 000C  8B 3E 0000 R        MOV  DI,MSGNM
   76 0010  D1 E7               SHL  DI,1   ;DOUBLE MSG #
   77 0012  8B B5 0000 E        MOV  SI,MSGTAB[DI]  ;MSG OFFSET
   78 0016  2B 36 0000 E        SUB  SI,MSGTAB  ;LESS 1ST MSG
   79 001A  81 C6 0000 E        ADD  SI,OFFSET DGROUP:MSG0 ;PLUS ACTUAL 1ST MSG ADDRESS
   80                       ;
   81                       ;THIS SENDS A MESSAGE BASED ON DS:SI
   82 001E                  DIRMSG    LABEL    NEAR
   83 001E  B4 0F               MOV  AH,0FH
   84 0020  CD 10               INT  ROMVID    ;GET VIDEO MODE
   85 0022  32 C9               XOR  CL,CL     ;PRESET TO NO FONT OFFSET
   86 0024  3C 02               CMP  AL,2
   87 0026  74 02               JE   SM1  ;JMP IF TEXT MODE
   88 0028  B1 80               MOV  CL,128    ;GRAPHICS FONT OFFSET
   89 002A  B3 07           SM1: MOV BL,7  ;WHITE
   90 002C  FC              CLD            ;COUNT UP
```

```
 9    91 002D AC          SM2:    LODSB            ;GET NEXT CHAR
10    92 002E 3C 24               CMP  AL,'$'
11    93 0030 74 08                JE   CRTMRT     ;JMP IF MSG END
12    94 0032 02 C1                ADD  AL,CL      ;ADD FONT OFFSET
13    95 0034 B4 0E                MOV  AH,0EH
14    96 0036 CD 10                INT  ROMVID     ;CHAR TO CRT
15    97 0038 EB F3                JMP  SM2        ;TRY AGAIN
16    98                   ;
17    99 003A C3          CRTMRT:  RET
18   100 003B                     CRTMSG   ENDP
19   101                   ;
20   102                   ;THIS PROCEDURE DISPLAYS A MESSAGE AND
21
22   103                   ;SCROLLS UP. MSGNM=MSG #
23   104 003B                     SNDMSG   PROC NEAR
24   105 003B E8 000C R            CALL CRTMSG     ;TO CRT
25   106 003E E8 0000 E            CALL CHKCRS     ;CHECK CURSOR
26   107 0041 C3                   RET
27   108 0042                     SNDMSG   ENDP
28   109                   ;
29   110                  COMMENT *
30   111                  DESCRIPTION:   THIS PROCEDURE GETS A USER TYPED VALUE 0-32767
32   112                                 IN SI. ELSE DISPLAYS ERROR MESSAGE AND RETS CY SET
34   113                  INPUT:    USER TYPED ASCII STRING
35   114                  OUTPUT:   SI=INTEGER VALUE
36   115                  DATA:     TEN BYTES 1   116                  REGISTERS:
```

^HMicrosoft (R) Macro Assembler Version 5.10                9/2/89 09:14:42

IN/OUT LIBRARY FUNCTIONS                                         Page 1-3

```
 8   117                          *
 9   118 0042                     RCVVAL   PROC NEAR
10   119 0042 B1 06                MOV  CL,6       ;5 DIGITS MAX
11   120 0044 88 0E 0002 R         MOV  VALIN,CL   ;TO BUFFER
12   121 0048 BA 0002 R            MOV  DX,OFFSET DGROUP:VALIN   ;BUFFER
```

```
14      122 004B  B4 0A              MOV     AH,0AH
15      123 004D  CD 21              INT     DOSINT      ;GET RESPONSE
16      124 004F  8A 0E 0003 R       MOV     CL,VALIN+1  ;GET #
17 DIGITS
18      125 0053  32 ED              XOR     CH,CH
19      126 0055  BB 0004 R          MOV     B X , O F F S E T
20 DGROUP:VALBUF           ;BUFFER ADR
21      127 0058  E8 0000 E          CALL    ASCBIN     ;CNVT TO BINARY
22      128 005B  72 01              JC      RV1 ;JMP IF ERROR
23      129 005D  C3                 RET              ;RET WITH NO CY
24      130                          ;
25      131 005E  E8 003B R          RV1: CALL SNDMSG    ;DIS ERR MSG
26      132 0061  F9                 STC
27      133 0062  C3                 RET              ;RET WITH CY SET
28      134 0063                     RCVVAL   ENDP
29      135                          ;
30      136                          COMMENT *
31      137                          DESCRIPTION: MISCELLANEOUS FILE HANDLING
32 ROUTINES.
33      138                          INPUT:       SEE ROUTINE
34      139                          OUTPUT:      SEE ROUTINE
35      140                          DATA:
36      141                          REGISTERS:

1       142                          *
2       143                          ;THIS PROCEDURE READS BYTES FROM FILE
3  AT NEXT
4       144                          ;POSITION. CY=ERROR. DX=DEST. CX=#
5  BYTES
6       145 0063                     RDFIL    PROC NEAR
7       146 0063  8B 1E 0000 E       MOV     BX,FHANDL ;GET FILE HANDLE
8       147 0067                     RDIND    LABEL    NEAR
9       148 0067  B4 3F              MOV     AH,3FH
10      149 0069  CD 21              INT     DOSINT      ;READ FROM FILE
11      150 006B  73 08              JNC     RDF1 ;JMP IF NO ERROR FLAG
12      151 006D  C7 06 0000 R 0002  MOV     MSGNM,2    ;INVALID MSG
13      152 0073  EB 0A              JMP     SHORT RDF2
14      153                          ;
15      154 0075  0B C0              RDF1:    OR   AX,AX
16.     155 0077  75 0A              JNZ     RDFRT     ;JMP IF ALL BYTES
17 READ
18      156 0079  C7 06 0000 R 000A  MOV     MSGNM,10  ;RD PAST EOF MSG
19      157 007F  E8 003B R          RDF2:    CALL SNDMSG   ;DISPLAY
20 ERROR MSG
21      158 0082  F9                 STC
```

```
 22      159 0083  C3           RDFRT:   RET
 23      160 0084                RDFIL   ENDP
 24      161                     ;
 25      162                     ;THIS PROCEDURE WRITES BYTES TO FILE AT NEXT
 27      163                     ;POSITION. CY=ERROR RET. DX=SOURCE. CX=# BYTES
 29      164 0084                WRTFIL  PROC NEAR
 30      165 0084  8B 1E 0000 E          MOV   BX,FHANDL ;GET FILE HANDLE
 31      166 0088                WRTIND  LABEL   NEAR
 32      167 0088  B4 40                 MOV   AH,40H
 33      168 008A  CD 21                 INT   DOSINT    ;WRITE TO FILE
 34      169 008C  73 08                 JNC   WRTF1     ;JMP IF NO ERROR FLAG
 36      170 008E  C7 06 0000 R 0002     MOV   MSGNM,2   ;INVALID MSG
  1      171 0094  EB 0A                 JMP   SHORT WRTF2
  2      172                     ;
  3      173 0096  3B C1          WRTF1: CMP   AX,CX
  4      174 0098  73 0A                 JNC   WRTFRT    ;JMP IF ALL BYTES WRITTEN
```

Microsoft (R) Macro Assembler Version 5.10                9/2/89 09:14:42

IN/OUT LIBRARY FUNCTIONS                                   Page 1-4

```
  8      175 009A  C7 06 0000 R 0000     MOV   MSGNM,0   ;INSUFFICIENT MEM MSG
 10      176 00A0  E8 003B R      WRTF2: CALL  SNDMSG    ;DISPLAY ERROR MSG
 12      177 00A3  F9                    STC
 13      178 00A4  C3             WRTFRT: RET
 14      179 00A5                 WRTFIL  ENDP
 15      180                      ;
 16      181                      ;THIS PROCEDURE CLEARS FILE HANDLE AND CLOSES
 18      182                      ;FILE IF OPEN. ON RETURN AL=1 IF NO FILE WAS OPEN
 20      183 00A5                 CLRHDL  PROC NEAR
 21      184 00A5  B0 01                  MOV  AL,1 ;PRESET AS NO FILE OPEN
 23      185 00A7  8B 1E 0000 E           MOV  BX,FHANDL ;GET FILE HANDLE
```

```
24      186 00AB  83 FB 05              CMP  BX,5
25      187 00AE  72 06                 JB   CH1    ;JMP IF 0-4
26      188 00B0  B4 3E                 MOV  AH,3EH
27      189 00B2  CD 21                 INT  DOSINT    ;CLOSE FILE
28      190 00B4  32 C0                 XOR  AL,AL     ;SET TO FILE
CLOSED
30      191 00B6  BB 0000          CH1: MOV  BX,0
31      192 00B9  89 1E 0000 E         MOV  FHANDL,BX ;FILE HANDLE=0
32      193 00BD  C3                   RET
33      194 00BE                       CLRHDL  ENDP
34      195                            ;
35      196 00BE                       CODE ENDS
36      197                            END
```

194 Source Lines
194 Total  Lines
 40 Symbols

47198 + 387022 Bytes symbol space free

0 Warning Errors
  0 Severe  Errors

PROGRAM LISTING: VIEW.EXE
DATE: 9/09/89
^HMicrosoft (R) Macro Assembler Version 5.10                    9/8/89
12:29:48

PARSES GRAB VIEW FILE                                            Page
1-1
        1                    .8086
        2                    NAME VIEW
        3                    PAGE 62,120
        4                    TITLE    PARSES GRAB VIEW FILE
        5                    ;
        6              COMMENT *
        7
;;;;;;;;;;;;;;;;;;;;;;;;;;;;;;;;;;;;;;;;;;;;;;;;;;;;;;;;;;;;;;;;;;
;;;;;;;
        8              COPYRIGHT (C) 1989 GEOLOW PARTNERS. ALL RIGHTS RESERVED. NO PART OF PROGRAM
        9                      OR   PUBLICATION   MAY   BE TRANSCRIBED,REPRODUCED, TRANSMITTED, OR TRANSLATED
       10              INTO ANY LANGUAGE OR COMPUTER LANGUAGE BY

```
22   ANY MEANS ELECTRONIC, MECHANICAL,
23       11                         MAGNETIC, CHEMICAL, OPTICAL, MANUAL OR
24   OTHERWISE OR IN ANY FORM, WITHOUT
25       12                         THE PRIOR WRITTEN PERMISSION OF LOWELL
26   WEDEMEYER, 3112 THATCHER AVE,
27       13                         MARINA DEL REY CALIFORNIA, 90292.
28       14
29   ;;;;;;;;;;;;;;;;;;;;;;;;;;;;;;;;;;;;;;;;;;;;;;;;;;;;;;;;;;;;;;;;
30   ;;;;;;;
31       15
32       16                         PROGRAMMING BY G. E. SOMERVILLE, 7315
33   BROCADE DR., CITRUS HEIGHTS, CA 95621
34       17                         *
35       18                         ;
36       19 = 001A                  EOF       EQU    1AH
 1       20 = 000D                  CR        EQU    0DH
 2       21 = 000A                  LF        EQU    0AH
 3       22 = 0021                  DOSINT    EQU    21H
 4       23                         ;
 5       24                         INCLUDELIB    IOR03MN
 6       25                         INCLUDELIB    CVN03MN
 7       26                         INCLUDELIB    CRT03MN
 8       27                         ;
 9       28 0000                    DATA SEGMENT   PUBLIC    'DATA'
10       29                         ;
11       30 0000  49 6E 73 75 66 66 MSG0 DB   'Insufficient memory$'
12       31       69 63 69 65 6E 74
13       32       20 6D 65 6D 6F 72
14       33       79 24
15       34 0014  45 6E 74 65 72 20 MSG1 DB   'Enter basic source file
16   name (omit .ext): $'
17       35       62 61 73 69 63 20
18       36       73 6F 75 72 63 65
19       37       20 66 69 6C 65 20
20       38       6E 61 6D 65 20 28
21       39       6F 6D 69 74 20 2E
22       40       65 78 74 29 3A 20
23       41       24
24       42 003F  41 63 63 65 73 73 MSG2 DB   'Access denied or invalid$'
25
26       43       20 64 65 6E 69 65
27       44       64 20 6F 72 20 69
28       45       6E 76 61 6C 69 64
29       46       24
```

```
30      47 0058  54 6F 6F 20 6D 61  MSG3  DB    'Too many files open$'
31      48       6E 79 20 66 69 6C
32      49       65 73 20 6F 70 65
33      50       6E 24
34      51 006C  4E 65 77 20 66 69  MSG4  DB    'New file Y(CR) or N=$'
35      52       6C 65 20 59 28 43
36      53       52 29 20 6F 72 20
 1      54       4E 3D 24
 2      55 0081  50 61 74 68 20 6E  MSG5  DB    'Path not found$'
 3      56       6F 74 20 66 6F 75
 4      57       6E 64 24
 5      58 0090  4E 6F 20 66 69 6C  MSG6  DB    'No file open$'
 6
```

1 ^HMicrosoft (R) Macro Assembler Version 5.10                       9/8/89
2 12:29:48
3
4 PARSES GRAB VIEW FILE                                              Page
5 1-2
6
7

```
 8      59       65 20 6F 70 65 6E
 9      60       24
10      61 009D  4F 6C 64 20 66 69  MSG7  DB    'Old file Y(CR) or N=$'
11      62       6C 65 20 59 28 43
12      63       52 29 20 6F 72 20
13      64       4E 3D 24
14      65 00B2  3A 24              MSG8  DB    ':$'
15      66 00B4  20 20 20 20 20 20  MSG9  DB    '
16 $'
17      67       20 20 20 20 20 20
18      68       20 20 20 20 20 20
19      69       20 20 20 20 20 20
20      70       20 20 20 20 24
21      71 00D1  41 74 74 65 6D 70  MSG10      DB    'Attempt to read past
22 end of file$'
23      72       74 20 74 6F 20 72
24      73       65 61 64 20 70 61
25      74       73 74 20 65 6E 64
26      75       20 6F 66 20 66 69
27      76       6C 65 24
28      77 00F2  45 6E 74 65 72 20  MSG11      DB    'Enter    view    file
29 extension (.V1): $'
30      78       76 69 65 77 20 66
31      79       69 6C 65 20 65 78
```

```
32        80       74 65 6E 73 69 6F
33        81       6E 20 28 2E 56 31
34        82       29 3A 20 24
35        83 0114  45 72 72 6F 72 20  MSG12    DB    'Error opening output
36  file$'

1        84       6F 70 65 6E 69 6E
 2        85       67 20 6F 75 74 70
 3        86       75 74 20 66 69 6C
 4        87       65 24
 5        88 012E  45 72 72 6F 72 20  MSG13    DB    'Error reading .LSP
 6  file$'
 7        89       72 65 61 64 69 6E
 8        90       67 20 2E 4C 53 50
 9        91       20 66 69 6C 65 24
10        92 0146  45 72 72 6F 72 20  MSG14    DB    'Error reading .V file
11  headings$'
12        93       72 65 61 64 69 6E
13        94       67 20 2E 56 20 66
14        95       69 6C 65 20 68 65
15        96       61 64 69 6E 67 73
16        97       24
17        98 0165  54 6F 74 61 6C 20  MSG15    DB    'Total base entities
18  do not match .LSP total$'
19        99       62 61 73 65 20 65
20       100       6E 74 69 74 69 65
21       101       73 20 64 6F 20 6E
22       102       6F 74 20 6D 61 74
23       103       63 68 20 2E 4C 53
24       104       50 20 74 6F 74 61
25       105       6C 24
26       106 0191  45 72 72 6F 72 20  MSG16    DB    'Error reading .V file
27  entity number$'
28       107       72 65 61 64 69 6E
29       108       67 20 2E 56 20 66
30       109       69 6C 65 20 65 6E
31       110       74 69 74 79 20 6E
32       111       75 6D 62 65 72 24
33       112 01B5  52 65 66 65 72 65  MSG17    DB    'Reference to raw data
34  file? Y(CR) or N :$'
35       113       6E 63 65 20 74 6F
36       114       20 72 61 77 20 64
 1       115       61 74 61 20 66 69
 2       116       6C 65 3F 20 59 28
 3
```

```
 1  ^HMicrosoft (R) Macro Assembler Version 5.10                    9/8/89
 2  12:29:48
 3
 4  PARSES GRAB VIEW FILE                                            Page
 5  1-3
 6       117         43 52 29 20 6F 72
 7       118         20 4E 20 3A 24
 8       119 01DE    45 6E 74 65 72 20   MSG18      DB    'Enter actual starting
 9  trial number :$'
10       120         61 63 74 75 61 6C
11       121         20 73 74 61 72 74
12       122         69 6E 67 20 74 72
13       123         69 61 6C 20 6E 75
14       124         6D 62 65 72 20 3A
15       125         24
16       126 0203    45 6E 74 65 72 20   MSG19      DB    'Enter actual starting
17  sample number :$'
18       127         61 63 74 75 61 6C
19       128         20 73 74 61 72 74
20       129         69 6E 67 20 73 61
21       130         6D 70 6C 65 20 6E
22       131         75 6D 62 65 72 20
23       132         3A 24
24       133 0229    6E 6F 6E 2D 6E 75   MSG20      DB    'non-numeric$'
25       134         6D 65 72 69 63 24
26       135                         ;
27       136 0235    0000 R 0014 R 003F R   MSGTAB   DW
28  MSG0,MSG1,MSG2,MSG3,MSG4,MSG5,MSG6,MSG7,MSG8
29       137         0058 R 006C R 0081 R
30       138         0090 R 009D R 00B2 R
31       139 0247    00B4 R 00D1 R 00F2 R            DW
32  MSG9,MSG10,MSG11,MSG12,MSG13,MSG14,MSG15,MSG16
33       140         0114 R 012E R 0146 R
34       141         0165 R 0191 R
35       142 0257    01B5 R 01DE R 0203 R            DW
36  MSG17,MSG18,MSG19,MSG20
 1       143         0229 R
 2       144                         ;
 3       145 025F    56 49 45 57 20 56   VERS DB    'VIEW VERSION 1.0  PARSES
 4  VIEW FILES '
 5       146         45 52 53 49 4F 4E
 6       147         20 31 2E 30 20 20
 7       148         50 41 52 53 45 53
 8       149         20 56 49 45 57 20
 9       150         46 49 4C 45 53 20
```

```
10      151          20
11      152  0284    43 4F 50 59 52 49    CPYRHT    DB      'COPYRIGHT     GEOLOW
12  PARTNERS',0DH,0AH,0AH,'$'
13      153          47 48 54 20 47 45
14      154          4F 4C 4F 57 20 50
15      155          41 52 54 4E 45 52
16      156          53 0D 0A 0A 24
17      157                                    ;
18      158  02A1    2E 4C 53 50 00       LISP      DB      '.LSP',00H
19      159                                    ;
20      160  02A6    54 52 49 41 4C 20    PRTLIN    DB      'TRIAL         SET
21  ',0DH,0AH,'    SAMPLES',0DH,0AH
22      161          20 20 20 20 20 53
23      162          45 54 20 20 20 20
24      163          20 0D 0A 20 20 20
25      164          53 41 4D 50 4C 45
26      165          53 0D 0A
27      166 = 0021                        PRTLTH    EQU     $-PRTLIN
28      167                                    ;
29      168  02C7    20 20 20 20 20 54    PRTSMP    DB      '     TO      ',0DH,0AH
30
31      169          4F 20 20 20 20 20
32      170          0D 0A
33      171 = 000E                        LTHPRT    EQU     $-PRTSMP
34      172                                    ;
35      173  02D5    41                   FLNAME    DB      65     ;MAX PATH BYTES
36      174  02D6    00                   FLNMLN    DB      ?      ;BYTES READ IN
37
```

```
Microsoft (R) Macro Assembler Version 5.10                        9/8/89
12:29:48

PARSES GRAB VIEW FILE                                             Page 1-4

175  02D7    0041[              FILNAM    DB    65 DUP(?) ;FILE NAME BUFFER
    176          ??
    177                   ]
    178
    179                                    ;
    180  0318    0000                FHANDL    DW    ?      ;FILE HANDLE
    181  031A    0000                VHANDL    DW    ?
    182  031C    0000                OHANDL    DW    ?
    183                                    ;
    184  031E    02                  REPLY     DB    2      ;ONE RESPONSE BYTE
```

```
17    185 031F  00              DB    ?
18    186 0320  0002[           DB    2 DUP(?)  ;RESPONSE
19    187       ??
20    188             ]
21    189
22    190                   ;
23    191 0322  0F      MSGIN    DB   15
24    192 0323  00      MSGLTH   DB   ?
25    193 0324  000F[       MSGBUF  DB   15 DUP(?)
26    194       ??
27    195             ]
28    196
29    197                   ;
30    198 0333  0000        NBASE   DW   ?
31    199 0335  0000        NENTS   DW   ?
32    200                   ;
33    201 0337  0000        NSETS   DW   ?      ;# SETS
34    202 0339  0000        NSMPS   DW   ?      ;# SAMPLES/TRIAL
35
36    203 033B  0000        NTRLS   DW   ?      ;# TRIALS/SET
 1    204                   ;
 2    205 033D  0000        NSET DW    ?      ;SET # TO FIND
 3    206 033F  0000        NSMP DW    ?      ;SAMPLES #
 4    207 0341  0000        NTRL DW    ?      ;TRIALS #
 5    208                   ;
 6    209 0343  0000        FSMP DW    ?      ;FIRST SAMP
 7    210 0345  0000        LSMP DW    ?      ;LAST SAMP
 8    211 0347  0000        CTRL DW    ?      ;CURR TRIAL
 9    212 0349  0000        XSMP DW    ?
10    213 034B  0000        FENT DW    ?
11    214 034D  0000        LENT DW    ?
12    215                   ;
13    216 034F  0000        RAWFLG  DW   ?
14    217 0351  00      RSMP DB    ?
15    218 0352  00      RTRL DB    ?
16    219 0353  0000        PTRL DW    ?
17    220                   ;
18    221 0355  0002[       FSIZ    DW   2 DUP(?)  ;BYTES IN FILE
19    222       ????
20    223             ]
21    224
22    225 0359  0002[       BYTSRD  DW   2 DUP(?)   ;BYTES READ
23    226       ????
24    227             ]
```

```
25      228
26      229 035D  0000            BUFSIZ  DW   ?       ;BYTES IN BUFF
27
28      230 035F  0000            BUFPTR  DW   ?       ;NEXT BUFF ADR
29
30      231
31      232 0361  8000[           FBUF DB   32768 DUP(?)
32
```

^HMicrosoft (R) Macro Assembler Version 5.10                9/8/89
12:29:48

PARSES GRAB VIEW FILE                                       Page 1-5

```
        233         ??
        234              ]
        235
        236 8361  0064[           BUFF DB   100 DUP(?)
        237         ??
        238              ]
        239
        240                       ;
        241 83C5  00FA[           SET1 DB   250 DUP(?)
        242         ??
        243              ]
        244
        245 84BF  00FA[           SET2 DB   250 DUP(?)
        246         ??
        247              ]
        248
        249 85B9  00FA[           SET3 DB   250 DUP(?)
        250         ??
        251              ]
        252
        253 86B3  00FA[           SET4 DB   250 DUP(?)
        254         ??
        255              ]
        256
        257 87AD  00FA[           SET5 DB   250 DUP(?)
        258         ??
        259              ]
        260
        261 88A7  00FA[           SET6 DB   250 DUP(?)
        262         ??
        263              ]
```

```
264
265                  ;
266 = 05DC           SETLTH   EQU    $-SET1
267 89A1 0000        SMPCNT   DW     ?       ;SAMPLE COUNT
268 89A3 00FA[       SMPTAB   DB     250 DUP(?)
269        ??
270              ]
271
272                  ;
273                  PUBLIC   BUFF,FHANDL,MSG0,MSGTAB
274                  EXTRN    MSGNM:WORD
275                  ;
276 8A9D             DATA ENDS
277                  ;
278 0000             STACK    SEGMENT  STACK   'STACK'
279 0000 0400[                DW       1024 DUP(?)
280       ????
281              ]
282
283 0800            STKTOP    LABEL    WORD
284 0800            STACK     ENDS
285                  ;
286                 DGROUP    GROUP    DATA,STACK
287                 CGROUP    GROUP    CODE
288 0000            CODE      SEGMENT  PUBLIC  'CODE'
289                           ASSUME   CS:CGROUP,DS:DGROUP,SS:DGROUP
290                  ;
```

Microsoft (R) Macro Assembler Version 5.10                        9/8/89
12:29:48

PARSES GRAB VIEW FILE                                              Page 1-6

```
291                 EXTRN    ASCBIN:NEAR,BNASC2:NEAR,BNASC4:NEAR,CLRHDL:NEAR,CRTMSG:NEAR
292                 EXTRN    DIRMSG:NEAR,RCVVAL:NEAR,RDIND:NEAR,SNDLF:NEAR
293                 EXTRN    UPRCAS:NEAR,WRTIND:NEAR
294                  ;
295 0000            START    LABEL    NEAR
296 0000 B8 ---- R           MOV      AX,DGROUP
297 0003 8E D8               MOV      DS,AX
```

```
15      298 0005  8E D0               MOV   SS,AX
16      299 0007  BC 0800 R           MOV   SP,OFFSET DGROUP:STKTOP
17      300 000A  BE 025F R           MOV   SI,OFFSET DGROUP:VERS
18      301 000D  E8 0000 E           CALL  DIRMSG      ;DISPLAY VERSION
19
20      302 0010  E8 0000 E           CALL  SNDLF
21      303 0013  E9 04F0 R           JMP   MAINPG      ;JMP TO MAIN
22 PROGRAM
23      304                           ;
24      305                           ;
25      306                           ;THIS GETS OLD/NEW RESPONSE FROM
26 MESSAGE IN MSGNM
27      307                           ;NZ FOR NO AND Z FOR YES
28      308 0016                      REPCHK    PROC NEAR
29      309 0016  E8 0000 E             CALL  SNDLF
30      310 0019  E8 0000 E             CALL  CRTMSG    ;ASK QUESTION
31      311 001C  BA 031E R             MOV   DX,OFFSET DGROUP:REPLY
32      312 001F  B0 0A                 MOV   AL,0AH
33      313 0021  B4 0C                 MOV   AH,0CH
34      314 0023  CD 21                 INT   DOSINT    ;GET REPLY
35      315 0025  8A 26 031F R          MOV   AH,REPLY+1     ;# BYTES
36 READ
1       316 0029  0A E4                 OR    AH,AH
2       317 002B  74 0C                 JZ    REPOK     ;JMP IF CR
3       318 002D  8A 26 0320 R          MOV   AH,REPLY+2     ;GET REPLY
4 BYTE
5       319 0031  80 FC 59              CMP   AH,'Y'
6       320 0034  74 03                 JZ    REPOK     ;JMP IF Y
7       321 0036  80 FC 79              CMP   AH,'y'
8       322 0039  C3              REPOK:    RET
9       323 003A                    REPCHK    ENDP
10      324                           ;
11      325                           ;THIS OPENS THE SOURCE FILES. CY=ERR
12
13      326 003A                    GETFIL    PROC NEAR
14      327 003A  E8 0000 E         GTF3:     CALL CRTMSG
15      328 003D  BA 02D5 R             MOV   DX,OFFSET DGROUP:FLNAME
16      329 0040  B0 0A                 MOV   AL,0AH
17      330 0042  B4 0C                 MOV   AH,0CH
18      331 0044  CD 21                 INT   DOSINT    ;G E T   F I L E
19 PATH/NAME
20      332 0046  E8 0000 E             CALL  SNDLF
21      333 0049  8A 0E 02D6 R          MOV   CL,FLNMLN ;# BYTES IN NAME
22      334 004D  80 F9 00              CMP   CL,0
23      335 0050  74 E8                 JE    GTF3 ;JMP IF JUST CR
```

```
24      336 0052  32 ED              XOR   CH,CH
25      337 0054  BF 02D7 R          MOV   DI,OFFSET DGROUP:FILNAM
26      338 0057  E8 0000 E          CALL  UPRCAS    ;ALL UPPER CASE
27
28      339 005A  BB 02D7 R          MOV   BX,OFFSET DGROUP:FILNAM
29      340 005D  8A 0E 02D6 R       MOV   CL,FLNMLN
30      341 0061  32 ED              XOR   CH,CH
31      342 0063  03 D9              ADD   BX,CX     ;BX=EXT LOCATION
32      343 0065  8B FB              MOV   DI,BX
33      344 0067  BE 02A1 R          MOV   SI,OFFSET DGROUP:LISP
34      345 006A  B9 0005            MOV   CX,5
35      346 006D  F3/ A4         REP MOVSB           ;ADD .LSP EXT
36      347 006F  BA 02D7 R          MOV   DX,OFFSET DGROUP:FILNAM
 1      348 0072  B4 3D              MOV   AH,3DH
 2
```

Microsoft (R) Macro Assembler Version 5.10                            9/8/89
12:29:48

PARSES GRAB VIEW FILE                                                 Page 1-7

```
 6      349 0074  B0 02              MOV   AL,2
 7      350 0076  CD 21              INT   DOSINT    ;OPEN FILE
 8      351 0078  73 17              JNC   GTF5 ;JMP IF EXISTS
 9      352                          ;
10      353 007A  C7 06 0000 E 0002 GTF4: MOV   MSGNM,2   ;BAD ACCESS
11      354 0080  E8 0000 E          CALL  CRTMSG
12      355 0083  E8 0000 E          CALL  SNDLF
13      356 0086  BE 02D7 R          MOV   SI,OFFSET DGROUP:FILNAM
14      357 0089  E8 0000 E          CALL  DIRMSG
15      358 008C  E8 0000 E          CALL  SNDLF
16      359 008F  F9                 STC
17      360 0090  C3                 RET
18      361                          ;
19      362 0091  A3 0318 R          GTF5: MOV   FHANDL,AX ;SAVE LISP FILE HANDLE
21      363 0094  53                 PUSH  BX        ;HOLD FILE EXT ADR
22      364 0095  C7 06 0000 E 000B GTF6: MOV   MSGNM,11
23      365 009B  E8 0000 E          CALL  CRTMSG    ;GET V EXT
24      366 009E  BA 0322 R          MOV   DX,OFFSET DGROUP:MSGIN
25      367 00A1  B0 0A              MOV   AL,0AH
26      368 00A3  B4 0C              MOV   AH,0CH
27      369 00A5  CD 21              INT   DOSINT    ;GET REPLY
28      370 00A7  E8 0000 E          CALL  SNDLF
29      371 00AA  8A 0E 0323 R       MOV   CL,MSGLTH ;# BYTES IN EXT
```

```
372 00AE  80 F9 00              CMP  CL,0
373 00B1  74 E2                 JE   GTF6 ;JMP IF JUST CR
374 00B3  32 ED                 XOR  CH,CH
375 00B5  BF 0324 R             MOV  DI,OFFSET DGROUP:MSGBUF
376 00B8  E8 0000 E             CALL UPRCAS    ;ALL UPPER CASE 377 00BB  BE 0324 R             MOV  SI,OFFSET DGROUP:MSGBUF
378 00BE  8A 0E 0323 R          MOV  CL,MSGLTH
379 00C2  32 ED                 XOR  CH,CH
380 00C4  5F              POP   DI   ;GET FILE NAME
381 00C5  F3/ A4          REP   MOVSB          ;ADD .V EXT
382 00C7  C6 05 00              MOV  BYTE PTR [DI],00H
383 00CA  BA 02D7 R             MOV  DX,OFFSET DGROUP:FILNAM
384 00CD  B4 3D                 MOV  AH,3DH
385 00CF  B0 02                 MOV  AL,2
386 00D1  CD 21                 INT  DOSINT    ;OPEN FILE
387 00D3  73 02                 JNC  GTF7 ;JMP IF EXISTS
388
389 00D5  EB A3                 JMP  GTF4 ;JMP IF DOESNT EXIST
390 00D7  A3 031A R       GTF7: MOV  VHANDL,AX ;SAVE VIEW FILE HANDLE
391 00DA  F8              CLC
392 00DB  C3              RET
393                       ;
394 00DC             GETFIL    ENDP
395                       ;
396                       ;THIS OPENS THE DESTINATION FILES. CY=ERR
397 00DC             MAKFIL    PROC NEAR
398 00DC  8A 0E 02D6 R          MOV  CL,FLNMLN
399 00E0  32 ED                 XOR  CH,CH
400 00E2  BB 02D7 R             MOV  BX,OFFSET DGROUP:FILNAM
401 00E5  03 D9                 ADD  BX,CX     ;POINT TO END OF NAME
402 00E7  43              INC   BX   ;POINT TO V
403 00E8  C6 07 4F              MOV  BYTE PTR [BX],'O' ;CHANGE V TO O
404                       ;
405 00EB  BA 02D7 R             MOV  DX,OFFSET DGROUP:FILNAM
406 00EE  B4 4E                 MOV  AH,4EH
```

PARSES GRAB VIEW FILE                                              Page 1-8

```
407 00F0 33 C9              XOR  CX,CX
408 00F2 CD 21              INT  DOSINT    ;SEARCH FOR FILE
409 00F4 3C 00              CMP  AL,0
410 00F6 75 0F              JNE  MKF2 ;JMP IF FILE NOT FOUND 411 00F8 C7 06 0000 E 0007  MOV  MSGNM,7
412 00FE 53                 PUSH BX       ;HOLD FILE NAME ADDR
413 00FF E8 0016 R          CALL REPCHK   ;SEE IF OK TO DESTROY EXISTING FILES
414 0102 5B                 POP  BX
415 0103 74 02              JZ   MKF2 ;JMP IF OKAY
416 0105 F9                 STC
417 0106 C3                 RET
418                         ;
419 0107 BA 02D7 R   MKF2:  MOV  DX,OFFSET DGROUP:FILNAM
420 010A B4 3C              MOV  AH,3CH
421 010C 33 C9              XOR  CX,CX
422 010E CD 21              INT  DOSINT    ;OPEN FILE
423 0110 72 05              JC   MKF4 ;JMP IF ERR
424 0112 A3 031C R          MOV  OHANDL,AX ;SAVE OUT FILE HANDLE
425 0115 F8                 CLC
426 0116 C3                 RET
427                         ;
428 0117 C7 06 0000 E 000C MKF4: MOV MSGNM,12
429 011D E8 0000 E          CALL CRTMSG   ;OUT FILE ERROR 430 0120 B4 4C              MOV  AH,4CH    ;STOP PROGRAM
431 0122 CD 21              INT  DOSINT
432                         ;
433 0124              MAKFIL  ENDP
434                         ;
435                         ;THIS GETS NEXT DECIMAL NUMBER FROM ASCII STRING
436 0124              GETDEC  PROC NEAR
437 0124 8B 36 035F R       MOV  SI,BUFPTR ;GET NEXT BUFF ADR
438 0128 B9 0038            MOV  CX,56     ;SET COUNTER
439 012B 80 3C 30    GD0:   CMP  BYTE PTR [SI],30H
440 012E 72 05              JB   GD1 ;JMP IF NOT NUMBER
441 0130 80 3C 3A           CMP  BYTE PTR [SI],3AH
```

```
12      442 0133  72 09                    JB    GD2    ;JMP IF NUMBER
13      443 0135  46              GD1: INC SI
14      444 0136  FF 0E 035D R         DEC   BUFSIZ
15      445 013A  E2 EF                LOOP  GD0    ;JMP IF MORE SPACE
16      446 013C  F9                   STC
17      447 013D  C3                   RET
18      448                             ;
19      449 013E  8B DE           GD2: MOV   BX,SI   ;HOLD FIRST ADR
20      450 0140  33 C9                XOR   CX,CX   ;CLR COUNTER
21      451 0142  41              GD3: INC   CX      ;COUNT ONE
22      452 0143  46                   INC   SI
23      453 0144  FF 0E 035D R         DEC   BUFSIZ
24      454 0148  80 3C 30             CMP   BYTE PTR [SI],30H
25      455 014B  72 07                JB    GD4    ;JMP IF NOT NUMBER
26      456 014D  80 3C 39             CMP   BYTE PTR [SI],39H
27      457 0150  77 02                JA    GD4    ;JMP IF NOT NUMBER
28      458 0152  EB EE                JMP   GD3    ;TRY NEXT ONE
29      459                             ;
30      460 0154  89 36 035F R    GD4: MOV   BUFPTR,SI ;SAVE NEXT BUFF ADR
32      461 0158  E8 0000 E            CALL  ASCBIN  ;GET VALUE
33      462 015B  C3                   RET
34      463 015C               GETDEC   ENDP
35      464                             ;
36
```

```
1  ^HMicrosoft (R) Macro Assembler Version 5.10                    9/8/89
2  12:29:48
3
4  PARSES GRAB VIEW FILE                                            Page
5  1-9
6      465                    ;THIS GETS NEXT ENTITY NUMBER FROM ASCII STRING
8      466 015C               GETHEX  PROC NEAR
9      467 015C  8B 36 035F R         MOV   SI,BUFPTR ;GET NEXT BUFF ADR
11     468 0160  B9 0024              MOV   CX,36    ;SET COUNTER
12     469 0163  80 3C 30        GH0: CMP   BYTE PTR [SI],30H
13     470 0166  74 09                JE    GH1    ;JMP IF A ZERO
14     471 0168  46                   INC   SI
15     472 0169  FF 0E 035D R         DEC   BUFSIZ
16     473 016D  E2 F4                LOOP  GH0    ;JMP IF MORE SPACE
17     474 016F  F9                   STC
18     475 0170  C3                   RET
19     476                             ;
```

```
20      477 0171    46              GH1: INC   SI
21      478 0172    FF 0E 035D R         DEC   BUFSIZ
22      479 0176    80 3C 30        GH2: CMP   BYTE PTR [SI],30H
23      480 0179    75 09                JNE   GH3   ;JMP IF NOT ZERO
24      481 017B    46                   INC   SI
25      482 017C    FF 0E 035D R         DEC   BUFSIZ
26      483 0180    E2 F4                LOOP  GH2   ;JMP IF MORE SPACE
27      484 0182    F9                   STC
28      485 0183    C3                   RET
29      486                               ;
30      487 0184    8B DE           GH3: MOV   BX,SI     ;HOLD FIRST ADR
31      488 0186    33 C9                XOR   CX,CX     ;CLR COUNTER
32      489 0188    41              GH4: INC   CX        ;COUNT ONE
33      490 0189    46                   INC   SI
34      491 018A    FF 0E 035D R         DEC   BUFSIZ
35      492 018E    80 3C 3E             CMP   BYTE PTR [SI],3EH
36      493 0191    74 07                JE    GH5   ;JMP IF CARROT
 1      494 0193    83 F9 08             CMP   CX,8
 2      495 0196    72 F0                JB    GH4   ;TRY NEXT ONE
 3      496 0198    F9                   STC
 4      497 0199    C3                   RET
 5      498                               ;
 6      499 019A    89 36 035F R    GH5: MOV   BUFPTR,SI ;SAVE NEXT BUFF
 7 ADR
 8      500 019E    33 F6                XOR   SI,SI     ;CLR RESULT
 9      501 01A0    8B C6           GH6: MOV   AX,SI     ;GET PREVIOUS
10 RESULT
11      502 01A2    BE 0010              MOV   SI,16
12      503 01A5    F7 E6                MUL   SI        ;TIMES 16
13      504 01A7    8B F0                MOV   SI,AX     ;HOLD RESULT
14      505 01A9    32 E4                XOR   AH,AH
15      506 01AB    8A 07                MOV   AL,[BX]   ;GET NEXT DIGIT
16      507 01AD    43                   INC   BX
17      508 01AE    2C 30                SUB   AL,30H    ;CLR ASCII
18      509 01B0    3C 0A                CMP   AL,10
19      510 01B2    72 02                JB    GH7   ;JMP IF 0-9
20      511 01B4    2C 07                SUB   AL,07H
21      512 01B6    03 F0           GH7: ADD   SI,AX     ;ADD TO CURR
22 RESULT
23      513 01B8    E2 E6                LOOP  GH6   ;JMP IF MORE
24      514 01BA    C3                   RET
25      515 01BB                    GETHEX      ENDP
26      516                               ;
27      517                               ;THIS READS THE .LSP FILE FOR
```

```
28  PARAMETERS
29       518 01BB                         GETLSP    PROC NEAR
30       519 01BB  B9 0037                          MOV   CX,55
31       520 01BE  8B 1E 0318 R                     MOV   BX,FHANDL
32       521 01C2  E8 0328 R                        CALL  INITBF      ;READ LSP FILE
33
34       522 01C5  73 0D                            JNC   GLSP2       ;JMP IF NO ERR
35
```

```
 1  ^HMicrosoft (R) Macro Assembler Version 5.10                    9/8/89
 2  12:29:48
 3
 4  PARSES GRAB VIEW FILE                                           Page
 5  1-10
 6       523 01C7  C7 06 0000 E 000D GLSP1:  MOV   MSGNM,13
 7       524 01CD  E8 0000 E                 CALL  CRTMSG      ;LSP FILE ERROR
 8
 9       525 01D0  B4 4C                     MOV   AH,4CH      ;STOP PROGRAM
10       526 01D2  CD 21                     INT   DOSINT
11       527                                 ;
12       528 01D4  E8 0124 R         GLSP2:  CALL  GETDEC      ;GET # TRLS
13
14       529 01D7  72 EE                     JC    GLSP1       ;JMP IF ERR
15       530 01D9  89 36 033B R              MOV   NTRLS,SI
16       531 01DD  E8 0124 R                 CALL  GETDEC      ;GET # SMPS
17       532 01E0  72 E5                     JC    GLSP1       ;JMP IF ERR
18       533 01E2  89 36 0339 R              MOV   NSMPS,SI
19       534 01E6  E8 0124 R                 CALL  GETDEC      ;GET # SETS
20       535 01E9  72 DC                     JC    GLSP1       ;JMP IF ERR
21       536 01EB  89 36 0337 R              MOV   NSETS,SI
22       537 01EF  83 3E 034F R 01           CMP   RAWFLG,1
23       538 01F4  74 0B                     JE    GLSP3       ;JMP IF RAW
24  REFERENCE
25       539 01F6  C6 06 0352 R 00           MOV   RTRL,0      ;ELSE USE
26  DXF DATA
27       540 01FB  C6 06 0351 R 00           MOV   RSMP,0
28       541 0200  C3                        RET
29       542                                 ;
30       543 0201  83 3E 035D R 3C   GLSP3:  CMP   BUFSIZ,60
31       544 0206  72 19                     JB    GLSP4       ;JMP IF OLDER LSP
32  FILE
33       545 0208  E8 0124 R                 CALL  GETDEC      ;GET STARTING
34  TRIAL
35       546 020B  72 BA                     JC    GLSP1       ;JMP IF ERR
36       547 020D  8B C6                     MOV   AX,SI
```

```
548 020F  FE C8              DEC   AL
549 0211  A2 0352 R          MOV   RTRL,AL
550 0214  E8 0124 R          CALL  GETDEC    ;GET STARTING SAMPLE
551 0217  72 AE              JC    GLSP1     ;JMP IF ERR
552 0219  8B C6              MOV   AX,SI
553 021B  FE C8              DEC   AL
554 021D  A2 0351 R          MOV   RSMP,AL
555 0220  C3                 RET
556                          ;
557 0221  E8 0000 E    GLSP4: CALL SNDLF
558 0224  C7 06 0000 E 0012  MOV  MSGNM,18
559 022A  E8 0000 E          CALL CRTMSG
560 022D  C7 06 0000 E 0014  MOV  MSGNM,20
561 0233  E8 0000 E          CALL RCVVAL    ;GET STARTING TRIAL
562 0236  72 E9              JC   GLSP4     ;TRY AGAIN IF ERR
563 0238  8B C6              MOV  AX,SI
564 023A  FE C8              DEC  AL
565 023C  A2 0352 R          MOV  RTRL,AL
566 023F  E8 0000 E    GLSP5: CALL SNDLF
567 0242  C7 06 0000 E 0013  MOV  MSGNM,19
568 0248  E8 0000 E          CALL CRTMSG
569 024B  C7 06 0000 E 0014  MOV  MSGNM,20
570 0251  E8 0000 E          CALL RCVVAL    ;GET STARTING SAMPLE
571 0254  72 E9              JC   GLSP5     ;TRY AGAIN IF ERR
572 0256  8B C6              MOV  AX,SI
573 0258  FE C8              DEC  AL
574 025A  A2 0351 R          MOV  RSMP,AL
575 025D  C3                 RET
576 025E              GETLSP  ENDP
577                          ;
578                          ;THIS GETS THE ENTITY SAMP,SET AND TRIAL #'S
579 025E              GETENT  PROC NEAR
580 025E  8B C6              MOV  AX,SI     ;GET ENTITY
                             ;FORMULA 1
```

Microsoft (R) Macro Assembler Version 5.10                    9/8/89
12:29:48

PARSES GRAB VIEW FILE                                          Page 1-11

```
581 0260  F7 36 034B R         DIV  FENT     ;DIVIDED BY 1ST
582 0264  8B F8                MOV  DI,AX    ;AS ENTITY #
583 0266  33 D2                XOR  DX,DX
;FORMULA 2
584 0268  F7 36 0349 R         DIV  XSMP     ;DIVIDED BY TOT SMPS
585 026C  83 FA 00             CMP  DX,0
586 026F  74 01                JE   GE0      ;JMP IF NO REMAINDER
587 0271  40                   INC  AX       ;ELSE ADD 1
588 0272  A3 0341 R       GE0: MOV  NTRL,AX  ;AS TRIAL #
589 0275  48                   DEC  AX       ;FORMULA 3
590 0276  F7 26 0349 R         MUL  XSMP     ;# SMPS IN PREV TRIALS 591 027A  2B F8                SUB  DI,AX    ;GIVES ENTITY # WITHIN TRIAL
592 027C  8B C7                MOV  AX,DI
;FORMULA 4
593 027E  33 D2                XOR  DX,DX
594 0280  F7 36 0337 R         DIV  NSETS    ;DIVIDED BY # SETS
595 0284  83 FA 00             CMP  DX,0
596 0287  74 01                JE   GE1      ;JMP IF NO RMDR
597 0289  40                   INC  AX
598 028A  A3 033F R       GE1: MOV  NSMP,AX  ;AS SAMPLE #
599 028D  48                   DEC  AX       ;FORMULA 5
600 028E  F7 26 0337 R         MUL  NSETS    ;# SMPS IN PREV SETS
601 0292  2B F8                SUB  DI,AX    ;GIVES SET #
602 0294  89 3E 033D R         MOV  NSET,DI  ;AS SET #
603                            ;
604 0298  A1 0347 R            MOV  AX,CTRL  ;GET CURR TRIAL #

605 029B  3D 0000              CMP  AX,0
606 029E  74 08                JE   GE2      ;JMP IF 1ST SMP OF NEW TRIAL
607 02A0  3B 06 0341 R         CMP  AX,NTRL
608 02A4  74 02                JE   GE2      ;JMP IF CURR TRIAL
609 02A6  F9                   STC
610 02A7  C3                   RET
```

```
 8    611                          ;
 9    612 02A8                     PSTENT   LABEL    NEAR
10    613 02A8  BF 83C5 R          GE2: MOV DI,OFFSET DGROUP:SET1
11    614 02AB  B9 00FA                 MOV CX,250
12    615 02AE  A1 033D R               MOV AX,NSET
13    616 02B1  48                 DEC  AX
14    617 02B2  3D 0000                 CMP AX,0
15    618 02B5  74 02                   JE  GE3      ;JMP IF 0
16    619 02B7  F7 E1                   MUL CX       ;GET SET TABLE ADR
17 OFFSET
18    620 02B9  03 F8              GE3: ADD DI,AX   ;GET SET TABLE
19 START
20    621 02BB  FF 0E 033F R            DEC NSMP
21    622 02BF  03 3E 033F R            ADD DI,NSMP
22    623 02C3  C6 05 01                MOV BYTE PTR [DI],1
23 ;POST SAMP
24    624 02C6  F8                      CLC
25    625 02C7  C3                      RET
26    626 02C8                     GETENT   ENDP
27    627                          ;
28    628                          ;THIS FILLS THE INPUT BUFFER
29    629 02C8                     FILLBF   PROC NEAR
30    630 02C8  BB 8000                 MOV BX,32768 ;MAX SIZE
31    631 02CB  8B 0E 035D R            MOV CX,BUFSIZ ;CURR SIZE
32    632 02CF  BF 0361 R               MOV DI,OFFSET DGROUP:FBUF
33    633 02D2  83 F9 00                CMP CX,0
34    634 02D5  74 06                   JE  FBF0    ;JMP IF EMPTY
35    635 02D7  8B 36 035F R            MOV SI,BUFPTR ;NXT DATA ADR 1    636 02DB  F3/ A4             REP  MOVSB          ;DATA TO HEAD OF
 2 BUFFER
 3    637 02DD  89 3E 035F R       FBF0:   MOV BUFPTR,DI ;NXT DATA
 4 ADR
 5    638 02E1  2B 1E 035D R            SUB BX,BUFSIZ ;SPACE AVAIL
 6
```

```
1 ^HMicrosoft (R) Macro Assembler Version 5.10              9/8/89
2 12:29:48
3
4 PARSES GRAB VIEW FILE                                    Page
5 1-12
6    639 02E5  8B 0E 0355 R            MOV CX,FSIZ   ;GET FILE SIZE
7    640 02E9  8B 16 0357 R            MOV DX,FSIZ+2
8    641 02ED  2B 0E 0359 R            SUB CX,BYTSRD ;LESS BYTES READ
9    642 02F1  1B 16 035B R            SBB DX,BYTSRD+2
```

```
10      643 02F5  0B D2                       OR   DX,DX
11      644 02F7  75 08                       JNZ  FBF1   ;JMP IF OVER 65535
12      645 02F9  0B C9                       OR   CX,CX
13      646 02FB  74 29                       JZ   FBF5   ;JMP IF DONE
14      647 02FD  3B CB                       CMP  CX,BX
15      648 02FF  72 02                       JB   FBF2   ;JMP IF LT SPACE AVAIL
16
17      649 0301  8B CB            FBF1:      MOV  CX,BX         ;SET TO MAX
18      650 0303  8B 1E 0318 R     FBF2:      MOV  BX,FHANDL
19      651 0307  8B 16 035F R                MOV  DX,BUFPTR ;1ST ADR
20      652 030B  E8 0000 E                   CALL RDIND         ;READ INPUT FILE
21
22      653 030E  72 16                       JC   FBF5   ;JMP IF ERR
23      654 0310  01 06 035D R                ADD  BUFSIZ,AX ;CURR SIZE
24      655 0314  01 06 0359 R                ADD  BYTSRD,AX ;TOTAL BYTES READ
25
26      656 0318  83 16 035B R 00             ADC  BYTSRD+2,0
27      657 031D  BE 0361 R                   MOV  SI,OFFSET DGROUP:FBUF
28      658 0320  89 36 035F R                MOV  BUFPTR,SI
29      659 0324  F8                          CLC
30      660 0325  C3                          RET
31      661 0326  F9               FBF5:      STC
32      662 0327  C3                          RET
33      663 0328                   FILLBF     ENDP
34      664                                   ;
35      665                                   ;THIS INITIALIZES THE BUFFER FROM A
36 FILE 1      666 0328                   INITBF     PROC NEAR
 2      667 0328  33 C9                       XOR  CX,CX
 3      668 032A  33 D2                       XOR  DX,DX
 4      669 032C  B0 02                       MOV  AL,2
 5      670 032E  B4 42                       MOV  AH,42H
 6      671 0330  CD 21                       INT  DOSINT        ;GET END OF FILE
 7      672 0332  A3 0355 R                   MOV  FSIZ,AX       ;POST FILE SIZE
 8
 9      673 0335  89 16 0357 R                MOV  FSIZ+2,DX
10      674 0339  33 C9                       XOR  CX,CX
11      675 033B  33 D2                       XOR  DX,DX
12      676 033D  32 C0                       XOR  AL,AL
13      677 033F  B4 42                       MOV  AH,42H
14      678 0341  CD 21                       INT  DOSINT        ;SET START OF
15 FILE
16      679 0343  BE 0361 R                   MOV  SI,OFFSET DGROUP:FBUF
17      680 0346  89 36 035F R                MOV  BUFPTR,SI ;SET INIT BUFF
```

```
18  ADR
19        681 034A  C7 06 035D R 0000      MOV    BUFSIZ,0
20        682 0350  C7 06 0359 R 0000      MOV    BYTSRD,0
21       .683 0356  C7 06 035B R 0000      MOV    BYTSRD+2,0
22        684 035C  E8 02C8 R              CALL   FILLBF     ;READ SOME DATA
23  INTO BUFF
24        685 035F  C3                     RET
25        686 0360                  INITBF     ENDP
26        687                       ;
27        688                       ;THIS PARSES THE VIEW FILE
28        689 0360                  PARSE      PROC NEAR
29        690 0360  E8 0124 R              CALL   GETDEC     ;GET # ENTITIES
30  IN BASE
31        691 0363  72 21                  JC     PAR1 ;JMP IF ERR
32        692 0365  89 36 0333 R           MOV    NBASE,SI
33        693 0369  E8 015C R              CALL   GETHEX     ;GET LAST ENTITY
34  NUMBER
35        694 036C  72 18                  JC     PAR1 ;JMP IF ERR
36        695 036E  89 36 034D R           MOV    LENT,SI 1         696 0372  E8 015C R              CALL   GETHEX     ;GET FIRST ENTITY
2   NUMBER
3
1   ^HMicrosoft (R) Macro Assembler Version 5.10                        9/8/89
2   12:29:48
3
4   PARSES GRAB VIEW FILE                                                Page
5   1-13
6         697 0375  72 0F                  JC     PAR1 ;JMP IF ERR
7         698 0377  89 36 034B R           MOV    FENT,SI
8         699 037B  E8 0124 R              CALL   GETDEC     ;GET # ENTITIES
9   IN VIEW
10        700 037E  72 06                  JC     PAR1 ;JMP IF ERR
11        701 0380  89 36 0335 R           MOV    NENTS,SI
12        702 0384  EB 0D                  JMP    SHORT PAR3
13        703                       ;
14        704 0386  C7 06 0000 E 000E PAR1:    MOV    MSGNM,14
15        705 038C  E8 0000 E        PAR2:    CALL   CRTMSG
16        706 038F  B4 4C                  MOV    AH,4CH     ;STOP PROGRAM
17        707 0391  CD 21                  INT    DOSINT
18        708                       ;
19        709 0393  A1 0339 R        PAR3:    MOV    AX,NSMPS   ;GET  .LSP
20  SAMPS
21        710 0396  F7 26 0337 R           MUL    NSETS      ;TIMES .LSP SETS
22        711 039A  A3 0349 R              MOV    XSMP,AX    ; S A V E    A S
```

SMPS/TRIAL

```
712 039D  F7 26 033B R              MUL  NTRLS    ;TIMES   .LSP TRIALS
713 03A1  3B 06 0333 R              CMP  AX,NBASE
714 03A5  74 08                     JE   PAR4 ;JMP IF EQUAL TO VIEW BASE
715 03A7  C7 06 0000 E 000F         MOV  MSGNM,15
716 03AD  EB DD                     JMP  PAR2 ;JMP AS ERROR
717                         ;
718 03AF  C7 06 0347 R 0000  PAR4:  MOV  CTRL,0   ;CLR CURR TRIAL #
719 03B5  BF 83C5 R          PARLP: MOV  DI,OFFSET DGROUP:SET1
720 03B8  B9 05DC                   MOV  CX,SETLTH
721 03BB  32 C0                     XOR  AL,AL
722 03BD  F3/ AA                    REP  STOSB    ;ZERO SET ARRAYS
723 03BF  83 3E 0347 R 00           CMP  CTRL,0
724 03C4  74 0B                     JE   TLP0 ;JMP IF FIRST PASS
725 03C6  A1 0341 R                 MOV  AX,NTRL  ;GET NEXT TRIAL #
726 03C9  A3 0347 R                 MOV  CTRL,AX  ;AS CURR TRIAL
727 03CC  E8 02A8 R                 CALL PSTENT   ;POST ENT
728 03CF  EB 18                     JMP  SHORT NXTENT
729                         ;
730 03D1  E8 015C R          TLP0:  CALL GETHEX   ;GET FIRST VIEW ENTITY OF FILE
731 03D4  72 05                     JC   TLP1 ;JMP IF ERR
732 03D6  E8 025E R                 CALL GETENT   ;GET ENTITY DATA
733 03D9  EB 08                     JMP  SHORT TLP2
734                         ;
735 03DB  C7 06 0000 E 0010  TLP1:  MOV  MSGNM,16
736 03E1  EB A9                     JMP  PAR2
737                         ;
738 03E3  A1 0341 R          TLP2:  MOV  AX,NTRL   ;GET TRIAL #
739 03E6  A3 0347 R                 MOV  CTRL,AX  ;AS CURR TRIAL
740                         ;
741 03E9  FF 0E 0335 R       NXTENT: DEC NENTS    ;COUNT AN ENTITY
742 03ED  74 17                     JZ   NE2 ;JMP IF NO MORE
743 03EF  83 3E 035D R 24           CMP  BUFSIZ,36
```

```
31      744 03F4  77 06                JA   NE1    ;JMP IF ROOM
32      745 03F6  E8 02C8 R            CALL FILLBF ;ELSE GET MORE DATA
33
34      746 03F9  73 01                JNC  NE1    ;JMP IF NO ERR
35      747 03FB  C3                   RET
36      748                            ;
 1      749 03FC  E8 015C R       NE1: CALL GETHEX ;GET NXT ENT
 2      750 03FF  72 DA                JC   TLP1   ;JMP IF ERR
 3      751 0401  E8 025E R            CALL GETENT ;GET NXT ENT
 4      752 0404  73 E3                JNC  NXTENT ;JMP IF CURR TRIAL
 5
 6      753                            ;
 7      754 0406  8B 0E 0337 R    NE2: MOV  CX,NSETS ;# SETS IN TRIAL
 8
```

Microsoft (R) Macro Assembler Version 5.10                 9/8/89 12:29:48

PARSES GRAB VIEW FILE                                            Page 1-14

```
 6      755 040A  BB 83C5 R            MOV  BX,OFFSET DGROUP:SET1
 7      756 040D  51              NE3: PUSH CX
 8      757 040E  53                   PUSH BX
 9      758 040F  A1 0337 R            MOV  AX,NSETS
10      759 0412  2B C1                SUB  AX,CX
11      760 0414  40                   INC  AX
12      761 0415  50                   PUSH AX   ;HOLD SET #
13      762 0416  B9 00FA               MOV  CX,250    ;MAX SMPS
14      763 0419  33 F6                XOR  SI,SI     ;SOURCE POINTER
15      764 041B  B2 01                MOV  DL,1 ;SOURCE NUMBER
16      765 041D  02 16 0351 R         ADD  DL,RSMP   ;PLUS RAW OFFSET (IF ANY)
17
18      766 0421  C7 06 89A1 R 0000    MOV  SMPCNT,0 ;DEST COUNTER
19      767 0427  BF 89A3 R            MOV  DI,OFFSET DGROUP:SMPTAB
20      768 042A  80 38 00        NE4: CMP  BYTE PTR [BX][SI],0
21
22      769 042D  74 07                JE   NE5    ;JMP IF NO SAMP
23      770 042F  88 15                MOV  [DI],DL ;POST SAMP #
24      771 0431  47                   INC  DI
25      772 0432  FF 06 89A1 R         INC  SMPCNT
26      773 0436  46              NE5: INC  SI
27      774 0437  FE C2                INC  DL
28      775 0439  E2 EF                LOOP NE4    ;JMP IF MORE
29      776 043B  83 3E 89A1 R 00      CMP  SMPCNT,0
30      777 0440  75 04                JNE  NE5A   ;JMP IF SAMPS FOUND
```

```
778 0442  58              POP  AX
779 0443  E9 04D9 R       JMP  NE12     ;ELSE SKIP
780                       ;
781 0446  A1 0347 R  NE5A: MOV AX,CTRL   ;GET CURR TRIAL #
782 0449  02 06 0352 R    ADD  AL,RTRL   ;PLUS RAW OFFSET (IF ANY)
783 044D  A3 0353 R       MOV  PTRL,AX
784 0450  BB 0353 R       MOV  BX,OFFSET DGROUP:PTRL
785 0453  BF 02AC R       MOV  DI,OFFSET DGROUP:PRTLIN+6

786 0456  E8 0000 E       CALL BNASC4    ;POST TRIAL #
787 0459  58              POP  AX        ;GET SET #
788 045A  B1 20           MOV  CL,' '
789 045C  BF 02B5 R       MOV  DI,OFFSET DGROUP:PRTLIN+15

790 045F  E8 0000 E       CALL BNASC2    ;POST SET #
791 0462  8B 1E 031C R    MOV  BX,OHANDL
792 0466  B9 0021         MOV  CX,PRTLTH
793 0469  BA 02A6 R       MOV  DX,OFFSET DGROUP:PRTLIN
794 046C  E8 0000 E       CALL WRTIND
795 046F  73 01           JNC  NE6       ;JMP IF NO ERR
796 0471  C3              RET
797 0472  8B 0E 89A1 R  NE6: MOV CX,SMPCNT ;GET # SAMPLES
798 0476  49              DEC  CX        ;LESS FIRST ONE
799 0477  BE 89A3 R       MOV  SI,OFFSET DGROUP:SMPTAB
800 047A  8A 14           MOV  DL,[SI]   ;GET 1ST NUMBER
801 047C  8A F2           MOV  DH,DL
802 047E  FE C6           INC  DH        ;NXT NUMBER IN SERIES
803 0480  46              INC  SI        ;NEXT TABLE ADR
804 0481  38 34      NE7: CMP [SI],DH
805 0483  75 05           JNE  NE8       ;JMP IF NOT IN SEQUENCE
806 0485  FE C6           INC  DH        ;NEXT SERIES #
807 0487  46              INC  SI
808 0488  E2 F7           LOOP NE7       ;JMP IF MORE
809                       ;
810 048A  FE CE      NE8: DEC DH
811 048C  51              PUSH CX        ;HOLD COUNT
812 048D  56              PUSH SI        ;HOLD ADR
```

Microsoft (R) Macro Assembler Version 5.10        9/8/89
12:29:48

PARSES GRAB VIEW FILE                                                          Page
1-15

```
813  048E  52                PUSH DX            ;HOLD #'S
814  048F  8A C6                  MOV  AL,DH    ;GET LAST SAMP
815  0491  32 E4                  XOR  AH,AH
816  0493  A3 0345 R              MOV  LSMP,AX
817  0496  8A C2                  MOV  AL,DL    ;GET 1ST SAMP
818  0498  A3 0343 R              MOV  FSMP,AX
819  049B  BB 0343 R              MOV  BX,OFFSET DGROUP:FSMP
820  049E  BF 02C7 R              MOV  DI,OFFSET DGROUP:PRTSMP
821  04A1  E8 0000 E              CALL BNASC4   ;POST SAMP #
822  04A4  BB 0345 R              MOV  BX,OFFSET DGROUP:LSMP
823  04A7  BF 02CF R              MOV  DI,OFFSET DGROUP:PRTSMP+8

824  04AA  E8 0000 E              CALL BNASC4   ;POST SAMP #
825  04AD  8B 1E 031C R           MOV  BX,OHANDL
826  04B1  B9 000E                MOV  CX,LTHPRT
827  04B4  BA 02C7 R              MOV  DX,OFFSET DGROUP:PRTSMP
828  04B7  E8 0000 E              CALL WRTIND
829  04BA  5A           POP DX
830  04BB  5E           POP SI
831  04BC  59           POP CX
832  04BD  73 01              JNC  NE9   ;JMP IF NO ERR
833  04BF  C3           RET
834  04C0  83 F9 00           NE9: CMP  CX,0
835  04C3  75 02              JNE  NE10  ;JMP IF NOT DONE
836  04C5  EB 12              JMP  SHORT NE12
837                     ;
838  04C7  8A 14        NE10:    MOV  DL,[SI]   ;GET NEXT #
839  04C9  8A F2              MOV  DH,DL
840  04CB  FE C6              INC  DH   ;NEXT SERIES #
841  04CD  46           INC SI
842  04CE  83 F9 00           CMP  CX,0
843  04D1  75 02              JNE  NE11  ;JMP IF MORE
844  04D3  EB 04              JMP  SHORT NE12
845                     ;
846  04D5  E2 AA        NE11:    LOOP NE7   ;JMP IF MORE
847  04D7  EB B1              JMP  NE8   ;POST LAST SAMP
848                     ;
849  04D9  5B           NE12:    POP  BX
850  04DA  59           POP CX
851  04DB  81 C3 00FA         ADD  BX,250
852  04DF  49           DEC CX
```

```
12     853 04E0  74 03                  JZ    NE13  ;JMP IF DONE
13     854 04E2  E9 040D R              JMP   NE3   ;ELSE DO NEXT SET
14     855                              ;
15     856 04E5  83 3E 0335 R 00   NE13: CMP  NENTS,0
16     857 04EA  74 03                  JE    NE14  ;JMP IF ALL DONE
17     858 04EC  E9 03B5 R              JMP   PARLP ;DO NEXT TRIAL
18
19     859                              ;
20     860 04EF  C3                NE14: RET
21     861                              ;
22     862 04F0                    PARSE    ENDP
23     863                              ;
24     864                         ;THIS IS THE START OF THE MAIN PROGRAM
25
26     865 04F0  8C D8             MAINPG:  MOV  AX,DS
27     866 04F2  8E C0                      MOV  ES,AX
28     867 04F4  FC                         CLD
29     868 04F5  C7 06 0000 E 0001          MOV  MSGNM,1   ;SOURCE FILE MSG
30     869 04FB  E8 003A R                  CALL GETFIL    ;OPEN THEM
31     870 04FE  73 04                      JNC  MPG1 ;JMP IF NO ERROR
32
```

```
Microsoft (R) Macro Assembler Version 5.10                    9/8/89
12:29:48

PARSES GRAB VIEW FILE                                         Page 1-16

871 0500  B4 4C             MPG0:    MOV  AH,4CH    ; S T O P PROGRAM
      872 0502  CD 21                      INT  DOSINT
      873                                  ;
      874 0504  E8 00DC R         MPG1:    CALL MAKFIL    ;OPEN OUTPUT FILE
      875                                  ;
      876 0507  C7 06 034F R 0000          MOV  RAWFLG,0  ;SET TO DXF REFERENCE
      877 050D  C7 06 0000 E 0011          MOV  MSGNM,17
      878 0513  E8 0016 R                  CALL REPCHK
      879 0516  75 04                      JNZ  MPG2 ;JMP IF DXF
      880 0518  FF 06 034F R               INC  RAWFLG    ;ELSE REFERENCE TO RAW DATA
      881                                  ;
      882 051C  E8 0000 E         MPG2:    CALL SNDLF
      883 051F  E8 01BB R                  CALL GETLSP    ;GET DXF FILE PARAMETERS
```

```
884 0522  E8 0000 E
885 0525  8B 1E 031A R
886 0529  89 1E 0318 R
887 052D  E8 0328 R                  BUFFER
888
889 0530  72 03                      ERR
890 0532  E8 0360 R                  BUFFER
891
892 0535  8B 1E 031A R
893 0539  89 1E 0318 R
894 053D  E8 0000 E
895 0540  8B 1E 031C R
896 0544  89 1E 0318 R
897 0548  C6 06 0324 R 1A
898 054D  B9 0001
899 0550  BA 0324 R
900 0553  E8 0000 E
901 0556  E8 0000 E
902 0559  B4 4C
903 055B  CD 21
904
905 055D
906

755 Source  Lines
    755 Total   Lines
    174 Symbols

47120 + 372763 Bytes symbol space free

0 Warning Errors
      0 Severe  Errors
```

```
        CALL CLRHDL    ;CLOSE LSP
        MOV  BX,VHANDL
        MOV  FHANDL,BX
        CALL INITBF    ;READ V FILE TO
;
        JC   MPG20     ;JMP IF END OR
        CALL PARSE     ;PROCESS   THE
;
MPG20:  MOV  BX,VHANDL
        MOV  FHANDL,BX
        CALL CLRHDL    ;CLOSE FILE
        MOV  BX,OHANDL
        MOV  FHANDL,BX
        MOV  MSGBUF,EOF
        MOV  CX,1
        MOV  DX,OFFSET DGROUP:MSGBUF
        CALL WRTIND
        CALL CLRHDL    ;CLOSE FILE
        MOV  AH,4CH
        INT  DOSINT
;
CODE ENDS
END  START
```

We claim:

1. A method of programming and operating a computer to automatically graphically display signal values as graphic drawing entites which form a graphic phase space portrait, and to automatically identify a subset of said signal values corresponding to a manually selected subset of one or more graphic drawing entities which form a visually identified pattern within said graphic phase space portrait, comprising the following steps:

1.1 automatically composing by computer a graphic phase space portrait of signal values collected from a series of two or three signal detectors D1, D2 and D3, said signal values comprising substantially simultaneous signal values D1S1, D2S1, and D3S1 collected at discrete time t1, and substantially simultaneous signal values D1S2, D2S2, and D3S2 collected at discrete time t2, by the following steps:

1.1.1 constructing a graphic drawing point entity P1 having as its drawing coordinates in space at least two of the respective signal values D1S1, D2S1, and D3S1;

1.1.2 constructing a graphic drawing point entity P2 having as its drawing coordinates in space at least two of the respective signal values D1S2, D2S2, and D3S2;

1.1.3 constructing a graphic drawing line entity Ll1 connecting and terminating at said two graphic drawing point entities P1 and P2;

1.2 Iterating steps 1.1, 1.1.1, 1.1.2, and 1.1.3 with additional signal values collected substantially simultaneously from at least two of said detectors D1, D2, and D3, at at least one of additional discrete signal times t3, t4, . . . tn;

1.3 visually identifying a pattern within said graphic phase space portrait;

1.4 manually commanding the computer to select from within said graphic phase space portrait a subset of one or more graphic drawing entities which form said visually identified pattern; and 1.5 automatically retrieving by computer the subset of signal values that comprise the drawing coordinates of said selected subset of one or more graphic drawing entities which form said visually identified pattern within said graphic phase space portrait.

2. A method of graphically displaying the time sequence of signal values as a variable dimension within a graphic phase space portrait of said signal values, comprising the following steps:

2.1 automatically composing by computer a graphic phase space portrait of signal values collected from a series of one or more signal detectors D1, D2, and D3, said signal values comprising substantially simultaneous signal values D1S1, D2S1, and D3S1 collected at discrete time t1, and substantially simultaneous signal values D1S2, D2S2, and D3S2 collected at discrete time t2, by the following steps:

2.1.1 constructing a graphic drawing entity P1 having as its drawing coordinates in space at least two of the respective signal values D1S1, D2S1, and D3S1;

2.1.2 constructing a graphic drawing entity P2 having as its drawing coordinates in space at least two of the respective signal values D1S2, D2S2, and D3S2;

2.2 Iterating steps 2.1, 2.1.1, and 2.1.2 with additional signal values collected substantially simultaneously from at least two of said detectors D1, D2, and D3, at at least one of additional discrete signal times t3, t4, . . . . tn;

2.3 assigning to each of said drawing entities P1, P2, P3, . . . . Pn, in accord with temporal sequence, a visually distinctive color from a pre-determined sequence of colors C1t1, C2t2, C3t3, . . . . Cntn.

3. A method of displaying the time sequence of signal values as a variable dimension in a graphic phase space portrait, as stated in claim 2, including display of periodic increments of a defined time period, further comprising:

3.1 defining a color sequence having a number of distinctive colors corresponding to the number and sequence of periodic increments in a defined time period; and 3.2 serially iterating said color sequence in said line drawing entities in said graphic phase space portrait, one iteration of said color sequence representing one expiration of the defined time period within the displayed time sequence of signal values.

4. A method of graphically displaying signal values, comprising the steps of claim 3, and further comprising:

4.1 defining a series of visually-distinctive different color sequences, wherein the number of said different colors is a different prime number in each color sequence;

4.2 iterating said graphic phase space portrait, but substituting a different prime-number color sequence in each iteration.

5. A method of identifying periodicity in signal values, comprising the steps of claim 3 or claim 4, and further comprising:

inspecting each such iteration of said graphic portrait for periodic patterns.

6. A method of constructing by computer a composite graphic phase space portrait of signal data which has been collected from a set of at least four signal detectors D1, D2, D3, D4, . . . . Dn, comprising substantially simultaneous signal values D1S1, D2S1, D3S1, D4S1, . . . . DnS1 at discrete time t1; and substantially simultaneous signal values D1S2, D2S2, D3S2, D4S2 . . . . DnS2 at discrete time t2, comprising the following steps:

6.1 automatically composing by computer a first layer LA1 graphic phase space portrait of a subset of said signal values by:

6.1.1 selecting a unique detector subset 1 comprised of two or three detectors Da, Db, and Dc taken from said set of at least four signal detectors D1, D2, D3, D4, . . . . Dn;

6.1.2 constructing a graphic drawing entity P1LA1 having as its drawing coordinates in space the respective signal values DaS1, DbS1, DcS1 . . . . DxS1, collected at time t1 from said unique subset 1 of detectors, Da, Db, and Dc.

6.1.3 constructing a graphic drawing entity P2LA1 having as its drawing coordinates in space the respective signal values DaS2, DbS2, DcS2, . . . . DxS2, collected at time t2 from said unique subset 1 of detectors Da, Db, and Dc;

6.2 iterating the steps of paragraph 6.1 and its subparts with additional signal data for at least one of discrete signal times t3, t4, . . . . tn;

6.3 composing additional layers LA2, LA3, . . . . LAn, of graphic phase space portraits by iterating the steps of paragraph 6.2 and its subparts, but in each additional layer substituting for the signal values of said unique subset 1 of detectors Da, Db, and Dc, the signal values from another unique subset of two or three detectors selected from said set of at least four detectors D1, D2, D3, D4 . . . Dn;

6.4 forming a composite graphic phase space portrait by graphically overlaying the phase space portraits of two or more of said layers LA1, LA2, LA3, . . . . LAn.

7. A method of visually distinguishing the layers of a composite graphic phase space portrait, composed by the method of claim 6, further comprising:

assigning to each layer of said composite graphic phase space portrait a color visually distinctive from the colors of other layers of said composite portrait.

8. A method of visually distinguishing the layers of a composite phase space portrait, composed by the method of claim 6, further comprising:

assigning to each layer of said composite phase space portrait a drawing entity type visually distinctive from the drawing entity types of other layers of said composite portrait.

9. A method of visually distinguishing the layers of a computer-generated composite graphic phase space portrait, composed by the method of claim 6, further comprising:

assigning to each layer of said composite graphic phase space portrait both a visually distinctive color and a visually distinctive line type, thus enabling each drawing line entity to display up to seven variables consisting of three drawing coordinates, a direction, a color and a line type.

10. A method, as in claim 2, of visually displaying within a graphic phase portrait of a computer-recorded stream of signal values the timing of an event relative to the timing of said signal values, denoted by a graphic drawing event symbol adjacent to the graphic drawing entity which has drawing coordinates corresponding to the signal values recorded substantially simultaneously with said event, comprising:

10.1 inserting automatically by computer a flag symbol into the computer-recorded stream of signal values corresponding to the timing of an event relative to said signal values; and 10.2 drawing a visually distinctive graphic drawing event symbol nearly adjacent to the drawing point entity having drawing coordinates derived from the signal values recorded nearest in time to said flag symbol in said computer-recorded stream of data.

11. A computer-assisted method of visually identifying and manually segregating a pattern-containing subset of signal values from a stream of computer-recorded signal values, which is displayed as graphic drawing entities to form a graphic phase space portrait as in any of claims 2, 3, 4, 6, 7, 8, 9, or 10, further comprising:

11.1 visually identifying a pattern within said graphic phase space portrait;

11.2 manually commanding the computer to select from within said graphic phase space portrait a subset of one or more graphic drawing entities which form said visually identified pattern; and 11.3 automatically retrieving by computer the subset of signal values that comprise the drawing coordinates of said selected subset of one or more graphic drawing entities which form said visually identified patterns within said graphic phase space portrait.

12. A computer-generated graphic image comprising:

12.1 a graphic drawing point entity P1 having drawing coordinates corresponding to the values of at least two of signals $D1S1$, $D2S1$, and $D3S1$ which have been collected substantially simultaneously from signal detectors D1, D2 and D3 at discrete time t1;

12.2 a graphic drawing point entity P2 having drawing coordinates corresponding to at least two of signal values $D1S2$, $D2S2$, and $D3S2$ which have been collected substantially simultaneously from signal detectors D1, D2 and D3 at discrete time t2;

12.2.1 a graphic line drawing entity LI1 connecting and terminating at said two drawing point entities P1 and P2;

12.3 Additional drawing point entities P3, P4, .... Pn, and drawing line entities LI2, LI3, .... LIn, said drawing point and line entities having as their respective drawing coordinates values corresponding respectively to additional signal values $D1S3$, $D2S3$, $D3S3$; and $D1S4$, $D2S4$, $D3S4$, .... $DnS4$, collected from said detectors D1, D2, and D3, at at least one of additional discrete signal times t3, t4, .... tn; and 12.4 each of said line drawing entities LI1, LI2, LI3 .... LIn, having a visually distinctive color from a predetermined sequence of colors $C1t1$, $C2t2$, $C3t3$, .... $Cntn$, such that 12.4.1 drawing line LI1 connecting drawing points P1 and P2 has color C1 and thus corresponds to the time interval from t1 to t2;

12.4.2 drawing line LI2 has color C2 corresponding to the time interval between t2 and t3; .....

12.4.3 drawing line LIn has color Cn.

13. A computer-generated graphic image, as stated in claim 12, further comprising:

13.1 a color sequence having a number of distinctive colors corresponding to a prime number, 13.2 which color sequence is serially iterated for as many multiples of said prime number of drawing line entities as desired.

14. A series of graphic images, comprising iterations of the graphic image of claim 13, but substituting a different prime-number color sequence in each iteration.

15. A composite graphic display of signal data which has been collected from a set of at least four signal detectors D1, D2, D3, D4, .... Dn, said signal data comprising substantially simultaneous signal values $D1S1$, $D2S1$, $D3S1$, $D4S1$ .... $DnS1$ at discrete time t1; and substantially simultaneous signal values $D1S2$, $D2S2$, $D3S2$, $D4S2$ .... $DnS2$ at discrete time t2, and $D1Sn$, $D2Sn$, $D3Sn$, $D4Sn$ .... $DnSn$ at time tn, said composite graphic display comprising the following elements:

15.1 a first layer LA1 graphic phase space portrait of a signal subset 1, 15.1.1 said signal subset 1 comprising the signals from a unique detector subset 1 comprised of two or three detectors Da, Db, and Dc taken from said set of at least four signal detectors D1, D2, D3, D4, .... Dn;

15.1.2 a graphic drawing point entity P1LA1 on said first layer LA1 having as its drawing coordinates in space the respective signal values $DaS1$, $DbS1$, $DcS1$, collected at time t1 from said unique subset 1 of detectors, Da, Db, and Dc;

15.1.3 a graphic drawing point entity P2LA1 on said first layer LA1 having as its drawing coordinates in space the respective signal values $DaS2$, $DbS2$, $DcS2$, collected at time t2 from said unique subset 1 of detectors Da, Db, and Dc;

15.1.4 a graphic line drawing entity LI1LA1 on said first layer LA1 between and terminating at said two drawing point entities P1LA1 and P2LA1;

15.2 additional drawing points P3LA1, P4LA1, ... PnLA1, whose drawing coordinates comprise additional signal values collected from said detector subset 1 for at least one of discrete signal times t3, t4, .... tn;

15.3 One or more different layers LA2, LA3, .... LAn, of graphic images overlaid with said first layer LA1, wherein the drawing coordinates of the point and line drawing entities on each such different layer correspond to the signal values of a different unique detector subset from said set of detectors D1, D2, D3, D4, .... Dn.

16. A composite graphic image, as in claim 15, further comprising a visually distinctive different color assigned to each different layer of said composite graphic image.

17. A composite graphic image, as in claim 15, further comprising a visually distinctive different line type assigned to each different layer of said composite graphic image.

18. A composite graphic computer image, as in claim 15, further comprising:

18.1 visually distinctive different colors assigned to each of one or more of said different layers, and 18.2 visually distinctive different line types assigned to each of one or more of said different layers, such that each line on a layer can display at least seven variable dimensions, consisting of three spatial coordinates, a direction, a scalar magnitude, a distinctive color, and a distinctive line type.

19. A pattern-containing subset of signal values segregated from a stream of signal values comprising:

a subset of signal values which has been segregated from a stream of signal values by the method of claim 1.

20. A pattern-containing subset of signal values, from a stream of signal values which has been displayed as graphic drawing entities to form a graphic phase space portrait as in any of claims 2, 3, 4, 6, 7, 8, 9, or 10, where said pattern-containing subset of signal values has been segregated by the method comprising:

20.1 visually identifying a pattern within said graphic phase space portrait;

20.2 manually commanding the computer to select from within said graphic phase space portrait a subset of one or more graphic drawing entities which form said visually identified pattern; and 20.3 automatically retrieving by computer the subset of signal values that comprise the drawing coordinates of said selected subset of one or more graphic drawing entities which form said visually identified patterns within said graphic phase space portrait.

21. A graphically displayed image, formed by the method of any of claims 2, 3, 4, 6, 7, 8, 9, or 10, comprising:

graphic phase space portrait of signal values.

22. A method of operating a computer to automatically graphically display signal data as graphic drawing entities which form a graphic phase space portrait, as in claim 1, and further to automatically identify both (i) a pattern-containing subset of said signal data and (ii) events temporally related to said pattern-containing subset of signal data, from a computer-recorded stream of signal values and temporally related events that correspond to a manually selected subset of one or more graphic drawing entities which form a visually identified pattern within said graphic phase space portrait, comprising the following steps:

22.1 inserting, automatically by computer, one or more flag symbols into a computer-recorded stream of signal values corresponding to the timing of one or more events relative to said signal values;

22.2 performing steps 1.1 through 1.4, inclusive, of claim 1; and 22.3 automatically retrieving by computer, from the computer-recorded stream of signal data and flag symbols, (i) the subset of signal values that comprise the drawing coordinates of said selected subset of one or more graphic drawing entities which form said visually identified patterns within said graphic phase space portrait, and (ii) any flag symbols previously inserted into said subset of signal values.

23. A method of programming and operating a computer to automatically graphically display signal values as graphic drawing entites which form a graphic phase space portrait, and to automatically identify a subset of said signal values corresponding to a manually selected subset of one or more graphic drawing entities which form a visually identified pattern within said graphic phase space portrait, comprising the following steps:

23.1 automatically composing by computer a graphic phase space portrait of signal values collected from a series of two or three signal detectors D1, D2 and D3, said signal values comprising substantially simultaneous signal values D1S1, D2S1, and D3S1 collected at discrete time t1, and substantially simultaneous signal values D1S2, D2S2, and D3S2 collected at discrete time t2, by the following steps:

23.1.1 constructing a graphic drawing point entity P1 having as its drawing coordinates in space at least two of the respective signal values D1S1, D2S1, and D3S1;

23.1.2 constructing a graphic drawing point entity P2 having as its drawing coordinates in space at least two of the respective signal values D1S2, D2S2, and D3S2;

23.2 Iterating steps 23.1, 23.1.1, and 23.1.2 with additional signal values collected substantially simultaneously from at least two of said detectors D1, D2, and D3, at at least one of additional discrete signal times t3, t4, . . . tn;

23.3 visually identifying a pattern within said graphic phase space portrait;

23.4 manually commanding the computer to select from within said graphic phase space portrait a subset of one or more graphic drawing entities which form said visually identified pattern; and 23.5 automatically retrieving by computer the subset of signal values that comprise the drawing coordinates of said selected subset of one or more graphic drawing entities which form said visually identified pattern within said graphic phase space portrait.

24. A method of programming and operating a computer, as in claim 23, further comprising:

24.1 inserting, automatically by computer, one or more flag symbols into a computer-recorded stream of signal values corresponding to the timing of one or more events relative to said signal values;

24.2 Performing steps 23.1 through 23.4, inclusive, of claim 23, and 24.3 automatically retrieving by computer, from the computer-recorded stream of signal data and flag symbols, (i) the subset of signal values that comprise the drawing coordinates of said selected subset of one or more graphic drawing entities which form said visually identified patterns within said graphic phase space portrait, and (ii) any flag symbols previously inserted into said subset of signal values.

25. A pattern-containing subset of signal values segregated from a stream of signal values comprising:

a subset of signal values which has been segregated from a stream of signal values by the method of claim 23.

26. A method of programming and operating a computer to automatically graphically display signal values as graphic drawing entites which form a graphic phase space portrait, and to automatically identify a subset of said signal values corresponding to a manually selected subset of one or more graphic drawing entities which form a visually identified pattern within said graphic phase space portrait, comprising the following steps:

26.1 automatically composing by computer a graphic phase space portrait of signal values collected from a series of one or more signal detectors D1, D2 and D3, said signal values comprising substantially simultaneous signal values D1S1, D2S1, and D3S1 collected at discrete time t1, and substantially simultaneous signal values D1S2, D2S2, and D3S2 collected at discrete time t2, by the following steps:

26.1.1 constructing a graphic drawing point entity P1 having as its drawing coordinates in space at least two of the respective signal values D1S1, D2S1, and D3S1;

26.1.2 constructing a graphic drawing point entity P2 having as its drawing coordinates in space at least two of the respective signal values D1S2, D2S2, and D3S2;

26.2 Iterating steps 26.1.1, 26.1.1, and 26.1.2 with additional signal values collected substantially simultaneously from at least two of said detectors D1, D2, and D3, at at least one of additional discrete signal times t3, t4, . . . . tn;

26.3 visually identifying a pattern within said graphic phase space portrait;

26.4 manually commanding the computer to select from within said graphic phase space portrait a subset of one or more graphic drawing entities which form said visually identified pattern; and 26.5 automatically retrieving by computer the subset of signal values that comprise the drawing coordinates of said selected subset of one or more graphic drawing entities which form said visually identified pattern within said graphic phase space portrait.

27. A method of graphically displaying the time sequence of signal values as a variable dimension within a graphic phase space portrait of said signal values, comprising the following steps:

27.1 automatically composing by computer a graphic phase space portrait of signal values collected from a series of one or more signal detectors D1, D2, and D3, said signal values comprising substantially simultaneous signal values D1S1, D2S1, and D3S1 collected at discrete time t1, and substantially simultaneous signal values D1S2, D2S2, and D3S2 collected at discrete time t2, by the following steps:

27.1.1 constructing a graphic drawing entity P1 having as its drawing coordinates in space at least two of the respective signal values D1S1, and D2S1, and D3S1;

27.1.2 constructing a graphic drawing entity P2 having as its drawing coordinates in space at least two of the respective signal values D1S2, D2S2, and D3S2;

27.2 Iterating steps 27.1, 27.1.1, and 27.1.2 with additional signal values collected substantially simultaneously from at least two of said detectors D1, D2, and D3, at at least one of additional discrete signal times t3, t4, . . . . tn;

27.3 assigning to each of said drawing entities P1, P2, P3, . . . . Pn, in accord with temporal sequence, a visually distinctive color from a pre-determined sequence of colors C1t1, C2t2, C3t3, . . . . Cntn.

* * * * *